(12) United States Patent
Anantha et al.

(10) Patent No.: US 10,266,574 B2
(45) Date of Patent: Apr. 23, 2019

(54) TUBERCULOSIS COMPOSITIONS AND METHODS OF USING THE SAME

(71) Applicant: Aeras Global TB Vaccine Foundation, Rockville, MD (US)

(72) Inventors: Ravi Anantha, Rockville, MD (US); Nathalie Cadieux, Rockville, MD (US); Thomas G. Evans, Rockville, MD (US); Michele Stone, Rockville, MD (US); Barry Walker, Rockville, MD (US)

(73) Assignee: International AIDS Vaccine Initiative, Inc., New York, NY (US)

( * ) Notice: Subject to any disclaimer, the term of this patent is extended or adjusted under 35 U.S.C. 154(b) by 0 days.

(21) Appl. No.: 14/313,694

(22) Filed: Jun. 24, 2014

(65) Prior Publication Data

US 2014/0377300 A1 Dec. 25, 2014

Related U.S. Application Data

(60) Provisional application No. 61/838,872, filed on Jun. 25, 2013.

(51) Int. Cl.
*A61K 39/00* (2006.01)
*A61K 39/04* (2006.01)
*C07K 14/35* (2006.01)

(52) U.S. Cl.
CPC .............. *C07K 14/35* (2013.01); *A61K 39/04* (2013.01); *A61K 2039/523* (2013.01); *A61K 2039/545* (2013.01); *A61K 2039/55561* (2013.01); *A61K 2039/55572* (2013.01); *A61K 2039/70* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,593,972 A | 1/1997 | Weiner et al. | |
| 5,962,428 A | 10/1999 | Carrano | |
| 7,670,609 B2 * | 3/2010 | Shafferman | A61K 39/04 424/185.1 |
| 8,703,151 B2 | 4/2014 | Aagaard | |
| 2009/0136534 A1 | 5/2009 | Shafferman et al. | |
| 2011/0117133 A1 | 5/2011 | Shafferman et al. | |
| 2012/0003256 A1 | 1/2012 | Han et al. | |
| 2012/0219582 A1 | 8/2012 | Yasutomi et al. | |
| 2012/0244173 A1 | 9/2012 | Wu et al. | |
| 2012/0294882 A1 | 11/2012 | Blais et al. | |
| 2013/0142800 A1 | 6/2013 | Carroll et al. | |
| 2014/0377300 A1 | 12/2014 | Anantha et al. | |

FOREIGN PATENT DOCUMENTS

| | | | |
|---|---|---|---|
| CN | 101289496 | 10/2008 | |
| JP | 2013517783 | 5/2013 | |
| WO | 94016737 | 8/1994 | |
| WO | 2007/058663 | 5/2007 | |
| WO | WO2008124647 | 10/2008 | |
| WO | WO 2011045612 A1 * | 4/2011 | ............ C07K 14/435 |
| WO | WO2014009438 | 1/2014 | |

OTHER PUBLICATIONS

Cruse et al., Illustrated Dict. of Immunology, 2nd ed., CRC Press, 2003, p. 46.*
McGuinness et al. (Mol. Microbiol., 7:505-514, 1993).*
Moudallal et al. (EMBO Journal, 1:1005-1010, 1982).*
Abaza et al. (J. Prot. Chem., 11:433-444, 1992).*
Commandeur et al., "The in vivo expressed *Mycobacterium tuberculosis* (IVE-TB) antigen Rv2034 induces CD4+ T-cells that protect against pulmonary infection in HLA-DR transgenic mice and guinea pigs", Vaccine, 2014, 32, pp. 3580-3588.
Millington et al., "Rv3615c is a highly immunodominant RD1 (Region of Difference 1)-dependent secreted antigen specific for *Mycobacterium tuberculosis* infection", PNAS, 2011, 108(14), pp. 5730-5735.
Office Action dated Sep. 11, 2018 in related U.S. Appl. No. 15/624,853.
Kaufmann, Stefan H. et al., "Tuberculosis Vaccines: Time to think about the next generation", Seminars in Immunology, 2013, 25(2):172-181.

* cited by examiner

*Primary Examiner* — Brian Gangle
(74) *Attorney, Agent, or Firm* — Stradley Ronon Stevens & Young, LLP

(57) ABSTRACT

The present disclosure provides fusion proteins comprising *Mycobacterium tuberculosis* (Mtb) antigens, nucleic acid molecules encoding the same, vectors comprising nucleic acid molecules, compositions comprising the same, and methods of eliciting an immune response against tuberculosis.

6 Claims, 6 Drawing Sheets

Specification includes a Sequence Listing.

```
                             SEQUENCE LISTING

<160> NUMBER OF SEQ ID NOS: 100

<210> SEQ ID NO 1
<211> LENGTH: 977
<212> TYPE: DNA
<213> ORGANISM: Artificial Sequence
<220> FEATURE:
<223> OTHER INFORMATION: Description of Artificial Sequence:
      Mycobacterium Ag85B

<400> SEQUENCE: 1
atgacagacg tgagccgaaa gattcgagct tggggacgcc gattgatgat cggcacggca        60
gcggctgtag tccttccggg cctggtgggg cttgccgcgc agcggcaacc gcgggcgcgt       120
tctcccggcc ggggctgccg gtcgagtacc tgcaggtgcc gtcgccgtcg atgggccgcg       180
acatcaaggt tcagttccag agcggtggga acaactcacc tgcggtttat ctgctcgacg       240
gcctgcgcgc ccaagacgac tacaacggct gggatatcaa caccccggcg ttcgagtggt       300
actaccagtc gggactgtcg atagtcatgc cggtcggcgg gcagtccagc ttctacagcg       360
actggtacag cccggcctgc ggtaaggctg gctgccagac ttacaagtgg gaaaccttcc       420
tgaccagcga gctgccgcaa tggttgtccg ccaacagggc cgtgaagccc accggcagcg       480
ctgcaatcgg cttgtcgatg gccggctcgt cggcaatgat cttggccgcc taccaccccc       540
agcagttcat ctacgccggc tcgctgtcgg ccctgctgga ccccctcag gggatggggc       600 ctagcctgat cggcctcgcg atgggtgacg ccggcggtta caaggccgca gacatgtggg       660
gtccctcgag tgacccggca tgggagcgca acgaccctac gcagcagatc cccaagctgg       720
tcgcaaacaa cacccggcta tgggtttatt gcgggaacgg caccccgaac gagttgggcg       780
gtgccaacat acccgccgag ttcttggaga acttcgttcg tagcagcaac ctgaagttcc       840
aggatgcgta caacgccgcg ggcgggcaca acgccgtgtt caacttcccg cccaacggca       900
cgcacagctg ggagtactgg ggcgctcagc tcaacgccat gaagggtgac ctgcagagtt       960
cgttaggcgc cggctga                                                     977

<210> SEQ ID NO 2
<211> LENGTH: 858
<212> TYPE: DNA
<213> ORGANISM: Artificial Sequence
<220> FEATURE:
```

<223> OTHER INFORMATION: Description of Artificial Sequence:
       Mycobacterium Ag85B (E. coli optimized)

<400> SEQUENCE: 2

```
atgtttag

-continued

<212> TYPE: PRT
<213> ORGANISM: Artificial Sequence
<220> FEATURE:
<223> OTHER INFORMATION: Description of Artificial Sequence:
Mycobacterium Ag85B

<400> SEQUENCE: 4

```
Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325
```

<210> SEQ ID NO 5
<211> LENGTH: 286
<212> TYPE: PRT
<213> ORGANISM: Artificial Sequence
<220> FEATURE:
<223> OTHER INFORMATION: Description of Artificial Sequence:
Mycobacterium Ag85B (E. coli and human optimized)

<400> SEQUENCE: 5

```
Met Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Asn
            20                  25                  30

Asn Ser Pro Ala Val Tyr Leu Leu Asp Gly Leu Arg Ala Gln Asp Asp
        35                  40                  45

Tyr Asn Gly Trp Asp Ile Asn Thr Pro Ala Phe Glu Trp Tyr Tyr Gln
    50                  55                  60

Ser Gly Leu Ser Ile Val Met Pro Val Gly Gly Gln Ser Ser Phe Tyr
65                  70                  75                  80

Ser Asp Trp Tyr Ser Pro Ala Cys Gly Lys Ala Gly Cys Gln Thr Tyr
                85                  90                  95

Lys Trp Glu Thr Phe Leu Thr Ser Glu Leu Pro Gln Trp Leu Ser Ala
            100                 105                 110

Asn Arg Ala Val Lys Pro Thr Gly Ser Ala Ala Ile Gly Leu Ser Met
        115                 120                 125

Ala Gly Ser Ser Ala Met Ile Leu Ala Ala Tyr His Pro Gln Gln Phe
130                 135                 140

Ile Tyr Ala Gly Ser Leu Ser Ala Leu Leu Asp Pro Ser Gln Gly Met
145                 150                 155                 160

Gly Pro Ser Leu Ile Gly Leu Ala Met Gly Asp Ala Gly Gly Tyr Lys
                165                 170                 175

Ala Ala Asp Met Trp Gly Pro Ser Ser Asp Pro Ala Trp Glu Arg Asn
            180                 185                 190

Asp Pro Thr Gln Gln Ile Pro Lys Leu Val Ala Asn Asn Thr Arg Leu
        195                 200                 205

Trp Val Tyr Cys Gly Asn Gly Thr Pro Asn Glu Leu Gly Gly Ala Asn
210                 215                 220

Ile Pro Ala Glu Phe Leu Glu Asn Phe Val Arg Ser Ser Asn Leu Lys
225                 230                 235                 240

Phe Gln Asp Ala Tyr Asn Ala Ala Gly Gly His Asn Ala Val Phe Asn
                245                 250                 255

Phe Pro Pro Asn Gly Thr His Ser Trp Glu Tyr Trp Gly Ala Gln Leu
            260                 265                 270

Asn Ala Met Lys Gly Asp Leu Gln Ser Ser Leu Gly Ala Gly
        275                 280                 285
```

<210> SEQ ID NO 6
<211> LENGTH: 288
<212> TYPE: DNA
<213> ORGANISM: Artificial Sequence
<220> FEATURE:
<223> OTHER INFORMATION: Description of Artificial Sequence:
    Mycobacterium ESAT-6

<400> SEQUENCE: 6

```
atgacagagc agcagtggaa tttcgcgggt atcgaggccg cggcaagcgc aatccaggga      60
aatgtcacgt ccattcattc cctccttgac gagggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcatag                  288
```

<210> SEQ ID NO 7
<211> LENGTH: 282
<212> TYPE: DNA
<213> ORGANISM: Artificial Sequence
<220> FEATURE:
<223> OTHER INFORMATION: Description of Artificial Sequence:
      Mycobacterium ESAT-6 (human optimized)

<400> SEQUENCE: 7

```
accgagcagc agtggaactt cgccggcatc gaagctgccg ctagcgccat ccaaggcaac     60
gtgaccagca tccacagcct gctggacgag ggcaagcaga gcctgaccaa gctggctgct    120
gcttggggcg gatccggaag cgaagcctac cagggcgtgc agcagaagtg ggacgccaca    180
gccaccgagc tgaacaacgc cctgcagaac ctcgccagaa ccatcagcga ggccggacag    240
gctatggcca gcacagaggg caatgtgacc ggcatgttcg cc                       282
```

<210> SEQ ID NO 8
<211> LENGTH: 94
<212> TYPE: PRT
<213> ORGANISM: Artificial Sequence
<220> FEATURE:
<223> OTHER INFORMATION: Description of Artificial Sequence: ESAT-6

<400> SEQUENCE: 8

```
Thr Glu Gln Gln Trp Asn Phe Ala Gly Ile Glu Ala Ala Ala Ser Ala
1               5                   10                  15

Ile Gln Gly Asn Val Thr Ser Ile His Ser Leu Leu Asp Glu Gly Lys
            20                  25                  30

Gln Ser Leu Thr Lys Leu Ala Ala Ala Trp Gly Gly Ser Gly Ser Glu
        35                  40                  45

Ala Tyr Gln Gly Val Gln Gln Lys Trp Asp Ala Thr Ala Thr Glu Leu
    50                  55                  60

Asn Asn Ala Leu Gln Asn Leu Ala Arg Thr Ile Ser Glu Ala Gly Gln
65                  70                  75                  80

Ala Met Ala Ser Thr Glu Gly Asn Val Thr Gly Met Phe Ala
                85                  90
```

<210> SEQ ID NO 9
<211> LENGTH: 687
<212> TYPE: DNA
<213> ORGANISM: Artificial Sequence
<220> FEATURE:
<223> OTHER INFORMATION: Description of Artificial Sequence:
      Mycobacterium Rv1980c

<400> SEQUENCE: 9

```
gtgcgcatca agatcttcat gctggtcacg gctgtcgttt tgctctgttg ttcgggtgtg     60
gccacggccg cgcccaagac ctactgcgag gagttgaaag gcaccgatac cggccaggcg    120
tgccagattc aaatgtccga cccggcctac aacatcaaca tcagcctgcc cagttactac    180
cccgaccaga agtcgctgga aaattacatc gcccagacgc gcgacaagtt cctcagcgcg    240
gccacatcgt ccactccacg cgaagccccc tacgaattga atatcacctc ggccacatac    300
cagtccgcga taccgccgcg tggtacgcag gccgtggtgc tcaaggtcta ccagaacgcc    360
ggcggcacgc acccaacgac cacgtacaag gccttcgatt gggaccaggc ctatcgcaag    420
ccaatcacct atgacacgct gtggcaggct gacaccgatc cgctgccagt cgtcttcccc    480
attgtgcaag gtgaactgag caagcagacc ggacaacagg tatcgatagc gccgaatgcc    540
ggcttggacc cggtgaatta tcagaacttc gcagtcacga acgacggggt gattttcttc    600
```

```
ttcaacccgg gggagttgct gcccgaagca gccggcccaa cccaggtatt ggtcccacgt    660
tccgcgatcg actcgatgct ggcctag                                        687

<210> SEQ ID NO 10
<211> LENGTH: 690
<212> TYPE: DNA
<213> ORGANISM: Artificial Sequence
<220> FEATURE:
<223> OTHER INFORMATION: Description of Artificial Sequence:
      Mycobacterium Rv1980c (human optimized)

<400> SEQUENCE: 10
atggtcagga tcaagatctt catgctcgtg accgccgtgg tgctcctgtg ttgttccggc    60
gtggctaccg ctgctcccaa gacctactgc gaggagctga agggaaccga caccggccag   120
gcctgccaga tccaaatgag cgaccccgcc tacaacatca catctcccct ccctcctac    180 taccccgatc agaagtccct cgagaactac atcgctcaga ccagggacaa gttcctgagc   240
gccgccacaa gcagcacacc cagagaggcc ccctacgagc tgaacatcac ctccgccacc   300
taccagtccg ctattcctcc cagaggcacc caggctgtgg tgctcaaggt ctaccaaaac   360
gctggcggaa cacccccac caccacctac aaggccttcg actgggacca ggcctacagg   420
aagcccatca catacgacac cctgtggcag gctgataccg atccctgcc cgtggtgttc    480 cccatcgtgc agggcgagct ctccaagcag accggccagc aagtgagcat cgcccccaat   540
gctggactgg accccgtgaa ctaccagaac ttcgccgtca ccaacgacgg cgtgatcttc    600
ttcttcaatc ccggcgaact gctgcctgaa gctgctggcc ccacccaagt gctggtgcct    660
agaagcgcca tcgactccat gctggcctga                                     690

<210> SEQ ID NO 11
<211> LENGTH: 228
<212> TYPE: PRT
<213> ORGANISM: Artificial Sequence
<220> FEATURE:
<223> OTHER INFORMATION: Description of Artificial Sequence: Rv1980c

<400> SEQUENCE: 11

Val Arg Ile Lys Ile Phe Met Leu Val Thr Ala Val Val Leu Leu Cys
1               5                   10                  15

Cys Ser Gly Val Ala Thr Ala Ala Pro Lys Thr Tyr Cys Glu Glu Leu
            20                  25                  30

Lys Gly Thr Asp Thr Gly Gln Ala Cys Gln Ile Gln Met Ser Asp Pro
        35                  40                  45

Ala Tyr Asn Ile Asn Ile Ser Leu Pro Ser Tyr Pro Asp Gln Lys
    50                  55                  60

Ser Leu Glu Asn Tyr Ile Ala Gln Thr Arg Asp Lys Phe Leu Ser Ala
65                  70                  75                  80

Ala Thr Ser Ser Thr Pro Arg Glu Ala Pro Tyr Glu Leu Asn Ile Thr
                85                  90                  95

Ser Ala Thr Tyr Gln Ser Ala Ile Pro Pro Arg Gly Thr Gln Ala Val
            100                 105                 110

Val Leu Lys Val Tyr Gln Asn Ala Gly Gly Thr His Pro Thr Thr Thr
        115                 120                 125

Tyr Lys Ala Phe Asp Trp Asp Gln Ala Tyr Arg Lys Pro Ile Thr Tyr
    130                 135                 140

Asp Thr Leu Trp Gln Ala Asp Thr Asp Pro Leu Pro Val Val Phe Pro
145                 150                 155                 160
```

```
Ile Val Gln Gly Glu Leu Ser Lys Gln Thr Gly Gln Gln Val Ser Ile
            165                 170                 175

Ala Pro Asn Ala Gly Leu Asp Pro Val Asn Tyr Gln Asn Phe Ala Val
        180                 185                 190

Thr Asn Asp Gly Val Ile Phe Phe Phe Asn Pro Gly Glu Leu Leu Pro
    195                 200                 205

Glu Ala Ala Gly Pro Thr Gln Val Leu Val Pro Arg Ser Ala Ile Asp
210                 215                 220

Ser Met Leu Ala
225

<210> SEQ ID NO 12
<211> LENGTH: 1176
<212> TYPE: DNA
<213> ORGANISM: Artificial Sequence
<220> FEATURE:
<223> OTHER INFORMATION: Description of Artificial Sequence:
      Mycobacterium Rv1039c

<400> SEQUENCE: 12
atggatttcg gagctttacc ccctgagatc aactccgcac gcatgtacgc cggcgcgggt      60
gcaggaccga tgatggccgc cggggccgca tggaacggcc tggccgccga gttgggtacg     120
acggccgcgt cgtatgagtc ggtgatcacc cggctgacca ccgagtcgtg gatgggtccg     180
gcctcgatgg cgatggtcgc cgcagcccag ccctatctgg cttggttgac ctacaccgcc     240
gaagccgctg cgcatgccgg ctcgcaggcc atggcgtcgg cggccgccta cgaggcggcc     300
tatgcgatga cagtgccgcc ggaggtggtc gcggccaacc gggcgctgct ggcggccctg     360
gtcgcgacga acgtcctggg gatcaacaca ccggcaatca tggcgaccga agccctctat     420
gccgagatgt gggctcagga cgctctggct atgtacggct acgcgccgc ttcgggagcc     480
gccgggatgc tgcaaccgtt aagcccgccg tcgcagacca ccaacccggg cgggctggcc     540
gcccagtccg ccgcggtcgg ctcggctgcc gccaccgccg ccgtcaacca ggtgagcgta     600
gcggacctga tcagtagcct gcccaacgcg gtgagtgggc tcgcctcccc agtcacatcg     660
gttctcgact cgacggggct gagcggaatc attgccgaca tcgacgccct gctcgcgacc     720
ccgttcgtgg caaacatcat caacagcgca gtcaacaccg ccgcttggta tgtcaacgcc     780
gccatcccca ccgcgatatt cctagcaaat gccctgaaca gtggggcgcc ggtagcgatc     840
gccgaaggcg ccatcgaggc tgccgagggt gccgccagtg cggccgccgc ggggttggcg     900
gactcggtga cgccagcggg gctcggcgca agtttaggcg aggccaccct ggtcggccgg     960
ctgtcagtgc cggcggcctg gtctacggcc gcaccggcga caaccgccgg cgccacagcg    1020
ctcgaaggca gcggctggac cgtcgccgcc gaagaagccg gcccagttac cgggatgatg    1080
ccgggaatgg cctcggccgc caagggcacc ggtgcctatg ccgggccgcg gtacggattc    1140
aagcccactg tcatgcccaa acaggtcgtc gtgtga                             1176

<210> SEQ ID NO 13
<211> LENGTH: 1176
<212> TYPE: DNA
<213> ORGANISM: Artificial Sequence
<220> FEATURE:
<223> OTHER INFORMATION: Description of Artificial Sequence:
      Mycobacterium Rv1039c (human optimized)

<400> SEQUENCE: 13
atggattttg gcgccctgcc tcccgagatc aacagcgcta ggatgtatgc tggcgctgga      60
```

```
gccggaccta tgatggccgc tggagccgcc tggaatggac tggctgccga actgggcaca    120
acagccgctt cctacgagtc cgtgatcacc agactcacca cagagtcctg gatgggacct    180
gccagcatgg ctatggtcgc cgctgctcaa ccctacctgg cctggctgac ctatacagct    240
gaagccgctg ctcacgccgg aagccaagct atggctagcg ccgccgctta tgaggccgct    300
tatgccatga ccgtgcctcc cgaggtcgtg gctgccaaca gagctctcct ggccgccctc    360
gtggctacca acgtgctggg aatcaacacc ccgctatta tggccaccga ggctctgtac    420
gctgagatgt gggcccagga tgccctcgcc atgtacggat acgccgctgc ttccggagct    480
gctggaatgc tgcagcccct gtcccccccct tcccagacca ccaacccccgg aggactggct    540
gctcaaagcg ctgctgtggg atccgctgct gctaccgctg ccgtcaatca ggtcagcgtc    600
gccgacctca tctccagcct gcctaacgct gtgagcggac tggcctcccc tgtcacatcc    660
gtgctcgata gcaccggcct gtccggcatc atcgccgaca ttgatgctct cctcgccacc    720
cccttgtcg ccaacatcat caattccgcc gtgaacaccg ctgcctggta cgtcaacgct    780
gccattccca ccgccatctt cctcgccaac gccctgaact ccggagctcc tgtcgccatc    840
gctgagggcg ctattgaggc tgctgaagga gccgctagcg ctgctgctgc tggactggct    900
gatagcgtca cccctgctgg actcggagct agcctgggag aagccaccct ggtcggcaga    960
ctgtccgtgc ctgctgcttg gagcaccgct gctcctgcta caaccgctgg agctaccgct    1020
ctggagggat ccggatggac agtggctgct gaggaagctg acccgtgac cggaatgatg    1080
cctggcatgg ccagcgctgc taagggaacc ggcgcctatg ccggacccag atacggattc    1140
aagcccaccg tcatgcccaa gcaggtcgtc gtctaa                              1176
```

<210> SEQ ID NO 14
<211> LENGTH: 391
<212> TYPE: PRT
<213> ORGANISM: Artificial Sequence
<220> FEATURE:
<223> OTHER INFORMATION: Description of Artificial Sequence: Rv1039c

<400> SEQUENCE: 14

```
Met Asp Phe Gly Ala Leu Pro Pro Glu Ile Asn Ser Ala Arg Met Tyr
1               5                  10                  15

Ala Gly Ala Gly Ala Gly Pro Met Met Ala Gly Ala Ala Trp Asn
            20                  25                  30

Gly Leu Ala Ala Glu Leu Gly Thr Thr Ala Ala Ser Tyr Glu Ser Val
        35                  40                  45

Ile Thr Arg Leu Thr Thr Glu Ser Trp Met Gly Pro Ala Ser Met Ala
    50                  55                  60

Met Val Ala Ala Ala Gln Pro Tyr Leu Ala Trp Leu Thr Tyr Thr Ala
65                  70                  75                  80

Glu Ala Ala Ala His Ala Gly Ser Gln Ala Met Ala Ser Ala Ala Ala
                85                  90                  95

Tyr Glu Ala Ala Tyr Ala Met Thr Val Pro Pro Glu Val Val Ala Ala
            100                 105                 110

Asn Arg Ala Leu Leu Ala Ala Leu Val Ala Thr Asn Val Leu Gly Ile
        115                 120                 125

Asn Thr Pro Ala Ile Met Ala Thr Glu Ala Leu Tyr Ala Glu Met Trp
    130                 135                 140

Ala Gln Asp Ala Leu Ala Met Tyr Gly Tyr Ala Ala Ala Ser Gly Ala
145                 150                 155                 160

Ala Gly Met Leu Gln Pro Leu Ser Pro Pro Ser Gln Thr Thr Asn Pro
```

```
                165                 170                 175
Gly Gly Leu Ala Ala Gln Ser Ala Ala Val Gly Ser Ala Ala Ala Thr
            180                 185                 190
Ala Ala Val Asn Gln Val Ser Val Ala Asp Leu Ile Ser Ser Leu Pro
        195                 200                 205
Asn Ala Val Ser Gly Leu Ala Ser Pro Val Thr Ser Val Leu Asp Ser
    210                 215                 220
Thr Gly Leu Ser Gly Ile Ile Ala Asp Ile Asp Ala Leu Leu Ala Thr
225                 230                 235                 240
Pro Phe Val Ala Asn Ile Ile Asn Ser Ala Val Asn Thr Ala Ala Trp
                245                 250                 255
Tyr Val Asn Ala Ala Ile Pro Thr Ala Ile Phe Leu Ala Asn Ala Leu
            260                 265                 270
Asn Ser Gly Ala Pro Val Ala Ile Ala Glu Gly Ala Ile Glu Ala Ala
        275                 280                 285
Glu Gly Ala Ala Ser Ala Ala Ala Gly Leu Ala Asp Ser Val Thr
    290                 295                 300
Pro Ala Gly Leu Gly Ala Ser Leu Gly Glu Ala Thr Leu Val Gly Arg
305                 310                 315                 320
Leu Ser Val Pro Ala Ala Trp Ser Thr Ala Ala Pro Ala Thr Thr Ala
                325                 330                 335
Gly Ala Thr Ala Leu Glu Gly Ser Gly Trp Thr Val Ala Ala Glu Glu
            340                 345                 350
Ala Gly Pro Val Thr Gly Met Met Pro Gly Met Ala Ser Ala Ala Lys
        355                 360                 365
Gly Thr Gly Ala Tyr Ala Gly Pro Arg Tyr Gly Phe Lys Pro Thr Val
    370                 375                 380
Met Pro Lys Gln Val Val Val
385                 390

<210> SEQ ID NO 15
<211> LENGTH: 1143
<212> TYPE: DNA
<213> ORGANISM: Artificial Sequence
<220> FEATURE:
<223> OTHER INFORMATION: Description of Artificial Sequence:
      Mycobacterium Rv3136

<400> SEQUENCE: 15
atggatttcg cactgttacc accggaagtc aactccgccc ggatgtacac cggccctggg    60
gcaggatcgc tgttggctgc cgcgggcggc tgggattcgc tggccgccga gttggccacc    120
acagccgagg catatggatc ggtgctgtcc ggactggccg ccttgcattg cgtggaccg    180 gcagcggaat cgatggcggt gacggccgct ccctatatcg gttggctgta cacgaccgcc    240
gaaaagacac agcaaacagc gatccaagcc agggcggcag cgctggcctt cgagcaagca    300
tacgcaatga ccctgccgcc accggtggta gcggccaacc ggatacagct gctagcactg    360
atcgcgacga acttcttcgg ccagaacact gcggcgatcg cggccaccga ggcacagtac    420
gccgagatgt gggcccagga cgccgccgcg atgtacggtt acgccaccgc ctcagcggct    480
gcggccctgc tgacaccgtt ctccccgccg cggcagacca ccaacccggc cggcctgacc    540
gctcaggccg ccgcggtcag ccaggccacc gacccactgt cgctgctgat tgagacggtg    600
acccaagcgc tgcaagcgct gacgattccg agcttcatcc ctgaggactt caccttcctt    660
gacgccatat tcgctggata tgccacggta ggtgtgacgc aggatgtcga gtcctttgtt    720
```

| | |
|---|---|
| gccgggacca tcggggccga gagcaaccta ggccttttga acgtcggcga cgagaatccc | 780 |
| gcggaggtga caccgggcga ctttgggatc ggcgagttgg tttccgcgac cagtcccggc | 840 |
| ggtggggtgt ctgcgtcggg tgccggcggt gcggcgagcg tcggcaacac ggtgctcgcg | 900 |
| agtgtcggcc gggcaaactc gattgggcaa ctatccggtcc caccgagctg ggccgcgccc | 960 |
| tcgacgcgcc ctgtctcggc attgtcgccc gccggcctga ccacactccc ggggaccgac | 1020 |
| gtggccgagc acgggatgcc aggtgtaccg ggggtgccag tggcagcagg gcgagcctcc | 1080 |
| ggcgtcctac ctcgatacgg ggttcggctc acggtgatgg cccacccacc cgcggcaggg | 1140 |
| taa | 1143 |

<210> SEQ ID NO 16
<211> LENGTH: 1146
<212> TYPE: DNA
<213> ORGANISM: Artificial Sequence
<220> FEATURE:
<223> OTHER INFORMATION: Description of Artificial Sequence:
      Mycobacterium Rv3136 (E. coli optimized)

<400> SEQUENCE: 16

| | |
|---|---|
| atggattttg cgctgctgcc gccggaagtg aacagcgcgc gcatgtatac cggcccgggc | 60 |
| gcgggcagcc tgctggcggc ggcgggcggc tgggatagcc tggcggcgga actggcgacc | 120 |
| accgcggaag cgtatggcag cgtgctgagc ggcctggcgg cgctgcattg cgcggcccg | 180 |
| gcggcggaaa gcatggcggt gaccgcggcg ccgtatattg gctggctgta taccaccgcg | 240 |
| gaaaaaaccc agcagaccgc gattcaggcg cgcgcggcgg cgctggcgtt tgaacaggcg | 300 |
| tatgcgatga ccctgccgcc gccggtggtg gcggcgaacc gcattcagct gctggcgctg | 360 |
| attgcgacca acttttttgg ccagaacacc gcggcgattg cggcgaccga agcgcagtat | 420 |
| gcggaaatgt gggcgcagga tgcggcggcg atgtatggct atgcgaccgc gagcgcggcg | 480 |
| gcggcgctgc tgaccccgtt tagcccgccg cgccagacca ccaacccggc gggcctgacc | 540 |
| gcgcaggcgg cggcggtgag ccaggcgacc gatccgctga gcctgctgat tgaaaccgtg | 600 |
| acccaggcgc tgcaggcgct gaccattccg agctttattc cggaagattt tacctttctg | 660 |
| gatgcgattt ttgcgggcta tgcgaccgtg gcgtgaccc aggatgtgga aagctttgtg | 720 |
| gcgggcacca ttggcgcgga aagcaacctg gcctgctga acgtgggcga tgaaaacccg | 780 |
| gcggaagtga cccggggcga ttttggcatt ggcgaactgg tgagcgcgac cagcccgggc | 840 |
| ggcggcgtga gcgcgagcgg cgcgggcggc gcggcgagcg tgggcaacac cgtgctggcg | 900 |
| agcgtgggcc gcgcgaacag cattggccag ctgagcgtgc cgccgagctg gcggcgccg | 960 |
| agcacccgcc cggtgagcgc gctgagcccg gcgggcctga ccaccctgcc gggcaccgat | 1020 |
| gtggcggaac atggcatgcc gggcgtgccg gcgtgccgg tggcggcggg ccgcgcgagc | 1080 |
| ggcgtgctgc cgcgctatgg cgtgcgcctg accgtgatgg cgcatccgcc ggcggcgggc | 1140 |
| gaattt | 1146 |

<210> SEQ ID NO 17
<211> LENGTH: 1143
<212> TYPE: DNA
<213> ORGANISM: Artificial Sequence
<220> FEATURE:
<223> OTHER INFORMATION: Description of Artificial Sequence:
      Mycobacterium Rv3136 (human optimized)

<400> SEQUENCE: 17

| | |
|---|---|
| atggatttcg ctctgctccc ccccgaggtg aatagcgcta ggatgtacac aggacccgga | 60 |

```
gctggaagcc tcctggctgc tgctggagga tgggactccc tggctgccga gctcgctaca    120
accgctgagg cttacggaag cgtgctctcc ggcctggctg ctctccattg gagaggccct    180
gctgccgagt ccatggctgt cacagccgct ccctacattg gatggctgta caccaccgcc    240
gagaagaccc agcaaaccgc tattcaggcc agagctgccg ccctggcctt cgaacaggcc    300
tacgctatga cactcccccc ccctgtcgtg gctgccaata ggatccagct cctggccctc    360
atcgccacca acttcttcgg ccaaaacacc gctgccatcg ctgccaccga agcccagtac    420
gccgaaatgt gggcccagga tgccgctgct atgtacggct atgccacagc tagcgctgcc    480
gctgctctgc tcacaccctt cagcccccca aggcaaacaa ccaaccctgc cggactgaca    540
gcccaagctg ctgccgtcag ccaagctacc gaccccctga gcctcctgat cgaaaccgtg    600
acacaggccc tgcaggccct gaccattccc agctttatcc ccgaggactt cacctttctg    660
gacgctatct cgctggcta cgccaccgtg ggcgtgacac aagacgtcga gtccttcgtc    720
gccggcacaa tcggagccga gtccaacctc ggactcctca acgtcggcga cgaaaatccc    780
gccgaagtga cacctggaga cttcggcatt ggagaactcg tcagcgccac atcccctggc    840
ggaggagtga gcgcttccgg agctggagga gctgcttccg tgggcaatac cgtgctggcc    900
agcgtgggaa gggccaactc cattggccag ctcagcgtcc cccttcctg ggctgcccct     960 tccacaaggc ctgtgtccgc tctcagccct gctggactga ccacactccc tggcacagac   1020
gtggctgagc atggcatgcc cggagtgcct ggagtccctg tggctgctgg cagagcttcc   1080
ggagtcctcc ctaggtatgg cgtgaggctg acagtgatgg ctcatccccc cgctgccgga   1140
taa                                                                  1143
```

<210> SEQ ID NO 18
<211> LENGTH: 380
<212> TYPE: PRT
<213> ORGANISM: Artificial Sequence
<220> FEATURE:
<223> OTHER INFORMATION: Description of Artificial Sequence: Rv3136

<400> SEQUENCE: 18

```
Met Asp Phe Ala Leu Leu Pro Pro Glu Val Asn Ser Ala Arg Met Tyr
1               5                   10                  15

Thr Gly Pro Gly Ala Gly Ser Leu Leu Ala Ala Gly Gly Trp Asp
            20                  25                  30

Ser Leu Ala Ala Glu Leu Ala Thr Thr Ala Glu Ala Tyr Gly Ser Val
        35                  40                  45

Leu Ser Gly Leu Ala Ala Leu His Trp Arg Gly Pro Ala Ala Glu Ser
    50                  55                  60

Met Ala Val Thr Ala Ala Pro Tyr Ile Gly Trp Leu Tyr Thr Thr Ala
65                  70                  75                  80

Glu Lys Thr Gln Gln Thr Ala Ile Gln Ala Arg Ala Ala Ala Leu Ala
                85                  90                  95

Phe Glu Gln Ala Tyr Ala Met Thr Leu Pro Pro Val Val Ala Ala
            100                 105                 110

Asn Arg Ile Gln Leu Leu Ala Leu Ile Ala Thr Asn Phe Phe Gly Gln
        115                 120                 125

Asn Thr Ala Ala Ile Ala Ala Thr Glu Ala Gln Tyr Ala Glu Met Trp
    130                 135                 140

Ala Gln Asp Ala Ala Ala Met Tyr Gly Tyr Ala Thr Ala Ser Ala Ala
145                 150                 155                 160
```

```
Ala Ala Leu Leu Thr Pro Phe Ser Pro Pro Arg Gln Thr Thr Asn Pro
            165                 170                 175

Ala Gly Leu Thr Ala Gln Ala Ala Val Ser Gln Ala Thr Asp Pro
        180                 185                 190

Leu Ser Leu Leu Ile Glu Thr Val Thr Gln Ala Leu Gln Ala Leu Thr
            195                 200                 205

Ile Pro Ser Phe Ile Pro Glu Asp Phe Thr Phe Leu Asp Ala Ile Phe
            210                 215                 220

Ala Gly Tyr Ala Thr Val Gly Val Thr Gln Asp Val Glu Ser Phe Val
225                 230                 235                 240

Ala Gly Thr Ile Gly Ala Glu Ser Asn Leu Gly Leu Leu Asn Val Gly
            245                 250                 255

Asp Glu Asn Pro Ala Glu Val Thr Pro Gly Asp Phe Gly Ile Gly Glu
            260                 265                 270

Leu Val Ser Ala Thr Ser Pro Gly Gly Val Ser Ala Ser Gly Ala
            275                 280                 285

Gly Gly Ala Ala Ser Val Gly Asn Thr Val Leu Ala Ser Val Gly Arg
            290                 295                 300

Ala Asn Ser Ile Gly Gln Leu Ser Val Pro Pro Ser Trp Ala Ala Pro
305                 310                 315                 320

Ser Thr Arg Pro Val Ser Ala Leu Ser Pro Ala Gly Leu Thr Thr Leu
            325                 330                 335

Pro Gly Thr Asp Val Ala Glu His Gly Met Pro Gly Val Pro Gly Val
            340                 345                 350

Pro Val Ala Ala Gly Arg Ala Ser Gly Val Leu Pro Arg Tyr Gly Val
            355                 360                 365

Arg Leu Thr Val Met Ala His Pro Pro Ala Ala Gly
            370                 375                 380

<210> SEQ ID NO 19
<211> LENGTH: 312
<212> TYPE: DNA
<213> ORGANISM: Artificial Sequence
<220> FEATURE:
<223> OTHER INFORMATION: Description of Artificial Sequence:
      Mycobacterium Rv3615c

<400> SEQUENCE: 19
atgacggaaa acttgaccgt ccagcccgag cgtctcggtg tactggcgtc gcaccatgac    60
aacgcggcgg tcgatgcctc ctcgggcgtc gaagctgccg ctggcctagg cgaatctgtg   120
gcgatcactc acggtccgta ctgctcacag ttcaacgaca cgttaaatgt gtacttgact   180
gcccacaatg ccctgggctc gtccttgcat acggccggtg tcgatctcgc caaaagtctt   240
cgaattgcgg cgaagatata tagcgaggcc gacgaagcgt ggcgcaaggc tatcgacggg   300
ttgtttacct ga                                                       312

<210> SEQ ID NO 20
<211> LENGTH: 312
<212> TYPE: DNA
<213> ORGANISM: Artificial Sequence
<220> FEATURE:
<223> OTHER INFORMATION: Description of Artificial Sequence:
      Mycobacterium Rv3615c (human optimized)

<400> SEQUENCE: 20
atgaccgaga acctgaccgt gcagcctgag aggctgggag tgctggccag ccaccacgac    60
aacgctgccg tggacgcttc cagcggagtg gaggctgctg ctggactggg agagagcgtg   120
```

```
gccatcaccc acggacccta ctgcagccag ttcaacgaca ccctgaacgt gtacctgaca    180
gcccacaacg ccctgggaag cagcctgcat acagccggcg tggacctggc taagtccctg    240
aggatcgccg ccaagatcta cagcgaggcc gacgaggcct ggaggaaagc catcgacggc    300
ctgttcacct aa                                                        312
```

```
<210> SEQ ID NO 21
<211> LENGTH: 103
<212> TYPE: PRT
<213> ORGANISM: Artificial Sequence
<220> FEATURE:
<223> OTHER INFORMATION: Description of Artificial Sequence: Rv3615c

<400> SEQUENCE: 21

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
            20                  25                  30

Ala Ala Gly Leu Gly Glu Ser Val Ala Ile Thr His Gly Pro Tyr Cys
        35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100
```

```
<210> SEQ ID NO 22
<211> LENGTH: 633
<212> TYPE: DNA
<213> ORGANISM: Artificial Sequence
<220> FEATURE:
<223> OTHER INFORMATION: Description of Artificial Sequence:
      Mycobacterium Rv1733c

<400> SEQUENCE: 22
atgatcgcca caacccgcga tcgtgaagga gccaccatga tcacgtttag gctgcgcttg     60
ccgtgccgga cgatactgcg ggtgttcagc cgcaatccgc tggtgcgtgg acggatcga    120 ctcgaggcgg tcgtcatgct gctggccgtc acggtctcgc tgctgactat cccgttcgcc    180
gccgcggccg gcaccgcagt ccaggattcc cgcagccacg tctatgccca ccaggcccag    240
acccgccatc ccgcaaccgc gaccgtgatc gatcacgagg gggtgatcga cagcaacacg    300
accgccacgt cagcgccgcc gcgcacgaag atcaccgtgc ctgcccgatg ggtcgtgaac    360
ggaatagaac gcagcggtga ggtcaacgcg aagccgggaa ccaaatccgg tgaccgcgtc    420
ggcatttggg tcgacagtgc cggtcagctg gtcgatgaac cagctccgcc ggcccgtgcc    480
attgcggatg cggccctggc cgccttggga ctctggttga gcgtcgccgc ggttgcgggc    540
gccctgctgg cgctcactcg ggcgattctg atccgcgttc gcaacgccag ttggcaacac    600
gacatcgaca gcctgttctg cacgcagcgg tga                                 633
```

```
<210> SEQ ID NO 23
<211> LENGTH: 630
<212> TYPE: DNA
<213> ORGANISM: Artificial Sequence
<220> FEATURE:
```

<223> OTHER INFORMATION: Description of Artificial Sequence:
      Mycobacterium Rv1733c (E. coli optimized)

<400> SEQUENCE: 23

```
atgattgcga ctacccgtga tcgtgagggc gcgaccatga tcacgttccg tctgcgtctg      60
ccgtgtcgca ccattttgcg cgtgttttcg cgtaacccgc tggtccgcgg taccgaccgt     120
ctggaggccg ttgtcatgct gctggcggtt accgtgagcc tgctgacgat cccattcgca     180
gcggcagctg gcacggccgt ccaagacagc cgtagccatg tgtatgctca ccaggctcaa     240
acccgtcacc cggctactgc cactgttatc gatcacgaag gcgtgattga ctccaatacc     300
acggcaacct ccgcaccgcc tcgcaccaag attacggttc ctgcgcgttg ggtggtgaat     360
ggtattgaac gcagcggcga agttaatgcc aaaccgggta ccaaaagcgg tgaccgtgtg     420
ggcatctggg tcgatagcgc cggtcagctg gtcgacgagc cggcaccgcc agcgcgtgcg     480
atcgccgatg cggcgctggc tgccctgggt ctgtggctga gcgtggcagc ggtcgccggt     540
gcgttgctgg cgctgacgcg cgcaattctg atccgcgttc gcaatgcgag ctggcagcac     600
gatattgata gcctgttttg cacccaacgt                                      630
```

<210> SEQ ID NO 24
<211> LENGTH: 210
<212> TYPE: PRT
<213> ORGANISM: Artificial Sequence
<220> FEATURE:
<223> OTHER INFORMATION: Description of Artificial Sequence: Rv1733c

<400> SEQUENCE: 24

```
Met Ile Ala Thr Thr Arg Asp Arg Glu Gly Ala Thr Met Ile Thr Phe
1               5                   10                  15

Arg Leu Arg Leu Pro Cys Arg Thr Ile Leu Arg Val Phe Ser Arg Asn
            20                  25                  30

Pro Leu Val Arg Gly Thr Asp Arg Leu Glu Ala Val Val Met Leu Leu
        35                  40                  45

Ala Val Thr Val Ser Leu Leu Thr Ile Pro Phe Ala Ala Ala Ala Gly
    50                  55                  60

Thr Ala Val Gln Asp Ser Arg Ser His Val Tyr Ala His Gln Ala Gln
65                  70                  75                  80

Thr Arg His Pro Ala Thr Ala Thr Val Ile Asp His Glu Gly Val Ile
                85                  90                  95

Asp Ser Asn Thr Thr Ala Thr Ser Ala Pro Pro Arg Thr Lys Ile Thr
            100                 105                 110

Val Pro Ala Arg Trp Val Val Asn Gly Ile Glu Arg Ser Gly Glu Val
        115                 120                 125

Asn Ala Lys Pro Gly Thr Lys Ser Gly Asp Arg Val Gly Ile Trp Val
    130                 135                 140

Asp Ser Ala Gly Gln Leu Val Asp Glu Pro Ala Pro Pro Ala Arg Ala
145                 150                 155                 160

Ile Ala Asp Ala Ala Leu Ala Ala Leu Gly Leu Trp Leu Ser Val Ala
                165                 170                 175

Ala Val Ala Gly Ala Leu Leu Ala Leu Thr Arg Ala Ile Leu Ile Arg
            180                 185                 190

Val Arg Asn Ala Ser Trp Gln His Asp Ile Asp Ser Leu Phe Cys Thr
        195                 200                 205

Gln Arg
    210
```

<210> SEQ ID NO 25
<211> LENGTH: 504
<212> TYPE: DNA
<213> ORGANISM: Artificial Sequence
<220> FEATURE:
<223> OTHER INFORMATION: Description of Artificial Sequence:
    Mycobacterium Rv1733c (transmembrane deleted; E. coli optimized)

<400> SEQUENCE: 25

```
atgattgcga

```
                50                  55                  60
Thr Ala Thr Val Ile Asp His Glu Gly Val Ile Asp Ser Asn Thr Thr
 65                  70                  75                  80

Ala Thr Ser Ala Pro Pro Arg Thr Lys Ile Thr Val Pro Ala Arg Trp
                 85                  90                  95

Val Val Asn Gly Ile Glu Arg Ser Gly Glu Val Asn Ala Lys Pro Gly
            100                 105                 110

Thr Lys Ser Gly Asp Arg Val Gly Ile Trp Val Asp Ser Ala Gly Gln
        115                 120                 125

Leu Val Asp Glu Pro Ala Pro Pro Ala Arg Ala Ile Ala Asp Ser Arg
130                 135                 140

Arg Ala Ile Leu Ile Arg Val Arg Asn Ala Ser Trp Gln His Asp Ile
145                 150                 155                 160

Asp Ser Leu Phe Cys Thr Gln Arg
                165

<210> SEQ ID NO 28
<211> LENGTH: 163
<212> TYPE: PRT
<213> ORGANISM: Artificial Sequence
<220> FEATURE:
<223> OTHER INFORMATION: Description of Artificial Sequence: Rv1733c
      (both transmembrane regions deleted; human optimized)

<400> SEQUENCE: 28

Ile Ala Thr Thr Arg Asp Arg Glu Gly Ala Thr Met Ile Thr Phe Arg
  1               5                  10                  15

Leu Arg Leu Pro Cys Arg Thr Ile Leu Arg Val Phe Ser Arg Asn Pro
                 20                  25                  30

Leu Val Arg Gly Thr Asp Arg Leu Glu Ala Val Gln Asp Ser Arg Ser
             35                  40                  45

His Val Tyr Ala His Gln Ala Gln Thr Arg His Pro Ala Thr Ala Thr
         50                  55                  60

Val Ile Asp His Glu Gly Val Ile Asp Ser Asn Thr Thr Ala Thr Ser
 65                  70                  75                  80

Ala Pro Pro Arg Thr Lys Ile Thr Val Pro Ala Arg Trp Val Val Asn
                 85                  90                  95

Gly Ile Glu Arg Ser Gly Glu Val Asn Ala Lys Pro Gly Thr Lys Ser
            100                 105                 110

Gly Asp Arg Val Gly Ile Trp Val Asp Ser Ala Gly Gln Leu Val Asp
        115                 120                 125

Glu Pro Ala Pro Pro Ala Arg Ala Ile Ala Asp Arg Ala Ile Leu Ile
    130                 135                 140

Arg Val Arg Asn Ala Ser Trp Gln His Asp Ile Asp Ser Leu Phe Cys
145                 150                 155                 160

Thr Gln Arg

<210> SEQ ID NO 29
<211> LENGTH: 432
<212> TYPE: DNA
<213> ORGANISM: Artificial Sequence
<220> FEATURE:
<223> OTHER INFORMATION: Description of Artificial Sequence:
      Mycobacterium Rv2626c

<400> SEQUENCE: 29
atgaccaccg cacgcgacat catgaacgca ggtgtgacct gtgttggcga acacgagacg    60
```

```
ctaaccgctg ccgctcaata catgcgtgag cacgacatcg gcgcgttgcc gatctgcggg      120
gacgacgacc ggctgcacgg catgctcacc gaccgcgaca ttgtgatcaa aggcctggct      180
gcgggcctag acccgaatac cgccacggct ggcgagttgg cccgggacag catctactac      240
gtcgatgcga acgcaagcat ccaggagatg ctcaacgtca tggaagaaca tcaggtccgc      300
cgtgttccgg tcatctcaga gcaccgcttg gtcggaatcg tcaccgaagc cgacatcgcc      360
cgacacctgc ccgagcacgc cattgtgcag ttcgtcaagg caatctgctc gcccatggcc      420
ctcgccagct ag                                                         432

<210> SEQ ID NO 30
<211> LENGTH: 428
<212> TYPE: DNA
<213> ORGANISM: Artificial Sequence
<220> FEATURE:
<223> OTHER INFORMATION: Description of Artificial Sequence:
      Mycobacterium Rv2626c (E. coli optimized)

<400> SEQUENCE: 30
atgaccacgg cgcgtgatat catgaatgcg ggtgtcacct gtgttggcga gcacgaaacg      60
ttgaccgcag cagcacagta catgcgcgaa catgatatcg gcgcattgcc gatttgcggc      120
gacgatgatc gtctgcacgg tatgctgacc gaccgcgata tcgttatcaa gggtctggcc      180
gcaggcttgg acccgaacac cgcgaccgcc ggtgaactgg cacgtgacag catctattac      240
gtcgacgcga acgccagcat tcaagagatg ctgaacgtga tggaagagca tcaggtgcgt      300
cgtgtcccgg ttatcagcga acatcgtctg gttggtatcg ttaccgaagc cgacatcgca      360
cgtcacctgc cggagcacgc gattgttcag ttcgtgaaag cgatttgcag cccgatggcg      420
ttggcgtc                                                              428

<210> SEQ ID NO 31
<211> LENGTH: 426
<212> TYPE: DNA
<213> ORGANISM: Artificial Sequence
<220> FEATURE:
<223> OTHER INFORMATION: Description of Artificial Sequence:
      Mycobacterium Rv2626c (human optimized)

<400> SEQUENCE: 31
acaacagcca gggacatcat gaacgccggc gtgacctgcg tgggagagca tgaaaccctc      60
accgccgccg cccaatacat gagggagcac gacatcggcg ccctgcccat ctgtggagac      120
gacgacaggc tgcacggcat gctgaccgac agggacatcg tgatcaaggg cctggctgcc      180
ggcctcgatc ctaacaccgc tacagccggc gagctggcca gagacagcat ctactacgtg      240
gacgccaacg ccagcatcca ggagatgctc aacgtgatgg aggagcacca ggtgagaagg      300
gtgcctgtga tcagcgagca caggctggtg ggcatcgtga ccgaggccga tatcgctagg      360
cacctgcccg agcacgccat cgtgcagttc gtgaaggcca tctgcagccc catggctctg      420
gccagc                                                                426

<210> SEQ ID NO 32
<211> LENGTH: 143
<212> TYPE: PRT
<213> ORGANISM: Artificial Sequence
<220> FEATURE:
<223> OTHER INFORMATION: Description of Artificial Sequence: Rv2626c

<400> SEQUENCE: 32

Met Thr Thr Ala Arg Asp Ile Met Asn Ala Gly Val Thr Cys Val Gly
```

```
            1               5                  10                  15
         Glu His Glu Thr Leu Thr Ala Ala Gln Tyr Met Arg Glu His Asp
                         20                  25                  30
         Ile Gly Ala Leu Pro Ile Cys Gly Asp Asp Arg Leu His Gly Met
                         35                  40                  45
         Leu Thr Asp Arg Asp Ile Val Ile Lys Gly Leu Ala Ala Gly Leu Asp
                         50              55                  60
         Pro Asn Thr Ala Thr Ala Gly Glu Leu Ala Arg Asp Ser Ile Tyr Tyr
         65                      70                  75                  80
         Val Asp Ala Asn Ala Ser Ile Gln Glu Met Leu Asn Val Met Glu Glu
                                 85                  90                  95
         His Gln Val Arg Arg Val Pro Val Ile Ser Glu His Arg Leu Val Gly
                         100                 105                 110
         Ile Val Thr Glu Ala Asp Ile Ala Arg His Leu Pro Glu His Ala Ile
                         115                 120                 125
         Val Gln Phe Val Lys Ala Ile Cys Ser Pro Met Ala Leu Ala Ser
                         130                 135                 140
```

<210> SEQ ID NO 33
<211> LENGTH: 300
<212> TYPE: DNA
<213> ORGANISM: Artificial Sequence
<220> FEATURE:
<223> OTHER INFORMATION: Description of Artificial Sequence:
      Mycobacterium Rv3407

<400> SEQUENCE: 33

```
atgcgtgcta ccgttgggct tgtggaggca atcggaatcc gagaactaag acagcacgca      60
tcgcgatacc tcgcccgggt tgaagccggc gaggaacttg gcgtcaccaa caaaggaaga     120
cttgtggccc gactcatccc ggtgcaggcc gcggagcgtt ctcgcgaagc cctgattgaa     180
tcaggtgtcc tgattccggc tcgtcgtcca caaaaccttc tcgacgtcac cgccgaaccg     240
gcgcgcggcc gcaagcgcac cctgtccgat gttctcaacg aaatgcgcga cgagcagtga    300
```

<210> SEQ ID NO 34
<211> LENGTH: 297
<212> TYPE: DNA
<213> ORGANISM: Artificial Sequence
<220> FEATURE:
<223> OTHER INFORMATION: Description of Artificial Sequence:
      Mycobacterium Rv3407 (E. coli optimized)

<400> SEQUENCE: 34

```
atgcgtgcga ctgtgggtct ggttgaggcg attggcattc gcgagctgcg ccaacatgcc      60
agccgttact tggctcgtgt cgaggcgggt gaagaactgg gcgtgacgaa taagggtcgt     120
ctggtcgccc gtctgattcc ggttcaggca gctgagcgtt ctcgcgaggc gctgattgaa     180
tccggcgtcc tgatcccggc tcgccgtccg caaaacctgc tggacgtgac ggcggagcca     240
gctcgtggtc gcaaacgcac gctgtctgat gtcctgaacg aaatgcgcga cgagcag       297
```

<210> SEQ ID NO 35
<211> LENGTH: 297
<212> TYPE: DNA
<213> ORGANISM: Artificial Sequence
<220> FEATURE:
<223> OTHER INFORMATION: Description of Artificial Sequence:
      Mycobacterium Rv3407 (human optimized)

<400> SEQUENCE: 35

```
atgagggcga ccgtcgggct ggtggaggcg ataggtatcc gggagttgcg acagcacgca    60
tcacgatatc tggcacgggt ggaagctggg gaggaactgg gcgtgaccaa caagggcgg   120 ctggtcgcga ggctgatccc cgtgcaggcc gccgagcggt cccgcgaagc cctcatcgag   180
tctggggtgc tcattccagc acgcaggccg caaaatctcc tggacgtcac tgcggagccc   240
gccagaggca gaaagaggac gctgagtgac gtgctgaacg agatgaggga cgaacag     297
```

```
<210> SEQ ID NO 36
<211> LENGTH: 99
<212> TYPE: PRT
<213> ORGANISM: Artificial Sequence
<220> FEATURE:
<223> OTHER INFORMATION: Description of Artificial Sequence: Rv3407

<400> SEQUENCE: 36
```

```
Met Arg Ala Thr Val Gly Leu Val Glu Ala Ile Gly Ile Arg Glu Leu
1               5                   10                  15

Arg Gln His Ala Ser Arg Tyr Leu Ala Arg Val Glu Ala Gly Glu Glu
            20                  25                  30

Leu Gly Val Thr Asn Lys Gly Arg Leu Val Ala Arg Leu Ile Pro Val
        35                  40                  45

Gln Ala Ala Glu Arg Ser Arg Glu Ala Leu Ile Glu Ser Gly Val Leu
    50                  55                  60

Ile Pro Ala Arg Arg Pro Gln Asn Leu Leu Asp Val Thr Ala Glu Pro
65                  70                  75                  80

Ala Arg Gly Arg Lys Arg Thr Leu Ser Asp Val Leu Asn Glu Met Arg
                85                  90                  95

Asp Glu Gln
```

```
<210> SEQ ID NO 37
<211> LENGTH: 363
<212> TYPE: DNA
<213> ORGANISM: Artificial Sequence
<220> FEATURE:
<223> OTHER INFORMATION: Description of Artificial Sequence:
      Mycobacterium Rv2628c

<400> SEQUENCE: 37
```

```
atgtccacgc aacgaccgag gcactccggt attcgggctg ttggccccta cgcatgggcc    60
ggccgatgtg gtcggatagg caggtggggg gtgcaccagg aggcgatgat gaatctagcg   120
atatggcacc cgcgcaaggt gcaatccgcc accatctatc aggtgaccga tcgctcgcac   180
gacgggcgca cagcacgggt gcctggtgac gagatcacta gcaccgtgtc cggttggttg   240
tcggagttgg gcacccaaag cccgttggcc gatgagcttg cgcgtgcggt gcggatcggc   300
gactggcccg ctgcgtacgc aatcggtgag cacctgtccg ttgagattgc cgttgcggtc   360
taa                                                                363
```

```
<210> SEQ ID NO 38
<211> LENGTH: 363
<212> TYPE: DNA
<213> ORGANISM: Artificial Sequence
<220> FEATURE:
<223> OTHER INFORMATION: Description of Artificial Sequence:
      Mycobacterium Rv2628c (human optimized)

<400> SEQUENCE: 38
```

```
atgagcaccc agagacccag gcacagcggc attagggccg tgggacctta tgcttgggcc    60
ggcagatgcg gaaggatcgg cagatggggc gtgcaccaag aggccatgat gaacctggcc   120
```

| | |
|---|---|
| atctggcacc ccaggaaggt gcagagcgcc accatctacc aggtgaccga caggagccat | 180 |
| gacggaagga ccgccagagt gcccggcgat gagatcacca gcaccgtgag cggctggctg | 240 |
| agcgaactgg gcacccaatc cccccctggct gatgaactgg ccagggctgt gaggatcggc | 300 |
| gattggcctg ccgcctatgc catcggcgag catctgagcg tggagatcgc cgtggccgtg | 360 |
| taa | 363 |

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Rv2628c

<400> SEQUENCE: 39

Met Ser Thr Gln Arg Pro Arg His Ser Gly Ile Arg Ala Val Gly Pro
1               5                   10                  15

Tyr Ala Trp Ala Gly Arg Cys Gly Arg Ile Gly Arg Trp Gly Val His
            20                  25                  30

Gln Glu Ala Met Met Asn Leu Ala Ile Trp His Pro Arg Lys Val Gln
        35                  40                  45

Ser Ala Thr Ile Tyr Gln Val Thr Asp Arg Ser His Asp Gly Arg Thr
    50                  55                  60

Ala Arg Val Pro Gly Asp Glu Ile Thr Ser Thr Val Ser Gly Trp Leu
65                  70                  75                  80

Ser Glu Leu Gly Thr Gln Ser Pro Leu Ala Asp Glu Leu Ala Arg Ala
                85                  90                  95

Val Arg Ile Gly Asp Trp Pro Ala Ala Tyr Ala Ile Gly Glu His Leu
            100                 105                 110

Ser Val Glu Ile Ala Val Ala Val
        115                 120

<210> SEQ ID NO 40
<211> LENGTH: 1089
<212> TYPE: DNA
<213> ORGANISM: Artificial Sequence
<220> FEATURE:
<223> OTHER INFORMATION: Description of Artificial Sequence:
      Mycobacterium Rv1009

<400> SEQUENCE: 40

| | |
|---|---|
| atgttgcgcc tggtagtcgg tgcgctgctg ctggtgttgg cgttcgccgg tggctatgcg | 60 |
| gtcgccgcat gcaaaacggt gacgttgacc gtcgacggaa ccgcgatgcg ggtgaccacg | 120 |
| atgaaatcgc gggtgatcga catcgtcgaa gagaacgggt tctcagtcga cgaccgcgac | 180 |
| gacctgtatc ccgcggccgg cgtgcaggtc catgacgcc acaccatcgt gctgcggcgt | 240 |
| agccgtccgc tgcagatctc gctggatggt cacgacgcta agcaggtgtg gacgaccgcg | 300 |
| tcgacggtgg acgaggcgct ggcccaactc gcgatgaccg acacgcgcc ggccgcggct | 360 |
| tctcgcgcca gccgcgtccc gctgtccggg atggcgctac cggtcgtcag cgccaagacg | 420 |
| gtgcagctca cgacggcgg gttggtgcgc acggtgcact tgccggcccc caatgtcgcg | 480 |
| gggctgctga gtgcggccgg cgtgccgctg ttgcaaagcg accacgtggt gcccgccgcg | 540 |
| acggccccga tcgtcgaagg catgcagatc caggtgaccc gcaatcggat caagaaggtc | 600 |
| accgagcggc tgccgctgcc gccgaacgcg cgtcgtgtcg aggacccgga gatgaacatg | 660 |
| agccgggagg tcgtcgaaga cccgggggtt ccggggaccc aggatgtgac gttcgcggta | 720 |

```
gctgaggtca acggcgtcga gaccggccgt ttgcccgtcg ccaacgtcgt ggtgaccccg      780
gcccacgaag ccgtggtgcg ggtgggcacc aagcccggta ccgaggtgcc cccggtgatc      840
gacggaagca tctgggacgc gatcgccggc tgtgaggccg gtggcaactg ggcgatcaac      900
accggcaacg ggtattacgg tggtgtgcag tttgaccagg gcacctggga ggccaacggc      960
gggctgcggt atgcaccccg cgctgacctc gccacccgcg aagagcagat cgccgttgcc     1020
gaggtgaccc gactgcgtca aggttggggc gcctggccgg tatgtgctgc acgagcgggt     1080
gcgcgctga                                                             1089
```

<210> SEQ ID NO 41
<211> LENGTH: 1023
<212> TYPE: DNA
<213> ORGANISM: Artificial Sequence
<220> FEATURE:
<223> OTHER INFORMATION: Description of Artificial Sequence:
      Mycobacterium Rv1009 (signal sequence deleted)

<400> SEQUENCE: 41

```
gcatgcaaaa cggtgacgtt gaccgtcgac ggaaccgcga tgcgggtgac cacgatgaaa       60
tcgcgggtga tcgacatcgt cgaagagaac gggttctcag tcgacgaccg cgacgacctg      120
tatcccgcgg ccggcgtgca ggtccatgac gccgacacca tcgtgctgcg gcgtagccgt      180
ccgctgcaga tctcgctgga tggtcacgac gctaagcagg tgtggacgac cgcgtcgacg      240
gtggacgagg cgctggccca actcgcgatg accgacacgg cgccggccgc ggcttctcgc      300
gccagccgcg tcccgctgtc cgggatggcg ctaccggtcg tcagcgccaa gacggtgcag      360
ctcaacgacg gcgggttggt gcgcacggtg cacttgccgg ccccaatgt cgcggggctg       420 ctgagtgcgg ccggcgtgcc gctgttgcaa agcgaccacg tggtgcccgc cgcgacggcc      480
ccgatcgtcg aaggcatgca gatccaggtg acccgcaatc ggatcaagaa ggtcaccgag      540
cggctgccgc tgccgccgaa cgcgcgtcgt gtcgaggacc cggagatgaa catgagccgg      600
gaggtcgtcg aagacccggg ggttccgggg acccaggatg tgacgttcgc ggtagctgag      660
gtcaacggcg tcgagaccgg ccgtttgccc gtcgccaacg tcgtggtgac cccggcccac      720
gaagccgtgg tgcgggtggg caccaagccc ggtaccgagg tgcccccggt gatcgacgga      780
agcatctggg acgcgatcgc cggctgtgag gccggtggca actgggcgat caacaccggc      840
aacgggtatt acggtggtgt gcagtttgac cagggcacct gggaggccaa cggcgggctg      900
cggtatgcac cccgcgctga cctcgccacc cgcgaagagc agatcgccgt tgccgaggtg      960
acccgactgc gtcaaggttg gggcgcctgg ccggtatgtg ctgcacgagc gggtgcgcgc     1020
tga                                                                  1023
```

<210> SEQ ID NO 42
<211> LENGTH: 362
<212> TYPE: PRT
<213> ORGANISM: Artificial Sequence
<220> FEATURE:
<223> OTHER INFORMATION: Description of Artificial Sequence: RpfB
      (mycobacterial sequence)

<400> SEQUENCE: 42

```
Met Leu Arg Leu Val Val Gly Ala Leu Leu Leu Val Leu Ala Phe Ala
1               5                   10                  15

Gly Gly Tyr Ala Val Ala Ala Cys Lys Thr Val Thr Leu Thr Val Asp
            20                  25                  30
```

Gly Thr Ala Met Arg Val Thr Thr Met Lys Ser Arg Val Ile Asp Ile
                35                  40                  45

Val Glu Glu Asn Gly Phe Ser Val Asp Asp Arg Asp Leu Tyr Pro
 50                  55                  60

Ala Ala Gly Val Gln Val His Asp Ala Asp Thr Ile Val Leu Arg Arg
 65                  70                  75                  80

Ser Arg Pro Leu Gln Ile Ser Leu Asp Gly His Asp Ala Lys Gln Val
                 85                  90                  95

Trp Thr Thr Ala Ser Thr Val Asp Glu Ala Leu Ala Gln Leu Ala Met
                100                 105                 110

Thr Asp Thr Ala Pro Ala Ala Ser Arg Ala Ser Arg Val Pro Leu
                115                 120                 125

Ser Gly Met Ala Leu Pro Val Val Ser Ala Lys Thr Val Gln Leu Asn
130                 135                 140

Asp Gly Gly Leu Val Arg Thr Val His Leu Pro Ala Pro Asn Val Ala
145                 150                 155                 160

Gly Leu Leu Ser Ala Ala Gly Val Pro Leu Leu Gln Ser Asp His Val
                165                 170                 175

Val Pro Ala Ala Thr Ala Pro Ile Val Glu Gly Met Gln Ile Gln Val
                180                 185                 190

Thr Arg Asn Arg Ile Lys Lys Val Thr Glu Arg Leu Pro Leu Pro Pro
                195                 200                 205

Asn Ala Arg Arg Val Glu Asp Pro Glu Met Asn Met Ser Arg Glu Val
                210                 215                 220

Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
                260                 265                 270

Gly Thr Glu Val Pro Pro Val Ile Asp Gly Ser Ile Trp Asp Ala Ile
                275                 280                 285

Ala Gly Cys Glu Ala Gly Gly Asn Trp Ala Ile Asn Thr Gly Asn Gly
                290                 295                 300

Tyr Tyr Gly Gly Val Gln Phe Asp Gln Gly Thr Trp Glu Ala Asn Gly
305                 310                 315                 320

Gly Leu Arg Tyr Ala Pro Arg Ala Asp Leu Ala Thr Arg Glu Glu Gln
                325                 330                 335

Ile Ala Val Ala Glu Val Thr Arg Leu Arg Gln Gly Trp Gly Ala Trp
                340                 345                 350

Pro Val Cys Ala Ala Arg Ala Gly Ala Arg
                355                 360

<210> SEQ ID NO 43
<211> LENGTH: 340
<212> TYPE: PRT
<213> ORGANISM: Artificial Sequence
<220> FEATURE:
<223> OTHER INFORMATION: Description of Artificial Sequence: RpfB
      (mycobacterial sequence; signal sequence deleted)

<400> SEQUENCE: 43

Ala Cys Lys Thr Val Thr Leu Thr Val Asp Gly Thr Ala Met Arg Val
1               5                   10                  15

Thr Thr Met Lys Ser Arg Val Ile Asp Ile Val Glu Glu Asn Gly Phe
                20                  25                  30

```
Ser Val Asp Asp Arg Asp Leu Tyr Pro Ala Ala Gly Val Gln Val
    35                  40                  45

His Asp Ala Asp Thr Ile Val Leu Arg Arg Ser Arg Pro Leu Gln Ile
 50                  55                  60

Ser Leu Asp Gly His Asp Ala Lys Gln Val Trp Thr Thr Ala Ser Thr
 65                  70                  75                  80

Val Asp Glu Ala Leu Ala Gln Leu Ala Met Thr Asp Thr Ala Pro Ala
                 85                  90                  95

Ala Ala Ser Arg Ala Ser Arg Val Pro Leu Ser Gly Met Ala Leu Pro
            100                 105                 110

Val Val Ser Ala Lys Thr Val Gln Leu Asn Asp Gly Gly Leu Val Arg
        115                 120                 125

Thr Val His Leu Pro Ala Pro Asn Val Ala Gly Leu Leu Ser Ala Ala
130                 135                 140

Gly Val Pro Leu Leu Gln Ser Asp His Val Val Pro Ala Ala Thr Ala
145                 150                 155                 160

Pro Ile Val Glu Gly Met Gln Ile Gln Val Thr Arg Asn Arg Ile Lys
                165                 170                 175

Lys Val Thr Glu Arg Leu Pro Leu Pro Pro Asn Ala Arg Arg Val Glu
            180                 185                 190

Asp Pro Glu Met Asn Met Ser Arg Glu Val Val Glu Asp Pro Gly Val
        195                 200                 205

Pro Gly Thr Gln Asp Val Thr Phe Ala Val Ala Glu Val Asn Gly Val
210                 215                 220

Glu Thr Gly Arg Leu Pro Val Ala Asn Val Val Val Thr Pro Ala His
225                 230                 235                 240

Glu Ala Val Val Arg Val Gly Thr Lys Pro Gly Thr Glu Val Pro Pro
                245                 250                 255

Val Ile Asp Gly Ser Ile Trp Asp Ala Ile Ala Gly Cys Glu Ala Gly
            260                 265                 270

Gly Asn Trp Ala Ile Asn Thr Gly Asn Gly Tyr Tyr Gly Gly Val Gln
        275                 280                 285

Phe Asp Gln Gly Thr Trp Glu Ala Asn Gly Gly Leu Arg Tyr Ala Pro
290                 295                 300

Arg Ala Asp Leu Ala Thr Arg Glu Glu Gln Ile Ala Val Ala Glu Val
305                 310                 315                 320

Thr Arg Leu Arg Gln Gly Trp Gly Ala Trp Pro Val Cys Ala Ala Arg
                325                 330                 335

Ala Gly Ala Arg
            340

<210> SEQ ID NO 44
<211> LENGTH: 465
<212> TYPE: DNA
<213> ORGANISM: Artificial Sequence
<220> FEATURE:
<223> OTHER INFORMATION: Description of Artificial Sequence:
      Mycobacterium Rv2389c

<400> SEQUENCE: 44
atgacaccgg gtttgcttac tactgcgggt gctggccgac cacgtgacag gtgcgccagg      60
atcgtatgca cggtgttcat cgaaaccgcc gttgtcgcga ccatgtttgt cgcgttgttg     120
ggtctgtcca ccatcagctc gaaagccgac gacatcgatt gggacgccat cgcgcaatgc     180
gaatccggcg gcaattgggc ggccaacacc ggtaacgggt atacggtgg tctgcagatc      240
```

-continued

```
agccaggcga cgtgggattc aacggtggt gtcgggtcgc cggcggccgc gagtccccag    300
caacagatcg aggtcgcaga caacattatg aaaacccaag gcccgggtgc gtggccgaaa    360
tgtagttctt gtagtcaggg agacgcaccg ctgggctcgc tcacccacat cctgacgttc    420
ctcgcggccg agactggagg ttgttcgggg agcagggacg attga                    465
```

<210> SEQ ID NO 45
<211> LENGTH: 354
<212> TYPE: DNA
<213> ORGANISM: Artificial Sequence
<220> FEATURE:
<223> OTHER INFORMATION: Description of Artificial Sequence:
    Mycobacterium Rv2389c (E. coli optimized; leader sequence deleted)

<400> SEQUENCE: 45

```
aagcttttgc tgggcctgag caccattagc agcaaagcgg atgacatcga ctgggatgcg    60
attgcgcagt gtgagagcgg tggcaattgg gcagcgaata ccggcaatgg cctgtacggc   120
ggtctgcaga tctcccaggc gacgtgggac agcaatggtg gcgtcggcag cccggctgcc   180
gcgtccccac aacaacagat cgaggtggca gataacatta tgaaaacgca gggtccgggt   240
gcttggccaa aatgctccag ctgcagccag ggtgacgcac cgctgggcag cctgaccccac  300 attctgacgt tcctggcagc ggaaaccggt ggttgtagcg gtagccgcga tgac           354
```

<210> SEQ ID NO 46
<211> LENGTH: 465
<212> TYPE: DNA
<213> ORGANISM: Artificial Sequence
<220> FEATURE:
<223> OTHER INFORMATION: Description of Artificial Sequence:
    Mycobacterium Rv2389c (human optimized; leader sequence present)

<400> SEQUENCE: 46

```
accccggac tcctcaccac agctggagct ggcaggccca gagacagatg cgccaggatc     60
gtgtgcaccg tgttcatcga accgccgtg gtggctacca tgttcgtggc cctgctgggc    120
ctgagcacca tcagcagcaa ggccgacgac atcgactggg acgccatcgc ccagtgtgaa   180
tccggcggaa actgggccgc caataccggc aatggcctgt acgcggcct gcagatcagc    240 caggctacct gggactccaa cggaggagtg ggaagccctg ccgctgcttc ccctcagcag    300
cagatcgagg tggccgacaa catcatgaag acccaaggcc ctggcgcctg gcctaagtgt    360
tccagctgta gccagggcga tgctcctctg ggcagcctga cccacatcct gacctttctc    420
gccgccgaga caggcggatg tagcggaagc agggacgact aatga                    465
```

<210> SEQ ID NO 47
<211> LENGTH: 116
<212> TYPE: PRT
<213> ORGANISM: Artificial Sequence
<220> FEATURE:
<223> OTHER INFORMATION: Description of Artificial Sequence: RpfD (E.
    coli optimized)

<400> SEQUENCE: 47

```
Leu Leu Gly Leu Ser Thr Ile Ser Ser Lys Ala Asp Asp Ile Asp Trp
 1               5                  10                  15

Asp Ala Ile Ala Gln Cys Glu Ser Gly Gly Asn Trp Ala Ala Asn Thr
            20                  25                  30

Gly Asn Gly Leu Tyr Gly Gly Leu Gln Ile Ser Gln Ala Thr Trp Asp
        35                  40                  45
```

Ser Asn Gly Gly Val Gly Ser Pro Ala Ala Ala Ser Pro Gln Gln Gln
 50                  55                  60

Ile Glu Val Ala Asp Asn Ile Met Lys Thr Gln Gly Pro Gly Ala Trp
 65                  70                  75                  80

Pro Lys Cys Ser Ser Cys Ser Gln Gly Asp Ala Pro Leu Gly Ser Leu
                 85                  90                  95

Thr His Ile Leu Thr Phe Leu Ala Ala Glu Thr Gly Gly Cys Ser Gly
            100                 105                 110

Ser Arg Asp Asp
        115

<210> SEQ ID NO 48
<211> LENGTH: 153
<212> TYPE: PRT
<213> ORGANISM: Artificial Sequence
<220> FEATURE:
<223> OTHER INFORMATION: Description of Artificial Sequence: RpfD
      (mycobacterial sequence and human optimized)

<400> SEQUENCE: 48

Thr Pro Gly Leu Leu Thr Thr Ala Gly Ala Gly Arg Pro Arg Asp Arg
  1               5                  10                  15

Cys Ala Arg Ile Val Cys Thr Val Phe Ile Glu Thr Ala Val Val Ala
                 20                  25                  30

Thr Met Phe Val Ala Leu Leu Gly Leu Ser Thr Ile Ser Ser Lys Ala
             35                  40                  45

Asp Asp Ile Asp Trp Asp Ala Ile Ala Gln Cys Glu Ser Gly Gly Asn
 50                  55                  60

Trp Ala Ala Asn Thr Gly Asn Gly Leu Tyr Gly Gly Leu Gln Ile Ser
 65                  70                  75                  80

Gln Ala Thr Trp Asp Ser Asn Gly Gly Val Gly Ser Pro Ala Ala Ala
                 85                  90                  95

Ser Pro Gln Gln Gln Ile Glu Val Ala Asp Asn Ile Met Lys Thr Gln
            100                 105                 110

Gly Pro Gly Ala Trp Pro Lys Cys Ser Ser Cys Ser Gln Gly Asp Ala
        115                 120                 125

Pro Leu Gly Ser Leu Thr His Ile Leu Thr Phe Leu Ala Ala Glu Thr
    130                 135                 140

Gly Gly Cys Ser Gly Ser Arg Asp Asp
145                 150

<210> SEQ ID NO 49
<211> LENGTH: 519
<212> TYPE: DNA
<213> ORGANISM: Artificial Sequence
<220> FEATURE:
<223> OTHER INFORMATION: Description of Artificial Sequence:
      Mycobacterium Rv2450c

<400> SEQUENCE: 49
ttgaagaacg cccgtacgac gctcatcgcc gccgcgattg ccgggacgtt ggtgaccacg      60
tcaccagccg gtatcgccaa tgccgacgac gcgggcttgg acccaaacgc cgcagccggc     120
ccggatgccg tgggctttga cccgaacctg ccgccgccc cggacgctgc acccgtcgat     180
actccgccgg ctccggagga cgcgggcttt gatcccaacc tcccccgcc gctggccccg     240 gacttcctgt ccccgcctgc ggaggaagcg cctcccgtgc ccgtggccta cagcgtgaac     300
tgggacgcga tcgcgcagtg cgagtccggt ggaaactggg cgatcaacac cggtaacggt     360
tactacggcg gcctgcggtt caccgccggc acctggcgtg ccaacggtgg ctcggggtcc 420
gcggccaacg cgagccggga ggagcagatc cgggtggctg agaacgtgct gcgttcgcag 480
ggtatccgcg cctggccggt ctgcggccgc cgcggctga 519

<210> SEQ ID NO 50
<211> LENGTH: 172
<212> TYPE: PRT
<213> ORGANISM: Artificial Sequence
<220> FEATURE:
<223> OTHER INFORMATION: Description of Artificial Sequence: RpfE

<400> SEQUENCE: 50

Leu Lys Asn Ala Arg Thr Thr Leu Ile Ala Ala Ala Ile Ala Gly Thr
1 5 10 15

Leu Val Thr Thr Ser Pro Ala Gly Ile Ala Asn Ala Asp Asp Ala Gly
20 25 30

Leu Asp Pro Asn Ala Ala Ala Gly Pro Asp Ala Val Gly Phe Asp Pro
35 40 45

Asn Leu Pro Pro Ala Pro Asp Ala Ala Pro Val Asp Thr Pro Pro Ala
50 55 60

Pro Glu Asp Ala Gly Phe Asp Pro Asn Leu Pro Pro Pro Leu Ala Pro
65 70 75 80

Asp Phe Leu Ser Pro Pro Ala Glu Glu Ala Pro Pro Val Pro Val Ala
85 90 95

Tyr Ser Val Asn Trp Asp Ala Ile Ala Gln Cys Glu Ser Gly Gly Asn
100 105 110

Trp Ser Ile Asn Thr Gly Asn Gly Tyr Tyr Gly Gly Leu Arg Phe Thr
115 120 125

Ala Gly Thr Trp Arg Ala Asn Gly Gly Ser Gly Ser Ala Ala Asn Ala
130 135 140

Ser Arg Glu Glu Gln Ile Arg Val Ala Glu Asn Val Leu Arg Ser Gln
145 150 155 160

Gly Ile Arg Ala Trp Pro Val Cys Gly Arg Arg Gly
165 170

<210> SEQ ID NO 51
<211> LENGTH: 1584
<212> TYPE: DNA
<213> ORGANISM: Artificial Sequence
<220> FEATURE:
<223> OTHER INFORMATION: Description of Artificial Sequence: Mycobacterium ESAT6-Rv1733c-Rv2626c-RpfD fusion protein (E. coli optimized)

<400> SEQUENCE: 51
atgacagagc agcagtggaa tttcgcgggt atcgaggccg cggcaagcgc aatccaggga 60
aatgtcacgt ccattcattc cctccttgac gaggggaagc agtccctgac caagctcgca 120
gcggcctggg gcggtagcgg ttcggaggcg taccagggtg tccagcaaaa atgggacgcc 180
acggctaccg agctgaacaa cgcgctgcag aacctggcgc ggacgatcag cgaagccggt 240
caggcaatgg cttcgaccga aggcaacgtc actgggatgt tcgcagaatt catgattgcg 300
actacccgtg atcgtgaggg cgcgaccatg atcacgttcc gtctgcgtct gccgtgtcgc 360
accattttgc gcgtgttttc gcgtaacccg ctggtccgcg gtaccgaccg tctggaggcc 420
cccggggtcc aagacagccg tagccatgtg tatgctcacc aggctcaaac ccgtcacccg 480
gctactgcca ctgttatcga tcacgaaggc gtgattgact ccaataccac ggcaacctcc 540

-continued

```
gcaccgcctc gcaccaagat tacggttcct gcgcgttggg tggtgaatgg tattgaacgc    600
agcggcgaag ttaatgccaa accgggtacc aaaagcggtg accgtgtggg catctgggtc    660
gatagcgccg gtcagctggt cgacgagccg gcaccgccag cgcgtgcgat cgccgattct    720
agacgcgcaa ttctgatccg cgttcgcaat gcgagctggc agcacgatat tgatagcctg    780
ttttgcaccc aacgtgagct catgaccacg gcgcgtgata tcatgaatgc gggtgtcacc    840
tgtgttggcg agcacgaaac gttgaccgca gcagcacagt acatgcgcga acatgatatc    900
ggcgcattgc cgatttgcgg cgacgatgat cgtctgcacg gtatgctgac cgaccgcgat    960
atcgttatca agggtctggc cgcaggcttg gacccgaaca ccgcgaccgc cggtgaactg   1020
gcacgtgaca gcatctatta cgtcgacgcg aacgccagca ttcaagagat gctgaacgtg   1080
atggaagagc atcaggtgcg tcgtgtcccg gttatcagcg aacatcgtct ggttggtatc   1140
gttaccgaag ccgacatcgc acgtcacctg ccggagcacg cgattgttca gttcgtgaaa   1200
gcgatttgca gcccgatggc gttggcgtct aagcttttgc tgggcctgag caccattagc   1260
agcaaagcgg atgacatcga ctgggatgcg attgcgcagt gtgagagcgg tggcaattgg   1320
gcagcgaata ccggcaatgg cctgtacggc ggtctgcaga tctcccaggc gacgtgggac   1380
agcaatggtg gcgtcggcag cccggctgcc gcgtccccac aacaacagat cgaggtggca   1440
gataacatta tgaaaacgca gggtccgggt gcttggccaa aatgctccag ctgcagccag   1500
ggtgacgcac cgctgggcag cctgacccac attctgacgt tcctggcagc ggaaaccggt   1560
ggttgtagcg gtagccgcga tgac                                          1584
```

<210> SEQ ID NO 52
<211> LENGTH: 1689
<212> TYPE: DNA
<213> ORGANISM: Artificial Sequence
<220> FEATURE:
<223> OTHER INFORMATION: Description of Artificial Sequence: Mycobacterium ESAT6-Rv1733c-Rv2626c-RpfD fusion protein (human optimized)

<400> SEQUENCE: 52

```
atgaccgagc agcagtggaa cttcgccggc atcgaagctg ccgctagcgc catccaaggc     60
aacgtgacca gcatccacag cctgctggac gagggcaagc agagcctgac caagctggct    120
gctgcttggg gcggatccgg aagcgaagcc taccagggcg tgcagcagaa gtgggacgcc    180
acagccaccg agctgaacaa cgccctgcag aacctcgcca gaaccatcag cgaggccgga    240
caggctatgg ccagcacaga gggcaatgtg accggcatgt tcgccttcga aatcgccacc    300
accagggaca gggaaggcgc taccatgatc accttcaggc tgaggctccc ctgcaggacc    360
atcctgaggg tgttcagcag gaacccctg gtgaggggca ccgacagact ggaagccgtg     420
caggacagca ggagccacgt gtatgcccac caggctcaga ccaggcaccc tgctaccgcc    480
accgtgatcg accacgaggg cgtgatcgac tccaacacca ccgccaccag cgctcctccc    540
agaaccaaga tcacagtgcc cgccaggtgg gtggtgaacg gcatcgagag gagcggcgag    600
gtgaacgcca agcctggaac caagagcggc gacagggtgg gcatttgggt cgatagcgcc    660
ggccagctgg tggatgaacc tgctccccct gccagagcca tcgccgatag ggccatcctg    720
atcagggtga ggaacgccag ctggcagcac gacatcgaca gcctgttctg cacccaaagg    780
cgatcgacaa cagccaggga catcatgaac gccggcgtga cctgcgtggg agagcatgaa    840
accctcaccg ccgccgccca atacatgagg gagcacgaca tcggcgccct gcccatctgt    900
ggagacgacg acaggctgca cggcatgctg accgacaggg acatcgtgat caagggcctg    960
```

```
gctgccggcc tcgatcctaa caccgctaca gccggcgagc tggccagaga cagcatctac    1020
tacgtggacg ccaacgccag catccaggag atgctcaacg tgatggagga gcaccaggtg    1080
agaagggtgc ctgtgatcag cgagcacagg ctggtgggca tcgtgaccga ggccgatatc    1140
gctaggcacc tgcccgagca cgccatcgtg cagttcgtga aggccatctg cagccccatg    1200
gctctggcca gcggcgcgcc caccccggga ctcctcacca cagctggagc tggcaggccc    1260
agagacagat gcgccaggat cgtgtgcacc gtgttcatcg agaccgccgt ggtggctacc    1320
atgttcgtgg ccctgctggg cctgagcacc atcagcagca aggccgacga catcgactgg    1380
gacgccatcg cccagtgtga atccggcgga aactgggccg ccaataccgg caatggcctg    1440
tacggcggcc tgcagatcag ccaggctacc tgggactcca acggaggagt gggaagccct    1500
gccgctgctt cccctcagca gcagatcgag gtggccgaca acatcatgaa gacccaaggc    1560
cctggcgcct ggcctaagtg ttccagctgt agccagggcg atgctcctct gggcagcctg    1620
acccacatcc tgacctttct cgccgccgag acaggcggat gtagcggaag cagggacgac    1680
taatgatag                                                             1689
```

<210> SEQ ID NO 53
<211> LENGTH: 528
<212> TYPE: PRT
<213> ORGANISM: Artificial Sequence
<220> FEATURE:
<223> OTHER INFORMATION: Description of Artificial Sequence: ESAT6-Rv1733c-Rv2626c-RpfD (E. coli optimized)

<400> SEQUENCE: 53

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala Glu
                85                  90                  95

Phe Met Ile Ala Thr Thr Arg Asp Arg Glu Gly Ala Thr Met Ile Thr
            100                 105                 110

Phe Arg Leu Arg Leu Pro Cys Arg Thr Ile Leu Arg Val Phe Ser Arg
        115                 120                 125

Asn Pro Leu Val Arg Gly Thr Arg Leu Glu Ala Pro Gly Val Gln
    130                 135                 140

Asp Ser Arg Ser His Val Tyr Ala His Gln Ala Gln Thr Arg His Pro
145                 150                 155                 160

Ala Thr Ala Thr Val Ile Asp His Glu Gly Val Ile Asp Ser Asn Thr
                165                 170                 175

Thr Ala Thr Ser Ala Pro Pro Thr Lys Ile Thr Val Pro Ala Arg
            180                 185                 190

Trp Val Val Asn Gly Ile Glu Arg Ser Gly Glu Val Asn Ala Lys Pro
        195                 200                 205

Gly Thr Lys Ser Gly Asp Arg Val Gly Ile Trp Val Asp Ser Ala Gly
    210                 215                 220
```

Gln Leu Val Asp Glu Pro Ala Pro Pro Ala Arg Ala Ile Ala Asp Ser
225                 230                 235                 240

Arg Arg Ala Ile Leu Ile Arg Val Arg Asn Ala Ser Trp Gln His Asp
            245                 250                 255

Ile Asp Ser Leu Phe Cys Thr Gln Arg Glu Leu Met Thr Thr Ala Arg
        260                 265                 270

Asp Ile Met Asn Ala Gly Val Thr Cys Val Gly Glu His Glu Thr Leu
    275                 280                 285

Thr Ala Ala Ala Gln Tyr Met Arg Glu His Asp Ile Gly Ala Leu Pro
290                 295                 300

Ile Cys Gly Asp Asp Arg Leu His Gly Met Leu Thr Asp Arg Asp
305                 310                 315                 320

Ile Val Ile Lys Gly Leu Ala Ala Gly Leu Asp Pro Asn Thr Ala Thr
                325                 330                 335

Ala Gly Glu Leu Ala Arg Asp Ser Ile Tyr Tyr Val Asp Ala Asn Ala
            340                 345                 350

Ser Ile Gln Glu Met Leu Asn Val Met Glu Glu His Gln Val Arg Arg
        355                 360                 365

Val Pro Val Ile Ser Glu His Arg Leu Val Gly Ile Val Thr Glu Ala
    370                 375                 380

Asp Ile Ala Arg His Leu Pro Glu His Ala Ile Val Gln Phe Val Lys
385                 390                 395                 400

Ala Ile Cys Ser Pro Met Ala Leu Ala Ser Lys Leu Leu Gly Leu
                405                 410                 415

Ser Thr Ile Ser Ser Lys Ala Asp Asp Ile Asp Trp Asp Ala Ile Ala
            420                 425                 430

Gln Cys Glu Ser Gly Gly Asn Trp Ala Ala Asn Thr Gly Asn Gly Leu
        435                 440                 445

Tyr Gly Gly Leu Gln Ile Ser Gln Ala Thr Trp Asp Ser Asn Gly Gly
    450                 455                 460

Val Gly Ser Pro Ala Ala Ala Ser Pro Gln Gln Gln Ile Glu Val Ala
465                 470                 475                 480

Asp Asn Ile Met Lys Thr Gln Gly Pro Gly Ala Trp Pro Lys Cys Ser
                485                 490                 495

Ser Cys Ser Gln Gly Asp Ala Pro Leu Gly Ser Leu Thr His Ile Leu
            500                 505                 510

Thr Phe Leu Ala Ala Glu Thr Gly Gly Cys Ser Gly Ser Arg Asp Asp
        515                 520                 525

<210> SEQ ID NO 54
<211> LENGTH: 559
<212> TYPE: PRT
<213> ORGANISM: Artificial Sequence
<220> FEATURE:
<223> OTHER INFORMATION: Description of Artificial Sequence:
      ESAT6-Rv1733c-Rv2626c-RpfD (human optimized)

<400> SEQUENCE: 54

Met Thr Glu Gln Gln Trp Asn Phe Ala Gly Ile Glu Ala Ala Ala Ser
1 5 10 15

Ala Ile Gln Gly Asn Val Thr Ser Ile His Ser Leu Leu Asp Glu Gly
20 25 30

Lys Gln Ser Leu Thr Lys Leu Ala Ala Ala Trp Gly Gly Ser Gly Ser
35 40 45

Glu Ala Tyr Gln Gly Val Gln Gln Lys Trp Asp Ala Thr Ala Thr Glu

```
            50                  55                  60
Leu Asn Asn Ala Leu Asn Leu Ala Arg Thr Ile Ser Glu Ala Gly Gln
 65                  70                  75                  80

Ala Met Ala Ser Thr Glu Gly Asn Val Thr Gly Met Phe Ala Phe Glu
                 85                  90                  95

Ile Ala Thr Thr Arg Asp Arg Glu Gly Ala Thr Met Ile Thr Phe Arg
                100                 105                 110

Leu Arg Leu Pro Cys Arg Thr Ile Leu Arg Val Phe Ser Arg Asn Pro
                115                 120                 125

Leu Val Arg Gly Thr Asp Arg Leu Glu Ala Val Gln Asp Ser Arg Ser
130                 135                 140

His Val Tyr Ala His Gln Ala Gln Thr Arg His Pro Ala Thr Ala Thr
145                 150                 155                 160

Val Ile Asp His Glu Gly Val Ile Asp Ser Asn Thr Thr Ala Thr Ser
                165                 170                 175

Ala Pro Pro Arg Thr Lys Ile Thr Val Pro Ala Arg Trp Val Val Asn
                180                 185                 190

Gly Ile Glu Arg Ser Gly Glu Val Asn Ala Lys Pro Gly Thr Lys Ser
                195                 200                 205

Gly Asp Arg Val Gly Ile Trp Val Asp Ser Ala Gly Gln Leu Val Asp
210                 215                 220

Glu Pro Ala Pro Ala Arg Ala Ile Ala Asp Arg Ala Ile Leu Ile
225                 230                 235                 240

Arg Val Arg Asn Ala Ser Trp Gln His Asp Ile Asp Ser Leu Phe Cys
                245                 250                 255

Thr Gln Arg Arg Ser Thr Thr Ala Arg Asp Ile Met Asn Ala Gly Val
                260                 265                 270

Thr Cys Val Gly Glu His Glu Thr Leu Thr Ala Ala Gln Tyr Met
                275                 280                 285

Arg Glu His Asp Ile Gly Ala Leu Pro Ile Cys Gly Asp Asp Asp Arg
                290                 295                 300

Leu His Gly Met Leu Thr Asp Arg Asp Ile Val Ile Lys Gly Leu Ala
305                 310                 315                 320

Ala Gly Leu Asp Pro Asn Thr Ala Thr Ala Gly Glu Leu Ala Arg Asp
                325                 330                 335

Ser Ile Tyr Tyr Val Asp Ala Asn Ala Ser Ile Gln Glu Met Leu Asn
                340                 345                 350

Val Met Glu Glu His Gln Val Arg Arg Val Pro Val Ile Ser Glu His
                355                 360                 365

Arg Leu Val Gly Ile Val Thr Glu Ala Asp Ile Ala Arg His Leu Pro
370                 375                 380

Glu His Ala Ile Val Gln Phe Val Lys Ala Ile Cys Ser Pro Met Ala
385                 390                 395                 400

Leu Ala Ser Gly Ala Pro Thr Pro Gly Leu Leu Thr Thr Ala Gly Ala
                405                 410                 415

Gly Arg Pro Arg Asp Arg Cys Ala Arg Ile Val Cys Thr Val Phe Ile
                420                 425                 430

Glu Thr Ala Val Val Ala Thr Met Phe Val Ala Leu Leu Gly Leu Ser
                435                 440                 445

Thr Ile Ser Ser Lys Ala Asp Asp Ile Asp Trp Asp Ala Ile Ala Gln
                450                 455                 460

Cys Glu Ser Gly Gly Asn Trp Ala Ala Asn Thr Gly Asn Gly Leu Tyr
465                 470                 475                 480
```

```
Gly Gly Leu Gln Ile Ser Gln Ala Thr Trp Asp Ser Asn Gly Gly Val
            485                 490                 495

Gly Ser Pro Ala Ala Ser Pro Gln Gln Ile Glu Val Ala Asp
        500                 505                 510

Asn Ile Met Lys Thr Gln Gly Pro Gly Ala Trp Pro Lys Cys Ser Ser
        515                 520                 525

Cys Ser Gln Gly Asp Ala Pro Leu Gly Ser Leu Thr His Ile Leu Thr
        530                 535                 540

Phe Leu Ala Ala Glu Thr Gly Gly Cys Ser Gly Ser Arg Asp Asp
545                 550                 555

<210> SEQ ID NO 55
<211> LENGTH: 2421
<212> TYPE: DNA
<213> ORGANISM: Artificial Sequence
<220> FEATURE:
<223> OTHER INFORMATION: Description of Artificial Sequence:
      Mycobacterium ESAT6-Rv1733c-Rv2626c-RpfB fusion protein

<400> SEQUENCE: 55
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcagaatt catgattgcg     300
actacccgtg atcgtgaggg cgcgaccatg atcacgttcc gtctgcgtct gccgtgtcgc     360
accattttgc gcgtgttttc gcgtaacccg ctggtccgcg gtaccgaccg tctggaggcc     420
gttgtcatgc tgctggcggt taccgtgagc ctgctgacga tcccattcgc agcggcagct     480
ggcacggccg tccaagacag ccgtagccat gtgtatgctc accaggctca aacccgtcac     540
ccggctactg ccactgttat cgatcacgaa ggcgtgattg actccaatac cacggcaacc     600
tccgcaccgc ctcgcaccaa gattacggtt cctgcgcgtt gggtggtgaa tggtattgaa     660
cgcagcggcg aagttaatgc caaaccgggt accaaaagcg tgaccgtgt gggcatctgg      720 gtcgatagcg ccggtcagct ggtcgacgag ccggcaccgc cagcgcgtgc gatcgccgat     780
gcggcgctgg ctgccctggg tctgtggctg agctggcag cggtcgccgg tgcgttgctg      840
gcgctgacgc gcgcaattct gatccgcgtt cgcaatgcga gctggcagca cgatattgat     900
agcctgtttt gcacccaacg tgagctcatg accacggcgc gtgatatcat gaatgcgggt     960
gtcacctgtg ttggcgagca cgaaacgttg accgcagcag cacagtacat gcgcgaacat    1020
gatatcggcg cattgccgat tgcggcgac gatgatcgtc tgcacggtat gctgaccgac    1080
cgcgatatcg ttatcaaggg tctggccgca ggcttggacc cgaacaccgc gaccgccggt    1140
gaactggcac gtgacagcat ctattacgtc gacgcgaacg ccagcattca agagatgctg    1200
aacgtgatgg aagagcatca ggtgcgtcgt gtcccggtta tcagcgaaca tcgtctggtt    1260
ggtatcgtta ccgaagccga catcgcacgt cacctgccgg agcacgcgat tgttcagttc    1320
gtgaaagcga tttgcagccc gatggcgttg gcgtctcgtc aaaagggcga cacaaaattt    1380
attctaaatg caaagcttgc atgcaaaacg gtgacgttga ccgtcgacgg aaccgcgatg    1440
cgggtgacca cgatgaaatc gcgggtgatc gacatcgtcg aagagaacgg gttctcagtc    1500
gacgaccgcg acgacctgta tccgcgcgcc ggcgtgcagg tccatgacgc cgacaccatc    1560
```

```
gtgctgcggc gtagccgtcc gctgcagatc tcgctggatg gtcacgacgc taagcaggtg   1620
tggacgaccg cgtcgacggt ggacgaggcg ctggcccaac tcgcgatgac cgacacggcg   1680
ccggccgcgg cttctcgcgc cagccgcgtc ccgctgtccg ggatggcgct accggtcgtc   1740
agcgccaaga cggtgcagct caacgacggc gggttggtgc gcacggtgca cttgccggcc   1800
cccaatgtcg cggggctgct gagtgcggcc ggcgtgccgc tgttgcaaag cgaccacgtg   1860
gtgcccgccg cgacggcccc gatcgtcgaa ggcatgcaga tccaggtgac cgcaatcgg    1920 atcaagaagg tcaccgagcg gctgccgctg ccgccgaacg cgcgtcgtgt cgaggacccg   1980
gagatgaaca tgagccggga ggtcgtcgaa gacccggggg ttccggggac ccaggatgtg   2040
acgttcgcgg tagctgaggt caacggcgtc gagaccggcc gtttgcccgt cgccaacgtc   2100
gtggtgaccc cggcccacga agccgtggtg cgggtgggca ccaagcccgg taccgaggtg   2160
cccccggtga tcgacggaag catctgggac gcgatcgccg gctgtgaggc cggtggcaac   2220
tgggcgatca acaccggcaa cgggtattac ggtggtgtgc agtttgacca gggcacctgg   2280
gaggccaacg gcgggctgcg gtatgcaccc cgcgctgacc tcgccacccg cgaagagcag   2340
atcgccgttg ccgaggtgac ccgactgcgt caaggttggg gcgcctggcc ggtatgtgct   2400
gcacgagcgg gtgcgcgctg a                                              2421

<210> SEQ ID NO 56
<211> LENGTH: 806
<212> TYPE: PRT
<213> ORGANISM: Artificial Sequence
<220> FEATURE:
<223> OTHER INFORMATION: Description of Artificial Sequence:
      ESAT6-Rv1733c-Rv2626c-RpfB

<400> SEQUENCE: 56

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala Glu
                85                  90                  95

Phe Met Ile Ala Thr Thr Arg Asp Arg Glu Gly Ala Thr Met Ile Thr
            100                 105                 110

Phe Arg Leu Arg Leu Pro Cys Arg Thr Ile Leu Arg Val Phe Ser Arg
        115                 120                 125

Asn Pro Leu Val Arg Gly Thr Asp Arg Leu Glu Ala Val Val Met Leu
    130                 135                 140

Leu Ala Val Thr Val Ser Leu Leu Thr Ile Pro Phe Ala Ala Ala Ala
145                 150                 155                 160

Gly Thr Ala Val Gln Asp Ser Arg Ser His Val Tyr Ala His Gln Ala
                165                 170                 175

Gln Thr Arg His Pro Ala Thr Ala Thr Val Ile Asp His Glu Gly Val
            180                 185                 190

Ile Asp Ser Asn Thr Thr Ala Thr Ser Ala Pro Pro Arg Thr Lys Ile
        195                 200                 205
```

```
Thr Val Pro Ala Arg Trp Val Val Asn Gly Ile Glu Arg Ser Gly Glu
    210                 215                 220

Val Asn Ala Lys Pro Gly Thr Lys Ser Gly Asp Arg Val Gly Ile Trp
225                 230                 235                 240

Val Asp Ser Ala Gly Gln Leu Val Asp Glu Pro Ala Pro Ala Arg
                245                 250                 255

Ala Ile Ala Asp Ala Ala Leu Ala Ala Leu Gly Leu Trp Leu Ser Val
            260                 265                 270

Ala Ala Val Ala Gly Ala Leu Leu Ala Leu Thr Arg Ala Ile Leu Ile
        275                 280                 285

Arg Val Arg Asn Ala Ser Trp Gln His Asp Ile Asp Ser Leu Phe Cys
    290                 295                 300

Thr Gln Arg Glu Leu Met Thr Thr Ala Arg Asp Ile Met Asn Ala Gly
305                 310                 315                 320

Val Thr Cys Val Gly Glu His Glu Thr Leu Thr Ala Ala Gln Tyr
                325                 330                 335

Met Arg Glu His Asp Ile Gly Ala Leu Pro Ile Cys Gly Asp Asp Asp
            340                 345                 350

Arg Leu His Gly Met Leu Thr Asp Arg Asp Ile Val Ile Lys Gly Leu
        355                 360                 365

Ala Ala Gly Leu Asp Pro Asn Thr Ala Thr Ala Gly Glu Leu Ala Arg
    370                 375                 380

Asp Ser Ile Tyr Tyr Val Asp Ala Asn Ala Ser Ile Gln Glu Met Leu
385                 390                 395                 400

Asn Val Met Glu Glu His Gln Val Arg Arg Val Pro Val Ile Ser Glu
                405                 410                 415

His Arg Leu Val Gly Ile Val Thr Glu Ala Asp Ile Ala Arg His Leu
            420                 425                 430

Pro Glu His Ala Ile Val Gln Phe Val Lys Ala Ile Cys Ser Pro Met
        435                 440                 445

Ala Leu Ala Ser Arg Gln Lys Gly Asp Thr Lys Phe Ile Leu Asn Ala
    450                 455                 460

Lys Leu Ala Cys Lys Thr Val Thr Leu Thr Val Asp Gly Thr Ala Met
465                 470                 475                 480

Arg Val Thr Thr Met Lys Ser Arg Val Ile Asp Ile Val Glu Glu Asn
                485                 490                 495

Gly Phe Ser Val Asp Asp Arg Asp Leu Tyr Pro Ala Ala Gly Val
            500                 505                 510

Gln Val His Asp Ala Asp Thr Ile Val Leu Arg Arg Ser Arg Pro Leu
        515                 520                 525

Gln Ile Ser Leu Asp Gly His Asp Ala Lys Gln Val Trp Thr Thr Ala
    530                 535                 540

Ser Thr Val Asp Glu Ala Leu Ala Gln Leu Ala Met Thr Asp Thr Ala
545                 550                 555                 560

Pro Ala Ala Ala Ser Arg Ala Ser Arg Val Pro Leu Ser Gly Met Ala
                565                 570                 575

Leu Pro Val Val Ser Ala Lys Thr Val Gln Leu Asn Asp Gly Gly Leu
            580                 585                 590

Val Arg Thr Val His Leu Pro Ala Pro Asn Val Ala Gly Leu Leu Ser
        595                 600                 605

Ala Ala Gly Val Pro Leu Leu Gln Ser Asp His Val Val Pro Ala Ala
    610                 615                 620
```

-continued

Thr Ala Pro Ile Val Glu Gly Met Gln Ile Gln Val Thr Arg Asn Arg
625 630 635 640

Ile Lys Lys Val Thr Glu Arg Leu Pro Leu Pro Pro Asn Ala Arg Arg
645 650 655

Val Glu Asp Pro Glu Met Asn Met Ser Arg Glu Val Val Glu Asp Pro
660 665 670

Gly Val Pro Gly Thr Gln Asp Val Thr Phe Ala Val Ala Glu Val Asn
675 680 685

Gly Val Glu Thr Gly Arg Leu Pro Val Ala Asn Val Val Val Thr Pro
690 695 700

Ala His Glu Ala Val Val Arg Val Gly Thr Lys Pro Gly Thr Glu Val
705 710 715 720

Pro Pro Val Ile Asp Gly Ser Ile Trp Asp Ala Ile Ala Gly Cys Glu
725 730 735

Ala Gly Gly Asn Trp Ala Ile Asn Thr Gly Asn Gly Tyr Tyr Gly Gly
740 745 750

Val Gln Phe Asp Gln Gly Thr Trp Glu Ala Asn Gly Gly Leu Arg Tyr
755 760 765

Ala Pro Arg Ala Asp Leu Ala Thr Arg Glu Glu Gln Ile Ala Val Ala
770 775 780

Glu Val Thr Arg Leu Arg Gln Gly Trp Gly Ala Trp Pro Val Cys Ala
785 790 795 800

Ala Arg Ala Gly Ala Arg
805

<210> SEQ ID NO 57
<211> LENGTH: 2430
<212> TYPE: DNA
<213> ORGANISM: Artificial Sequence
<220> FEATURE:
<223> OTHER INFORMATION: Description of Artificial Sequence: Mycobacterium RpfB-ESAT6-Rv1733c-Rv2626c fusion protein

<400> SEQUENCE: 57
atgaagcttg catgcaaaac ggtgacgttg accgtcgacg gaaccgcgat gcgggtgacc 60
acgatgaaat cgcgggtgat cgacatcgtc gaagagaacg ggttctcagt cgacgaccgc 120
gacgacctgt atcccgcggc cggcgtgcag gtccatgacg ccgacaccat cgtgctgcgg 180
cgtagccgtc cgctgcagat ctcgctggat ggtcacgacg ctaagcaggt gtggacgacc 240
gcgtcgacgg tggacgaggc gctggcccaa ctcgcgatga ccgacacggc gccggccgcg 300
gcttctcgcg ccagccgcgt cccgctgtcc gggatggcgc taccggtcgt cagcgccaag 360
acggtgcagc tcaacgacgg cgggttggtg cgcacggtgc acttgccggc ccccaatgtc 420
gcggggctgc tgagtgcggc cggcgtgccg ctgttgcaaa gcgaccacgt ggtgcccgcc 480
gcgacggccc cgatcgtcga aggcatgcag atccaggtga cccgcaatcg gatcaagaag 540
gtcaccgagc ggctgccgct gccgccgaac gcgcgtcgtg tcgaggaccc ggagatgaac 600
atgagccggg aggtcgtcga agacccgggg gttccgggga cccaggatgt gacgttcgcg 660
gtagctgagg tcaacggcgt cgagaccggc cgtttgcccg tcgccaacgt cgtggtgacc 720
ccggcccacg aagccgtggt gcgggtgggc accaagcccg gtaccgaggt gcccccggtg 780
atcgacggaa gcatctggga cgcgatcgcc ggctgtgagg ccggtggcaa ctgggcgatc 840
aacaccggca acgggtatta cggtggtgtg cagtttgacc agggcacctg ggaggccaac 900
ggcgggctgc ggtatgcacc ccgcgctgac ctcgccaccc gcgaagagca gatcgccgtt 960

```
gccgaggtga cccgactgcg tcaaggttgg ggcgcctggc cggtatgtgc tgcacgagcg    1020
ggtgcgcgcg gatccatgac agagcagcag tggaatttcg cgggtatcga ggccgcggca    1080
agcgcaatcc agggaaatgt cacgtccatt cattccctcc ttgacgaggg gaagcagtcc    1140
ctgaccaagc tcgcagcggc ctggggcggt agcggttcgg aggcgtacca gggtgtccag    1200
caaaaatggg acgccacggc taccgagctg aacaacgcgc tgcagaacct ggcgcggacg    1260
atcagcgaag ccggtcaggc aatggcttcg accgaaggca acgtcactgg gatgttcgca    1320
gaattcatga ttgcgactac ccgtgatcgt gagggcgcga ccatgatcac gttccgtctg    1380
cgtctgccgt gtcgcaccat tttgcgcgtg ttttcgcgta cccgctggt ccgcggtacc    1440 gaccgtctgg aggccgttgt catgctgctg gcggttaccg tgagcctgct gacgatccca    1500
ttcgcagcgg cagctggcac ggccgtccaa gacagccgta gccatgtgta tgctcaccag    1560
gctcaaaccc gtcacccggc tactgccact gttatcgatc acgaaggcgt gattgactcc    1620
aataccacgg caacctccgc accgcctcgc accaagatta cggttcctgc gcgttgggtg    1680
gtgaatggta ttgaacgcag cggcgaagtt aatgccaaac cgggtaccaa aagcggtgac    1740
cgtgtgggca tctgggtcga tagcgccggt cagctggtcg acgagccggc accgccagcg    1800
cgtgcgatcg ccgatgcggc gctggctgcc ctgggtctgt ggctgagcgt ggcagcggtc    1860
gccggtgcgt tgctggcgct gacgcgcgca attctgatcc gcgttcgcaa tgcgagctgg    1920
cagcacgata ttgatagcct gttttgcacc caacgtgagc tcatgaccac ggcgcgtgat    1980
atcatgaatg cgggtgtcac ctgtgttggc gagcacgaaa cgttgaccgc agcagcacag    2040
tacatgcgcg aacatgatat cggcgcattg ccgatttgcg cgacgatga tcgtctgcac    2100 ggtatgctga ccgaccgcga tatcgttatc aagggtctgg ccgcaggctt ggacccgaac    2160
accgcgaccg ccggtgaact ggcacgtgac agcatctatt acgtcgacgc gaacgccagc    2220
attcaagaga tgctgaacgt gatggaagag catcaggtgc gtcgtgtccc ggttatcagc    2280
gaacatcgtc tggttggtat cgttaccgaa gccgacatcg cacgtcacct gccggagcac    2340
gcgattgttc agttcgtgaa agcgatttgc agcccgatgg cgttggcgtc tcgtcaaaag    2400
ggcgacacaa aatttattct aaatgcatga                                     2430
```

<210> SEQ ID NO 58
<211> LENGTH: 809
<212> TYPE: PRT
<213> ORGANISM: Artificial Sequence
<220> FEATURE:
<223> OTHER INFORMATION: Description of Artificial Sequence:
      RpfB-ESAT6-Rv1733c-Rv2626c

<400> SEQUENCE: 58

```
Met Lys Leu Ala Cys Lys Thr Val Thr Leu Thr Val Asp Gly Thr Ala
1               5                   10                  15

Met Arg Val Thr Thr Met Lys Ser Arg Val Ile Asp Ile Val Glu Glu
                20                  25                  30

Asn Gly Phe Ser Val Asp Asp Arg Asp Asp Leu Tyr Pro Ala Ala Gly
            35                  40                  45

Val Gln Val His Asp Ala Asp Thr Ile Val Leu Arg Arg Ser Arg Pro
        50                  55                  60

Leu Gln Ile Ser Leu Asp Gly His Asp Ala Lys Gln Val Trp Thr Thr
65                  70                  75                  80

Ala Ser Thr Val Asp Glu Ala Leu Ala Gln Leu Ala Met Thr Asp Thr
                85                  90                  95
```

```
Ala Pro Ala Ala Ala Ser Arg Ala Ser Arg Val Pro Leu Ser Gly Met
            100                 105                 110

Ala Leu Pro Val Val Ser Ala Lys Thr Val Gln Leu Asn Asp Gly Gly
        115                 120                 125

Leu Val Arg Thr Val His Leu Pro Ala Pro Asn Val Ala Gly Leu Leu
    130                 135                 140

Ser Ala Ala Gly Val Pro Leu Leu Gln Ser Asp His Val Val Pro Ala
145                 150                 155                 160

Ala Thr Ala Pro Ile Val Glu Gly Met Gln Ile Gln Val Thr Arg Asn
                165                 170                 175

Arg Ile Lys Lys Val Thr Glu Arg Leu Pro Leu Pro Pro Asn Ala Arg
            180                 185                 190

Arg Val Glu Asp Pro Glu Met Asn Met Ser Arg Glu Val Val Glu Asp
        195                 200                 205

Pro Gly Val Pro Gly Thr Gln Asp Val Thr Phe Ala Val Ala Glu Val
    210                 215                 220

Asn Gly Val Glu Thr Gly Arg Leu Pro Val Ala Asn Val Val Val Thr
225                 230                 235                 240

Pro Ala His Glu Ala Val Val Arg Val Gly Thr Lys Pro Gly Thr Glu
                245                 250                 255

Val Pro Pro Val Ile Asp Gly Ser Ile Trp Asp Ala Ile Ala Gly Cys
            260                 265                 270

Glu Ala Gly Gly Asn Trp Ala Ile Asn Thr Gly Asn Gly Tyr Tyr Gly
        275                 280                 285

Gly Val Gln Phe Asp Gln Gly Thr Trp Glu Ala Asn Gly Gly Leu Arg
    290                 295                 300

Tyr Ala Pro Arg Ala Asp Leu Ala Thr Arg Glu Gln Ile Ala Val
305                 310                 315                 320

Ala Glu Val Thr Arg Leu Arg Gln Gly Trp Gly Ala Trp Pro Val Cys
                325                 330                 335

Ala Ala Arg Ala Gly Ala Arg Gly Ser Met Thr Glu Gln Gln Trp Asn
            340                 345                 350

Phe Ala Gly Ile Glu Ala Ala Ala Ser Ala Ile Gln Gly Asn Val Thr
        355                 360                 365

Ser Ile His Ser Leu Leu Asp Glu Gly Lys Gln Ser Leu Thr Lys Leu
    370                 375                 380

Ala Ala Ala Trp Gly Gly Ser Gly Ser Glu Ala Tyr Gln Gly Val Gln
385                 390                 395                 400

Gln Lys Trp Asp Ala Thr Ala Thr Glu Leu Asn Asn Ala Leu Gln Asn
                405                 410                 415

Leu Ala Arg Thr Ile Ser Glu Ala Gly Gln Ala Met Ala Ser Thr Glu
            420                 425                 430

Gly Asn Val Thr Gly Met Phe Ala Glu Phe Met Ile Ala Thr Thr Arg
        435                 440                 445

Asp Arg Glu Gly Ala Thr Met Ile Thr Phe Arg Leu Arg Leu Pro Cys
    450                 455                 460

Arg Thr Ile Leu Arg Val Phe Ser Arg Asn Pro Leu Val Arg Gly Thr
465                 470                 475                 480

Asp Arg Leu Glu Ala Val Val Met Leu Leu Ala Val Thr Val Ser Leu
                485                 490                 495

Leu Thr Ile Pro Phe Ala Ala Ala Gly Thr Ala Val Gln Asp Ser
            500                 505                 510

Arg Ser His Val Tyr Ala His Gln Ala Gln Thr Arg His Pro Ala Thr
```

Ala Thr Val Ile Asp His Glu Gly Val Ile Asp Ser Asn Thr Thr Ala
     530                 535                 540

Thr Ser Ala Pro Pro Arg Thr Lys Ile Thr Val Pro Ala Arg Trp Val
545                 550                 555                 560

Val Asn Gly Ile Glu Arg Ser Gly Glu Val Asn Ala Lys Pro Gly Thr
                565                 570                 575

Lys Ser Gly Asp Arg Val Gly Ile Trp Val Asp Ser Ala Gly Gln Leu
            580                 585                 590

Val Asp Glu Pro Ala Pro Pro Ala Arg Ala Ile Ala Asp Ala Ala Leu
        595                 600                 605

Ala Ala Leu Gly Leu Trp Leu Ser Val Ala Val Ala Gly Ala Leu
    610                 615                 620

Leu Ala Leu Thr Arg Ala Ile Leu Ile Arg Val Arg Asn Ala Ser Trp
625                 630                 635                 640

Gln His Asp Ile Asp Ser Leu Phe Cys Thr Gln Arg Glu Leu Met Thr
                645                 650                 655

Thr Ala Arg Asp Ile Met Asn Ala Gly Val Thr Cys Val Gly Glu His
            660                 665                 670

Glu Thr Leu Thr Ala Ala Ala Gln Tyr Met Arg Glu His Asp Ile Gly
        675                 680                 685

Ala Leu Pro Ile Cys Gly Asp Asp Arg Leu His Gly Met Leu Thr
    690                 695                 700

Asp Arg Asp Ile Val Ile Lys Gly Leu Ala Ala Gly Leu Asp Pro Asn
705                 710                 715                 720

Thr Ala Thr Ala Gly Glu Leu Ala Arg Asp Ser Ile Tyr Tyr Val Asp
                725                 730                 735

Ala Asn Ala Ser Ile Gln Glu Met Leu Asn Val Met Glu Glu His Gln
            740                 745                 750

Val Arg Arg Val Pro Val Ile Ser Glu His Arg Leu Val Gly Ile Val
        755                 760                 765

Thr Glu Ala Asp Ile Ala Arg His Leu Pro Glu His Ala Ile Val Gln
    770                 775                 780

Phe Val Lys Ala Ile Cys Ser Pro Met Ala Leu Ala Ser Arg Gln Lys
785                 790                 795                 800

Gly Asp Thr Lys Phe Ile Leu Asn Ala
                805

<210> SEQ ID NO 59
<211> LENGTH: 2448
<212> TYPE: DNA
<213> ORGANISM: Artificial Sequence
<220> FEATURE:
<223> OTHER INFORMATION: Description of Artificial Sequence:
    Mycobacterium Ag85B-ESAT6-Rv1733c-Rv2626c-RpfD fusion protein (E.
    coli optimized)

<400> SEQUENCE: 59
atgtttagcc gtcctggcct gccagttgaa tacctgcaag ttccgagccc gtccatgggt     60
cgtgacatta aggtgcagtt ccagagcggc ggtaacaata gcccggctgt gtacctgctg    120
gacggtctgc gtgcgcagga tgattacaac ggctgggaca tcaatacccc ggcatttgag    180
tggtattacc agtcgggtct gagcattgtg atgccggttg cggtcaaag cagcttctat    240 agcgattggt acagcccggc atgcggcaag gctggttgcc aaacctacaa gtgggaaact    300
ttcttgacca gcgagctgcc gcaatggttg agcgccaacc gtgcggtcaa accgaccggt    360

```
agcgctgcta ttggcctgtc catggccggc agcagcgcga tgatcttggc ggcataccat     420
ccgcagcagt ttatctacgc cggtagcctg agcgcattgc tggacccgag ccaaggcatg     480
ggtccgagcc tgattggtct ggcaatgggt gacgcaggtg gttacaaagc ggccgatatg     540
tggggcccat ctagcgaccc ggcatgggag cgtaatgacc cgacccagca aattccgaaa     600
ctggtggcga taacacgcg cctgtgggtc tactgtggca atggtacgcc gaacgagctg      660
ggtggcgcga atatccctgc ggagtttctg gaaaactttg ttcgcagcag caacctgaaa     720
ttccaggacg cgtataacgc agccggtggt cacaatgcgg ttttcaattt cccgccaaat     780
ggcactcata gctgggagta ctggggtgcg cagttgaacg caatgaaagg cgatctgcaa     840
tcctctctgg gtgcgggcgg atccatgaca gagcagcagt ggaatttcgc gggtatcgag     900
gccgcggcaa gcgcaatcca gggaaatgtc acgtccattc attccctcct tgacgagggg     960
aagcagtccc tgaccaagct cgcagcggcc tggggcggta gcggttcgga ggcgtaccag    1020
ggtgtccagc aaaaatggga cgccacggct accgagctga acaacgcgct gcagaacctg    1080
gcgcggacga tcagcgaagc cggtcaggca atggcttcga ccgaaggcaa cgtcactggg    1140
atgttcgcag aattcatgat tgcgactacc cgtgatcgtg agggcgcgac catgatcacg    1200
ttccgtctgc gtctgccgtg tcgcaccatt ttgcgcgtgt tttcgcgtaa cccgctggtc    1260
cgcggtaccg accgtctgga ggcccccggg gtccaagaca gccgtagcca tgtgtatgct    1320
caccaggctc aaacccgtca cccggctact gccactgtta tcgatcacga aggcgtgatt    1380
gactccaata ccacggcaac ctccgcaccg cctcgcacca agattacggt tcctgcgcgt    1440
tgggtggtga atggtattga acgcagcggc gaagttaatg ccaaaccggg taccaaaagc    1500
ggtgaccgtg tgggcatctg ggtcgatagc gccggtcagc tggtcgacga gccggcaccg    1560
ccagcgcgtg cgatcgccga ttctagacgc gcaattctga tccgcgttcg caatgcgagc    1620
tggcagcacg atattgatag cctgttttgc acccaacgtg agctcatgac cacggcgcgt    1680
gatatcatga atgcgggtgt cacctgtgtt ggcgagcacg aaacgttgac cgcagcagca    1740
cagtacatgc gcgaacatga tatcggcgca ttgccgattt gcggcgacga tgatcgtctg    1800
cacggtatgc tgaccgaccg cgatatcgtt atcaagggtc tggccgcagg cttggacccg    1860
aacaccgcga ccgccggtga actggcacgt gacagcatct attacgtcga cgcgaacgcc    1920
agcattcaag agatgctgaa cgtgatgaa gagcatcagg tgcgtcgtgt cccggttatc    1980
agcgaacatc gtctggttgg tatcgttacc gaagccgaca tcgcacgtca cctgccggag    2040
cacgcgattg ttcagttcgt gaaagcgatt tgcagcccga tggcgttggc gtctaagctt    2100
ttgctgggcc tgagcaccat tagcagcaaa gcggatgaca tcgactggga tgcgattgcg    2160
cagtgtgaga gcggtggcaa ttgggcagcg aataccggca atggcctgta cggcggtctg    2220
cagatctccc aggcgacgtg ggacagcaat ggtggcgtcg gcagcccggc tgccgcgtcc    2280
ccacaacaac agatcgaggt ggcagataac attatgaaaa cgcagggtcc gggtgcttgg    2340
ccaaaatgct ccagctgcag ccagggtgac gcaccgctgg gcagcctgac ccacattctg    2400
acgttcctgg cagcggaaac cggtggttgt agcggtagcc gcgatgac                 2448
```

<210> SEQ ID NO 60
<211> LENGTH: 2550
<212> TYPE: DNA
<213> ORGANISM: Artificial Sequence
<220> FEATURE:
<223> OTHER INFORMATION: Description of Artificial Sequence:
      Mycobacterium Ag85B-ESAT6-Rv1733c-Rv2626c-RpfD fusion protein (human optimized)

<400> SEQUENCE: 60

```
atgttctcca ggcccggcct gcctgtcgag tatctgcagg tccctcccc ctccatgggc      60
agagacatca aggtgcagtt ccaatccgga ggcaacaaca gccccgccgt gtatctcctc    120
gacggcctga gggctcagga cgactacaac ggctgggaca tcaacacccc cgccttcgag    180
tggtactacc agtccggact gagcatcgtc atgcccgtgg cggccagag ctccttctac     240
agcgactggt atagccctgc ctgcggcaaa gccggatgcc agacctacaa gtgggagacc    300
tttctgacca gcgaactgcc ccagtggctg tccgccaata gggccgtcaa acctaccggc    360
tccgctgcca tcggactcag catggccgga agctccgcta tgatcctggc cgcctaccac    420
ccccagcaat ttatctacgc tggcagcctg tccgctctgc tggatcctag ccaaggcatg    480
ggccctagcc tcattggcct ggccatgggc gatgctggcg gctataaggc cgccgatatg    540
tggggcccta gctccgatcc tgcctggag aggaatgacc ccacccagca gatccccaag     600
ctggtggcca acaacacaag gctctggtg tactgcggca atggcacccc caacgaactg     660
ggcggagcca acattcccgc cgagttcctg gagaacttcg tcaggagcag caacctgaag    720
ttccaggacc cctacaatgc cgccggaggc cacaacgctg tgttcaactt ccctcccaac    780
ggcacccaca gctgggagta ttgggcgct cagctgaacg ccatgaaagg cgacctccag    840
agctccctgg gagctggacc cgggaccgag cagcagtgga acttcgccgg catcgaagct    900
gccgctagcg ccatccaagg caacgtgacc agcatccaca gcctgctgga cgagggcaag    960
cagagcctga ccaagctggc tgctgcttgg ggcggatccg aagcgaagc ctaccagggc    1020
gtgcagcaga agtgggacgc cacagccacc gagctgaaca cgccctgca gaacctcgcc   1080
agaaccatca gcgaggccgg acaggctatg gccagcacag agggcaatgt gaccggcatg   1140
ttcgccttcg aaatcgccac caccagggac agggaaggcg ctaccatgat caccttcagg   1200
ctgaggctcc cctgcaggac catcctgagg gtgttcagca ggaaccccct ggtgaggggc   1260
accgacagac tggaagccgt gcaggacagc aggagccacg tgtatgccca ccaggctcag   1320
accaggcacc ctgctaccgc caccgtgatc gaccacgagg gcgtgatcga ctccaacacc   1380
accgccacca gcgctcctcc cagaaccaag atcacagtgc ccgccaggtg ggtggtgaac   1440
ggcatcgaga ggagcggcga ggtgaacgcc aagcctggaa ccaagagcgg cgacagggtg   1500
ggcatttggg tcgatagcgc cggccagctg gtggatgaac ctgctcccc tgccagagcc   1560
atcgccgata gggccatcct gatcagggtg aggaacgcca gctggcagca cgacatcgac   1620
agcctgttct gcacccaaag gcgatcgaca acagccaggg acatcatgaa cgccggcgtg   1680
acctgcgtgg agagcatga aaccctcacc gccgccgccc aatacatgag ggagcacgac   1740
atcggcgccc tgcccatctg tggagacgac gacaggctgc acggcatgct gaccgacagg   1800
gacatcgtga tcaagggcct ggctgccggc ctcgatccta caccgctac agccggcgag   1860
ctggccagag acagcatcta ctacgtggac gccaacgcca gcatccagga gatgctcaac   1920
gtgatggagg agcaccaggt gagaagggtg cctgtgatca gcgagcacag gctggtgggc   1980
atcgtgaccg aggccgatat cgctaggcac ctgcccgagc acgccatcgt gcagttcgtg   2040
aaggccatct gcagcccat ggctctggcc agcggcgcgc ccaccccgg actcctcacc    2100
acagctggag ctggcaggcc cagagacaga tgcgccagga tcgtgtgcac cgtgttcatc   2160
gagaccgccg tggtggctac catgttcgtg gccctgctgg gcctgagcac catcagcagc   2220
aaggccgacg acatcgactg ggacgccatc gcccagtgtg aatccggcgg aaactgggcc   2280
```

-continued

```
gccaataccg gcaatggcct gtacggcggc ctgcagatca gccaggctac ctgggactcc   2340
aacggaggag tgggaagccc tgccgctgct tcccctcagc agcagatcga ggtggccgac   2400
aacatcatga agacccaagg ccctggcgcc tggcctaagt gttccagctg tagccagggc   2460
gatgctcctc tgggcagcct gacccacatc ctgacctttc tcgccgccga gacaggcgga   2520
tgtagcggaa gcagggacga ctaatgatag                                    2550

<210> SEQ ID NO 61
<211> LENGTH: 816
<212> TYPE: PRT
<213> ORGANISM: Artificial Sequence
<220> FEATURE:
<223> OTHER INFORMATION: Description of Artificial Sequence:
      Ag85B-ESAT6-Rv1733c-Rv2626c-RpfD  (E. coli optimized)

<400> SEQUENCE: 61

Met Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Asn
            20                  25                  30

Asn Ser Pro Ala Val Tyr Leu Leu Asp Gly Leu Arg Ala Gln Asp Asp
        35                  40                  45

Tyr Asn Gly Trp Asp Ile Asn Thr Pro Ala Phe Glu Trp Tyr Tyr Gln
    50                  55                  60

Ser Gly Leu Ser Ile Val Met Pro Val Gly Gly Gln Ser Ser Phe Tyr
65                  70                  75                  80

Ser Asp Trp Tyr Ser Pro Ala Cys Gly Lys Ala Gly Cys Gln Thr Tyr
                85                  90                  95

Lys Trp Glu Thr Phe Leu Thr Ser Glu Leu Pro Gln Trp Leu Ser Ala
            100                 105                 110

Asn Arg Ala Val Lys Pro Thr Gly Ser Ala Ala Ile Gly Leu Ser Met
        115                 120                 125

Ala Gly Ser Ser Ala Met Ile Leu Ala Ala Tyr His Pro Gln Gln Phe
    130                 135                 140

Ile Tyr Ala Gly Ser Leu Ser Ala Leu Leu Asp Pro Ser Gln Gly Met
145                 150                 155                 160

Gly Pro Ser Leu Ile Gly Leu Ala Met Gly Asp Ala Gly Gly Tyr Lys
                165                 170                 175

Ala Ala Asp Met Trp Gly Pro Ser Ser Asp Pro Ala Trp Glu Arg Asn
            180                 185                 190

Asp Pro Thr Gln Gln Ile Pro Lys Leu Val Ala Asn Asn Thr Arg Leu
        195                 200                 205

Trp Val Tyr Cys Gly Asn Gly Thr Pro Asn Glu Leu Gly Gly Ala Asn
    210                 215                 220

Ile Pro Ala Glu Phe Leu Glu Asn Phe Val Arg Ser Ser Asn Leu Lys
225                 230                 235                 240

Phe Gln Asp Ala Tyr Asn Ala Ala Gly Gly His Asn Ala Val Phe Asn
                245                 250                 255

Phe Pro Pro Asn Gly Thr His Ser Trp Glu Tyr Trp Gly Ala Gln Leu
            260                 265                 270

Asn Ala Met Lys Gly Asp Leu Gln Ser Ser Leu Gly Ala Gly Gly Ser
        275                 280                 285

Met Thr Glu Gln Gln Trp Asn Phe Ala Gly Ile Glu Ala Ala Ala Ser
    290                 295                 300
```

```
Ala Ile Gln Gly Asn Val Thr Ser Ile His Ser Leu Leu Asp Glu Gly
305                 310                 315                 320

Lys Gln Ser Leu Thr Lys Leu Ala Ala Ala Trp Gly Gly Ser Gly Ser
            325                 330                 335

Glu Ala Tyr Gln Gly Val Gln Gln Lys Trp Asp Ala Thr Ala Thr Glu
            340                 345                 350

Leu Asn Asn Ala Leu Gln Asn Leu Ala Arg Thr Ile Ser Glu Ala Gly
            355                 360                 365

Gln Ala Met Ala Ser Thr Glu Gly Asn Val Thr Gly Met Phe Ala Glu
370                 375                 380

Phe Met Ile Ala Thr Thr Arg Asp Arg Glu Gly Ala Thr Met Ile Thr
385                 390                 395                 400

Phe Arg Leu Arg Leu Pro Cys Arg Thr Ile Leu Arg Val Phe Ser Arg
            405                 410                 415

Asn Pro Leu Val Arg Gly Thr Asp Arg Leu Glu Ala Pro Gly Val Gln
            420                 425                 430

Asp Ser Arg Ser His Val Tyr Ala His Gln Ala Gln Thr Arg His Pro
            435                 440                 445

Ala Thr Ala Thr Val Ile Asp His Glu Gly Val Ile Asp Ser Asn Thr
450                 455                 460

Thr Ala Thr Ser Ala Pro Pro Arg Thr Lys Ile Thr Val Pro Ala Arg
465                 470                 475                 480

Trp Val Val Asn Gly Ile Glu Arg Ser Gly Glu Val Asn Ala Lys Pro
            485                 490                 495

Gly Thr Lys Ser Gly Asp Arg Val Gly Ile Trp Val Asp Ser Ala Gly
            500                 505                 510

Gln Leu Val Asp Glu Pro Ala Pro Ala Arg Ala Ile Ala Asp Ser
515                 520                 525

Arg Arg Ala Ile Leu Ile Arg Val Arg Asn Ala Ser Trp Gln His Asp
530                 535                 540

Ile Asp Ser Leu Phe Cys Thr Gln Arg Glu Leu Met Thr Thr Ala Arg
545                 550                 555                 560

Asp Ile Met Asn Ala Gly Val Thr Cys Val Gly Glu His Glu Thr Leu
            565                 570                 575

Thr Ala Ala Gln Tyr Met Arg Glu His Asp Ile Gly Ala Leu Pro
            580                 585                 590

Ile Cys Gly Asp Asp Arg Leu His Gly Met Leu Thr Asp Arg Asp
        595                 600                 605

Ile Val Ile Lys Gly Leu Ala Ala Gly Leu Asp Pro Asn Thr Ala Thr
        610                 615                 620

Ala Gly Glu Leu Ala Arg Asp Ser Ile Tyr Tyr Val Asp Ala Asn Ala
625                 630                 635                 640

Ser Ile Gln Glu Met Leu Asn Val Met Glu Glu His Gln Val Arg Arg
                645                 650                 655

Val Pro Val Ile Ser Glu His Arg Leu Val Gly Ile Val Thr Glu Ala
            660                 665                 670

Asp Ile Ala Arg His Leu Pro Glu His Ala Ile Val Gln Phe Val Lys
            675                 680                 685

Ala Ile Cys Ser Pro Met Ala Leu Ala Ser Lys Leu Leu Gly Leu
            690                 695                 700

Ser Thr Ile Ser Ser Lys Ala Asp Asp Ile Asp Trp Asp Ala Ile Ala
705                 710                 715                 720

Gln Cys Glu Ser Gly Gly Asn Trp Ala Ala Asn Thr Gly Asn Gly Leu
```

```
                725                 730                 735

Tyr Gly Gly Leu Gln Ile Ser Gln Ala Thr Trp Asp Ser Asn Gly Gly
            740                 745                 750

Val Gly Ser Pro Ala Ala Ala Ser Pro Gln Gln Gln Ile Glu Val Ala
        755                 760                 765

Asp Asn Ile Met Lys Thr Gln Gly Pro Gly Ala Trp Pro Lys Cys Ser
    770                 775                 780

Ser Cys Ser Gln Gly Asp Ala Pro Leu Gly Ser Leu Thr His Ile Leu
785                 790                 795                 800

Thr Phe Leu Ala Ala Glu Thr Gly Gly Cys Ser Gly Ser Arg Asp Asp
                805                 810                 815

<210> SEQ ID NO 62
<211> LENGTH: 847
<212> TYPE: PRT
<213> ORGANISM: Artificial Sequence
<220> FEATURE:
<223> OTHER INFORMATION: Description of Artificial Sequence:
      Ag85B-ESAT6-Rv1733c-Rv2626c-RpfD  (human optimized)

<400> SEQUENCE: 62

Met Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Asn
            20                  25                  30

Asn Ser Pro Ala Val Tyr Leu Leu Asp Gly Leu Arg Ala Gln Asp Asp
        35                  40                  45

Tyr Asn Gly Trp Asp Ile Asn Thr Pro Ala Phe Glu Trp Tyr Tyr Gln
    50                  55                  60

Ser Gly Leu Ser Ile Val Met Pro Val Gly Gly Gln Ser Ser Phe Tyr
65                  70                  75                  80

Ser Asp Trp Tyr Ser Pro Ala Cys Gly Lys Ala Gly Cys Gln Thr Tyr
                85                  90                  95

Lys Trp Glu Thr Phe Leu Thr Ser Glu Leu Pro Gln Trp Leu Ser Ala
            100                 105                 110

Asn Arg Ala Val Lys Pro Thr Gly Ser Ala Ala Ile Gly Leu Ser Met
        115                 120                 125

Ala Gly Ser Ser Ala Met Ile Leu Ala Ala Tyr His Pro Gln Gln Phe
    130                 135                 140

Ile Tyr Ala Gly Ser Leu Ser Ala Leu Leu Asp Pro Ser Gln Gly Met
145                 150                 155                 160

Gly Pro Ser Leu Ile Gly Leu Ala Met Gly Asp Ala Gly Gly Tyr Lys
                165                 170                 175

Ala Ala Asp Met Trp Gly Pro Ser Ser Asp Pro Ala Trp Glu Arg Asn
            180                 185                 190

Asp Pro Thr Gln Gln Ile Pro Lys Leu Val Ala Asn Asn Thr Arg Leu
        195                 200                 205

Trp Val Tyr Cys Gly Asn Gly Thr Pro Asn Glu Leu Gly Gly Ala Asn
    210                 215                 220

Ile Pro Ala Glu Phe Leu Glu Asn Phe Val Arg Ser Ser Asn Leu Lys
225                 230                 235                 240

Phe Gln Asp Ala Tyr Asn Ala Ala Gly Gly His Asn Ala Val Phe Asn
                245                 250                 255

Phe Pro Pro Asn Gly Thr His Ser Trp Glu Tyr Trp Gly Ala Gln Leu
            260                 265                 270
```

```
Asn Ala Met Lys Gly Asp Leu Gln Ser Ser Leu Gly Ala Gly Pro Gly
            275                 280                 285

Thr Glu Gln Gln Trp Asn Phe Ala Gly Ile Glu Ala Ala Ala Ser Ala
290                 295                 300

Ile Gln Gly Asn Val Thr Ser Ile His Ser Leu Leu Asp Glu Gly Lys
305                 310                 315                 320

Gln Ser Leu Thr Lys Leu Ala Ala Ala Trp Gly Gly Ser Gly Ser Glu
            325                 330                 335

Ala Tyr Gln Gly Val Gln Gln Lys Trp Asp Ala Thr Ala Thr Glu Leu
            340                 345                 350

Asn Asn Ala Leu Gln Asn Leu Ala Arg Thr Ile Ser Glu Ala Gly Gln
            355                 360                 365

Ala Met Ala Ser Thr Glu Gly Asn Val Thr Gly Met Phe Ala Phe Glu
            370                 375                 380

Ile Ala Thr Thr Arg Asp Arg Glu Gly Ala Thr Met Ile Thr Phe Arg
385                 390                 395                 400

Leu Arg Leu Pro Cys Arg Thr Ile Leu Arg Val Phe Ser Arg Asn Pro
                405                 410                 415

Leu Val Arg Gly Thr Asp Arg Leu Glu Ala Val Gln Asp Ser Arg Ser
            420                 425                 430

His Val Tyr Ala His Gln Ala Gln Thr Arg His Pro Ala Thr Ala Thr
            435                 440                 445

Val Ile Asp His Glu Gly Val Ile Asp Ser Asn Thr Thr Ala Thr Ser
            450                 455                 460

Ala Pro Pro Arg Thr Lys Ile Thr Val Pro Ala Arg Trp Val Val Asn
465                 470                 475                 480

Gly Ile Glu Arg Ser Gly Glu Val Asn Ala Lys Pro Gly Thr Lys Ser
                485                 490                 495

Gly Asp Arg Val Gly Ile Trp Val Asp Ser Ala Gly Gln Leu Val Asp
            500                 505                 510

Glu Pro Ala Pro Pro Ala Arg Ala Ile Ala Asp Arg Ala Ile Leu Ile
            515                 520                 525

Arg Val Arg Asn Ala Ser Trp Gln His Asp Ile Asp Ser Leu Phe Cys
530                 535                 540

Thr Gln Arg Arg Ser Thr Thr Ala Arg Asp Ile Met Asn Ala Gly Val
545                 550                 555                 560

Thr Cys Val Gly Glu His Glu Thr Leu Thr Ala Ala Ala Gln Tyr Met
                565                 570                 575

Arg Glu His Asp Ile Gly Ala Leu Pro Ile Cys Gly Asp Asp Arg
            580                 585                 590

Leu His Gly Met Leu Thr Asp Arg Asp Ile Val Ile Lys Gly Leu Ala
            595                 600                 605

Ala Gly Leu Asp Pro Asn Thr Ala Thr Ala Gly Glu Leu Ala Arg Asp
610                 615                 620

Ser Ile Tyr Tyr Val Asp Ala Asn Ala Ser Ile Gln Glu Met Leu Asn
625                 630                 635                 640

Val Met Glu Glu His Gln Val Arg Arg Val Pro Val Ile Ser Glu His
                645                 650                 655

Arg Leu Val Gly Ile Val Thr Glu Ala Asp Ile Ala Arg His Leu Pro
            660                 665                 670

Glu His Ala Ile Val Gln Phe Val Lys Ala Ile Cys Ser Pro Met Ala
            675                 680                 685

Leu Ala Ser Gly Ala Pro Thr Pro Gly Leu Leu Thr Thr Ala Gly Ala
```

```
                690               695               700
Gly Arg Pro Arg Asp Arg Cys Ala Arg Ile Val Cys Thr Val Phe Ile
705                 710               715                 720

Glu Thr Ala Val Val Ala Thr Met Phe Val Ala Leu Leu Gly Leu Ser
                725               730               735

Thr Ile Ser Ser Lys Ala Asp Asp Ile Asp Trp Asp Ala Ile Ala Gln
                740               745               750

Cys Glu Ser Gly Gly Asn Trp Ala Ala Asn Thr Gly Asn Gly Leu Tyr
                755               760               765

Gly Gly Leu Gln Ile Ser Gln Ala Thr Trp Asp Ser Asn Gly Gly Val
770               775               780

Gly Ser Pro Ala Ala Ser Pro Gln Gln Gln Ile Glu Val Ala Asp
785                 790               795                 800

Asn Ile Met Lys Thr Gln Gly Pro Gly Ala Trp Pro Lys Cys Ser Ser
                805               810               815

Cys Ser Gln Gly Asp Ala Pro Leu Gly Ser Leu Thr His Ile Leu Thr
                820               825               830

Phe Leu Ala Ala Glu Thr Gly Gly Cys Ser Gly Ser Arg Asp Asp
                835               840               845
```

<210> SEQ ID NO 63
<211> LENGTH: 2499
<212> TYPE: DNA
<213> ORGANISM: Artificial Sequence
<220> FEATURE:
<223> OTHER INFORMATION: Description of Artificial Sequence:
      Mycobacterium PPE51-Rv1733c-Rv2628c-RpfD fusion protein

<400> SEQUENCE: 63

```
atggattttg cgctgctgcc gccggaagtg aacagcgcgc gcatgtatac cggcccgggc      60
gcgggcagcc tgctggcggc ggcgggcggc tgggatagcc tggcggcgga actggcgacc     120
accgcggaag cgtatggcag cgtgctgagc ggcctggcgg cgctgcattg cgcggcccg     180
gcggcggaaa gcatggcggt gaccgcggcg ccgtatattg gctggctgta ccaccgcg      240
gaaaaaaccc agcagaccgc gattcaggcg cgcgcggcgg cgctggcgtt tgaacaggcg     300
tatgcgatga ccctgccgcc gccggtggtg gcggcgaacc gcattcagct gctggcgctg     360
attgcgacca cttttttgg ccagaacacc gcggcgattg cggcgaccga agcgcagtat     420
gcggaaatgt gggcgcagga tgcggcggcg atgtatggct atgcgaccgc gagcgcggcg     480
gcggcgctgc tgaccccgtt tagcccgccg cgccagacca ccaacccggc gggcctgacc     540
gcgcaggcgg cggcggtgag ccaggcgacc gatccgctga gcctgctgat tgaaaccgtg     600
acccaggcgc tgcaggcgct gaccattccg agctttattc cggaagattt tacctttctg     660
gatgcgattt ttgcgggcta tgcgaccgtg ggcgtgaccc aggatgtgga aagctttgtg     720
gcgggcacca ttggcgcgga aagcaacctg gcctgctga acgtgggcga tgaaaacccg     780
gcggaagtga ccccgggcga ttttggcatt ggcgaactgg tgagcgcgac cagcccgggc     840
ggcggcgtga gcgcgagcgg cgcgggcggc gcggcgagcg tgggcaacac cgtgctggcg     900
agcgtgggcc gcgcgaacag cattggccag ctgagcgtgc gccgagctg gcggcgccg     960
agcacccgcc cggtgagcgc gctgagcccg gcgggcctga ccaccctgcc gggcaccgat    1020
gtggcggaac atggcatgcc gggcgtgccg gcgtgccgg tggcggcggg ccgcgcgagc    1080
ggcgtgctgc cgcgctatgg cgtgcgcctg accgtgatgg cgcatccgcc ggcggcgggc    1140
gaattcatga ttgcgactac cgtgatcgt gagggcgcga ccatgatcac gttccgtctg    1200
```

```
cgtctgccgt gtcgcaccat tttgcgcgtg ttttcgcgta acccgctggt ccgcggtacc    1260
gaccgtctgg aggccgttgt catgctgctg gcggttaccg tgagcctgct gacgatccca    1320
ttcgcagcgg cagctggcac ggccgtccaa gacagccgta gccatgtgta tgctcaccag    1380
gctcaaaccc gtcaccccgg ctactgccact gttatcgatc acgaaggcgt gattgactcc    1440
aataccacgg caacctccgc accgcctcgc accaagatta cggttcctgc gcgttgggtg    1500
gtgaatggta ttgaacgcag cggcgaagtt aatgccaaac cgggtaccaa aagcggtgac    1560
cgtgtgggca tctgggtcga tagcgccggt cagctggtcg acgagccggc accgccagcg    1620
cgtgcgatcg ccgatgcggc gctggctgcc ctgggtctgt ggctgagcgt ggcagcggtc    1680
gccggtgcgt tgctggcgct gacgcgcgca attctgatcc gcgttcgcaa tgcgagctgg    1740
cagcacgata ttgatagcct gttttgcacc caacgtgagc tcatgtccac gcaacgaccg    1800
aggcactccg gtattcgggc tgttggcccc tacgcatggg ccggccgatg tggtcggata    1860
ggcaggtggg gggtgcacca ggaggcgatg atgaatctag cgatatggca cccgcgcaag    1920
gtgcaatccg ccaccatcta tcaggtgacc gatcgctcgc acgacgggcg cacagcacgg    1980
gtgcctggtg acgagatcac tagcaccgtg tccggttggt tgtcggagtt gggcaccccaa   2040 agcccgttgg ccgatgagct tgcgcgtgcg gtgcggatcg gcgactggcc cgctgcgtac    2100
gcaatcggtg agcacctgtc cgttgagatt gccgttgcgg tcaagctttt gctgggcctg    2160
agcaccatta gcagcaaagc ggatgacatc gactgggatg cgattgcgca gtgtgagagc    2220
ggtggcaatt gggcagcgaa taccggcaat ggcctgtacg gcggtctgca gatctcccag    2280
gcgacgtggg acagcaatgg tggcgtcggc agcccggctg ccgcgtcccc acaacaacag    2340
atcgaggtgg cagataacat tatgaaaacg cagggtccgg gtgcttggcc aaaatgctcc    2400
agctgcagcc agggtgacgc accgctgggc agcctgaccc acattctgac gttcctggca    2460
gcggaaaccg gtggttgtag cggtagccgc gatgactga                           2499
```

<210> SEQ ID NO 64  
<211> LENGTH: 834  
<212> TYPE: PRT  
<213> ORGANISM: Artificial Sequence  
<220> FEATURE:  
<223> OTHER INFORMATION: Description of Artificial Sequence: PPE51-Rv1733c-Rv2628c-RpfD

<400> SEQUENCE: 64

```
Met Asp Phe Ala Leu Leu Pro Pro Glu Val Asn Ser Ala Arg Met Tyr
1               5                   10                  15

Thr Gly Pro Gly Ala Gly Ser Leu Leu Ala Ala Ala Gly Gly Trp Asp
                20                  25                  30

Ser Leu Ala Ala Glu Leu Ala Thr Thr Ala Glu Ala Tyr Gly Ser Val
            35                  40                  45

Leu Ser Gly Leu Ala Ala Leu His Trp Arg Gly Pro Ala Ala Glu Ser
        50                  55                  60

Met Ala Val Thr Ala Ala Pro Tyr Ile Gly Trp Leu Tyr Thr Thr Ala
65                  70                  75                  80

Glu Lys Thr Gln Gln Thr Ala Ile Gln Ala Arg Ala Ala Ala Leu Ala
                85                  90                  95

Phe Glu Gln Ala Tyr Ala Met Thr Leu Pro Pro Val Val Ala Ala
                100                 105                 110

Asn Arg Ile Gln Leu Leu Ala Leu Ile Ala Thr Asn Phe Phe Gly Gln
            115                 120                 125
```

```
Asn Thr Ala Ala Ile Ala Ala Thr Glu Ala Gln Tyr Ala Glu Met Trp
    130                 135                 140
Ala Gln Asp Ala Ala Ala Met Tyr Gly Tyr Ala Thr Ala Ser Ala Ala
145                 150                 155                 160
Ala Ala Leu Leu Thr Pro Phe Ser Pro Pro Arg Gln Thr Thr Asn Pro
                165                 170                 175
Ala Gly Leu Thr Ala Gln Ala Ala Val Ser Gln Ala Thr Asp Pro
                180                 185                 190
Leu Ser Leu Leu Ile Glu Thr Val Thr Gln Ala Leu Gln Ala Leu Thr
            195                 200                 205
Ile Pro Ser Phe Ile Pro Glu Asp Phe Thr Phe Leu Asp Ala Ile Phe
210                 215                 220
Ala Gly Tyr Ala Thr Val Gly Val Thr Gln Asp Val Glu Ser Phe Val
225                 230                 235                 240
Ala Gly Thr Ile Gly Ala Glu Ser Asn Leu Gly Leu Leu Asn Val Gly
                245                 250                 255
Asp Glu Asn Pro Ala Glu Val Thr Pro Gly Asp Phe Gly Ile Gly Glu
                260                 265                 270
Leu Val Ser Ala Thr Ser Pro Gly Gly Val Ser Ala Ser Gly Ala
            275                 280                 285
Gly Gly Ala Ala Ser Val Gly Asn Thr Val Leu Ala Ser Val Gly Arg
290                 295                 300
Ala Asn Ser Ile Gly Gln Leu Ser Val Pro Pro Ser Trp Ala Ala Pro
305                 310                 315                 320
Ser Thr Arg Pro Val Ser Ala Leu Ser Pro Ala Gly Leu Thr Thr Leu
                325                 330                 335
Pro Gly Thr Asp Val Ala Glu His Gly Met Pro Gly Val Pro Gly Val
                340                 345                 350
Pro Val Ala Ala Gly Arg Ala Ser Gly Val Leu Pro Arg Tyr Gly Val
                355                 360                 365
Arg Leu Thr Val Met Ala His Pro Pro Ala Ala Gly Glu Phe Glu Phe
            370                 375                 380
Met Ile Ala Thr Thr Arg Asp Arg Glu Gly Ala Thr Met Ile Thr Phe
385                 390                 395                 400
Arg Leu Arg Leu Pro Cys Arg Thr Ile Leu Arg Val Phe Ser Arg Asn
                405                 410                 415
Pro Leu Val Arg Gly Thr Asp Arg Leu Glu Ala Val Val Met Leu Leu
                420                 425                 430
Ala Val Thr Val Ser Leu Leu Thr Ile Pro Phe Ala Ala Ala Ala Gly
            435                 440                 445
Thr Ala Val Gln Asp Ser Arg Ser His Val Tyr Ala His Gln Ala Gln
    450                 455                 460
Thr Arg His Pro Ala Thr Ala Thr Val Ile Asp His Glu Gly Val Ile
465                 470                 475                 480
Asp Ser Asn Thr Thr Ala Thr Ser Ala Pro Pro Arg Thr Lys Ile Thr
                485                 490                 495
Val Pro Ala Arg Trp Val Val Asn Gly Ile Glu Arg Ser Gly Glu Val
                500                 505                 510
Asn Ala Lys Pro Gly Thr Lys Ser Gly Asp Arg Val Gly Ile Trp Val
            515                 520                 525
Asp Ser Ala Gly Gln Leu Val Asp Glu Pro Ala Pro Pro Ala Arg Ala
    530                 535                 540
```

| | | | | | | | | | | | | | | |
|---|---|---|---|---|---|---|---|---|---|---|---|---|---|---|
|Ile|Ala|Asp|Ala|Ala|Leu|Ala|Leu|Gly|Leu|Trp|Leu|Ser|Val|Ala|
|545| | | |550| | | |555| | | |560| | |
|Ala|Val|Ala|Gly|Ala|Leu|Leu|Ala|Leu|Thr|Arg|Ala|Ile|Leu|Ile|Arg|
| | | | |565| | | |570| | | |575| | |
|Val|Arg|Asn|Ala|Ser|Trp|Gln|His|Asp|Ile|Asp|Ser|Leu|Phe|Cys|Thr|
| | | |580| | | |585| | | |590| | | |
|Gln|Arg|Glu|Leu|Met|Ser|Thr|Gln|Arg|Pro|Arg|His|Ser|Gly|Ile|Arg|
| | |595| | | |600| | | |605| | | | |
|Ala|Val|Gly|Pro|Tyr|Ala|Trp|Ala|Gly|Arg|Cys|Gly|Arg|Ile|Gly|Arg|
| |610| | | |615| | | |620| | | | | |
|Trp|Gly|Val|His|Gln|Glu|Ala|Met|Met|Asn|Leu|Ala|Ile|Trp|His|Pro|
|625| | | |630| | | |635| | | |640| | | |
|Arg|Lys|Val|Gln|Ser|Ala|Thr|Ile|Tyr|Gln|Val|Thr|Asp|Arg|Ser|His|
| | | |645| | | |650| | | |655| | | |
|Asp|Gly|Arg|Thr|Ala|Arg|Val|Pro|Gly|Asp|Glu|Ile|Thr|Ser|Thr|Val|
| | |660| | | |665| | | |670| | | | |
|Ser|Gly|Trp|Leu|Ser|Glu|Leu|Gly|Thr|Gln|Ser|Pro|Leu|Ala|Asp|Glu|
| |675| | | |680| | | |685| | | | | |
|Leu|Ala|Arg|Ala|Val|Arg|Ile|Gly|Asp|Trp|Pro|Ala|Ala|Tyr|Ala|Ile|
|690| | | |695| | | |700| | | | | | |
|Gly|Glu|His|Leu|Ser|Val|Glu|Ile|Ala|Val|Ala|Val|Lys|Leu|Leu|Leu|
|705| | | |710| | | |715| | | |720| | | |
|Gly|Leu|Ser|Thr|Ile|Ser|Ser|Lys|Ala|Asp|Ile|Asp|Trp|Asp|Ala|
| | | |725| | | |730| | | |735| | | |
|Ile|Ala|Gln|Cys|Glu|Ser|Gly|Gly|Asn|Trp|Ala|Ala|Asn|Thr|Gly|Asn|
| | | |740| | | |745| | | |750| | | |
|Gly|Leu|Tyr|Gly|Gly|Leu|Gln|Ile|Ser|Gln|Ala|Thr|Trp|Asp|Ser|Asn|
| | |755| | | |760| | | |765| | | | |
|Gly|Gly|Val|Gly|Ser|Pro|Ala|Ala|Ser|Pro|Gln|Gln|Gln|Ile|Glu|
| | |770| | | |775| | | |780| | | | |
|Val|Ala|Asp|Asn|Ile|Met|Lys|Thr|Gln|Gly|Pro|Gly|Ala|Trp|Pro|Lys|
|785| | | |790| | | |795| | | |800| | | |
|Cys|Ser|Ser|Cys|Ser|Gln|Gly|Asp|Ala|Pro|Leu|Gly|Ser|Leu|Thr|His|
| | | |805| | | |810| | | |815| | | |
|Ile|Leu|Thr|Phe|Leu|Ala|Ala|Glu|Thr|Gly|Gly|Cys|Ser|Gly|Ser|Arg|
| | | |820| | | |825| | | |830| | | |
|Asp|Asp| | | | | | | | | | | | | | |

<210> SEQ ID NO 65
<211> LENGTH: 3171
<212> TYPE: DNA
<213> ORGANISM: Artificial Sequence
<220> FEATURE:
<223> OTHER INFORMATION: Description of Artificial Sequence:
     Mycobacterium PPE51-Rv1733c-Rv2628c-RpfB fusion protein

<400> SEQUENCE: 65

```
atggattttg cgctgctgcc gccggaagtg aacagcgcgc gcatgtatac cggcccgggc      60
gcgggcagcc tgctggcggc ggcgggcggc tgggatagcc tggcggcgga actggcgacc     120
accgcgaaag cgtatggcag cgtgctgagc ggcctggcgg cgctgcattg cgcggcccg     180 gcggcggaaa gcatggcggt gaccgcggcg ccgtatattg ctggctgta taccaccgcg      240 gaaaaaaccc agcagaccgc gattcaggcg cgcgcggcgg cgctggcgtt tgaacaggcg     300
tatgcgatga ccctgccgcc gccggtggtg gcggcgaacc gcattcagct gctggcgctg     360
```

```
attgcgacca acttttttgg ccagaacacc gcggcgattg cggcgaccga agcgcagtat      420
gcggaaatgt gggcgcagga tgcggcggcg atgtatggct atgcgaccgc gagcgcggcg      480
gcggcgctgc tgaccccgtt tagcccgccg cgccagacca ccaacccggc gggcctgacc      540
gcgcaggcgg cggcggtgag ccaggcgacc gatccgctga gcctgctgat tgaaaccgtg      600
acccaggcgc tgcaggcgct gaccattccg agctttattc cggaagattt tacctttctg      660
gatgcgattt ttgcgggcta tgcgaccgtg ggcgtgaccc aggatgtgga aagctttgtg      720
gcgggcacca ttggcgcgga aagcaacctg ggcctgctga acgtgggcga tgaaaacccg      780
gcggaagtga ccccgggcga ttttggcatt ggcgaactgg tgagcgcgac cagcccgggc      840
ggcggcgtga gcgcgagcgg cgcgggcggc gcggcgagcg tgggcaacac cgtgctggcg      900
agcgtgggcc gcgcgaacag cattggccag ctgagcgtgc cgccgagctg ggcggcgccg      960
agcacccgcc cggtgagcgc gctgagcccg gcgggcctga ccaccctgcc gggcaccgat     1020
gtggcggaac atggcatgcc gggcgtgccg ggcgtgccgg tggcggcggg ccgcgcgagc     1080
ggcgtgctgc cgcgctatgg cgtgcgcctg accgtgatgg cgcatccgcc ggcggcgggc     1140
gaattcatga ttgcgactac ccgtgatcgt gagggcgcga ccatgatcac gttccgtctg     1200
cgtctgccgt gtcgcaccat ttttgcgcgtg ttttcgcgta acccgctggt ccgcggtacc     1260
gaccgtctgg aggccgttgt catgctgctg gcggttaccg tgagcctgct gacgatccca     1320
ttcgcagcgg cagctggcac ggccgtccaa gacagccgta gccatgtgta tgctcaccag     1380
gctcaaaccc gtcacccggc tactgccact gttatcgatc acgaaggcgt gattgactcc     1440
aataccacgg caacctccgc accgcctcgc accaagatta cggttcctgc gcgttgggtg     1500
gtgaatggta ttgaacgcag cggcgaagtt aatgccaaac cgggtaccaa aagcggtgac     1560
cgtgtgggca tctgggtcga tagccgccgt cagctggtcg acgagccggc accgccagcg     1620
cgtgcgatcg ccgatgcggc gctggctgcc ctgggtctgt ggctgagcgt ggcagcggtc     1680
gccggtgcgt tgctggcgct gacgcgcgca attctgatcc gcgttcgcaa tgcgagctgg     1740
cagcacgata ttgatagcct gttttgcacc caacgtgagc tcatgtccac gcaacgaccg     1800
aggcactccg gtattcgggc tgttggcccc tacgcatggg ccggccgatg tggtcggata     1860
ggcaggtggg gggtgcacca ggaggcgatg atgaatctag cgatatggca cccgcgcaag     1920
gtgcaatccg ccaccatcta tcaggtgacc gatcgctcgc acgacgggcg cacagcacgg     1980
gtgcctggtg acgagatcac tagcaccgtg tccggttggt tgtcggagtt gggcacccaa     2040
agcccgttgg ccgatgagct tgcgcgtgcg gtgcggatcg gcgactggcc cgctgcgtac     2100
gcaatcggtg agcacctgtc cgttgagatt gccgttgcgg tcaagcttgc atgcaaaacg     2160
gtgacgttga ccgtcgacgg aaccgcgatg cgggtgacca cgatgaaatc gcgggtgatc     2220
gacatcgtcg aagagaacgg gttctcagtc gacgaccgcg acgacctgta tcccgcggcc     2280
ggcgtgcagg tccatgacgc cgacaccatc gtgctgcggc gtagccgtcc gctgcagatc     2340
tcgctggatg gtcacgacgc taagcaggtg tggacgaccg cgtcgacggt ggacgaggcg     2400
ctggcccaac tcgcgatgac cgacacggcg ccggccgcgg cttctcgcgc cagccgcgtc     2460
ccgctgtccg ggatggcgct accggtcgtc agcgccaaga cggtgcagct caacgacggc     2520
gggttggtgc gcacggtgca cttgccggcc cccaatgtcg cggggctgct gagtgcggcc     2580
ggcgtgccgc tgttgcaaag cgaccacgtg gtgcccgccg cgacggcccc gatcgtcgaa     2640
ggcatgcaga tccaggtgac ccgcaatcgg atcaagaagg tcaccgagcg gctgccgctg     2700
ccgccgaacg cgcgtcgtgt cgaggacccg gagatgaaca tgagccggga ggtcgtcgaa     2760
```

```
gacccggggg ttccggggac ccaggatgtg acgttcgcgg tagctgaggt caacggcgtc    2820
gagaccggcc gtttgccgt cgccaacgtc gtggtgaccc cggccacga agccgtggtg      2880 cgggtgggca ccaagcccgg taccgaggtg ccccggtga tcgacggaag catctgggac     2940
gcgatcgccg gctgtgaggc cggtggcaac tgggcgatca acaccggcaa cgggtattac    3000
ggtggtgtgc agtttgacca gggcacctgg gaggccaacg gcgggctgcg gtatgcaccc    3060
cgcgctgacc tcgccacccg cgaagagcag atcgccgttg ccgaggtgac ccgactgcgt    3120
caaggttggg gcgcctggcc ggtatgtgct gcacgagcgg gtgcgcgctg a             3171
```

<210> SEQ ID NO 66
<211> LENGTH: 1056
<212> TYPE: PRT
<213> ORGANISM: Artificial Sequence
<220> FEATURE:
<223> OTHER INFORMATION: Description of Artificial Sequence:
      PPE51-Rv1733c-Rv2628c-RpfB

<400> SEQUENCE: 66

```
Met Asp Phe Ala Leu Leu Pro Pro Glu Val Asn Ser Ala Arg Met Tyr
1               5                   10                  15

Thr Gly Pro Gly Ala Gly Ser Leu Leu Ala Ala Ala Gly Gly Trp Asp
            20                  25                  30

Ser Leu Ala Ala Glu Leu Ala Thr Thr Ala Glu Ala Tyr Gly Ser Val
        35                  40                  45

Leu Ser Gly Leu Ala Ala Leu His Trp Arg Gly Pro Ala Ala Glu Ser
    50                  55                  60

Met Ala Val Thr Ala Ala Pro Tyr Ile Gly Trp Leu Tyr Thr Thr Ala
65                  70                  75                  80

Glu Lys Thr Gln Gln Thr Ala Ile Gln Ala Arg Ala Ala Ala Leu Ala
                85                  90                  95

Phe Glu Gln Ala Tyr Ala Met Thr Leu Pro Pro Pro Val Val Ala Ala
            100                 105                 110

Asn Arg Ile Gln Leu Leu Ala Leu Ile Ala Thr Asn Phe Phe Gly Gln
        115                 120                 125

Asn Thr Ala Ala Ile Ala Ala Thr Glu Ala Gln Tyr Ala Glu Met Trp
    130                 135                 140

Ala Gln Asp Ala Ala Ala Met Tyr Gly Tyr Ala Thr Ala Ser Ala Ala
145                 150                 155                 160

Ala Ala Leu Leu Thr Pro Phe Ser Pro Pro Arg Gln Thr Thr Asn Pro
                165                 170                 175

Ala Gly Leu Thr Ala Gln Ala Ala Val Ser Gln Ala Thr Asp Pro
            180                 185                 190

Leu Ser Leu Leu Ile Glu Thr Val Thr Gln Ala Leu Gln Ala Leu Thr
        195                 200                 205

Ile Pro Ser Phe Ile Pro Glu Asp Phe Thr Phe Leu Asp Ala Ile Phe
    210                 215                 220

Ala Gly Tyr Ala Thr Val Gly Val Thr Gln Asp Val Glu Ser Phe Val
225                 230                 235                 240

Ala Gly Thr Ile Gly Ala Glu Ser Asn Leu Gly Leu Leu Asn Val Gly
                245                 250                 255

Asp Glu Asn Pro Ala Glu Val Thr Pro Gly Asp Phe Gly Ile Gly Glu
            260                 265                 270

Leu Val Ser Ala Thr Ser Pro Gly Gly Val Ser Ala Ser Gly Ala
        275                 280                 285
```

```
Gly Gly Ala Ala Ser Val Gly Asn Thr Val Leu Ala Ser Val Gly Arg
        290                 295                 300
Ala Asn Ser Ile Gly Gln Leu Ser Val Pro Pro Ser Trp Ala Ala Pro
305                 310                 315                 320
Ser Thr Arg Pro Val Ser Ala Leu Ser Pro Ala Gly Leu Thr Thr Leu
                325                 330                 335
Pro Gly Thr Asp Val Ala Glu His Gly Met Pro Gly Val Pro Gly Val
                340                 345                 350
Pro Val Ala Ala Gly Arg Ala Ser Gly Val Leu Pro Arg Tyr Gly Val
                355                 360                 365
Arg Leu Thr Val Met Ala His Pro Pro Ala Ala Gly Glu Phe Met Ile
        370                 375                 380
Ala Thr Thr Arg Asp Arg Glu Gly Ala Thr Met Ile Thr Phe Arg Leu
385                 390                 395                 400
Arg Leu Pro Cys Arg Thr Ile Leu Arg Val Phe Ser Arg Asn Pro Leu
                405                 410                 415
Val Arg Gly Thr Asp Arg Leu Glu Ala Val Val Met Leu Leu Ala Val
                420                 425                 430
Thr Val Ser Leu Leu Thr Ile Pro Phe Ala Ala Ala Ala Gly Thr Ala
        435                 440                 445
Val Gln Asp Ser Arg Ser His Val Tyr Ala His Gln Ala Gln Thr Arg
450                 455                 460
His Pro Ala Thr Ala Thr Val Ile Asp His Glu Gly Val Ile Asp Ser
465                 470                 475                 480
Asn Thr Thr Ala Thr Ser Ala Pro Pro Arg Thr Lys Ile Thr Val Pro
                485                 490                 495
Ala Arg Trp Val Val Asn Gly Ile Glu Arg Ser Gly Glu Val Asn Ala
                500                 505                 510
Lys Pro Gly Thr Lys Ser Gly Asp Arg Val Gly Ile Trp Val Asp Ser
                515                 520                 525
Ala Gly Gln Leu Val Asp Glu Pro Ala Pro Ala Arg Ala Ile Ala
        530                 535                 540
Asp Ala Ala Leu Ala Ala Leu Gly Leu Trp Leu Ser Val Ala Ala Val
545                 550                 555                 560
Ala Gly Ala Leu Leu Ala Leu Thr Arg Ala Ile Leu Ile Arg Val Arg
                565                 570                 575
Asn Ala Ser Trp Gln His Asp Ile Asp Ser Leu Phe Cys Thr Gln Arg
                580                 585                 590
Glu Leu Met Ser Thr Gln Arg Pro Arg His Ser Gly Ile Arg Ala Val
        595                 600                 605
Gly Pro Tyr Ala Trp Ala Gly Arg Cys Gly Arg Ile Gly Arg Trp Gly
        610                 615                 620
Val His Gln Glu Ala Met Met Asn Leu Ala Ile Trp His Pro Arg Lys
625                 630                 635                 640
Val Gln Ser Ala Thr Ile Tyr Gln Val Thr Asp Arg Ser His Asp Gly
                645                 650                 655
Arg Thr Ala Arg Val Pro Gly Asp Glu Ile Thr Ser Thr Val Ser Gly
                660                 665                 670
Trp Leu Ser Glu Leu Gly Thr Gln Ser Pro Leu Ala Asp Glu Leu Ala
        675                 680                 685
Arg Ala Val Arg Ile Gly Asp Trp Pro Ala Ala Tyr Ala Ile Gly Glu
        690                 695                 700
```

His Leu Ser Val Glu Ile Ala Val Ala Val Lys Leu Ala Cys Lys Thr
705                 710                 715                 720

Val Thr Leu Thr Val Asp Gly Thr Ala Met Arg Val Thr Thr Met Lys
            725                 730                 735

Ser Arg Val Ile Asp Ile Val Glu Glu Asn Gly Phe Ser Val Asp Asp
            740                 745                 750

Arg Asp Asp Leu Tyr Pro Ala Ala Gly Val Gln Val His Asp Ala Asp
            755                 760                 765

Thr Ile Val Leu Arg Arg Ser Arg Pro Leu Gln Ile Ser Leu Asp Gly
            770                 775                 780

His Asp Ala Lys Gln Val Trp Thr Thr Ala Ser Thr Val Asp Glu Ala
785                 790                 795                 800

Leu Ala Gln Leu Ala Met Thr Asp Thr Ala Pro Ala Ala Ser Arg
            805                 810                 815

Ala Ser Arg Val Pro Leu Ser Gly Met Ala Leu Pro Val Val Ser Ala
            820                 825                 830

Lys Thr Val Gln Leu Asn Asp Gly Gly Leu Val Arg Thr Val His Leu
            835                 840                 845

Pro Ala Pro Asn Val Ala Gly Leu Leu Ser Ala Ala Gly Val Pro Leu
850                 855                 860

Leu Gln Ser Asp His Val Val Pro Ala Ala Thr Ala Pro Ile Val Glu
865                 870                 875                 880

Gly Met Gln Ile Gln Val Thr Arg Asn Arg Ile Lys Lys Val Thr Glu
            885                 890                 895

Arg Leu Pro Leu Pro Pro Asn Ala Arg Arg Val Glu Asp Pro Glu Met
            900                 905                 910

Asn Met Ser Arg Glu Val Val Glu Asp Pro Gly Val Pro Gly Thr Gln
            915                 920                 925

Asp Val Thr Phe Ala Val Ala Glu Val Asn Gly Val Glu Thr Gly Arg
            930                 935                 940

Leu Pro Val Ala Asn Val Val Val Thr Pro Ala His Glu Ala Val Val
945                 950                 955                 960

Arg Val Gly Thr Lys Pro Gly Thr Glu Val Pro Pro Val Ile Asp Gly
            965                 970                 975

Ser Ile Trp Asp Ala Ile Ala Gly Cys Glu Ala Gly Gly Asn Trp Ala
            980                 985                 990

Ile Asn Thr Gly Asn Gly Tyr Tyr Gly Gly Val Gln Phe Asp Gln Gly
            995                 1000                1005

Thr Trp Glu Ala Asn Gly Gly Leu Arg Tyr Ala Pro Arg Ala Asp Leu
            1010                1015                1020

Ala Thr Arg Glu Glu Gln Ile Ala Val Ala Glu Val Thr Arg Leu Arg
1025                1030                1035                1040

Gln Gly Trp Gly Ala Trp Pro Val Cys Ala Ala Arg Ala Gly Ala Arg
            1045                1050                1055

<210> SEQ ID NO 67
<211> LENGTH: 2433
<212> TYPE: DNA
<213> ORGANISM: Artificial Sequence
<220> FEATURE:
<223> OTHER INFORMATION: Description of Artificial Sequence:
      Mycobacterium Rv3407-Rv1733c-Rv2626c-RpfB fusion protein

<400> SEQUENCE: 67
atgcgtgcga ctgtgggtct ggttgaggcg attggcattc gcgagctgcg ccaacatgcc        60

```
agccgttact tggctcgtgt cgaggcgggt gaagaactgg gcgtgacgaa taagggtcgt      120
ctggtcgccc gtctgattcc ggttcaggca gctgagcgtt ctcgcgaggc gctgattgaa      180
tccggcgtcc tgatcccggc tcgccgtccg caaaacctgc tggacgtgac ggcggagcca      240
gctcgtggtc gcaaacgcac gctgtctgat gtcctgaacg aaatgcgcga cgagcaggaa      300
ttcatgattg cgactacccg tgatcgtgag ggcgcgacca tgatcacgtt ccgtctgcgt      360
ctgccgtgtc gcaccatttt gcgcgtgttt tcgcgtaacc cgctggtccg cggtaccgac      420
cgtctggagg ccgttgtcat gctgctggcg gttaccgtga gcctgctgac gatcccattc      480
gcagcggcag ctggcacggc cgtccaagac agccgtagcc atgtgtatgc tcaccaggct      540
caaacccgtc acccggctac tgccactgtt atcgatcacg aaggcgtgat tgactccaat      600
accacgcaa cctccgcacc gcctcgcacc aagattacgg ttcctgcgcg ttgggtggtg       660
aatggtattg aacgcagcgg cgaagttaat gccaaaccgg gtaccaaaag cggtgaccgt      720
gtgggcatct gggtcgatag cgccggtcag ctggtcgacg agccggcacc gccagcgcgt      780
gcgatcgccg atgcggcgct ggctgccctg ggtctgtggc tgagcgtggc agcggtcgcc      840
ggtgcgttgc tggcgctgac gcgcgcaatt ctgatccgcg ttcgcaatgc gagctggcag      900
cacgatattg atagcctgtt ttgcacccaa cgtgagctca tgaccacggc gcgtgatatc      960
atgaatgcgg gtgtcacctg tgttggcgag cacgaaacgt tgaccgcagc agcacagtac     1020
atgcgcgaac atgatatcgg cgcattgccg atttgcggcg acgatgatcg tctgcacggt     1080
atgctgaccg accgcgatat cgttatcaag ggtctggccg caggcttgga cccgaacacc     1140
gcgaccgccg gtgaactggc acgtgacagc atctattacg tcgacgcgaa cgccagcatt     1200
caagagatgc tgaacgtgat ggaagagcat caggtgcgtc gtgtcccggt tatcagcgaa     1260
catcgtctgg ttggtatcgt taccgaagcc gacatcgcac gtcacctgcc ggagcacgcg     1320
attgttcagt tcgtgaaagc gatttgcagc ccgatggcgt tggcgtctcg tcaaaagggc     1380
gacacaaaat ttattctaaa tgcaaagctt gcatgcaaaa cggtgacgtt gaccgtcgac     1440
ggaaccgcga tgcgggtgac cacgatgaaa tcgcgggtga tcgacatcgt cgaagagaac     1500
gggttctcag tcgacgaccg cgacgacctg tatcccgcgg ccggcgtgca ggtccatgac     1560
gccgacacca tcgtgctgcg gcgtagccgt ccgctgcaga tctcgctgga tggtcacgac     1620
gctaagcagg tgtggacgac cgcgtcgacg gtggacgagg cgctggccca actcgcgatg     1680
accgacacgg cgccggccgc ggcttctcgc gccagccgcg tcccgctgtc cgggatggcg     1740
ctaccggtcg tcagcgccaa gacggtgcag ctcaacgacg gcgggttggt gcgcacggtg     1800
cacttgccgg ccccaatgt cgcggggctg ctgagtgcgg ccggcgtgcc gctgttgcaa     1860
agcgaccacg tggtgcccgc cgcgacggcc ccgatcgtcg aaggcatgca gatccaggtg     1920
acccgcaatc ggatcaagaa ggtcaccgag cggctgccgc tgccgccgaa cgcgcgtcgt     1980
gtcgaggacc cggagatgaa catgagccgg gaggtcgtcg aagacccggg ggttccgggg     2040
acccaggatg tgacgttcgc ggtagctgag gtcaacggcg tcgagaccgg ccgtttgccc     2100
gtcgccaacg tcgtggtgac cccggcccac gaagccgtgg tgcgggtggg caccaagccc     2160
ggtaccgagg tgcccccggt gatcgacgga agcatctggg acgcgatcgc cggctgtgag     2220
gccggtggca actgggcgat caacaccggc aacgggtatt acggtggtgt gcagtttgac     2280
cagggcacct gggaggccaa cggcgggctg cggtatgcac cccgcgctga cctcgccacc     2340
cgcgaagagc agatcgccgt tgccgagtg acccgactgc gtcaaggttg gggcgcctgg      2400
ccggtatgtg ctgcacgagc gggtgcgcgc tga                                   2433
```

<210> SEQ ID NO 68
<211> LENGTH: 810
<212> TYPE: PRT
<213> ORGANISM: Artificial Sequence
<220> FEATURE:
<223> OTHER INFORMATION: Description of Artificial Sequence: Rv3407-Rv1733c-Rv2626c-RpfB

<400> SEQUENCE: 68

```
Met Arg Ala Thr Val Gly Leu Val Glu Ala Ile Gly Ile Arg Glu Leu
1               5                   10                  15

Arg Gln His Ala Ser Arg Tyr Leu Ala Arg Val Glu Ala Gly Glu Glu
            20                  25                  30

Leu Gly Val Thr Asn Lys Gly Arg Leu Val Ala Arg Leu Ile Pro Val
        35                  40                  45

Gln Ala Ala Glu Arg Ser Arg Glu Ala Leu Ile Glu Ser Gly Val Leu
    50                  55                  60

Ile Pro Ala Arg Arg Pro Gln Asn Leu Leu Asp Val Thr Ala Glu Pro
65                  70                  75                  80

Ala Arg Gly Arg Lys Arg Thr Leu Ser Asp Val Leu Asn Glu Met Arg
                85                  90                  95

Asp Glu Gln Glu Phe Met Ile Ala Thr Thr Arg Asp Arg Glu Gly Ala
            100                 105                 110

Thr Met Ile Thr Phe Arg Leu Arg Leu Pro Cys Arg Thr Ile Leu Arg
        115                 120                 125

Val Phe Ser Arg Asn Pro Leu Val Arg Gly Thr Asp Arg Leu Glu Ala
    130                 135                 140

Val Val Met Leu Leu Ala Val Thr Val Ser Leu Leu Thr Ile Pro Phe
145                 150                 155                 160

Ala Ala Ala Ala Gly Thr Ala Val Gln Asp Ser Arg Ser His Val Tyr
                165                 170                 175

Ala His Gln Ala Gln Thr Arg His Pro Ala Thr Ala Thr Val Ile Asp
            180                 185                 190

His Glu Gly Val Ile Asp Ser Asn Thr Thr Ala Thr Ser Ala Pro Pro
        195                 200                 205

Arg Thr Lys Ile Thr Val Pro Ala Arg Trp Val Val Asn Gly Ile Glu
    210                 215                 220

Arg Ser Gly Glu Val Asn Ala Lys Pro Gly Thr Lys Ser Gly Asp Arg
225                 230                 235                 240

Val Gly Ile Trp Val Asp Ser Ala Gly Gln Leu Val Asp Glu Pro Ala
                245                 250                 255

Pro Pro Ala Arg Ala Ile Ala Asp Ala Ala Leu Ala Ala Leu Gly Leu
            260                 265                 270

Trp Leu Ser Val Ala Ala Val Ala Gly Ala Leu Leu Ala Leu Thr Arg
        275                 280                 285

Ala Ile Leu Ile Arg Val Arg Asn Ala Ser Trp Gln His Asp Ile Asp
    290                 295                 300

Ser Leu Phe Cys Thr Gln Arg Glu Leu Met Thr Thr Ala Arg Asp Ile
305                 310                 315                 320

Met Asn Ala Gly Val Thr Cys Val Gly Glu His Glu Thr Leu Thr Ala
                325                 330                 335

Ala Ala Gln Tyr Met Arg Glu His Asp Ile Gly Ala Leu Pro Ile Cys
            340                 345                 350

Gly Asp Asp Asp Arg Leu His Gly Met Leu Thr Asp Arg Asp Ile Val
```

```
                355                 360                 365
Ile Lys Gly Leu Ala Ala Gly Leu Asp Pro Asn Thr Ala Thr Ala Gly
370                 375                 380

Glu Leu Ala Arg Asp Ser Ile Tyr Tyr Val Asp Ala Asn Ala Ser Ile
385                 390                 395                 400

Gln Glu Met Leu Asn Val Met Glu Glu His Gln Val Arg Arg Val Pro
                405                 410                 415

Val Ile Ser Glu His Arg Leu Val Gly Ile Val Thr Glu Ala Asp Ile
                420                 425                 430

Ala Arg His Leu Pro Glu His Ala Ile Val Gln Phe Val Lys Ala Ile
                435                 440                 445

Cys Ser Pro Met Ala Leu Ala Ser Arg Gln Lys Gly Asp Thr Lys Phe
                450                 455                 460

Ile Leu Asn Ala Lys Leu Ala Cys Lys Thr Val Thr Leu Thr Val Asp
465                 470                 475                 480

Gly Thr Ala Met Arg Val Thr Thr Met Lys Ser Arg Val Ile Asp Ile
                485                 490                 495

Val Glu Glu Asn Gly Phe Ser Val Asp Asp Arg Asp Asp Leu Tyr Pro
                500                 505                 510

Ala Ala Gly Val Gln Val His Asp Ala Asp Thr Ile Val Leu Arg Arg
                515                 520                 525

Ser Arg Pro Leu Gln Ile Ser Leu Asp Gly His Asp Ala Lys Gln Val
                530                 535                 540

Trp Thr Thr Ala Ser Thr Val Asp Glu Ala Leu Ala Gln Leu Ala Met
545                 550                 555                 560

Thr Asp Thr Ala Pro Ala Ala Ser Arg Ala Ser Arg Val Pro Leu
                565                 570                 575

Ser Gly Met Ala Leu Pro Val Val Ser Ala Lys Thr Val Gln Leu Asn
                580                 585                 590

Asp Gly Gly Leu Val Arg Thr Val His Leu Pro Ala Pro Asn Val Ala
                595                 600                 605

Gly Leu Leu Ser Ala Ala Gly Val Pro Leu Leu Gln Ser Asp His Val
610                 615                 620

Val Pro Ala Ala Thr Ala Pro Ile Val Glu Gly Met Gln Ile Gln Val
625                 630                 635                 640

Thr Arg Asn Arg Ile Lys Lys Val Thr Glu Arg Leu Pro Leu Pro Pro
                645                 650                 655

Asn Ala Arg Arg Val Glu Asp Pro Glu Met Asn Met Ser Arg Glu Val
                660                 665                 670

Val Glu Asp Pro Gly Val Pro Gly Thr Gln Asp Val Thr Phe Ala Val
                675                 680                 685

Ala Glu Val Asn Gly Val Glu Thr Gly Arg Leu Pro Val Ala Asn Val
                690                 695                 700

Val Val Thr Pro Ala His Glu Ala Val Arg Val Gly Thr Lys Pro
705                 710                 715                 720

Gly Thr Glu Val Pro Pro Val Ile Asp Gly Ser Ile Trp Asp Ala Ile
                725                 730                 735

Ala Gly Cys Glu Ala Gly Gly Asn Trp Ala Ile Asn Thr Gly Asn Gly
                740                 745                 750

Tyr Tyr Gly Gly Val Gln Phe Asp Gln Gly Thr Trp Glu Ala Asn Gly
                755                 760                 765

Gly Leu Arg Tyr Ala Pro Arg Ala Asp Leu Ala Thr Arg Glu Glu Gln
                770                 775                 780
```

Ile Ala Val Ala Glu Val Thr Arg Leu Arg Gln Gly Trp Gly Ala Trp
785                 790                 795                 800

Pro Val Cys Ala Ala Arg Ala Gly Ala Arg
                805                 810

<210> SEQ ID NO 69
<211> LENGTH: 1761
<212> TYPE: DNA
<213> ORGANISM: Artificial Sequence
<220> FEATURE:
<223> OTHER INFORMATION: Description of Artificial Sequence:
      Mycobacterium Rv3407-Rv1733c-Rv2626c-RpfD fusion protein

<400> SEQUENCE: 69

| | |
|---|---|
| atgcgtgcga ctgtgggtct ggttgaggcg attggcattc gcgagctgcg ccaacatgcc | 60 |
| agccgttact tggctcgtgt cgaggcgggt gaagaactgg gcgtgacgaa taagggtcgt | 120 |
| ctggtcgccc gtctgattcc ggttcaggca gctgagcgtt ctcgcgaggc gctgattgaa | 180 |
| tccggcgtcc tgatcccggc tcgccgtccg caaaacctgc tggacgtgac ggcggagcca | 240 |
| gctcgtggtc gcaaacgcac gctgtctgat gtcctgaacg aaatgcgcga cgagcaggaa | 300 |
| ttcatgattg cgactacccg tgatcgtgag ggcgcgacca tgatcacgtt ccgtctgcgt | 360 |
| ctgccgtgtc gcaccatttt gcgcgtgttt tcgcgtaacc cgctggtccg cggtaccgac | 420 |
| cgtctggagg ccgttgtcat gctgctggcg gttaccgtga cctgctgac gatcccattc | 480 |
| gcagcggcag ctggcacggc cgtccaagac agccgtagcc atgtgtatgc tcaccaggct | 540 |
| caaacccgtc accggctac tgccactgtt atcgatcacg aaggcgtgat tgactccaat | 600 |
| accacggcaa cctccgcacc gcctcgcacc aagattacgg ttcctgcgcg ttgggtggtg | 660 |
| aatggtattg aacgcagcgg cgaagttaat gccaaaccgg gtaccaaaag cggtgaccgt | 720 |
| gtgggcatct gggtcgatag cgccggtcag ctggtcgacg agccggcacc gccagcgcgt | 780 |
| gcgatcgccg atgcggcgct ggctgccctg gtctgtggc tgagcgtggc agcggtcgcc | 840 |
| ggtgcgttgc tggcgctgac gcgcgcaatt ctgatccgcg ttcgcaatgc gagctggcag | 900 |
| cacgatattg atagcctgtt ttgcacccaa cgtgagctca tgaccacggc gcgtgatatc | 960 |
| atgaatgcgg gtgtcacctg tgttggcgag cacgaaacgt tgaccgcagc agcacagtac | 1020 |
| atgcgcgaac atgatatcgg cgcattgccg atttgcggcg acgatgatcg tctgcacggt | 1080 |
| atgctgaccg accgcgatat cgttatcaag ggtctggccg caggcttgga cccgaacacc | 1140 |
| gcgaccgccg gtgaactggc acgtgacagc atctattacg tcgacgcgaa cgccagcatt | 1200 |
| caagagatgc tgaacgtgat ggaagagcat caggtgcgtc gtgtcccggt tatcagcgaa | 1260 |
| catcgtctgg ttggtatcgt taccgaagcc gacatcgcac gtcacctgcc ggagcacgcg | 1320 |
| attgttcagt tcgtgaaagc gatttgcagc ccgatggcgt tggcgtctcg tcaaaagggc | 1380 |
| gacacaaaat ttattctaaa tgcaaagctt ttgctgggcc tgagcaccat tagcagcaaa | 1440 |
| gcggatgaca tcgactggga tgcgattgcg cagtgtgaga gcggtggcaa ttgggcagcg | 1500 |
| aataccggca atggcctgta cggcggtctg cagatctccc aggcgacgtg ggacagcaat | 1560 |
| ggtggcgtcg gcagcccggc tgccgcgtcc ccacaacaac agatcgaggt ggcagataac | 1620 |
| attatgaaaa cgcagggtcc gggtgcttgg ccaaaatgct ccagctgcag ccagggtgac | 1680 |
| gcaccgctgg gcagcctgac ccacattctg acgttcctgg cagcggaaac cggtggttgt | 1740 |
| agcggtagcc gcgatgactg a | 1761 |

-continued

```
<210> SEQ ID NO 70
<211> LENGTH: 586
<212> TYPE: PRT
<213> ORGANISM: Artificial Sequence
<220> FEATURE:
<223> OTHER INFORMATION: Description of Artificial Sequence:
      Rv3407-Rv1733c-Rv2626c-RpfD

<400> SEQUENCE: 70

Met Arg Ala Thr Val Gly Leu Val Glu Ala Ile Gly Ile Arg Glu Leu
1               5                   10                  15

Arg Gln His Ala Ser Arg Tyr Leu Ala Arg Val Glu Ala Gly Glu Glu
            20                  25                  30

Leu Gly Val Thr Asn Lys Gly Arg Leu Val Ala Arg Leu Ile Pro Val
        35                  40                  45

Gln Ala Ala Glu Arg Ser Arg Glu Ala Leu Ile Glu Ser Gly Val Leu
    50                  55                  60

Ile Pro Ala Arg Arg Pro Gln Asn Leu Leu Asp Val Thr Ala Glu Pro
65                  70                  75                  80

Ala Arg Gly Arg Lys Arg Thr Leu Ser Asp Val Leu Asn Glu Met Arg
                85                  90                  95

Asp Glu Gln Glu Phe Met Ile Ala Thr Thr Arg Asp Arg Glu Gly Ala
            100                 105                 110

Thr Met Ile Thr Phe Arg Leu Arg Leu Pro Cys Arg Thr Ile Leu Arg
        115                 120                 125

Val Phe Ser Arg Asn Pro Leu Val Arg Gly Thr Asp Arg Leu Glu Ala
    130                 135                 140

Val Val Met Leu Leu Ala Val Thr Val Ser Leu Leu Thr Ile Pro Phe
145                 150                 155                 160

Ala Ala Ala Ala Gly Thr Ala Val Gln Asp Ser Arg Ser His Val Tyr
                165                 170                 175

Ala His Gln Ala Gln Thr Arg His Pro Ala Thr Ala Thr Val Ile Asp
            180                 185                 190

His Glu Gly Val Ile Asp Ser Asn Thr Thr Ala Thr Ser Ala Pro Pro
        195                 200                 205

Arg Thr Lys Ile Thr Val Pro Ala Arg Trp Val Asn Gly Ile Glu
    210                 215                 220

Arg Ser Gly Glu Val Asn Ala Lys Pro Gly Thr Lys Ser Gly Asp Arg
225                 230                 235                 240

Val Gly Ile Trp Val Asp Ser Ala Gly Gln Leu Val Asp Glu Pro Ala
                245                 250                 255

Pro Pro Ala Arg Ala Ile Ala Asp Ala Leu Ala Ala Leu Gly Leu
            260                 265                 270

Trp Leu Ser Val Ala Ala Val Ala Gly Ala Leu Leu Ala Leu Thr Arg
        275                 280                 285

Ala Ile Leu Ile Arg Val Arg Asn Ala Ser Trp Gln His Asp Ile Asp
    290                 295                 300

Ser Leu Phe Cys Thr Gln Arg Glu Leu Met Thr Thr Ala Arg Asp Ile
305                 310                 315                 320

Met Asn Ala Gly Val Thr Cys Val Gly Glu His Glu Thr Leu Thr Ala
                325                 330                 335

Ala Ala Gln Tyr Met Arg Glu His Asp Ile Gly Ala Leu Pro Ile Cys
            340                 345                 350

Gly Asp Asp Asp Arg Leu His Gly Met Leu Thr Asp Arg Asp Ile Val
        355                 360                 365
```

-continued

```
Ile Lys Gly Leu Ala Ala Gly Leu Asp Pro Asn Thr Ala Thr Ala Gly
    370                 375                 380

Glu Leu Ala Arg Asp Ser Ile Tyr Tyr Val Asp Ala Asn Ala Ser Ile
385                 390                 395                 400

Gln Glu Met Leu Asn Val Met Glu Glu His Gln Val Arg Arg Val Pro
                405                 410                 415

Val Ile Ser Glu His Arg Leu Val Gly Ile Val Thr Glu Ala Asp Ile
            420                 425                 430

Ala Arg His Leu Pro Glu His Ala Ile Val Gln Phe Val Lys Ala Ile
        435                 440                 445

Cys Ser Pro Met Ala Leu Ala Ser Arg Gln Lys Gly Asp Thr Lys Phe
450                 455                 460

Ile Leu Asn Ala Lys Leu Leu Leu Gly Leu Ser Thr Ile Ser Ser Lys
465                 470                 475                 480

Ala Asp Asp Ile Asp Trp Asp Ala Ile Ala Gln Cys Glu Ser Gly Gly
                485                 490                 495

Asn Trp Ala Ala Asn Thr Gly Asn Gly Leu Tyr Gly Gly Leu Gln Ile
                500                 505                 510

Ser Gln Ala Thr Trp Asp Ser Asn Gly Gly Val Gly Ser Pro Ala Ala
        515                 520                 525

Ala Ser Pro Gln Gln Gln Ile Glu Val Ala Asp Asn Ile Met Lys Thr
530                 535                 540

Gln Gly Pro Gly Ala Trp Pro Lys Cys Ser Ser Cys Ser Gln Gly Asp
545                 550                 555                 560

Ala Pro Leu Gly Ser Leu Thr His Ile Leu Thr Phe Leu Ala Ala Glu
                565                 570                 575

Thr Gly Gly Cys Ser Gly Ser Arg Asp Asp
                580                 585
```

<210> SEQ ID NO 71
<211> LENGTH: 2895
<212> TYPE: DNA
<213> ORGANISM: Artificial Sequence
<220> FEATURE:
<223> OTHER INFORMATION: Description of Artificial Sequence:
      Mycobacterium PPE51-Rv1733c-Rv2626c-RpfD fusion protein

<400> SEQUENCE: 71

```
atggattttg cgctgctgcc gccggaagtg aacagcgcgc gcatgtatac cggcccgggc      60
gcgggcagcc tgctggcggc ggcgggcggc tgggatagcc tggcggcgga actggcgacc     120
accgcggaag cgtatggcag cgtgctgagc ggcctggcgg cgctgcattg cgcggcccg      180 gcggcggaaa gcatggcggt gaccgcggcg ccgtatattg gctggctgta ccaccgcg       240 gaaaaaccc agcagaccgc gattcaggcg cgcgcggcgg cgctggcgtt tgaacaggcg      300
tatgcgatga ccctgccgcc gccggtggtg gcggcgaacc gcattcagct gctggcgctg     360
attgcgacca actttttggg ccagaacacc gcggcgattg cggcgaccga agcgcagtat     420
gcggaaatgt gggcgcagga tgcggcggcg atgtatggct atgcgaccgc gagcgcggcg     480
gcggcgctgc tgaccccgtt tagcccgccg cgccagacca ccaacccggc gggcctgacc     540
gcgcaggcgc ggcggtgag ccaggcgacc gatccgctga cctgctgat tgaaaccgtg       600 acccaggcgc tgcaggcgct gaccattccg agctttattc cggaagattt tacctttctg     660
gatgcgattt ttgcgggcta tgcgaccgtg gcgtgaccc aggatgtgga agctttgtg       720 gcgggcacca ttggcgcgga aagcaacctg ggcctgctga acgtgggcga tgaaaacccg     780
```

```
gcggaagtga cccccgggcga ttttggcatt ggcgaactgg tgagcgcgac cagcccgggc    840
ggcggcgtga gcgcgagcgg cgcgggcggc cggcgagcg tgggcaacac cgtgctggcg    900
agcgtgggcc gcgcgaacag cattggccag ctgagcgtgc cgccgagctg ggcggcgccg    960
agcacccgcc cggtgagcgc gctgagcccg cggggcctga ccaccctgcc gggcaccgat   1020
gtggcggaac atggcatgcc gggcgtgccg ggcgtgccgg tggcggcggg ccgcgcgagc   1080
ggcgtgctgc cgcgctatgg cgtgcgcctg accgtgatgg cgcatccgcc ggcggcgggc   1140
gaatttatga cagagcagca gtggaatttc gcgggtatcg aggccgcggc aagcgcaatc   1200
cagggaaatg tcacgtccat tcattccctc cttgacgagg ggaagcagtc cctgaccaag   1260
ctcgcagcgg cctggggcgg tagcggttcg gaggcgtacc agggtgtcca gcaaaaatgg   1320
gacgccacgg ctaccgagct gaacaacgcg ctgcagaacc tggcgcggac gatcagcgaa   1380
gccggtcagg caatggcttc gaccgaaggc aacgtcactg ggatgttcgc agaattcatg   1440
attgcgacta cccgtgatcg tgagggcgcg accatgatca cgttccgtct gcgtctgccg   1500
tgtcgcacca ttttgcgcgt gttttcgcgt aacccgctgg tccgcggtac cgaccgtctg   1560
gaggccgttg tcatgctgct ggcggttacc gtgagcctgc tgacgatccc attcgcagcg   1620
gcagctggca cggccgtcca agacagccgt agccatgtgt atgctcacca ggctcaaacc   1680
cgtcacccgg ctactgccac tgttatcgat cacgaaggcg tgattgactc caataccacg   1740
gcaacctccg caccgcctcg caccaagatt acggttcctg cgccgttggg ggtgaatggt   1800
attgaacgca gcggcgaagt taatgccaaa ccgggtacca aaagcggtga ccgtgtgggc   1860
atctgggtcg atagccgcgg tcagctggtc gacgagccgg caccgccagc gcgtgcgatc   1920
gccgatgcgg cgctggctgc cctgggtctg tggctgagcg tggcagcggt cgccggtgcg   1980
ttgctggcgc tgacgcgcgc aattctgatc cgcgttcgca atgcgagctg gcagcacgat   2040
attgatagcc tgttttgcac ccaacgtgag ctcatgacca cggcgcgtga tatcatgaat   2100
gcgggtgtca cctgtgttgg cgagcacgaa acgttgaccg cagcagcaca gtacatgcgc   2160
gaacatgata tcggcgcatt gccgatttgc ggcgacgatg atcgtctgca cggtatgctg   2220
accgaccgcg atatcgttat caagggtctg gccgcaggct tggacccgaa caccgcgacc   2280
gccggtgaac tggcacgtga cagcatctat tacgtcgacg cgaacgccag cattcaagag   2340
atgctgaacg tgatggaaga gcatcaggtg cgtcgtgtcc cggttatcag cgaacatcgt   2400
ctggttggta tcgttaccga agccgacatc gcacgtcacc tgccggagca cgcgattgtt   2460
cagttcgtga aagcgatttg cagcccgatg gcgttggcgt ctcgtcaaaa gggcgacaca   2520
aaatttattc taaatgcaaa gcttttgctg ggcctgagca ccattagcag caaagcggat   2580
gacatcgact gggatgcgat tgcgcagtgt gagagcggtg gcaattgggc agcgaatacc   2640
ggcaatggcc tgtacggcgg tctgcagatc tcccaggcga cgtgggacag caatggtggc   2700
gtcggcagcc cggctgccgc gtccccacaa caacagatcg aggtggcaga taacattatg   2760
aaaacgcagg gtccgggtgc ttggccaaaa tgctccagct gcagccaggg tgacgcaccg   2820
ctgggcagcc tgacccacat tctgacgttc ctggcagcgg aaaccggtgg ttgtagcggt   2880
agccgcgatg actga                                                    2895

<210> SEQ ID NO 72
<211> LENGTH: 870
<212> TYPE: PRT
<213> ORGANISM: Artificial Sequence
<220> FEATURE:
<223> OTHER INFORMATION: Description of Artificial Sequence:
```

PPE51-Rv1733c-Rv2626c-RpfD

<400> SEQUENCE: 72

```
Met Asp Phe Ala Leu Leu Pro Pro Glu Val Asn Ser Ala Arg Met Tyr
1               5                   10                  15
Thr Gly Pro Gly Ala Gly Ser Leu Leu Ala Ala Ala Gly Gly Trp Asp
            20                  25                  30
Ser Leu Ala Ala Glu Leu Ala Thr Thr Ala Glu Ala Tyr Gly Ser Val
        35                  40                  45
Leu Ser Gly Leu Ala Ala Leu His Trp Arg Gly Pro Ala Ala Glu Ser
    50                  55                  60
Met Ala Val Thr Ala Ala Pro Tyr Ile Gly Trp Leu Tyr Thr Thr Ala
65                  70                  75                  80
Glu Lys Thr Gln Gln Thr Ala Ile Gln Ala Arg Ala Ala Ala Leu Ala
                85                  90                  95
Phe Glu Gln Ala Tyr Ala Met Thr Leu Pro Pro Pro Val Val Ala Ala
            100                 105                 110
Asn Arg Ile Gln Leu Leu Ala Leu Ile Ala Thr Asn Phe Phe Gly Gln
        115                 120                 125
Asn Thr Ala Ala Ile Ala Ala Thr Glu Ala Gln Tyr Ala Glu Met Trp
    130                 135                 140
Ala Gln Asp Ala Ala Ala Met Tyr Gly Tyr Ala Thr Ala Ser Ala Ala
145                 150                 155                 160
Ala Ala Leu Leu Thr Pro Phe Ser Pro Pro Arg Gln Thr Thr Asn Pro
                165                 170                 175
Ala Gly Leu Thr Ala Gln Ala Ala Val Ser Gln Ala Thr Asp Pro
            180                 185                 190
Leu Ser Leu Leu Ile Glu Thr Val Thr Gln Ala Leu Gln Ala Leu Thr
        195                 200                 205
Ile Pro Ser Phe Ile Pro Glu Asp Phe Thr Phe Leu Asp Ala Ile Phe
    210                 215                 220
Ala Gly Tyr Ala Thr Val Gly Val Thr Gln Asp Val Glu Ser Phe Val
225                 230                 235                 240
Ala Gly Thr Ile Gly Ala Glu Ser Asn Leu Gly Leu Leu Asn Val Gly
                245                 250                 255
Asp Glu Asn Pro Ala Glu Val Thr Pro Gly Asp Phe Gly Ile Gly Glu
            260                 265                 270
Leu Val Ser Ala Thr Ser Pro Gly Gly Val Ser Ala Ser Gly Ala
        275                 280                 285
Gly Gly Ala Ala Ser Val Gly Asn Thr Val Leu Ala Ser Val Gly Arg
    290                 295                 300
Ala Asn Ser Ile Gly Gln Leu Ser Val Pro Pro Ser Trp Ala Ala Pro
305                 310                 315                 320
Ser Thr Arg Pro Val Ser Ala Leu Ser Pro Ala Gly Leu Thr Thr Leu
                325                 330                 335
Pro Gly Thr Asp Val Ala Glu His Gly Met Pro Gly Val Pro Gly Val
            340                 345                 350
Pro Val Ala Ala Gly Arg Ala Ser Gly Val Leu Pro Arg Tyr Gly Val
        355                 360                 365
Arg Leu Thr Val Met Ala His Pro Pro Ala Ala Gly Glu Phe Met Ile
    370                 375                 380
Ala Thr Thr Arg Asp Arg Glu Gly Ala Thr Met Ile Thr Phe Arg Leu
385                 390                 395                 400
```

```
Arg Leu Pro Cys Arg Thr Ile Leu Arg Val Phe Ser Arg Asn Pro Leu
                405                 410                 415

Val Arg Gly Thr Asp Arg Leu Glu Ala Val Val Met Leu Leu Ala Val
            420                 425                 430

Thr Val Ser Leu Leu Thr Ile Pro Phe Ala Ala Ala Gly Thr Ala
        435                 440                 445

Val Gln Asp Ser Arg Ser His Val Tyr Ala His Gln Ala Gln Thr Arg
    450                 455                 460

His Pro Ala Thr Ala Thr Val Ile Asp His Glu Gly Val Ile Asp Ser
465                 470                 475                 480

Asn Thr Thr Ala Thr Ser Ala Pro Pro Arg Thr Lys Ile Thr Val Pro
                485                 490                 495

Ala Arg Trp Val Val Asn Gly Ile Glu Arg Ser Gly Glu Val Asn Ala
            500                 505                 510

Lys Pro Gly Thr Lys Ser Gly Asp Arg Val Gly Ile Trp Val Asp Ser
        515                 520                 525

Ala Gly Gln Leu Val Asp Glu Pro Ala Pro Ala Arg Ala Ile Ala
    530                 535                 540

Asp Ala Ala Leu Ala Ala Leu Gly Leu Trp Leu Ser Val Ala Ala Val
545                 550                 555                 560

Ala Gly Ala Leu Leu Ala Leu Thr Arg Ala Ile Leu Ile Arg Val Arg
            565                 570                 575

Asn Ala Ser Trp Gln His Asp Ile Asp Ser Leu Phe Cys Thr Gln Arg
        580                 585                 590

Glu Leu Met Thr Thr Ala Arg Asp Ile Met Asn Ala Gly Val Thr Cys
    595                 600                 605

Val Gly Glu His Glu Thr Leu Thr Ala Ala Gln Tyr Met Arg Glu
    610                 615                 620

His Asp Ile Gly Ala Leu Pro Ile Cys Gly Asp Asp Arg Leu His
625                 630                 635                 640

Gly Met Leu Thr Asp Arg Asp Ile Val Ile Lys Gly Leu Ala Ala Gly
            645                 650                 655

Leu Asp Pro Asn Thr Ala Thr Ala Gly Glu Leu Ala Arg Asp Ser Ile
        660                 665                 670

Tyr Tyr Val Asp Ala Asn Ala Ser Ile Gln Glu Met Leu Asn Val Met
    675                 680                 685

Glu Glu His Gln Val Arg Arg Val Pro Val Ile Ser Glu His Arg Leu
    690                 695                 700

Val Gly Ile Val Thr Glu Ala Asp Ile Ala Arg His Leu Pro Glu His
705                 710                 715                 720

Ala Ile Val Gln Phe Val Lys Ala Ile Cys Ser Pro Met Ala Leu Ala
            725                 730                 735

Ser Arg Gln Lys Gly Asp Thr Lys Phe Ile Leu Asn Ala Lys Leu Leu
        740                 745                 750

Leu Gly Leu Ser Thr Ile Ser Ser Lys Ala Asp Asp Ile Asp Trp Asp
    755                 760                 765

Ala Ile Ala Gln Cys Glu Ser Gly Gly Asn Trp Ala Ala Asn Thr Gly
    770                 775                 780

Asn Gly Leu Tyr Gly Gly Leu Gln Ile Ser Gln Ala Thr Trp Asp Ser
785                 790                 795                 800

Asn Gly Gly Val Gly Ser Pro Ala Ala Ala Ser Pro Gln Gln Gln Ile
            805                 810                 815

Glu Val Ala Asp Asn Ile Met Lys Thr Gln Gly Pro Gly Ala Trp Pro
```

|     |     | 820 |     |     | 825 |     |     |     | 830 |     |     |
| --- | --- | --- | --- | --- | --- | --- | --- | --- | --- | --- | --- |

Lys Cys Ser Ser Cys Ser Gln Gly Asp Ala Pro Leu Gly Ser Leu Thr
        835                 840                 845

His Ile Leu Thr Phe Leu Ala Ala Glu Thr Gly Gly Cys Ser Gly Ser
    850                 855                 860

Arg Asp Asp Lys Met Lys
865             870

<210> SEQ ID NO 73
<211> LENGTH: 3567
<212> TYPE: DNA
<213> ORGANISM: Artificial Sequence
<220> FEATURE:
<223> OTHER INFORMATION: Description of Artificial Sequence:
      Mycobacterium PPE51-Rv1733c-Rv2626c-RpfB fusion protein

<400> SEQUENCE: 73

| | |
|---|---|
| atggattttg cgctgctgcc gccggaagtg aacagcgcgc gcatgtatac cggcccgggc | 60 |
| gcgggcagcc tgctggcggc ggcgggcggc tgggatagcc tggcggcgga actggcgacc | 120 |
| accgcggaag cgtatggcag cgtgctgagc ggcctggcgg cgctgcattg cgcggcccgg | 180 |
| gcggcggaaa gcatggcggt gaccgcggcg ccgtatattg gctggctgta taccaccgcg | 240 |
| gaaaaaccc agcagaccgc gattcaggcg cgcgcggcgg cgctggcgtt tgaacaggcg | 300 |
| tatgcgatga ccctgccgcc gccggtggtg gcggcgaacc gcattcagct gctggcgctg | 360 |
| attgcgacca acttttttgg ccagaacacc gcggcgattg cggcgaccga agcgcagtat | 420 |
| gcggaaatgt gggcgcagga tgcggcgcg atgtatggct atgcgaccgc gagcgcggcg | 480 |
| gcggcgctgc tgacccgtt tagcccgccg cgccagacca ccaacccggc gggcctgacc | 540 |
| gcgcaggcgg cggcggtgag ccaggcgacc gatccgctga gcctgctgat tgaaaccgtg | 600 |
| acccaggcgc tgcaggcgct gaccattccg agctttattc cggaagattt tacctttctg | 660 |
| gatgcgattt ttgcgggcta tgcgaccgtg gcgtgaccc aggatgtgga agctttgtg | 720 |
| gcgggcacca ttggcgcgga aagcaacctg gcctgctga acgtgggcga tgaaaacccg | 780 |
| gcggaagtga ccccgggcga ttttggcatt ggcgaactgg tgagcgcgac cagcccgggc | 840 |
| ggcggcgtga gcgcgagcgg cgcgggcggc gcggcgagcg tgggcaacac cgtgctggcg | 900 |
| agcgtgggcc gcgcgaacag cattggccag ctgagcgtgc cgccgagctg gcggcgccg | 960 |
| agcacccgcc cggtgagcgc gctgagcccg gcgggcctga ccaccctgcc gggcaccgat | 1020 |
| gtggcggaac atggcatgcc gggcgtgccg gcgtgccgg tggcggcggg ccgcgcgagc | 1080 |
| ggcgtgctgc cgcgctatgg cgtgcgcctg accgtgatgg cgcatccgcc ggcggcgggc | 1140 |
| gaatttatga cagagcagca gtggaatttc gcgggtatcg aggccgcggc aagcgcaatc | 1200 |
| cagggaaatg tcacgtccat tcattccctc cttgacgagg ggaagcagtc cctgaccaag | 1260 |
| ctcgcagcgg cctgggggcgg tagcggttcg gaggcgtacc agggtgtcca gcaaaaatgg | 1320 |
| gacgccacgg ctaccgagct gaacaacgcg ctgcagaacc tggcgcggac gatcagcgaa | 1380 |
| gccggtcagg caatggcttc gaccgaaggc aacgtcactg gatgttcgc agaattcatg | 1440 |
| attgcgacta cccgtgatcg tgagggcgcg accatgatca cgttccgtct cgtctgccg | 1500 |
| tgtcgcacca ttttgcgcgt gttttcgcgt aacccgctgg tccgcggtac cgaccgtctg | 1560 |
| gaggccgttg tcatgctgct ggcggttacc gtgagcctgc tgacgatccc attcgcagcg | 1620 |
| gcagctggca cggccgtcca agacagccgt agccatgtgt atgctcacca ggctcaaacc | 1680 |
| cgtcacccgg ctactgccac tgttatcgat cacgaaggcg tgattgactc caataccacg | 1740 |

```
gcaacctccg caccgcctcg caccaagatt acggttcctg cgcgttgggt ggtgaatggt    1800
attgaacgca gcggcgaagt taatgccaaa ccgggtacca aaagcggtga ccgtgtgggc    1860
atctgggtcg atagcgccgg tcagctggtc gacgagccgg caccgccagc gcgtgcgatc    1920
gccgatgcgg cgctggctgc cctgggtctg tggctgagcg tggcagcggt cgccggtgcg    1980
ttgctggcgc tgacgcgcgc aattctgatc cgcgttcgca atgcgagctg cagcacgat    2040 attgatagcc tgttttgcac ccaacgtgag ctcatgacca cggcgcgtga tatcatgaat    2100
gcgggtgtca cctgtgttgg cgagcacgaa acgttgaccg cagcagcaca gtacatgcgc    2160
gaacatgata tcggcgcatt gccgatttgc ggcgacgatg atcgtctgca cggtatgctg    2220
accgaccgcg atatcgttat caagggtctg gccgcaggct tggacccgaa caccgcgacc    2280
gccggtgaac tggcacgtga cagcatctat tacgtcgacg cgaacgccag cattcaagag    2340
atgctgaacg tgatggaaga gcatcaggtg cgtcgtgtcc cggttatcag cgaacatcgt    2400
ctggttggta tcgttaccga agccgacatc gcacgtcacc tgccggagca cgcgattgtt    2460
cagttcgtga aagcgatttg cagcccgatg gcgttggcgt ctcgtcaaaa gggcgacaca    2520
aaatttattc taaatgcaaa gcttgcatgc aaaacggtga cgttgaccgt cgacggaacc    2580
gcgatgcggg tgaccacgat gaaatcgcgg gtgatcgaca tcgtcgaaga aacgggttc    2640 tcagtcgacg accgcgacga cctgtatccc cgggccggcg tgcaggtcca tgacgccgac    2700
accatcgtgc tgcggcgtag ccgtccgctg cagatctcgc tggatggtca cgacgctaag    2760
caggtgtgga cgaccgcgtc gacggtggac gaggcgctgg cccaactcgc gatgaccgac    2820
acggcgccgg ccgcggcttc tcgcgccagc cgcgtcccgc tgtccgggat ggcgctaccg    2880
gtcgtcagcg ccaagacggt gcagctcaac gacggcgggt tggtgcgcac ggtgcacttg    2940
ccggccccca atgtcgcggg gctgctgagt gcggccggcg tgccgctgtt gcaaagcgac    3000
cacgtggtgc ccgccgcgac ggccccgatc gtcgaaggca tgcagatcca ggtgacccgc    3060
aatcggatca agaaggtcac cgagcggctg ccgctgccgc cgaacgcgcg tcgtgtcgag    3120
gacccggaga tgaacatgag ccgggaggtc gtcgaagacc cggggggttcc ggggacccag    3180 gatgtgacgt tcgcggtagc tgaggtcaac ggcgtcgaga ccggccgttt gcccgtcgcc    3240
aacgtcgtgg tgaccccggc ccacgaagcc gtggtgcggg tgggcaccaa gcccggtacc    3300
gaggtgcccc cggtgatcga cggaagcatc tgggacgcga tcgccggctg tgaggccggt    3360
ggcaactggg cgatcaacac cggcaacggg tattacggtg gtgtgcagtt tgaccagggc    3420
acctgggagg ccaacggcgg gctgcggtat gcaccccgcg ctgacctcgc cacccgcgaa    3480
gagcagatcg ccgttgccga ggtgaccccga ctgcgtcaag gttggggcgc ctggccggta    3540
tgtgctgcac gagcgggtgc gcgctga                                         3567
```

<210> SEQ ID NO 74
<211> LENGTH: 1091
<212> TYPE: PRT
<213> ORGANISM: Artificial Sequence
<220> FEATURE:
<223> OTHER INFORMATION: Description of Artificial Sequence:
      PPE51-Rv1733c-Rv2626c-RpfB

<400> SEQUENCE: 74

Met Asp Phe Ala Leu Leu Pro Pro Glu Val Asn Ser Ala Arg Met Tyr
1               5                   10                  15

Thr Gly Pro Gly Ala Gly Ser Leu Leu Ala Ala Ala Gly Gly Trp Asp
            20                  25                  30

```
Ser Leu Ala Ala Glu Leu Ala Thr Thr Ala Glu Ala Tyr Gly Ser Val
        35                  40                  45

Leu Ser Gly Leu Ala Ala Leu His Trp Arg Gly Pro Ala Ala Glu Ser
        50                  55                  60

Met Ala Val Thr Ala Ala Pro Tyr Ile Gly Trp Leu Tyr Thr Thr Ala
65                  70                  75                  80

Glu Lys Thr Gln Gln Thr Ala Ile Gln Ala Arg Ala Ala Ala Leu Ala
                    85                  90                  95

Phe Glu Gln Ala Tyr Ala Met Thr Leu Pro Pro Val Val Ala Ala
                100                 105                 110

Asn Arg Ile Gln Leu Leu Ala Leu Ile Ala Thr Asn Phe Phe Gly Gln
                115                 120                 125

Asn Thr Ala Ala Ile Ala Ala Thr Glu Ala Gln Tyr Ala Glu Met Trp
        130                 135                 140

Ala Gln Asp Ala Ala Ala Met Tyr Gly Tyr Ala Thr Ala Ser Ala Ala
145                 150                 155                 160

Ala Ala Leu Leu Thr Pro Phe Ser Pro Pro Arg Gln Thr Thr Asn Pro
                165                 170                 175

Ala Gly Leu Thr Ala Gln Ala Ala Val Ser Gln Ala Thr Asp Pro
                180                 185                 190

Leu Ser Leu Leu Ile Glu Thr Val Thr Gln Ala Leu Gln Ala Leu Thr
        195                 200                 205

Ile Pro Ser Phe Ile Pro Glu Asp Phe Thr Phe Leu Asp Ala Ile Phe
        210                 215                 220

Ala Gly Tyr Ala Thr Val Gly Val Thr Gln Asp Val Glu Ser Phe Val
225                 230                 235                 240

Ala Gly Thr Ile Gly Ala Glu Ser Asn Leu Gly Leu Leu Asn Val Gly
                245                 250                 255

Asp Glu Asn Pro Ala Glu Val Thr Pro Gly Asp Phe Gly Ile Gly Glu
                260                 265                 270

Leu Val Ser Ala Thr Ser Pro Gly Gly Val Ser Ala Ser Gly Ala
        275                 280                 285

Gly Gly Ala Ala Ser Val Gly Asn Thr Val Leu Ala Ser Val Gly Arg
290                 295                 300

Ala Asn Ser Ile Gly Gln Leu Ser Val Pro Ser Trp Ala Pro
305                 310                 315                 320

Ser Thr Arg Pro Val Ser Ala Leu Ser Pro Ala Gly Leu Thr Thr Leu
                325                 330                 335

Pro Gly Thr Asp Val Ala Glu His Gly Met Pro Gly Val Pro Gly Val
                340                 345                 350

Pro Val Ala Ala Gly Arg Ala Ser Gly Val Leu Pro Arg Tyr Gly Val
                355                 360                 365

Arg Leu Thr Val Met Ala His Pro Pro Ala Ala Gly Glu Phe Met Ile
        370                 375                 380

Ala Thr Thr Arg Asp Arg Glu Gly Ala Thr Met Ile Thr Phe Arg Leu
385                 390                 395                 400

Arg Leu Pro Cys Arg Thr Ile Leu Arg Val Phe Ser Arg Asn Pro Leu
                405                 410                 415

Val Arg Gly Thr Asp Arg Leu Glu Ala Val Val Met Leu Leu Ala Val
                420                 425                 430

Thr Val Ser Leu Leu Thr Ile Pro Phe Ala Ala Ala Ala Gly Thr Ala
        435                 440                 445
```

-continued

Val Gln Asp Ser Arg Ser His Val Tyr Ala His Gln Ala Gln Thr Arg
450                 455                 460

His Pro Ala Thr Ala Thr Val Ile Asp His Glu Gly Val Ile Asp Ser
465                 470                 475                 480

Asn Thr Thr Ala Thr Ser Ala Pro Pro Arg Thr Lys Ile Thr Val Pro
                485                 490                 495

Ala Arg Trp Val Val Asn Gly Ile Glu Arg Ser Gly Glu Val Asn Ala
                500                 505                 510

Lys Pro Gly Thr Lys Ser Gly Asp Arg Val Gly Ile Trp Val Asp Ser
                515                 520                 525

Ala Gly Gln Leu Val Asp Glu Pro Ala Pro Ala Arg Ala Ile Ala
530                 535                 540

Asp Ala Ala Leu Ala Ala Leu Gly Leu Trp Leu Ser Val Ala Ala Val
545                 550                 555                 560

Ala Gly Ala Leu Leu Ala Leu Thr Arg Ala Ile Leu Ile Arg Val Arg
                565                 570                 575

Asn Ala Ser Trp Gln His Asp Ile Asp Ser Leu Phe Cys Thr Gln Arg
                580                 585                 590

Glu Leu Met Thr Thr Ala Arg Asp Ile Met Asn Ala Gly Val Thr Cys
                595                 600                 605

Val Gly Glu His Glu Thr Leu Thr Ala Ala Gln Tyr Met Arg Glu
610                 615                 620

His Asp Ile Gly Ala Leu Pro Ile Cys Gly Asp Asp Arg Leu His
625                 630                 635                 640

Gly Met Leu Thr Asp Arg Asp Ile Val Ile Lys Gly Leu Ala Ala Gly
                645                 650                 655

Leu Asp Pro Asn Thr Ala Thr Ala Gly Glu Leu Ala Arg Asp Ser Ile
                660                 665                 670

Tyr Tyr Val Asp Ala Asn Ala Ser Ile Gln Glu Met Leu Asn Val Met
                675                 680                 685

Glu Glu His Gln Val Arg Arg Val Pro Val Ile Ser Glu His Arg Leu
                690                 695                 700

Val Gly Ile Val Thr Glu Ala Asp Ile Ala Arg His Leu Pro Glu His
705                 710                 715                 720

Ala Ile Val Gln Phe Val Lys Ala Ile Cys Ser Pro Met Ala Leu Ala
                725                 730                 735

Ser Arg Gln Lys Gly Asp Thr Lys Phe Ile Leu Asn Ala Lys Leu Ala
                740                 745                 750

Cys Lys Thr Val Thr Leu Thr Val Asp Gly Thr Ala Met Arg Val Thr
                755                 760                 765

Thr Met Lys Ser Arg Val Ile Asp Ile Val Glu Glu Asn Gly Phe Ser
770                 775                 780

Val Asp Asp Arg Asp Asp Leu Tyr Pro Ala Ala Gly Val Gln Val His
785                 790                 795                 800

Asp Ala Asp Thr Ile Val Leu Arg Arg Ser Arg Pro Leu Gln Ile Ser
                805                 810                 815

Leu Asp Gly His Asp Ala Lys Gln Val Trp Thr Thr Ala Ser Thr Val
                820                 825                 830

Asp Glu Ala Leu Ala Gln Leu Ala Met Thr Asp Thr Ala Pro Ala Ala
                835                 840                 845

Ala Ser Arg Ala Ser Arg Val Pro Leu Ser Gly Met Ala Leu Pro Val
850                 855                 860

Val Ser Ala Lys Thr Val Gln Leu Asn Asp Gly Gly Leu Val Arg Thr

-continued

```
                865                 870                 875                 880
Val His Leu Pro Ala Pro Asn Val Ala Gly Leu Leu Ser Ala Ala Gly
                    885                 890                 895

Val Pro Leu Leu Gln Ser Asp His Val Val Pro Ala Ala Thr Ala Pro
                900                 905                 910

Ile Val Glu Gly Met Gln Ile Gln Val Thr Arg Asn Arg Ile Lys Lys
                915                 920                 925

Val Thr Glu Arg Leu Pro Leu Pro Pro Asn Ala Arg Arg Val Glu Asp
            930                 935                 940

Pro Glu Met Asn Met Ser Arg Glu Val Val Glu Asp Pro Gly Val Pro
945                 950                 955                 960

Gly Thr Gln Asp Val Thr Phe Ala Val Ala Glu Val Asn Gly Val Glu
                965                 970                 975

Thr Gly Arg Leu Pro Val Ala Asn Val Val Val Thr Pro Ala His Glu
                980                 985                 990

Ala Val Val Arg Val Gly Thr Lys Pro Gly Thr Glu Val Pro Pro Val
                995                 1000                1005

Ile Asp Gly Ser Ile Trp Asp Ala Ile Ala Gly Cys Glu Ala Gly Gly
            1010                1015                1020

Asn Trp Ala Ile Asn Thr Gly Asn Gly Tyr Tyr Gly Gly Val Gln Phe
1025                1030                1035                1040

Asp Gln Gly Thr Trp Glu Ala Asn Gly Gly Leu Arg Tyr Ala Pro Arg
                1045                1050                1055

Ala Asp Leu Ala Thr Arg Glu Glu Gln Ile Ala Val Ala Glu Val Thr
                1060                1065                1070

Arg Leu Arg Gln Gly Trp Gly Ala Trp Pro Val Cys Ala Ala Arg Ala
            1075                1080                1085

Gly Ala Arg
    1090

<210> SEQ ID NO 75
<211> LENGTH: 31
<212> TYPE: DNA
<213> ORGANISM: Artificial Sequence
<220> FEATURE:
<223> OTHER INFORMATION: Description of Artificial Sequence: 85B For
      NdeI primer

<400> SEQUENCE: 75
atagatcata tgtttagccg tcctggcctg c                                 31

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: 85B Rev
      EcoRI nostop primer

<400> SEQUENCE: 76
ttaagagaat tcgcccgcac ccagagagga t                                 31

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: ESAT-6 For
      BamHI primer
```

<400> SEQUENCE: 77
aacgttggat ccatgacaga gcagcagtgg aa        32

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: ESAT-6 Rev
      EcoRI ns primer

<400> SEQUENCE: 78
atactagaat tctgcgaaca tcccagtgac gt        32

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence: 1733 For
      EcoRI primer

<400> SEQUENCE: 79
aacttagaat tcatgattgc gactacccgt gat        33

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: 1733 In1
      Rev Xma primer

<400> SEQUENCE: 80
gatatacccg ggggcctcca gacggtcggt        30

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence: 1733 Out
      For Xma primer

<400> SEQUENCE: 81
aacgaacccg gggtccaaga cagccgtagc c        31

<210> SEQ ID NO 82
<211> LENGTH: 31
<212> TYPE: DNA
<213> ORGANISM: Artificial Sequence
<220> FEATURE:
<223> OTHER INFORMATION: Description of Artificial Sequence: 1733 Out
      Rev Xba primer

<400> SEQUENCE: 82
taagtatcta gaatcggcga tcgcacgcgc t        31

<210> SEQ ID NO 83
<211> LENGTH: 32
<212> TYPE: DNA
<213> ORGANISM: Artificial Sequence
<220> FEATURE:
<223> OTHER INFORMATION: Description of Artificial Sequence: 1733 In2
      For Xba primer

<400> SEQUENCE: 83
atagaatcta gacgcgcaat tctgatccgc gt                     32

<210> SEQ ID NO 84
<211> LENGTH: 32
<212> TYPE: DNA
<213> ORGANISM: Artificial Sequence
<220> FEATURE:
<223> OTHER INFORMATION: Description of Artificial Sequence: 1733 Rev ns
      SacI primer

<400> SEQUENCE: 84
agataagagc tcacgttggg tgcaaaacag gc                     32

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: 2626 For
      SacI primer

<400> SEQUENCE: 85
atagaagagc tcatgaccac ggcgcgtgat a                      31

<210> SEQ ID NO 86
<211> LENGTH: 36
<212> TYPE: DNA
<213> ORGANISM: Artificial Sequence
<220> FEATURE:
<223> OTHER INFORMATION: Description of Artificial Sequence: 2626 Rev
      HindIII ns primer

<400> SEQUENCE: 86
taaagaaagc tttgcattta gaataaattt tgtgtc                 36

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: RpfD For
      HindIII primer

<400> SEQUENCE: 87
taactaaagc ttttgctggg cctgagcacc                        30

<210> SEQ ID NO 88
<211> LENGTH: 33
<212> TYPE: DNA
<213> ORGANISM: Artificial Sequence
<220> FEATURE:
<223> OTHER INFORMATION: Description of Artificial Sequence: RpfD Rev
      XhoI stop primer

<400> SEQUENCE: 88
atctaactcg agctagtcat cgcggctacc gct                    33

<210> SEQ ID NO 89
<211> LENGTH: 33
<212> TYPE: DNA
<213> ORGANISM: Artificial Sequence
<220> FEATURE:
<223> OTHER INFORMATION: Description of Artificial Sequence: ESAT6 For
      NdeI primer

<400> SEQUENCE: 89
taagatcata tgacagagca gcagtggaat ttc                               33

<210> SEQ ID NO 90
<211> LENGTH: 32
<212> TYPE: DNA
<213> ORGANISM: Artificial Sequence
<220> FEATURE:
<223> OTHER INFORMATION: Description of Artificial Sequence: ESAT-6 Rev
      EcoRI ns primer

<400> SEQUENCE: 90
atactagaat tctgcgaaca tcccagtgac gt                                32

<210> SEQ ID NO 91
<211> LENGTH: 1263
<212> TYPE: DNA
<213> ORGANISM: Artificial Sequence
<220> FEATURE:
<223> OTHER INFORMATION: Description of Artificial Sequence: Ag85B-ESAT6
      fusion protein with Ag85B signal sequence

<400> SEQUENCE: 91
atgacagacg tgagccgaaa gattcgagct tggggacgcc gattgatgat cggcacggca    60
gcggctgtag tccttccggg cctggtgggg cttgccggcg agcggcaac cgcgggcgcg     120 ttctcccggc cggggctgcc ggtcgagtac ctgcaggtgc cgtcgccgtc gatgggccgc   180
gacatcaagg ttcagttcca gagcggtggg aacaactcac ctgcggttta tctgctcgac    240
ggcctgcgcg cccaagacga ctacaacggc tgggatatca caccccggc gttcgagtgg    300 tactaccagt cgggactgtc gatagtcatg ccggtcggcg ggcagtccag cttctacagc    360
gactggtaca gcccggcctg cggtaaggct ggctgccaga cttacaagtg gaaaccttc    420 ctgaccagcg agctgccgca atggttgtcc gccaacaggg ccgtgaagcc caccggcagc    480
gctgcaatcg gcttgtcgat ggccggctcg tcggcaatga tcttggccgc ctaccacccc    540
cagcagttca tctacgccgg ctcgctgtcg gccctgctgg acccctctca ggggatgggg    600
cctagcctga tcggcctcgc gatgggtgac gccggcggtt acaaggccgc agacatgtgg    660 ggtcccctcga gtgaccccggc atgggagcgc aacgaccta cgcagcagat ccccaagctg    720
gtcgcaaaca cacccggct atgggtttat tgcgggaacg gcaccccgaa cgagttgggc   780
ggtgccaaca tacccgccga gttcttggag aacttcgttc gtagcagcaa cctgaagttc    840
caggatgcgt acaacgccgc gggcgggcac aacgccgtgt tcaacttccc gcccaacggc    900
acgcacagct gggagtactg gggcgctcag ctcaacgcca tgaagggtga cctgcagagt    960
tcgttaggcg ccggcatgac agagcagcag tggaatttcg cgggtatcga ggccgcggca   1020
agcgcaatcc agggaaatgt cacgtccatt cattccctcc ttgacgaggg gaagcagtcc   1080
ctgaccaagc tcgcagcggc ctggggcggt agcggttcgg aggcgtacca gggtgtccag   1140
caaaaatggg acgccacggc taccgagctg aacaacgcgc tgcagaacct ggcgcggacg   1200
atcagcgaag ccggtcaggc aatggcttcg accgaaggca cgtcactgg gatgttcgca    1260 tga                                                               1263

<210> SEQ ID NO 92
<211> LENGTH: 420
<212> TYPE: PRT
<213> ORGANISM: Artificial Sequence
<220> FEATURE:
<223> OTHER INFORMATION: Description of Artificial Sequence: Ag85B-ESAT6
      (Ag85B signal sequence)

```
<400> SEQUENCE: 92

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly Met Thr Glu Gln Gln Trp Asn Phe Ala Gly Ile
                325                 330                 335

Glu Ala Ala Ala Ser Ala Ile Gln Gly Asn Val Thr Ser Ile His Ser
            340                 345                 350

Leu Leu Asp Glu Gly Lys Gln Ser Leu Thr Lys Leu Ala Ala Ala Trp
        355                 360                 365

Gly Gly Ser Gly Ser Glu Ala Tyr Gln Gly Val Gln Gln Lys Trp Asp
    370                 375                 380

Ala Thr Ala Thr Glu Leu Asn Asn Ala Leu Gln Asn Leu Ala Arg Thr
385                 390                 395                 400

Ile Ser Glu Ala Gly Gln Ala Met Ala Ser Thr Glu Gly Asn Val Thr
                405                 410                 415
```

```
Gly Met Phe Ala
        420

<210> SEQ ID NO 93
<211> LENGTH: 1272
<212> TYPE: DNA
<213> ORGANISM: Artificial Sequence
<220> FEATURE:
<223> OTHER INFORMATION: Description of Artificial Sequence: Ag85B-ESAT6
      fusion protein with 19 kDa lipoprotein signal sequence

<400> SEQUENCE: 93
atgaagcgtg gactgacggt cgcggtagcc ggagccgcca ttctggtcgc aggtctttcc      60
ggatgttcaa gcaacaagtc gactacagga agcggtgaga ccacgaccgc ggcaggtacc     120
acggcaagcc ccggccggcc ggggctgccg gtcgagtacc tgcaggtgcc gtcgccgtcg     180
atgggccgcg acatcaaggt tcagttccag agcggtggga caactcacc tgcggtttat      240 ctgctcgacg gcctgcgcgc ccaagacgac tacaacggct gggatatcaa caccccggcg     300
ttcgagtggt actaccagtc gggactgtcg atagtcatgc cggtcggcgg gcagtccagc     360
ttctacagcg actggtacag cccggcctgc ggtaaggctg gctgccagac ttacaagtgg     420
gaaaccttcc tgaccagcga gctgccgcaa tggttgtccg ccaacagggc cgtgaagccc     480
accggcagcg ctgcaatcgg cttgtcgatg gccggctcgt cggcaatgat cttggccgcc     540
taccaccccc agcagttcat ctacgccggc tcgctgtcgg ccctgctgga cccctctcag     600
gggatggggc ctagcctgat cggcctcgcg atgggtgacg ccggcggtta caaggccgca     660
gacatgtggg gtccctcgag tgacccggca tgggagcgca acgaccctac gcagcagatc     720
cccaagctgg tcgcaaacaa cacccggcta tgggtttatt gcgggaacgg cacccccgaac    780 gagttgggcg gtgccaacat cccgccgag ttcttggaga acttcgttcg tagcagcaac      840
ctgaagttcc aggatgcgta caacgccgcg ggcgggcaca acgccgtgtt caacttcccg     900
cccaacggca cgcacagctg ggagtactgg ggcgctcagc tcaacgccat gaagggtgac     960
ctgcagagtt cgttaggcgc cggcatgaca gagcagcagt ggaatttcgc gggtatcgag    1020
gccgcggcaa gcgcaatcca gggaaatgtc acgtccattc attccctcct tgacgagggg    1080
aagcagtccc tgaccaagct cgcagcggcc tggggcggta gcggttcgga ggcgtaccag    1140
ggtgtccagc aaaaatggga cgccacggct accgagctga acaacgcgct gcagaacctg    1200
gcgcggacga tcagcgaagc cggtcaggca atggcttcga ccgaaggcaa cgtcactggg    1260
atgttcgcat ga                                                       1272

<210> SEQ ID NO 94
<211> LENGTH: 423
<212> TYPE: PRT
<213> ORGANISM: Artificial Sequence
<220> FEATURE:
<223> OTHER INFORMATION: Description of Artificial Sequence: Ag85B-ESAT6
      (19 kDa lipopr Leu Pro Val Glu Tyr Leu Gln Val Pro Ser Pro Ser Met Gly Arg Asp
 50                  55                  60

Ile Lys Val Gln Phe Gln Ser Gly Gly Asn Asn Ser Pro Ala Val Tyr
 65                  70                  75                  80

Leu Leu Asp Gly Leu Arg Ala Gln Asp Tyr Asn Gly Trp Asp Ile
                 85                  90                  95

Asn Thr Pro Ala Phe Glu Trp Tyr Tyr Gln Ser Gly Leu Ser Ile Val
                100                 105                 110

Met Pro Val Gly Gly Gln Ser Ser Phe Tyr Ser Asp Trp Tyr Ser Pro
            115                 120                 125

Ala Cys Gly Lys Ala Gly Cys Gln Thr Tyr Lys Trp Glu Thr Phe Leu
130                 135                 140

Thr Ser Glu Leu Pro Gln Trp Leu Ser Ala Asn Arg Ala Val Lys Pro
145                 150                 155                 160

Thr Gly Ser Ala Ala Ile Gly Leu Ser Met Ala Gly Ser Ser Ala Met
                165                 170                 175

Ile Leu Ala Ala Tyr His Pro Gln Gln Phe Ile Tyr Ala Gly Ser Leu
                180                 185                 190

Ser Ala Leu Leu Asp Pro Ser Gln Gly Met Gly Pro Ser Leu Ile Gly
            195                 200                 205

Leu Ala Met Gly Asp Ala Gly Gly Tyr Lys Ala Ala Asp Met Trp Gly
210                 215                 220

Pro Ser Ser Asp Pro Ala Trp Glu Arg Asn Asp Pro Thr Gln Gln Ile
225                 230                 235                 240

Pro Lys Leu Val Ala Asn Asn Thr Arg Leu Trp Val Tyr Cys Gly Asn
                245                 250                 255

Gly Thr Pro Asn Glu Leu Gly Gly Ala Asn Ile Pro Ala Glu Phe Leu
                260                 265                 270

Glu Asn Phe Val Arg Ser Ser Asn Leu Lys Phe Gln Asp Ala Tyr Asn
            275                 280                 285

Ala Ala Gly Gly His Asn Ala Val Phe Asn Phe Pro Pro Asn Gly Thr
290                 295                 300

His Ser Trp Glu Tyr Trp Gly Ala Gln Leu Asn Ala Met Lys Gly Asp
305                 310                 315                 320

Leu Gln Ser Ser Leu Gly Ala Gly Met Thr Glu Gln Trp Asn Phe
                325                 330                 335

Ala Gly Ile Glu Ala Ala Ser Ala Ile Gln Gly Asn Val Thr Ser
                340                 345                 350

Ile His Ser Leu Leu Asp Glu Gly Lys Gln Ser Leu Thr Lys Leu Ala
                355                 360                 365

Ala Ala Trp Gly Gly Ser Gly Ser Glu Ala Tyr Gln Gly Val Gln Gln
370                 375                 380

Lys Trp Asp Ala Thr Ala Thr Glu Leu Asn Asn Ala Leu Gln Asn Leu
385                 390                 395                 400

Ala Arg Thr Ile Ser Glu Ala Gly Gln Ala Met Ala Ser Thr Glu Gly
                405                 410                 415

Asn Val Thr Gly Met Phe Ala
                420

<210> SEQ ID NO 95
<211> LENGTH: 1020
<212> TYPE: DNA
<213> ORGANISM: Artificial Sequence
<220> FEATURE:
<223> OTHER INFORMATION: Description of Artificial Sequence:

Rv2626c-RpfD fusion protein with Ag85B signal sequence

<400> SEQUENCE: 95

```
atgacagacg t

| Ile | Ala | Arg | His | Leu | Pro | Glu | His | Ala | Ile | Val | Gln | Phe | Val | Lys | Ala |
| | | | | 165 | | | | 170 | | | | | 175 | | |

| Ile | Cys | Ser | Pro | Met | Ala | Leu | Ala | Ser | Met | Thr | Pro | Gly | Leu | Leu | Thr |
| | | | 180 | | | | | 185 | | | | | 190 | | |

| Thr | Ala | Gly | Ala | Gly | Arg | Pro | Arg | Asp | Arg | Cys | Ala | Arg | Ile | Val | Cys |
| | | | 195 | | | | | 200 | | | | | 205 | | |

| Thr | Val | Phe | Ile | Glu | Thr | Ala | Val | Val | Ala | Thr | Met | Phe | Val | Ala | Leu |
| | | 210 | | | | | 215 | | | | | 220 | | | |

| Leu | Gly | Leu | Ser | Thr | Ile | Ser | Ser | Lys | Ala | Asp | Asp | Ile | Asp | Trp | Asp |
| 225 | | | | | 230 | | | | | 235 | | | | | 240 |

| Ala | Ile | Ala | Gln | Cys | Glu | Ser | Gly | Gly | Asn | Trp | Ala | Ala | Asn | Thr | Gly |
| | | | | 245 | | | | 250 | | | | | 255 | | |

| Asn | Gly | Leu | Tyr | Gly | Gly | Leu | Gln | Ile | Ser | Gln | Ala | Thr | Trp | Asp | Ser |
| | | | 260 | | | | | 265 | | | | | 270 | | |

| Asn | Gly | Gly | Val | Gly | Ser | Pro | Ala | Ala | Ala | Ser | Pro | Gln | Gln | Gln | Ile |
| | | | 275 | | | | | 280 | | | | | 285 | | |

| Glu | Val | Ala | Asp | Asn | Ile | Met | Lys | Thr | Gln | Gly | Pro | Gly | Ala | Trp | Pro |
| | | | 290 | | | | | 295 | | | | | 300 | | |

| Lys | Cys | Ser | Ser | Cys | Ser | Gln | Gly | Asp | Ala | Pro | Leu | Gly | Ser | Leu | Thr |
| 305 | | | | | 310 | | | | | 315 | | | | | 320 |

| His | Ile | Leu | Thr | Phe | Leu | Ala | Ala | Glu | Thr | Gly | Gly | Cys | Ser | Gly | Ser |
| | | | | 325 | | | | 330 | | | | | 335 | | |

Arg Asp Asp

<210> SEQ ID NO 97
<211> LENGTH: 1029
<212> TYPE: DNA
<213> ORGANISM: Artificial Sequence
<220> FEATURE:
<223> OTHER INFORMATION: Description of Artificial Sequence:
      Rv2626c-RpfD fusion protein with 19 kDa lipoprotein signal
      sequence

<400> SEQUENCE: 97

```
atgaagcgtg gactgacggt cgcggtagcc ggagccgcca ttctggtcgc aggtctttcc      60
ggatgttcaa gcaacaagtc gactacagga agcggtgaga ccacgaccgc ggcaggtacc     120
acggcaagcc ccggcatgac caccgcacgc gacatcatga acgcaggtgt gacctgtgtt     180
ggcgaacacg agacgctaac cgctgccgct caatacatgc gtgagcacga catcggcgcg     240
ttgccgatct gcggggacga cgaccggctg cacggcatgc tcaccgaccg cgacattgtg     300
atcaaaggcc tggctgcggg cctagacccg aataccgcca cggctggcga gttggcccgg     360
gacagcatct actacgtcga tgcgaacgca agcatccagg agatgctcaa cgtcatggaa     420
gaacatcagg tccgccgtgt tccggtcatc tcagagcacc gcttggtcgg aatcgtcacc     480
gaagccgaca tcgcccgaca cctgcccgag cacgccattg tgcagttcgt caaggcaatc     540
tgctcgccca tggccctcgc cagcatgaca ccgggttttgc ttactactgc gggtgctggc     600
cgaccacgtg acaggtgcgc caggatcgta tgcacggtgt tcatcgaaac cgccgttgtc     660
gcgaccatgt ttgtcgcgtt gttgggtctg tccaccatca gctcgaaagc cgacgacatc     720
gattgggacg ccatcgcgca atgcgaatcc ggcggcaatt gggcggccaa caccggtaac     780
gggttatacg gtggtctgca gatcagccag gcgacgtggg attccaacgg tggtgtcggg     840
tcgccggcgg ccgcgagtcc ccagcaacag atcgaggtcg cagacaacat tatgaaaacc     900
caaggcccgg gtgcgtggcc gaaatgtagt tcttgtagtc agggagacgc accgctgggc     960
```

```
tcgctcaccc acatcctgac gttcctcgcg gccgagactg gaggttgttc ggggagcagg   1020
gacgattag                                                           1029
```

<210> SEQ ID NO 98
<211> LENGTH: 342
<212> TYPE: PRT
<213> ORGANISM: Artificial Sequence
<220> FEATURE:
<223> OTHER INFORMATION: Description of Artificial Sequence:
      Rv2626c-RpfD (19 kDa lipoprotein signal sequence)

<400> SEQUENCE: 98

```
Met Lys Arg Gly Leu Thr Val Ala Val Ala Gly Ala Ala Ile Leu Val
1               5                   10                  15

Ala Gly Leu Ser Gly Cys Ser Ser Asn Lys Ser Thr Thr Gly Ser Gly
                20                  25                  30

Glu Thr Thr Thr Ala Ala Gly Thr Thr Ala Ser Pro Gly Met Thr Thr
            35                  40                  45

Ala Arg Asp Ile Met Asn Ala Gly Val Thr Cys Val Gly Glu His Glu
        50                  55                  60

Thr Leu Thr Ala Ala Ala Gln Tyr Met Arg Glu His Asp Ile Gly Ala
65                  70                  75                  80

Leu Pro Ile Cys Gly Asp Asp Arg Leu His Gly Met Leu Thr Asp
                85                  90                  95

Arg Asp Ile Val Ile Lys Gly Leu Ala Ala Gly Leu Asp Pro Asn Thr
            100                 105                 110

Ala Thr Ala Gly Glu Leu Ala Arg Asp Ser Ile Tyr Tyr Val Asp Ala
        115                 120                 125

Asn Ala Ser Ile Gln Glu Met Leu Asn Val Met Glu Glu His Gln Val
    130                 135                 140

Arg Arg Val Pro Val Ile Ser Glu His Arg Leu Val Gly Ile Val Thr
145                 150                 155                 160

Glu Ala Asp Ile Ala Arg His Leu Pro Glu His Ala Ile Val Gln Phe
                165                 170                 175

Val Lys Ala Ile Cys Ser Pro Met Ala Leu Ala Ser Met Thr Pro Gly
            180                 185                 190

Leu Leu Thr Thr Ala Gly Ala Gly Arg Pro Arg Asp Arg Cys Ala Arg
        195                 200                 205

Ile Val Cys Thr Val Phe Ile Glu Thr Ala Val Val Ala Thr Met Phe
    210                 215                 220

Val Ala Leu Leu Gly Leu Ser Thr Ile Ser Ser Lys Ala Asp Asp Ile
225                 230                 235                 240

Asp Trp Asp Ala Ile Ala Gln Cys Glu Ser Gly Gly Asn Trp Ala Ala
                245                 250                 255

Asn Thr Gly Asn Gly Leu Tyr Gly Gly Leu Gln Ile Ser Gln Ala Thr
            260                 265                 270

Trp Asp Ser Asn Gly Gly Val Gly Ser Pro Ala Ala Ser Pro Gln
        275                 280                 285

Gln Gln Ile Glu Val Ala Asp Asn Ile Met Lys Thr Gln Gly Pro Gly
    290                 295                 300

Ala Trp Pro Lys Cys Ser Ser Cys Ser Gln Gly Asp Ala Pro Leu Gly
305                 310                 315                 320

Ser Leu Thr His Ile Leu Thr Phe Leu Ala Ala Glu Thr Gly Gly Cys
                325                 330                 335

Ser Gly Ser Arg Asp Asp
```

-continued

```
                340

<210> SEQ ID NO 99
<211> LENGTH: 1062
<212> TYPE: PRT
<213> ORGANISM: Artificial Sequence
<220> FEATURE:
<223> OTHER INFORMATION: Description of Artificial Sequence:
      Ag85B-ESAT6-Rv1733c-Rv2626c-RpfB  (E. coli optimized)

<400> SEQUENCE: 99

Met Phe Ser Arg Pro Gly Leu Pro Val Glu Tyr Leu Gln Val Pro Ser
1               5                   10                  15

Pro Ser Met Gly Arg Asp Ile Lys Val Gln Phe Gln Ser Gly Gly Asn
            20                  25                  30

Asn Ser Pro Ala Val Tyr Leu Leu Asp Gly Leu Arg Ala Gln Asp Asp
        35                  40                  45

Tyr Asn Gly Trp Asp Ile Asn Thr Pro Ala Phe Glu Trp Tyr Tyr Gln
    50                  55                  60

Ser Gly Leu Ser Ile Val Met Pro Val Gly Gly Gln Ser Ser Phe Tyr
65              70                  75                  80

Ser Asp Trp Tyr Ser Pro Ala Cys Gly Lys Ala Gly Cys Gln Thr Tyr
                85                  90                  95

Lys Trp Glu Thr Phe Leu Thr Ser Glu Leu Pro Gln Trp Leu Ser Ala
            100                 105                 110

Asn Arg Ala Val Lys Pro Thr Gly Ser Ala Ala Ile Gly Leu Ser Met
        115                 120                 125

Ala Gly Ser Ser Ala Met Ile Leu Ala Ala Tyr His Pro Gln Gln Phe
    130                 135                 140

Ile Tyr Ala Gly Ser Leu Ser Ala Leu Leu Asp Pro Ser Gln Gly Met
145             150                 155                 160

Gly Pro Ser Leu Ile Gly Leu Ala Met Gly Asp Ala Gly Gly Tyr Lys
                165                 170                 175

Ala Ala Asp Met Trp Gly Pro Ser Ser Asp Pro Ala Trp Glu Arg Asn
            180                 185                 190

Asp Pro Thr Gln Gln Ile Pro Lys Leu Val Ala Asn Asn Thr Arg Leu
        195                 200                 205

Trp Val Tyr Cys Gly Asn Gly Thr Pro Asn Glu Leu Gly Gly Ala Asn
    210                 215                 220

Ile Pro Ala Glu Phe Leu Glu Asn Phe Val Arg Ser Ser Asn Leu Lys
225             230                 235                 240

Phe Gln Asp Ala Tyr Asn Ala Ala Gly Gly His Asn Ala Val Phe Asn
                245                 250                 255

Phe Pro Pro Asn Gly Thr His Ser Trp Glu Tyr Trp Gly Ala Gln Leu
            260                 265                 270

Asn Ala Met Lys Gly Asp Leu Gln Ser Ser Leu Gly Ala Gly Gly Ser
        275                 280                 285

Met Thr Glu Gln Gln Trp Asn Phe Ala Gly Ile Glu Ala Ala Ala Ser
    290                 295                 300

Ala Ile Gln Gly Asn Val Thr Ser Ile His Ser Leu Leu Asp Glu Gly
305             310                 315                 320

Lys Gln Ser Leu Thr Lys Leu Ala Ala Ala Trp Gly Gly Ser Gly Ser
                325                 330                 335

Glu Ala Tyr Gln Gly Val Gln Gln Lys Trp Asp Ala Thr Ala Thr Glu
            340                 345                 350
```

```
Leu Asn Asn Ala Leu Gln Asn Leu Ala Arg Thr Ile Ser Glu Ala Gly
            355                 360                 365

Gln Ala Met Ala Ser Thr Glu Gly Asn Val Thr Gly Met Phe Ala Glu
        370                 375                 380

Phe Met Ile Ala Thr Thr Arg Asp Arg Glu Gly Ala Thr Met Ile Thr
385                 390                 395                 400

Phe Arg Leu Arg Leu Pro Cys Arg Thr Ile Leu Arg Val Phe Ser Arg
                405                 410                 415

Asn Pro Leu Val Arg Gly Thr Asp Arg Leu Glu Ala Pro Gly Val Gln
            420                 425                 430

Asp Ser Arg Ser His Val Tyr Ala His Gln Ala Gln Thr Arg His Pro
        435                 440                 445

Ala Thr Ala Thr Val Ile Asp His Glu Gly Val Ile Asp Ser Asn Thr
    450                 455                 460

Thr Ala Thr Ser Ala Pro Pro Arg Thr Lys Ile Thr Val Pro Ala Arg
465                 470                 475                 480

Trp Val Val Asn Gly Ile Glu Arg Ser Gly Glu Val Asn Ala Lys Pro
                485                 490                 495

Gly Thr Lys Ser Gly Asp Arg Val Gly Ile Trp Val Asp Ser Ala Gly
            500                 505                 510

Gln Leu Val Asp Glu Pro Ala Pro Ala Arg Ala Ile Ala Asp Ser
        515                 520                 525

Arg Arg Ala Ile Leu Ile Arg Val Arg Asn Ala Ser Trp Gln His Asp
    530                 535                 540

Ile Asp Ser Leu Phe Cys Thr Gln Arg Glu Leu Met Thr Thr Ala Arg
545                 550                 555                 560

Asp Ile Met Asn Ala Gly Val Thr Cys Val Gly Glu His Glu Thr Leu
                565                 570                 575

Thr Ala Ala Ala Gln Tyr Met Arg Glu His Asp Ile Gly Ala Leu Pro
            580                 585                 590

Ile Cys Gly Asp Asp Asp Arg Leu His Gly Met Leu Thr Asp Arg Asp
        595                 600                 605

Ile Val Ile Lys Gly Leu Ala Ala Gly Leu Asp Pro Asn Thr Ala Thr
    610                 615                 620

Ala Gly Glu Leu Ala Arg Asp Ser Ile Tyr Tyr Val Asp Ala Asn Ala
625                 630                 635                 640

Ser Ile Gln Glu Met Leu Asn Val Met Glu Glu His Gln Val Arg Arg
                645                 650                 655

Val Pro Val Ile Ser Glu His Arg Leu Val Gly Ile Val Thr Glu Ala
            660                 665                 670

Asp Ile Ala Arg His Leu Pro Glu His Ala Ile Val Gln Phe Val Lys
        675                 680                 685

Ala Ile Cys Ser Pro Met Ala Leu Ala Ser Lys Leu Met Leu Arg Leu
    690                 695                 700

Val Val Gly Ala Leu Leu Leu Val Leu Ala Phe Ala Gly Gly Tyr Ala
705                 710                 715                 720

Val Ala Ala Cys Lys Thr Val Thr Leu Thr Val Asp Gly Thr Ala Met
                725                 730                 735

Arg Val Thr Thr Met Lys Ser Arg Val Ile Asp Ile Val Glu Glu Asn
            740                 745                 750

Gly Phe Ser Val Asp Asp Arg Asp Leu Tyr Pro Ala Ala Gly Val
        755                 760                 765

Gln Val His Asp Ala Asp Thr Ile Val Leu Arg Arg Ser Arg Pro Leu
```

```
                  770              775                780
Gln Ile Ser Leu Asp Gly His Asp Ala Lys Gln Val Trp Thr Thr Ala
785                 790                 795                 800

Ser Thr Val Asp Glu Ala Leu Ala Gln Leu Ala Met Thr Asp Thr Ala
                    805                 810                 815

Pro Ala Ala Ala Ser Arg Ala Ser Arg Val Pro Leu Ser Gly Met Ala
                820                 825                 830

Leu Pro Val Val Ser Ala Lys Thr Val Gln Leu Asn Asp Gly Gly Leu
            835                 840                 845

Val Arg Thr Val His Leu Pro Ala Pro Asn Val Ala Gly Leu Leu Ser
850                 855                 860

Ala Ala Gly Val Pro Leu Leu Gln Ser Asp His Val Val Pro Ala Ala
865                 870                 875                 880

Thr Ala Pro Ile Val Glu Gly Met Gln Ile Gln Val Thr Arg Asn Arg
                885                 890                 895

Ile Lys Lys Val Thr Glu Arg Leu Pro Leu Pro Pro Asn Ala Arg Arg
                900                 905                 910

Val Glu Asp Pro Glu Met Asn Met Ser Arg Glu Val Val Glu Asp Pro
            915                 920                 925

Gly Val Pro Gly Thr Gln Asp Val Thr Phe Ala Val Ala Glu Val Asn
930                 935                 940

Gly Val Glu Thr Gly Arg Leu Pro Val Ala Asn Val Val Thr Pro
945                 950                 955                 960

Ala His Glu Ala Val Arg Val Gly Thr Lys Pro Gly Thr Glu Val
                965                 970                 975

Pro Pro Val Ile Asp Gly Ser Ile Trp Asp Ala Ile Ala Gly Cys Glu
                980                 985                 990

Ala Gly Gly Asn Trp Ala Ile Asn Thr Gly Asn Gly Tyr Tyr Gly Gly
                995                 1000                1005

Val Gln Phe Asp Gln Gly Thr Trp Glu Ala Asn Gly Gly Leu Arg Tyr
            1010                1015                1020

Ala Pro Arg Ala Asp Leu Ala Thr Arg Glu Glu Gln Ile Ala Val Ala
1025                1030                1035                1040

Glu Val Thr Arg Leu Arg Gln Gly Trp Gly Ala Trp Pro Val Cys Ala
                    1045                1050                1055

Ala Arg Ala Gly Ala Arg
            1060

<210> SEQ ID NO 100
<211> LENGTH: 1034
<212> TYPE: PRT
<213> ORGANISM: Artificial Sequence
<220> FEATURE:
<223> OTHER INFORMATION: Description of Artificial Sequence:
      Ag85B-ESAT6-Rv1733c-Rv2626c-RpfB (human optimized)

<400> SEQUENCE:

```
Ser Gly Leu Ser Ile Val Met Pro Val Gly Gln Ser Ser Phe Tyr
 65                  70                  75                  80

Ser Asp Trp Tyr Ser Pro Ala Cys Gly Lys Ala Gly Cys Gln Thr Tyr
                 85                  90                  95

Lys Trp Glu Thr Phe Leu Thr Ser Glu Leu Pro Gln Trp Leu Ser Ala
            100                 105                 110

Asn Arg Ala Val Lys Pro Thr Gly Ser Ala Ala Ile Gly Leu Ser Met
        115                 120                 125

Ala Gly Ser Ser Ala Met Ile Leu Ala Ala Tyr His Pro Gln Gln Phe
    130                 135                 140

Ile Tyr Ala Gly Ser Leu Ser Ala Leu Leu Asp Pro Ser Gln Gly Met
145                 150                 155                 160

Gly Pro Ser Leu Ile Gly Leu Ala Met Gly Asp Ala Gly Gly Tyr Lys
                165                 170                 175

Ala Ala Asp Met Trp Gly Pro Ser Ser Asp Pro Ala Trp Glu Arg Asn
            180                 185                 190

Asp Pro Thr Gln Gln Ile Pro Lys Leu Val Ala Asn Asn Thr Arg Leu
        195                 200                 205

Trp Val Tyr Cys Gly Asn Gly Thr Pro Asn Glu Leu Gly Gly Ala Asn
    210                 215                 220

Ile Pro Ala Glu Phe Leu Glu Asn Phe Val Arg Ser Ser Asn Leu Lys
225                 230                 235                 240

Phe Gln Asp Ala Tyr Asn Ala Ala Gly Gly His Asn Ala Val Phe Asn
                245                 250                 255

Phe Pro Pro Asn Gly Thr His Ser Trp Glu Tyr Trp Gly Ala Gln Leu
            260                 265                 270

Asn Ala Met Lys Gly Asp Leu Gln Ser Ser Leu Gly Ala Gly Pro Gly
        275                 280                 285

Thr Glu Gln Gln Trp Asn Phe Ala Gly Ile Glu Ala Ala Ser Ala
    290                 295                 300

Ile Gln Gly Asn Val Thr Ser Ile His Ser Leu Leu Asp Glu Gly Lys
305                 310                 315                 320

Gln Ser Leu Thr Lys Leu Ala Ala Ala Trp Gly Gly Ser Gly Ser Glu
                325                 330                 335

Ala Tyr Gln Gly Val Gln Gln Lys Trp Asp Ala Thr Ala Thr Glu Leu
            340                 345                 350

Asn Asn Ala Leu Gln Asn Leu Ala Arg Thr Ile Ser Glu Ala Gly Gln
        355                 360                 365

Ala Met Ala Ser Thr Glu Gly Asn Val Thr Gly Met Phe Ala Phe Glu
    370                 375                 380

Ile Ala Thr Thr Arg Asp Arg Glu Gly Ala Thr Met Ile Thr Phe Arg
385                 390                 395                 400

Leu Arg Leu Pro Cys Arg Thr Ile Leu Arg Val Phe Ser Arg Asn Pro
                405                 410                 415

Leu Val Arg Gly Thr Asp Arg Leu Glu Ala Val Gln Asp Ser Arg Ser
            420                 425                 430

His Val Tyr Ala His Gln Ala Gln Thr Arg His Pro Ala Thr Ala Thr
        435                 440                 445

Val Ile Asp His Glu Gly Val Ile Asp Ser Asn Thr Thr Ala Thr Ser
    450                 455                 460

Ala Pro Pro Arg Thr Lys Ile Thr Val Pro Ala Arg Trp Val Asn
465                 470                 475                 480

Gly Ile Glu Arg Ser Gly Glu Val Asn Ala Lys Pro Gly Thr Lys Ser
```

```
                485                 490                 495
Gly Asp Arg Val Gly Ile Trp Val Asp Ser Ala Gly Gln Leu Val Asp
            500                 505                 510
Glu Pro Ala Pro Ala Arg Ala Ile Ala Asp Arg Ala Ile Leu Ile
        515                 520                 525
Arg Val Arg Asn Ala Ser Trp Gln His Asp Ile Asp Ser Leu Phe Cys
530                 535                 540
Thr Gln Arg Arg Ser Thr Thr Ala Arg Asp Ile Met Asn Ala Gly Val
545                 550                 555                 560
Thr Cys Val Gly Glu His Glu Thr Leu Thr Ala Ala Gln Tyr Met
            565                 570                 575
Arg Glu His Asp Ile Gly Ala Leu Pro Ile Cys Gly Asp Asp Arg
            580                 585                 590
Leu His Gly Met Leu Thr Asp Arg Asp Ile Val Ile Lys Gly Leu Ala
        595                 600                 605
Ala Gly Leu Asp Pro Asn Thr Ala Thr Ala Gly Glu Leu Ala Arg Asp
        610                 615                 620
Ser Ile Tyr Tyr Val Asp Ala Asn Ala Ser Ile Gln Glu Met Leu Asn
625                 630                 635                 640
Val Met Glu Glu His Gln Val Arg Arg Val Pro Val Ile Ser Glu His
                645                 650                 655
Arg Leu Val Gly Ile Val Thr Glu Ala Asp Ile Ala Arg His Leu Pro
            660                 665                 670
Glu His Ala Ile Val Gln Phe Val Lys Ala Ile Cys Ser Pro Met Ala
        675                 680                 685
Leu Ala Ser Gly Ala Pro Ala Cys Lys Thr Val Thr Leu Thr Val Asp
690                 695                 700
Gly Thr Ala Met Arg Val Thr Thr Met Lys Ser Arg Val Ile Asp Ile
705                 710                 715                 720
Val Glu Glu Asn Gly Phe Ser Val Asp Asp Arg Asp Asp Leu Tyr Pro
                725                 730                 735
Ala Ala Gly Val Gln Val His Asp Ala Asp Thr Ile Val Leu Arg Arg
            740                 745                 750
Ser Arg Pro Leu Gln Ile Ser Leu Asp Gly His Asp Ala Lys Gln Val
        755                 760                 765
Trp Thr Thr Ala Ser Thr Val Asp Glu Ala Leu Ala Gln Leu Ala Met
        770                 775                 780
Thr Asp Thr Ala Pro Ala Ala Ser Arg Ala Ser Arg Val Pro Leu
785                 790                 795                 800
Ser Gly Met Ala Leu Pro Val Val Ser Ala Lys Thr Val Gln Leu Asn
            805                 810                 815
Asp Gly Gly Leu Val Arg Thr Val His Leu Pro Ala Pro Asn Val Ala
            820                 825                 830
Gly Leu Leu Ser Ala Ala Gly Val Pro Leu Leu Gln Ser Asp His Val
        835                 840                 845
Val Pro Ala Ala Thr Ala Pro Ile Val Glu Gly Met Gln Ile Gln Val
        850                 855                 860
Thr Arg Asn Arg Ile Lys Lys Val Thr Glu Arg Leu Pro Leu Pro Pro
865                 870                 875                 880
Asn Ala Arg Arg Val Glu Asp Pro Glu Met Asn Met Ser Arg Glu Val
                885                 890                 895
Val Glu Asp Pro Gly Val Pro Gly Thr Gln Asp Val Thr Phe Ala Val
            900                 905                 910
```

```
Ala Glu Val Asn Gly Val Glu Thr Gly Arg Leu Pro Val Ala Asn Val
        915                 920                 925

Val Val Thr Pro Ala His Glu Ala Val Val Arg Val Gly Thr Lys Pro
    930                 935                 940

Gly Thr Glu Val Pro Pro Val Ile Asp Gly Ser Ile Trp Asp Ala Ile
945                 950                 955                 960

Ala Gly Cys Glu Ala Gly Gly Asn Trp Ala Ile Asn Thr Gly Asn Gly
                965                 970                 975

Tyr Tyr Gly Gly Val Gln Phe Asp Gln Gly Thr Trp Glu Ala Asn Gly
                980                 985                 990

Gly Leu Arg Tyr Ala Pro Arg Ala Asp Leu Ala Thr Arg Glu Glu Gln
        995                 1000                1005

Ile Ala Val Ala Glu Val Thr Arg Leu Arg Gln Gly Trp Gly Ala Trp
    1010                1015                1020

Pro Val Cys Ala Ala Arg Ala Gly Ala Arg
1025                1030
```

TUBERCULOSIS COMPOSITIONS AND METHODS OF USING THE SAME

FIELD

The present disclosure is directed, in part, to fusion proteins comprising *Mycobacterium tuberculosis* (Mtb) antigens, nucleic acid molecules encoding the same, vectors comprising nucleic acid molecules, compositions comprising the same, and methods of eliciting an immune response against tuberculosis.

BACKGROUND

Tuberculosis (TB) is a global health problem resulting in 8 million new cases and 2 million deaths each year. The emergence of multi-drug and totally-drug resistant strains of TB only makes this problem more severe. The life cycle of Mtb has 3 stages. In the acute phase following initial infection the bacteria replicate in the host and virulence factors are expressed, leading to the generation of an immune response by the host. As the immune response begins to control the infection, the Mtb enters a latent, asymptomatic state in which the bacteria become non-replicating and are encased in granulomas. The bacterium can persist in this latent state in infected individuals for many years, making diagnosis and treatment of disease difficult. In some cases, the bacteria are reactivated and begin replicating again, leading back to the disease state. Reactivation can occur for numerous reasons, including immune suppression caused by diseases such as HIV, treatments such as chemotherapy, or the weakening of the immune system due to aging. An estimated 2 billion people are latently infected with Mtb worldwide, and reactivation of latent Mtb accounts for most new cases of active TB disease. Reactivation is associated with inflammation, necrosis and cavitation of the lung, a process that results in draining of the lesions into the bronchus. Aerosols generated when individuals with bronchial lesions cough causes dissemination of the Mtb organism to uninfected, susceptible persons, and the transmission cycle is thus maintained.

The only currently available vaccine against TB, *Mycobacterium bovis* (Bacille Calmette-Guérin) (BCG), was first introduced in 1921. BCG has been widely utilized and while studies show that for some purposes BCG is effective (e.g. against disseminated TB), it is known to be ineffective with respect to preventing the development, persistence and reactivation of latent TB. There is an ongoing need to develop improved, more effective vaccines against TB. In particular, there is a need to develop vaccines that provide protection against the development, maintenance and/or reactivation of latent tuberculosis infection. With the availability of the entire genomic sequence of Mtb, and the tools for bioinformatic and experimental analysis of Mtb antigens, many new potential Mtb vaccine candidates have been identified in recent years. These include antigens that are involved in acute infection, maintenance of latency, or reactivation of Mtb. There are a range of delivery strategies in clinical development that are comprised of combinations of these and other antigens that have been tested in animal models and are currently or will soon be in clinical trials.

While vaccines are often effective to immunize individuals prophylactically or therapeutically against pathogen infection or human diseases, there is a need for improved vaccines. There is also a need for compositions and methods that produce an enhanced immune response. Likewise, while some immunotherapeutics are useful to modulate immune response in a patient, there remains a need for improved immunotherapeutic compositions and methods.

SUMMARY

This disclosure describes an antigen cassette (and specified variants) that can be used to create tuberculosis vaccines comprising specified *Mycobacterium tuberculosis* (Mtb) antigens which are involved with 3 identified stages of disease: 1) infection or acute infection, 2) latency or the latent state, and 3) resuscitation or reactivation of active disease. The disclosure also describes the strategic combination of antigens which are incorporated into a variety of delivery platforms in such a way as to provide pathways to a matrix of matched combinations of antigen delivery to obtain an optimized immune response. The subject matter described herein can be used as a prophylactic or therapeutic TB vaccine. The initial selection of antigens for inclusion into a usable cassette was based on a number of parameters including, for example, a thorough review of the literature, expression data, responses by human T cells, inclusion of human immunogenic regions, mouse protection studies, and conservation in sequence across most strains of TB with full genome sequences. Specific antigens were then probed to be sure they were able to be expressed in a variety of systems (BCG, protein, viral vectors, nucleic acids), that they were immunogenic, and they could be made as fusions in proteins or other vectors to simplify downstream manufacturing concerns. All of the selected antigens were then shown to be immunogenic in mice, either when used alone, or in a variety of combinations, to arrive at the present application.

The constructs described herein have been integrated into a specified range of delivery platforms that include the following classes (but not exhaustive) of representative delivery platforms: 1) viral vector delivery systems, 2) recombinant BCG, 3) recombinant purified protein fusions, 4) DNA plasmid vector systems, and 5) RNA vector systems. These delivery platforms can be used either in a single platform alone or in combinations as matched antigen prime-boost approaches. In addition, the use of these antigens in a single rBCG vector system, which is envisioned to be used as an antigen matched prime for a boost with any of the modalities above, including protein, viral vectors, nucleic acids, or others.

The present disclosure provides fusion proteins that comprise at least three *Mycobacterium tuberculosis* (Mtb) antigens, wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides nucleic acid molecules encoding fusion proteins that comprise at least three *Mycobacterium tuberculosis* (Mtb) antigens, wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides: compositions comprising the fusion proteins and a pharmaceutically acceptable carrier; vectors encoding the fusion proteins; compositions comprising the vectors and a pharmaceutically acceptable carrier; cells comprising the vectors; compositions comprising the cells and a pharmaceutically acceptable carrier.

The present disclosure also provides compositions that comprise at least three *Mycobacterium tuberculosis* (Mtb) antigens, wherein the composition comprises: at least one acute Mtb antigen, at least one latent Mtb antigen, and at least one resuscitation Mtb antigen; or at least two latent Mtb antigens, and at least one resuscitation Mtb antigen.

The present disclosure also provides compositions that comprise at least three *Mycobacterium tuberculosis* (Mtb) antigens, wherein the composition comprises: at least one acute Mtb antigen, at least one latent Mtb antigen, and at least one resuscitation Mtb antigen; or at least two latent Mtb antigens, and at least one resuscitation Mtb antigen; wherein the composition comprises at least one nucleic acid molecule encoding at least one of the Mtb antigens.

The present disclosure also provides methods of eliciting an immune response against *Mycobacterium tuberculosis* in a mammal comprising administering to the mammal an immunologically sufficient amount of one or more fusion proteins comprising at least three *Mycobacterium tuberculosis* (Mtb) antigens, wherein at least one fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides methods of eliciting an immune response against *Mycobacterium tuberculosis* in a mammal comprising administering to the mammal an immunologically sufficient amount of a composition comprising at least three *Mycobacterium tuberculosis* (Mtb) antigens, wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides methods of eliciting an immune response against *Mycobacterium tuberculosis* in a mammal comprising administering to the mammal an immunologically sufficient amount of a composition comprising at least three *Mycobacterium tuberculosis* (Mtb) antigens, wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides fusion proteins for use in the preparation of a medicament for treating or preventing a *Mycobacterium tuberculosis* infection, wherein the fusion protein comprises at least three *Mycobacterium tuberculosis* (Mtb) antigens, and wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides fusion proteins for use in treating or preventing a *Mycobacterium tuberculosis* infection, wherein the fusion protein comprises at least three *Mycobacterium tuberculosis* (Mtb) antigens, and wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides uses of a fusion protein in the preparation of a medicament for treating or preventing a *Mycobacterium tuberculosis* infection, wherein the fusion protein comprises at least three *Mycobacterium tuberculosis* (Mtb) antigens, and wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides uses of a fusion protein in treating or preventing a *Mycobacterium tuberculosis* infection, wherein the fusion protein comprises at least three *Mycobacterium tuberculosis* (Mtb) antigens, and wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides compositions for use in the preparation of a medicament for treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides composition for use in treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides uses of a composition in the preparation of a medicament for treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides uses of a composition in treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides compositions for use in the preparation of a medicament for treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides compositions for use in treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides uses of a composition in the preparation of a medicament for treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides uses of a composition in treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides fusion proteins, compositions, cells, vectors, methods, and uses, as described herein, substantially as described with reference to the accompanying examples and/or figures.

DESCRIPTION OF EMBODIMENTS

Figure 1A:
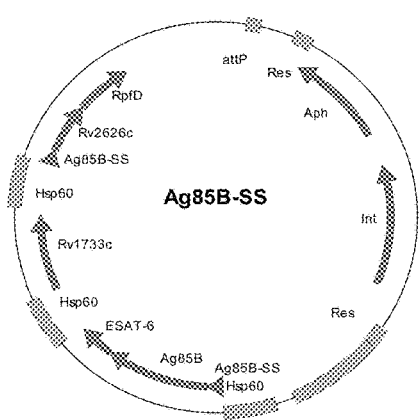
FIGS. 1A and 1B show maps of the plasmids used to insert the genes of interest into the chromosome of BCG SSI or other strains of BCG: (A) constructs with the Ag85B signal sequence for secretion of the fusions; and (B) constructs with the 19 kDa signal sequence to anchor the fusions into the membrane.
Figure 1B:
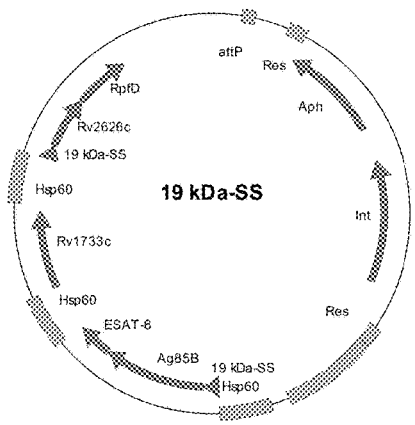
Figure 2:
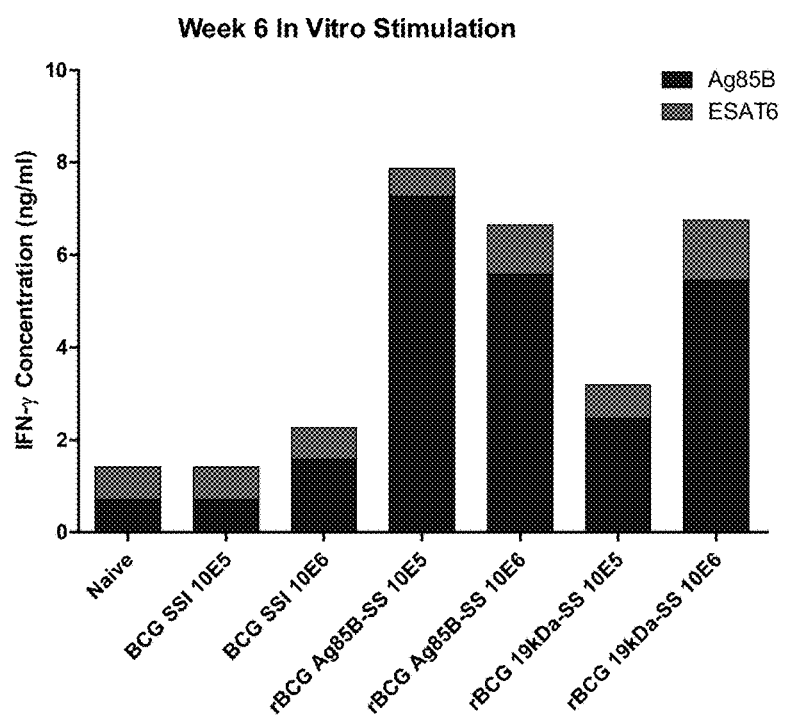
FIG. 2 shows in vitro antigen responsiveness after vaccination with BCG strains carrying antigen cassette.

The terminology used herein is for the purpose of describing particular embodiments only and is not intended to be limiting.

As used herein, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "acute Mtb antigen" means any Mtb antigen involved in the acute phase tuberculosis infection.

As used herein, "adjuvant" means any molecule added to any composition described herein to enhance the immunogenicity of the Mtb antigens.

As used herein, "coding sequence" or "encoding nucleic acid" means the nucleic acids (RNA or DNA molecule) that comprise a nucleotide sequence which encodes an Mtb antigen. The coding sequence can further include initiation and termination signals operably linked to regulatory elements including a promoter and polyadenylation signal capable of directing expression in the cells of an individual or mammal to which the nucleic acid is administered.

As used herein, "consensus" or "consensus sequence" means a polypeptide sequence based on analysis of an alignment of multiple subtypes of a particular Mtb antigen. Nucleic acid sequences that encode a consensus polypeptide sequence can be prepared. Vaccines comprising Mtb antigens that comprise consensus sequences and/or nucleic acid molecules that encode such antigens can be used to induce broad immunity against multiple subtypes or serotypes of a particular antigen.

As used herein, "electroporation" means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, "fragment" with respect to nucleic acid sequences, means a nucleic acid sequence or a portion thereof, that encodes a portion of an Mtb antigen capable of eliciting an immune response in a mammal that cross reacts with a full length wild type Mtb antigen. The fragments can be DNA fragments selected from at least one of the various nucleotide sequences that encode protein fragments set forth below.

As used herein, "fragment" or "immunogenic fragment" with respect to polypeptide sequences, means a portion of an MTB antigen capable of eliciting an immune response in a mammal that cross reacts with a full length wild type strain Mtb antigen. Fragments of consensus or wild type Mtb antigens can comprise at least 10%, at least 20%, at least 30%, at least 40%, at least 50%, at least 60%, at least 70%, at least 80%, at least 90% or at least 95% of a consensus or wild type Mtb antigen. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a consensus or wild type protein.

As used herein, "genetic construct" refers to the DNA or RNA molecules that comprise a nucleotide sequence which encodes an Mtb antigen. The coding sequence includes initiation and termination signals operably linked to regulatory elements including a promoter and polyadenylation signal capable of directing expression in the cells of the individual to whom the nucleic acid molecule is administered.

As used herein, "expressible form" refers to gene constructs that contain the necessary regulatory elements operable linked to a coding sequence that encodes an Mtb antigen such that when present in the cell of the individual, the coding sequence will be expressed.

As used herein, "homology" refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous" refers to a probe that can hybridize to a strand of the double-stranded nucleic acid sequence under conditions of low stringency. When used in reference to a single-stranded nucleic acid sequence, the term "substantially homologous" refers to a probe that can hybridize to (i.e., is the complement of) the single-stranded nucleic acid template sequence under conditions of low stringency.

As used herein, "identical" or "identity" in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) residues can be considered equivalent. Identity can be performed manually or by using a computer sequence algorithm such as BLAST or BLAST 2.0.

As used herein, "immune response" means the activation of a host's immune system, e.g., that of a mammal, in response to the introduction of an Mtb antigen. The immune response can be in the form of a cellular or humoral response, or both.

As used herein, "latent Mtb antigen" means any Mtb antigen involved in the latent phase tuberculosis infection.

As used herein, "Mtb antigen" means an antigen from *Mycobacterium tuberculosis*, which may be an isolated antigen, or an antigen that forms part of a fusion protein with other antigen(s).

As used herein, "nucleic acid" or "oligonucleotide" or "polynucleotide" means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

As used herein, "operably linked" means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

As used herein, "promoter" means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

As used herein, "resuscitation Mtb antigen" means any Mtb antigen involved in the resuscitation or reactivation of a tuberculosis infection.

As used herein, "signal peptide" and "leader sequence", used interchangeably, refer to an amino acid sequence that can be linked at the amino terminus of an Mtb antigenic protein set forth herein. Signal peptides/leader sequences typically direct localization of a protein. Signal peptides/leader sequences used herein can facilitate secretion of the protein from the cell in which it is produced or anchor it in the membrane. Signal peptides/leader sequences are often cleaved from the remainder of the protein, often referred to as the mature protein, upon secretion from the cell. Signal peptides/leader sequences are linked at the N terminus of the protein.

As used herein, "stringent hybridization conditions" means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5 to 10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01 to 1.0 M sodium ion concentration (or other salts) at pH 7.0 to 8.3 and the temperature is at least about 30° C. for short probes (e.g., about 10 to 50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

As used herein, "substantially complementary" means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used herein, "substantially identical" means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used herein, "variant" with respect to a nucleic acid means: i) a portion or fragment of a referenced nucleotide sequence; ii) the complement of a referenced nucleotide sequence or portion thereof; iii) a nucleic acid that is substantially identical to a referenced nucleic acid or the complement thereof; or iv) a nucleic acid that hybridizes under stringent conditions to the referenced nucleic acid, complement thereof, or a sequences substantially identical thereto.

As used herein, "variant" with respect to a peptide or polypeptide means that it differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change Amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "vector" means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector.

The present disclosure provides fusion proteins comprising at least three *Mycobacterium tuberculosis* (Mtb) antigens. In some embodiments, the fusion protein comprises at least one acute Mtb antigen, at least one latent Mtb antigen, and at least one resuscitation Mtb antigen. In some embodiments, the fusion protein comprises at least two latent Mtb antigens and at least one resuscitation Mtb antigen.

In some embodiments, the nucleic acid molecule encoding any particular Mtb antigen can be a mycobacterial sequence, a bacterial codon optimized sequence (such as an *E. coli* optimized sequence), or a mammalian optimized sequence (such as a human optimized sequence). The *E. coli* optimized sequences can be used, for example, to produce fusion proteins. The human optimized sequences can be used in, for example, viral vectors. Methods of codon optimization (whether for bacterial or mammalian) are well known to the skilled artisan.

In some embodiments, the acute Mtb antigen is Ag85B, ESAT6, MPT64, PPE15, PPE51, or Rv3615c. In some embodiments, the acute Mtb antigen is Ag85B, ESAT6, or Rv3615c. In some embodiments, the acute Mtb antigen is Ag85B or ESAT6. Additional acute Mtb antigens are well known to the skilled artisan.

The acute Mtb antigen Ag85B is also known as Rv1886c. A nucleotide sequence encoding Ag85B is shown in Table 1 as SEQ ID NO:1 (mycobacterial sequence; not codon optimized), SEQ ID NO:2 (*E. coli* optimized), and SEQ ID NO:3 (human optimized), and an amino acid sequence of Ag85B is shown in Table 1 as SEQ ID NO:4 (mycobacterial sequence) and SEQ ID NO:5 (*E. coli* and human optimized).

The acute Mtb antigen ESAT-6 is also known as Rv3875. A nucleotide sequence encoding ESAT-6 is shown in Table 1 as SEQ ID NO:6 (mycobacterial sequence; not codon optimized) and SEQ ID NO:7 (human optimized), and an amino acid sequence of ESAT-6 is shown in Table 1 as SEQ ID NO:8.

The acute Mtb antigen MPT64 is also known as Rv1980c. A nucleotide sequence encoding the acute Mtb antigen MPT64 is shown in Table 1 as SEQ ID NO:9 (mycobacterial sequence; not codon optimized) and as SEQ ID NO:10 (human optimized), and an amino acid sequence of MPT64 is shown in Table 1 as SEQ ID NO:11.

The acute Mtb antigen PPE15 is also known as Rv1039c. A nucleotide sequence encoding the acute Mtb antigen PPE15 is shown in Table 1 as SEQ ID NO:12 (mycobacterial sequence; not codon optimized) and as SEQ ID NO:13 (human optimized), and an amino acid sequence of PPE15 is shown in Table 1 as SEQ ID NO:14.

The acute Mtb antigen PPE51 is also known as Rv3136. A nucleotide sequence encoding the acute Mtb antigen PPE51 is shown in Table 1 as SEQ ID NO:15 (mycobacterial sequence; not codon optimized), SEQ ID NO:16 (*E. coli* optimized) and as SEQ ID NO:17 (human optimized), and an amino acid sequence of PPE51 is shown in Table 1 as SEQ ID NO:18.

A nucleotide sequence encoding the acute Mtb antigen Rv3615c is shown in Table 1 as SEQ ID NO:19 (mycobacterial sequence; not codon optimized) and as SEQ ID NO:20 (human optimized), and an amino acid sequence of Rv3615c is shown in Table 1 as SEQ ID NO:21.

TABLE 1

| Construct | nucleotide sequence<br>amino acid sequence |
|---|---|
| Ag85B | atgacagacgtgagccgaaagattcgagcttggggacgccgattgatgatcggcacggcagcggctgta<br>gtccttccgggcctggtggggcttgccgcggagcggcaaccgcgggcgcgttctcccggccggggctgc<br>cggtcgagtacctgcaggtgccgtcgccgtcgatgggccgcgacatcaaggttcagttccagagcggtg<br>ggaacaactcacctggggtttatctgctcgacggcctgcgcgcccaagacgactacaacggctgggata<br>tcaacacccggcgttcgagtggtactaccagtcggggactgtcgatagtcatgccggtcggcgggggcagt<br>ccagcttctacagcgactggtacagcccggcctgcggtaaggctggctgccagacttacaagtgggaaa<br>ccttcctgaccagcgagctgccgcaatggttgtccgccaacagggccgtgaagcccaccggcagcgctg<br>caatcggcttgtcgatggccggctcgtcggcaatgatcttggccgcctaccaccccagcagttcatct<br>acgccggctcgctgtcggccctgctggacccctctcaggggatggggcctagcctgatcggcctcgcga<br>tgggtgacgccggcggttacaaggccgcagacatgtggggtccctcgagtgacccggcatgggagcgca<br>acgaccctacgcagcagatccccaagctggtcgcaaacaacaccccggctatgggtttattggggaacg<br>gcaccccgaacgagttgggcggtgccaacataccccgccgagttcttggagaacttcgttcgtagcagca<br>acctgaagttccaggatgcgtacaacgccgcgggcgggcacaacgccgtgttcaacttccccgcccaacg<br>gcacgacagctggagtactgggcgctcagctcaacgccatgaaggggtgacctgcagagttcgttag<br>gcgccggctga (SEQ ID NO: 1)<br><br>atgtttagccgtcctggcctgccagttgaatacctgcaagttccgagcccgtccatgggtcgtgacatt<br>aaggtgcagttccagagcggcggtaacaatagcccggctgtgtacctgctggacggtctgcgtgcgcag<br>gatgattacaacggctgggacatcaatacccccggcatttgagtggtattaccagtcgggtctgagcatt<br>gtgatgccggttggcggtcaaagcagcttctatagcgattggtacagcccggcatgcggcaaggctggt<br>tgccaaacctacaagtgggaaactttatgaccagcgagctgccgcaatggttgagcgccaaccgtgcgg<br>tcaaaccgaccggtagcgctgctattggcctgtccatggccggcagcagcgcgatgatcttggcggcat<br>accatccgcagcagtttatctacgccggtagcctgagcgcattgctggacccgagccaaggcatggtc<br>cgagcctgattggtctggcaatgggtgacgcaggtggttacaaagcggccgatatgtggggcccatcta<br>gcgacccggcatgggagcgtaatgacccgacccagcaaattccgaaactggtggcgaataacacgcgcc<br>tgtgggtctactgtggcaatggtacgccgaacgagctgggtggcgcgaatatccctgcggagtttctgg<br>aaaactttgttcgcagcagcaacctgaaattccaggacgcgtataacgcagccggtggtcacaatgcgg<br>ttttcaatttccccgccaaatggcactcatagctgggagtactggggtgcgcagttgaacgcaatgaaag<br>gcgatctgcaatcctctctgggtgcgggc (SEQ ID NO: 2)<br><br>atgttctccaggcccgcctgcctgtcgagtatctgcaggtccccctccccctccatgggcagagacatc<br>aaggtgcagttccaatccggaggcaacaacagccccgccgtgtatctcctcgacggcctgagggctcag<br>gacgactacaacggctgggacatcaacacccccgccttcgagtggtactaccagtccggactgagcatc<br>gtcatgcccgtgggcggccagagctccttctacagcgactggtatagccctgcctgcggcaaagccgga<br>tgccagacctacaagtgggaaactttctgaccagcgaactgccccagtggctgtccgccaataggcga<br>gtcaaacctaccggctccgctgccatcggactcagcatggccggaagctccgctatgatcctggccgcc<br>taccaccccagcaatttatctacgctggcagcctgtccgctctgctggatcctagccaaggcatgggc<br>cctagcctcattggcctggccatgggcgatgctggcggctataaggccgccgatatgtggggcccctagc<br>tccgatcctgcctgggagaggaatgaccccaccccagcagatcccaaagctggtggccaacaacaaagg<br>ctctgggtgtactgggcaatggcaccccaacgaactgggcggagccaacattcccgccgagttcctg<br>gagaacttcgtcaggagcagcaacctgaagttccaggacgcctacaatgccgccggaggccacaacgct<br>gtgttcaacttccctcccaacggcacccacagctgggagtattgggcgctcagctgaacgccatgaaa<br>ggcgacctccagagctccctgggagctgga (SEQ ID NO: 3)<br><br>MTDVSRKIRAWGRRLMIGTAAAVVLPGLVGLAGGAATAGAFSRPGLPVEYLQVPSPSMGRDIKVQFQSG<br>GNNSPAVYLLDGLRAQDDYNGWDINTPAFEWYYQSGLSIVMPVGGQSSFYSDWYSPACGKAGCQTYKWE<br>TFLTSELPQWLSANRAVKPTGSAAIGLSMAGSSAMILAAYHPQQFIYAGSLSALLDPSQGMGPSLIGLA<br>MGDAGGYKAADMWGPSSDPAWERNDPTQQIPKLVANNTRLWVYCGNGTPNELGGANIPAEFLENFVRSS<br>NLKFQDAYNAAGGHNAVFNFPPNGTHSWEYWGAQLNAMKGDLQSSLGAG (SEQ ID NO: 4)<br><br>MFSRPGLPVEYLQVPSPSMGRDIKVQFQSGGNNSPAVYLLDGLRAQDDYNGWDINTPAFEWYYQSGLSI<br>VMPVGGQSSFYSDWYSPACGKAGCQTYKWETFLTSELPQWLSANRAVKPTGSAAIGLSMAGSSAMILAA<br>YHPQQFIYAGSLSALLDPSQGMGPSLIGLAMGDAGGYKAADMWGPSSDPAWERNDPTQQIPKLVANNTR<br>LWVYCGNGTPNELGGANIPAEFLENFVRSSNLKFQDAYNAAGGHNAVFNFPPNGTHSWEYWGAQLNAMK<br>GDLQSSLGAG (SEQ ID NO: 5) |
| ESAT6 | atgacagagcagcagtggaatttcgcgggtatcgaggccgcggcaagcgcaatccagggaaatgtcacg<br>tccattcattccctcctgacgaggggaagcagtccctgaccaagctcgcagcggcctggggcggtagc<br>ggttcggaggcgtaccagggtgtccagcaaaaatgggacgccacggctaccgagctgaacaacgcgctg<br>cagaacctggcgcggacgateagcgaagccggtcaggcaatggatcgaccgaaggcaacgtcactggga<br>tgttcgcatag (SEQ ID NO: 6)<br><br>accgagcagcagtggaacttcgccggcatcgaagctgccgctagcgccatccaaggcaacgtgaccagc<br>atccacagcctgctggacgagggcaagcagagcctgaccaagctgctgcttggggcggatccgga<br>agcgaagcctaccagggcgtgcagcagaagtgggacgccacagccaccgagctgaacaacgccctgcag<br>aacctcgccagaaccatcagcgaggccggacaggctatggccagcacagagggcaatgtgaccggcatg<br>ttcgcc (SEQ ID NO: 7)<br><br>TEQQWNFAGIEAAASAIQGNVTSIHSLLDEGKQSLTKLAAAWGSGSEAYQGVQQKWDATATELNNALQ<br>NLARTISEAGQAMASTEGNVTGMFA (SEQ ID NO: 8) |
| MPT64 | gtgcgcatcaagatctcatgctggtcacggctgtcgttttgctctgttgttcgggtgtggccacggcc<br>gcgcccaagaccactgcgaggagttgaaaggcaccgataccggccaggcgtgccagattcaaatgtcc<br>gacccggcctacaacatcaacatcagcctgcccagttactaccccgaccagaagtcgctggaaaattac<br>atcgcccagacgcgcgacaagttcctcagcgcggccacatcgtccactccacgcgaagcccctacgaa<br>ttgaatatcacctcggccacataccagtccgcgataccgccgcgtggtacgcaggccgtggtgctcaag<br>gtctaccagaacgccggcggcacgcacccaacgaccacgtacaaggccttcgattgggaccaggcctat |

TABLE 1-continued

| Construct | nucleotide sequence<br>amino acid sequence |
|---|---|
| | cgcaagccaatcacctatgacacgctgtggcaggctgacaccgatccgctgccagtcgtcttcccatt<br>gtgcaaggtgaactgagcaagcagaccggacaacaggtatcgatagcgccgaatgccggcttggacccg<br>gtgaattatcagaacttcgcagtcacgaacgacggggtgattttatcttcaacccgggggagttgctgc<br>ccgaagcagccggcccaacccaggtattggtcccacgttccgcgatcgactcgatgctggcctag<br>(SEQ ID NO: 9) |
| | atggtcaggatcaagatcttcatgctcgtgaccgccgtggtgctcctgtgttgttccggcgtggctacc<br>gctgctcccaagacctactgcgaggagctgaagggaaccgacaccggccaggcctgccagatccaaatg<br>agcgaccccgcctacaacatcaacatctcccteccctcctactaccccgateagaagtccctcgagaac<br>tacatcgctcagaccagggacaagttctgagcgccgccaagcagcacaccagagagccccctac<br>gagctgaacatcacctccgccacctaccagtccgctattctcccagaggcacccaggctgtggtgctc<br>aaggtctaccaaaacgctggcggaacacaccccaccaccacctacaaggccttcgactgggaccaggcc<br>tacaggaagccatcacatacgacaccctgtggcaggctgataccgatccctgcccgtggtgttcccc<br>atcgtgcaggcgagctctccaagcagaccggccagcaagtgagcatcgcccccaatgctggactggac<br>cccgtgaactaccagaacttcgccgtcaccaacgacggcgtgatcttcttcttcaatccggcgaactg<br>ctgcctgaagctgctggccccacccaagtgctggtgcctagaagcgccatcgactccatgctggcctga<br>(SEQ ID NO: 10) |
| | VRIKIFMLVTAVVLLCCSGVATAAPKTYCEELKGTDTGQACQIQMSDPAYNINISLPSYYPDQKSLENY<br>IAQTRDKFLSAATSSTPREAPYELNITSATYQSAIPPRGTQAVVLKVYQNAGGTHPTTTYKAFDWDQAY<br>RKPITYDTLWQADTDPLPVVFPIVQGELSKQTGQQVSIAPNAGLDPVNYQNFAVTNDGVIFFFNPGELL<br>PEAAGPTQVLVPRSAIDSMLA (SEQ ID NO: 11) |
| PPE15 | atggatttcggagattaccccctgagatcaactccgcacgcatgtacgccggcgcgggtgcaggaccga<br>tgatggccgccggggccgcatggaacggcctggccgccgagttgggtacgacggccgcgtcgtatgagt<br>cggtgatcaccggctgaccaccgagtcgtggatgggtccggcctcgatggcgatggtcgccgcagccc<br>agccctatctggcttggttgacctacaccgccgaagccgctgctcacgccggaagccatggcgt<br>cggcggccgcctacgaggcggcctatgcgatgacagtgccgccggaggtggtcgcggccaaccgggcgt<br>tgctggcggccctggtcgcgacgaacgtcctgggggatcaacacaccggcaatcatggcgaccgaagccc<br>tctatgccgagatgtgggctcaggacgctctggctatgtacggctacgcggccgcttcgggagccgccg<br>ggatgctgcaaccgttaagcccgccgtcgcagaccaccaaccccgggcgggctggccgccagtccgccg<br>cggtcggctcggctgccgccaccgccgccgtcaaccaggtgagcgtagcgacctgatcagtagcctgc<br>ccaacgcggtgagtgggctcgcctcccagtcacatcggttctcgactcgacggggctgagcggaatca<br>ttgccgacatcgacgccctgctcgcgaccccgttcgtggcaaacatcatcaacagcgcagtcaacaccg<br>ccgcttggtatgtcaacgccgccatccccaccgcgatattcctagcaaatgcctgaacagtggggcgc<br>cggtagcgatcgccgaaggcgccatcgaggctgccgaggtgccgccagtgcggccgccgcggggttgg<br>cggactcggtgacgccagcggggctcggcgcaagtttaggcgaggcaccctggtcggccggctgtcag<br>tgccggcggcctggtctacggccgcaccggcgacaaccgccggcgccacagcgctcgaaggcagcggct<br>ggaccgtcgccgccgaagaagccggccagttaccgggatgatgccgggaatggcctcggccgccaagg<br>gcaccggtgcctatgccgggccgcggtacggattcaagcccactgtcatgcccaaacaggtcgtcgtgt<br>ga (SEQ ID NO: 12) |
| | atggattttggcgccctgcctcccgagatcaacagcgctaggatgtatgctggcgctggagccggacct<br>atgatggccgctggagccgcctggaatggactggctgccgaactgggcacaacagccgcttcctacgag<br>tccgtgatcaccagactcaccacagagtcctggatgggacctgccagcatggctatggtcgccgctgct<br>caaccctacctggcctggctgacctatacagctgaagccgctgctcacgccggaagccaagctatggct<br>agcgccgccgcttatgaggccgcttatgccatgaccgtgcctccgaggtcgtggctgccaacagagct<br>ctcctggccgcctcgtggctaccaacgtgctgggaatcaacaccccgctattatggccaccgaggct<br>ctgtacgctgagatgtgggcccaggatgccctcgccatgtacggatacgccgctgcttccggagctgct<br>ggaatgctgcagcccctgtcccccccttccagaccaccaaccccggaggactggctgctcaaagcgct<br>gctgtgggatccgctgctgctaccgctgccgtcaatcaggtcagcgtcgccgacctcatctccagcctg<br>cctaacgctgtgagcggactggcctccctgtccacatccgtgctcgatagcaccggcctgtccggcatc<br>atcgccgacattgatgctctcctcgccaccccctttgtcgccaacatcatcaattccgccgtgaacacc<br>gctgcctggtacgtcaacgctgccattcccaccgccatcttcctcgccaacgccctgaactccggagct<br>ectgtcgccatcgctgagggcgctattgaggctgctgaaggagccgctagcgctgctgctgctggactg<br>gctgatagcgtcaccccctgctggactcggagctagcctgggagaagcaccctggtcggcaggctgtcc<br>gtgcctgctgcttggagcaccgctgctcctgctacaaccgctggagctaccgctctggagggatccgga<br>tggacagtggctgctgaggaagctggaccgtgaccggaatgatgcctggcatggccagcgctgctaag<br>ggaaccggcgcctatgccgacccagatacggattcaagcccaccgtcatgcccaagcaggtcgtcgtc<br>taa (SEQ ID NO: 13) |
| | MDFGALPPEINSARMYAGAGAGPMMAAGAAWNGLAAELGTTAASYESVITRLTTESWMGPASMAMVAAA<br>QPYLAWLTYTAEAAAHAGSQAMASAAAYEAAYAMTVPPEVVAANRALLAALVATNVLGINTPAIMATEA<br>LYAEMWAQDALAMYGYAAASGAAGMLQPLSPPSQTTNPGGLAAQSAAVGSAAATAAVNQVSVADLISSL<br>PNAVSGLASPVTSVLDSTGLSGIIADIDALLATPFVANIINSAVNTAAWYVNAAIPTAIFLANALNSGA<br>PVAIAEGAIEAAEGAASAAAAGLADSVTPAGLGASLGEATLVGRLSVPAAWSTAAPATTAGATALEGSG<br>WTVAAEEAGPVTGMMPGMASAAKGTGAYAGPRYGFKPTVMPKQVVV (SEQ ID NO: 14) |
| PPE51 | atggatttcgcactgttaccaccggaagtcaactccgcccggatgtacaccggccctggggcaggatcg<br>ctgttggctgccgcgggcggctgggattcgctggccgccgagttggccaccacagccgaggcatatgga<br>tcggtgctgtccggactggccgccttgcattggcgtggaccggcagcggaatcgatggcggtgacggcc<br>gctccctatatcggttggctgtacacgaccgccgaaaagacacagcaaacagcgatccaagccagggcg<br>gcagcgctggccttcgagaagcatacgcaatgaccctgccgccaccggtggtagcgccaaccggata<br>cagctgctagcactgatcgcgacgaacttatcggccagaacactgggcgatcgcggccaccgaggcac<br>agtacgccgagatgtgggcccaggacgccgccgcgatgtacggttacgccaccgcctcagcggctgcgg<br>ccctgctgacaccgttctccccgccgcggcagaccaccaacccgccggcctgaccgctcaggccgcg<br>cggtcagccaggccaccgacccactgtcgctgctgattgagacggtgacccaagcgctgcaagcgctga |

TABLE 1-continued

| Construct | nucleotide sequence<br>amino acid sequence |
|---|---|
| | cgattccgagatcatccctgaggacttcaccttccttgacgccatattcgctggatatgccacggtagg<br>tgtgacgcaggatgtcgagtectttgttgccgggaccatcggggccgagagcaacctaggcctttgaa<br>cgtcggcgacgagaatcccggaggtgacaccgggcgactttgggatcggcgagttggtttccgcgac<br>cagtccggcggtgggtgtctgcgtcgggtgccggcggtgcggcgagcgtcggcaacacggtgctcgc<br>gagtgtcggccgggcaaactcgattgggcaactatcggtcccaccgagctgggccgcgccctcgacgcg<br>ccctgtctcggcattgtcgcccgccggcctgaccacactcccggggaccgacgtggccgagcacgggat<br>gccaggtgtaccggggtgccagtggcagcagggcgagcctccggcgtcctacctcgatacggggtteg<br>gctcacggtgatggcccacccacccgcggcagggtaa (SEQ ID NO: 15) |
| | atggattttgcgctgctgccgccggaagtgaacagcgcgcgcatgtataccggcccgggcgcgggcagc<br>ctgctggcggcggcgggcggctgggatagcctggcggcggaactggcgaccaccgcggaagcgtatggc<br>agcgtgctgagcggcctggcggcgctgcattggcgcggcccggcggcggaaagcatggcggtgaccgcg<br>gcgccgtatattggctggctgtataccaccgcggaaaaaaccccagcagaccgcgattcaggcgcgcg<br>gcggcgctggcgtttgaacaggcgtatgcgatgaccctgccgccgccggtggtggcggcgaaccgcatt<br>cagctgctggcgctgattgcgaccaacttttttggccagaacaccgcggcgattgcggcgaccgaagcg<br>cagtatgcggaaatgtgggcgcaggatgcggcggcgatgtatggctatgcgaccgcgagcgcggccggcg<br>gcgctgctgaccccgtttagcccgccgcgccagaccaccaacccggcgggcctgaccgcgcaggcggcg<br>gcggtgagcccaggcgaccgatccgctgagcctgctgattgaaaccgtgacccaggcgctgcaggcgctg<br>accattccgagctttattccgaagattttacctttctggatgcgattttttgcgggctatgcgaccgtg<br>ggcgtgacccaggatgtggaaagattgtggcgggcaccattggcgcggaaagcaacctgggcctgctga<br>acgtgggcgatgaaacccggcggaagtgaccccgggcgattttggcattggcgaactggtgagcgcga<br>ccagcccgggcggcggcgtgagcgcgagcggcgcggcgggcgcggcggcgagtggggcaacaccgtgctgg<br>cgagcgtgggccgcgcgaacagcattggccagctgagcgtgccgccgagctgggcggcgccgagcaccc<br>gcccggtgagcgcgctgagcccggcgggcctgaccaccctgccgggcaccgatgtggcggaacatggca<br>tgccgggcgtgccgggcgtgccggtggcggcgggccgcgcgagcggcgtgctgccgcgctatggcgtgc<br>gcctgaccgtgatggcgcatccgccggcggcgggcgaattt (SEQ ID NO: 16) |
| | atggatttcgctctgctcccccccgaggtgaatagcgctaggatgtacacaggacccggagctggaagc<br>ctcctggctgctgctggaggatgggactccctggctgccgagctcgctacaaccgctgaggcttacgga<br>agcgtgctctccggcctggctgctctccattggagaggccctgctgccgagtccatggctgtcacagcc<br>gctccctacattggatggctgtacaccaccgccgagaagacccagcaaacgctattcaggccagagct<br>gccgccctggccttcgaacaggcctacgctatgacactcccccccccgtcgtggctgccaataggatc<br>cagctcctggccctcatcgccaccaacttcttcggccaaaacaccgctgccatcgctgccaccgaagcc<br>cagtacgccgaaatgtgggcccaggatgccgctgctatgtacggctatgccacagctagcgctgccgct<br>gctctgctcacacccttcagcccccccaggcaaacaaccaaccgctgccgactgacagcccaagctgct<br>gccgtcagccaagctaccgaccccctgagcctcctgatcgaaaccgtgacacaggccctgcaggccctg<br>accattcccagattatccccgaggacttcacctttctggacgctatcttcgctggctacgccaccgtgg<br>gcgtgacacaagacgtcgagtecttcgtcgccggcacaatcggagccgagtccaacctggactcctca<br>acgtcggcgacgaaaatcccgccgaagtgacacctggagacttcggcattggagaactcgtcagcgcca<br>catccctggcggaggagtgagcgcttccggagctggaggagctgcttccgtgggcaataccgtgctgg<br>ccagcgtgggaagggccaactccattggccagctcagcgtcccccttcctgggctgccccttccacaa<br>ggcctgtgtccgctctcagccctgctggactgaccacactccctggcacagacgtggctgagcatggca<br>tgcccggagtgcctggagtccctgtggctgctggcagagcttccggagtcctccctaggtatggcgtga<br>ggctgacagtgatggctcatccccccgctgccggataa (SEQ ID NO: 17) |
| | MDFALLPPEVNSARMYTGPGAGSLLAAAGGWDSLAAELATTAEAYGSVLSGLAALHWRGPAAESMAVTA<br>APYIGWLYTTAEKTQQTAIQARAAALAFEQAYAMTLPPPVVAANRIQLLALIATNFFGQNTAAIAATEA<br>QYAEMWAQDAAAMYGYATASAAAALLTPFSPPRQTTNPAGLTAQAAAVSQATDPLSLLIETVTQALQAL<br>TIPSFIPEDFTFLDAIFAGYATVGVTQDVESFVAGTIGAESNLGLLNVGDENPAEVTPGDFGIGELVSA<br>TSPGGGVSASGAGGAASVGNTVLASVGRANSIGQLSVPPSWAAPSTRPVSALSPAGLTTLPGTDVAEHG<br>MPGVPGVPVAAGRASGVLPRYGVRLTVMAHPPAAG (SEQ ID NO: 18) |
| Rv3615c | atgacggaaaacttgaccgtccagcccgagegtctcggtgtactggcgtcgcaccatgacaacgcggcg<br>gtcgatgcctcctcgggcgtcgaagctgccgctggcctaggcgaatctgtggcgateactcacggtccg<br>tactgctcacagttcaacgacacgttaaatgtgtacttgactgcccacaatgccctgggctcgtccttg<br>catacggccggtgtcgatctcgccaaaagtatcgaattgcggcgaagatatatagcgaggccgacgaag<br>cgtggcgcaaggctatcgacgggttgtttacctga (SEQ ID NO: 19) |
| | atgaccgagaacctgaccgtgcagcctgagaggctgggagtgctggccagccaccacgacaacgctgcc<br>gtggacgcttccageggagtggaggctgctgctggactgggagagcgtggccatcacccacggaccc<br>tactgcagccagttcaacgacaccctgaacgtgtacctgacagcccacaacgccctgggaagcagcctg<br>catacagccggcgtggacctggctaagtccctgaggatcgccgccaagatctacagcgaggccgacgag<br>gcctggaggaaagccatcgacggcctgttcacctaa (SEQ ID NO: 20) |
| | MTENLTVQPERLGVLASHHDNAAVDASSGVEAAAGLGESVAITHGPYCSQFNDTLNVYLTAHNALGSSL<br>HTAGVDLAKSLRIAAKIYSEADEAWRKAIDGLFT (SEQ ID NO: 21) |

In some embodiments, the latent Mtb antigen is Rv1733c, Rv2626c, Rv3407, or Rv2628c. In some embodiments, the latent Mtb antigen is Rv1733c or Rv2626c. Additional latent Mtb antigens are well known to the skilled artisan.

A nucleotide sequence encoding the wild type latent Mtb antigen Rv1733c is shown in Table 2 as SEQ ID NO:22 (mycobacterial sequence; not codon optimized), SEQ ID NO:23 (*E. coli* optimized), and an amino acid sequence of wild type Rv1733c is shown in Table 2 as SEQ ID NO:24. These sequences include two transmembrane regions of Rv1733c. A nucleotide sequence encoding Rv1733c, whereby both transmembrane regions are deleted is shown in Table 2 as SEQ ID NO:25 (*E. coli* optimized) and SEQ ID NO:26 (human optimized), and corresponding amino acid sequences are shown in Table 2 as SEQ ID NO:27 (*E. coli* optimized) and SEQ ID NO:28 (human optimized) (Rv1733c$_{ATM}$). In some embodiments, only a portion of the first and/or second or both transmembrane regions are deleted. In the *E. coli* optimized nucleotide sequence (SEQ ID NO:23), an XmaI restriction site was added, corresponding to an addition of amino acids PG; and an XbaI restriction site was added, corresponding to an addition of amino acids SR (see underlined and bolded added sequences).

A nucleotide sequence encoding the latent Mtb antigen Rv2626c is shown in Table 2 as SEQ ID NO:29 (mycobacterial sequence; not codon optimized), SEQ ID NO:30 (*E. coli* optimized), and SEQ ID NO:31 (human optimized), and an amino acid sequence of Rv2626c is shown in Table 2 as SEQ ID NO:32.

A nucleotide sequence encoding the latent Mtb antigen Rv3407 is shown in Table 2 as SEQ ID NO:33 (mycobacterial sequence; not codon optimized), SEQ ID NO:34 (*E. coli* optimized), and SEQ ID NO:35 (human optimized), and an amino acid sequence of Rv3407 is shown in Table 2 as SEQ ID NO:36.

A nucleotide sequence encoding the latent Mtb antigen Rv2628c is shown in Table 2 as SEQ ID NO:37 (mycobacterial sequence; not codon optimized) and as SEQ ID NO:38 (human optimized), and an amino acid sequence of Rv2628c is shown in Table 2 as SEQ ID NO:39.

TABLE 2

| Construct | nucleotide sequence<br>amino acid sequence |
|---|---|
| Rv1733c | atgatcgccacaacccgcgatcgtgaaggagccaccatgatcacgtttaggctgcgcttgccgtgccggac<br>gatactgcgggtgttcagccgcaatccgctggtgcgtgggacggatcgactcgaggcggtcgtcatgctgc<br>tggccgtcacggtctcgctgctgactatcccgttcgccgccgcggccggcaccgcagtccaggattcccgc<br>agccacgtctatgcccaccaggcccagacccgccatcccgcaaccgcgaccgtgatcgatcacgagggg<br>gtgatcgacagcaacacgaccgccacgtcagcgccgccgcgcacgaagatcaccgtgcctgcccgatgg<br>gtcgtgaacggaatagaacgcagcggtgaggtcaacgcgaagccgggaaccaaatccggtgaccgcgtc<br>ggcatttgggtcgacagtgccggtcagaggtcgatgaaccagaccgccggcccgtgccattgcggatgc<br>ggccctggccgccttgggactctggttgagcgtcgccgcggttgcgggcgccctgctggcgctcactcgg<br>gcgattctgatccgcgttcgcaacgccagttggcaacacgacatcgacagcctgttctgcacgcagcggtg<br>a (SEQ ID NO: 22)<br>atgattgcgactacccgtgatcgtgagggcgcgaccatgatcacgttccgtctgcgtctgccgtgtcgcacc<br>attttgcgcgtgttttcgcgtaacccgctggtccgcggtaccgaccgtctggaggccgttgtcatgctgctgg<br>cggttaccgtgagcctgctgacgatcccattcgcagcggcagaggcacggccgtccaagacagccgtag<br>ccatgtgtatgctcaccaggctcaaacccgtcacccggctactgccactgttatcgatcacgaaggcgtgatt<br>gactccaataccacggcaacctccgcaccgcctcgcaccaagattacggttcctgcgcgttgggtggtgaat<br>ggtattgaacgcagcggcgaagttaatgccaaaccgggtaccaaaagcggtgaccgtgtgggcatctggg<br>tcgatagcgccggtcagaggtcgacgagccggcaccgccagcgcgtgcgatcgccgatgcggcgctgg<br>ctgccctgggtctgtggctgagcgtggcagcggtcgccggtgcgttgctggcgctgacgcgcgcaattctg<br>atccgcgttcgcaatgcgagctggcagcacgatattgatagcctgttttgcacccaacgt (SEQ ID NO: 23)<br>MIATTRDREGATMITFRLRLPCRTILRVFSRNPLVRGTDRLEAVVML<br>LAVTVSLLTIPFAAAAGTAVQDSRSHVYAHQAQTRHPATATVIDHE<br>GVIDSNTTATSAPPRTKITVPARWVVNGIERSGEVNAKPGTKSGDRV<br>GIWVDSAGQLVDEPAPPARAIADAALAALGLWLSVAAVAGALLAL<br>TRAILIRVRNASWQHDIDSLFCTQR (SEQ ID NO: 24) |
| Rv1733c$_{\Delta TM}$ | atgattgcgactacccgtgatcgtgagggcgcgaccatgatcacgttccgtctgcgtctgccgtgtcgcacc<br>attttgcgcgtgttttcgcgtaacccgctggtccgcggtaccgaccgtctggaggcccccggggtccaagac<br>agccgtagccatgtgtatgctcaccaggctcaaacccgtcacccggctactgccactgttatcgatcacgaa<br>ggcgtgattgactccaataccacggcaacctccgcaccgcctcgcaccaagattacggttcctgcgcgttgg<br>gtggtgaatggtattgaacgcagcggcgaagttaatgccaaaccgggtaccaaaagcggtgaccgtgtgg<br>gcatctgggtcgatagcgccggtcagctggtcgacgagccggcaccgccagcgcgtgcgatcgccgatt<br>ctagacgcgcaattctgatccgcgttcgcaatgcgagctggcagcacgatattgatagcctgttttgcaccca<br>acgt (SEQ ID NO: 25)<br>atcgccaccaccagggacagggaaggcgctaccatgatcaccttcaggctgaggctcccctgcaggacca<br>tcctgagggtgttcagcaggaacccccctggtgaggggcaccgacagactggaagccgtgcaggacagca<br>ggagccacgtgtatgcccaccaggctcagaccaggcaccctgctaccgccaccgtgatcgaccacgagg<br>gcgtgatcgactccaacaccaccgccaccagcgctcctcccagaaccaagatcacagtgcccgccaggtg<br>ggtggtgaacggcatcgagaggagcggcgaggtgaacgccaagcctggaaccaagagcggcgacagg<br>gtgggcatttgggtcgatagcgccggccagctggtggatgaacctgctccccctgccagagccatcgccg<br>atagggccatcctgatcagggtgaggaacgccagctggcagcacgacatcgacagcctgttctgcaccca<br>aagg (SEQ ID NO: 26)<br>MIATTRDREGATMITFRLRLPCRTILRVFSRNPLVRGTDRLEAPGVQ<br>DSRSHVYAHQAQTRHPATATVIDHEGVIDSNTTATSAPPRTKITVPA<br>RWVVNGIERSGEVNAKPGTKSGDRVGIWVDSAGQLVDEPAPPARAI<br>ADSRRAILIRVRNASWQHDIDSLFCTQR (SEQ ID NO: 27)<br>IATTRDREGATMITFRLRLPCRTILRVFSRNPLVRGTDRLEAVQDSRS<br>HVYAHQAQTRHPATATVIDHEGVIDSNTTATSAPPRTKITVPARWV<br>VNGIERSGEVNAKPGTKSGDRVGIWVDSAGQLVDEPAPPARAIADR<br>AILIRVRNASWQHDIDSLFCTQR (SEQ ID NO: 28) |
| Rv2626c | atgaccaccgcacgcgacatcatgaacgcaggtgtgacctgtgttggcgaacacgagacgctaaccgctg<br>ccgctcaatacatgcgtgagcacgacatcggcgcgttgccgatctgcggggacgacgaccggctgcacg<br>gcatgctcaccgaccgcgacattgtgatcaaaggcctggctgcgggcctagacccgaataccgccacggc<br>tggcgagttggcccgggacagcatctactacgtcgatgcgaacgcaagcatccaggagatgctcaacgtc<br>atggaagaacatcaggtccgccgtgttccggtcatctcagagcaccgcttggtcggaatcgtcaccgaagc<br>cgacatcgcccgacacctgcccgagcacgccattgtgcagttcgtcaaggcaatctgctcgcccatggccc<br>tcgccagctag (SEQ ID NO: 29)<br>atgaccacggcgcgtgatatcatgaatgcgggtgtcacctgtgttggcgagcacgaaacgttgaccgcagc |

TABLE 2-continued

| Construct | nucleotide sequence<br>amino acid sequence |
|---|---|
| | agcacagtacatgcgcgaacatgatatcggcgcattgccgatttgcggcgacgatgatcgtctgcacggtat<br>gctgaccgaccgcgatatcgttatcaagggtctggccgcaggcttggacccgaacaccgcgaccgccggt<br>gaactggcacgtgacagcatctattacgtcgacgcgaacgccagcattcaagagatgctgaacgtgatgga<br>agagcatcaggtgcgtcgtgtcccggttatcagcgaacatcgtctggttggtatcgttaccgaagccgacatc<br>gcacgtcacctgccggagcacgcgattgttcagttcgtgaaagcgatttgcagcccgatggcgttggcgtc<br>(SEQ ID NO: 30)<br>acaacagccagggacatcatgaacgccggcgtgacctgcgtgggagagcatgaaaccctcaccgccgcc<br>gcccaatacatgagggagcacgacatcggcgccctgcccatctgtggagacgacgacaggctgcacggc<br>atgctgaccgacagggacatcgtgatcaagggcctggctgccggcctcgatcctaacaccgctacagccg<br>gcgagctggccagagacagcatctactacgtggacgccaacgccagcatccaggagatgctcaacgtgat<br>ggaggagcaccaggtgagaagggtgcctgtgatcagcgagcacaggctggtgggcatcgtgaccgagg<br>ccgatatcgctaggcacctgcccgagcacgccatcgtgcagttcgtgaaggccatctgcagcccatggct<br>ctggccagc (SEQ ID NO: 31)<br>MTTARDIMAGVTCVGEHETLTAAAQYMREHDIGALPICGDDDRL<br>HGMLTDRDIVIKGLAAGLDPNTATAGELARDSIYYVDANASIQEML<br>NVMEEHQVRRVPVISEHRLVGIVTEADIARHLPEHAIVQFVKAICSP<br>MALAS (SEQ ID NO: 32) |
| Rv3407 | atgcgtgctaccgttgggcttgtggaggcaatcggaatccgagaactaagacagcacgcatcgcgatacct<br>cgcccggggttgaagccggcgaggaacttggcgtcaccaacaaaggaagacttgtggcccgactcatcccg<br>gtgcaggccgcggagcgttctcgcgaagccctgattgaatcaggtgtcctgattccggctcgtcgtccacaa<br>aaccttctcgacgtcaccgccgaaccggcgcggccgcaagcgcaccctgtccgatgttctcaacgaaat<br>gcgcgacgagcagtga (SEQ ID NO: 33)<br>atgcgtgcgactgtgggtctggttgaggcgattggcattcgcgagctgcgccaacatgccagccgttacttg<br>gctcgtgtcgaggcgggtgaagaactgggcgtgacgaataagggtcgtctggtcgcccgtctgattccggt<br>tcaggcagctgagcgttctcgcgaggcgctgattgaatccggcgtcctgatcccggctcgccgtccgcaaa<br>acctgctggacgtgacggcggagccagctcgtggtcgcaaacgcacgctgtctgatgtcctgaacgaaatg<br>cgcgacgagcag (SEQ ID NO: 34)<br>atgagggcgaccgtcgggctggtggaggcgataggtatccgggagttgcgacagcacgcatcacgatatc<br>tggcacgggtggaagctggggaggaactgggcgtgaccaacaagggcggctggtcgcgaggctgatc<br>cccgtgcaggccgccgagcggtcccgcgaagccctcatcgagtctggggtgctcattccagcacgcagg<br>ccgcaaaatctcctggacgtcactgcggagcccgccagaggcagaaagaggacgctgagtgacgtgctg<br>aacgagatgagggacgaacag (SEQ ID NO: 35)<br>MRATVGLVEAIGIRELRQHASRYLARVEAGEELGVTNKGRLVARLI<br>PVQAAERSREALIESGVLIPARRPQNLLDVTAEPARGRKRTLSDVLN<br>EMRDEQ (SEQ ID NO: 36) |
| Rv2628 | atgtccacgcaacgaccgaggcactccggtattcgggctgttggcccctacgcatgggccggccgatgtg<br>gtcggataggcaggtgggggtgcaccaggaggcgatgatgaatctagcgatatggcacccgcgcaagg<br>tgcaatccgccaccatctatcaggtgaccgatcgctcgcacgacgggcgcacagcacgggtgcctggtga<br>cgagatcactagcaccgtgtccggttggttgtcggagttgggcacccaaagcccgttggccgatgagcttgc<br>gcgtgcggtgcggatcggcgactggccgctgcgtacgcaatcggtgagcacctgtccgttgagattgcc<br>gttgcggtctaa (SEQ ID NO: 37)<br>atgagcacccagagacccaggcacagcggcattagggccgtgggaccttatgatgggccggcagatgc<br>ggaaggatcggcagatggggcgtgcaccaagaggccatgatgaacctggccatctggcaccccaggaa<br>ggtgcagagcgccaccatctaccaggtgaccgacaggagccatgacggaaggaccgccagagtgcccg<br>gcgatgagatcaccagcaccgtgagcggctggctgagcgaactgggcacccaatcccccctggctgatga<br>actggccagggctgtgaggatcggcgattggcctgccgcctatgccatcggcgagcatctgagcgtggag<br>atcgccgtggccgtgtaa (SEQ ID NO: 38)<br>MSTQRPRHSGIRAVGPYAWAGRCGRIGRWGVHQEAMMNLAIWHP<br>RKVQSATIYQVTDRSHDGRTARVPGDEITSTVSGWLSELGTQSPLAD<br>ELARAVRIGDWPAAYAIGEHLSVEIAVAV (SEQ ID NO: 39) |

In some embodiments, the resuscitation Mtb antigen is RpfB, RpfD, or RpfE. In some embodiments, the resuscitation Mtb antigen is RpfB or RpfD. Additional resuscitation antigens include, but are not limited to, Rv0867c, Rv0288, Rv1009, Rv0685, Rv0824c, Rv2744c, Rv3347c, Rv1130, Rv1169c, Rv1884c, Rv2389c, and Rv2450c. In some embodiments, the resuscitation antigen is Rv0867c, Rv1884c, or Rv2389c. Additional resuscitation Mtb antigens are well known to the skilled artisan. In some embodiments, the resuscitation antigen is not any one or more of the following: Rv0867c, Rv0288, Rv1009, Rv0685, Rv0824c, Rv2744c, Rv3347c, Rv1130, Rv1169c, Rv1884c, Rv2389c, and Rv2450c. In some embodiments, the resuscitation antigen is not Rv0867c, Rv1884c, or Rv2389c.

The resuscitation Mtb antigen RpfB is also known as Rv1009. A nucleotide sequence encoding the resuscitation Mtb antigen RpfB is shown in Table 3 as SEQ ID NO:40 (mycobacterial sequence; not codon optimized) and SEQ ID NO:41 (mycobacterial sequence; signal sequence deleted), and amino acid sequences of RpfB corresponding thereto are shown in Table 3 as SEQ ID NO:42 and SEQ ID NO:43, respectively.

The resuscitation Mtb antigen RpfD is also known as Rv2389c. A nucleotide sequence encoding the resuscitation Mtb antigen RpfD is shown in Table 3 as SEQ ID NO:44 (mycobacterial sequence; not codon optimized), SEQ ID NO:45 (*E. coli* optimized; leader sequence deleted) and SEQ ID NO:46 (human optimized; leader sequence present), and amino acid sequences of RpfD are shown in Table 3 as SEQ ID NO:47 (*E. coli* optimized) and SEQ ID NO:48 (mycobacterial sequence and human optimized).

The resuscitation Mtb antigen RpfE is also known as Rv2450c. A nucleotide sequence encoding the resuscitation Mtb antigen RpfE is shown in Table 3 as SEQ ID NO:49 (mycobacterial sequence; not codon optimized), and an amino acid sequence of RpfE is shown in Table 3 as SEQ ID NO:50.

TABLE 3

| Construct | nucleotide sequence<br>amino acid sequence |
|---|---|
| RpfB | atgttgcgcctggtagtcggtgcgctgctgctggtgttggcgttcgccggtggctatgcggtcgcc<br>gcatgcaaaacggtgacgttgaccgtcgacgaaccgcgatgcgggtgaccacgatgaaatcgcgg<br>gtgatcgacatcgtcgaagagaacgggttctcagtcgacgaccgcgacgacctgtatcccgcggcc<br>ggcgtgcaggtccatgacgccgacaccatcgtgctgcggcgtagccgtccgctgcagatctcgctg<br>gatggtcacgacgctaagcaggtgtggacgaccgcgtcgacggtggacgaggcgctggcccaactc<br>gcgatgaccgacacggcgccggccgcggcttctcgcgccagccgcgtcccgctgtccgggatggcg<br>ctaccggtcgtcagcgccaagacggtgcagctcaacgacggcgggttggtgcgcacggtgcacttg<br>ccggcccccaatgtcgcggggctgctgagtgcggccggcgtgccgctgttgcaaagcgaccacgtg<br>gtgcccgccgcgacggccccgatcgtcgaaggcatgcagatccaggtgacccgcaatcggatcaag<br>aaggtcaccgagcggctgccgctgccgccgaacgcgcgtcgtgtcgaggacccggagatgaacatg<br>agccgggaggtcgtcgaagacccgggggttccggggacccaggatgtgacgttcgcggtagctgag<br>gtcaacggcgtcgagaccggccgtttgcccgtcgccaacgtcgtggtgacccggcccacgaagcc<br>gtggtgcgggtgggcaccaagcccggtaccgaggtgcccccggtgatcgacggaagcatctgggac<br>gcgatcgccggctgtgaggccggtggcaactgggcgatcaacaccggcaacgggtattacggtggt<br>gtgcagtttgaccagggcacctggaggccaacggcgggctgcggtatgcacccgcgctgacctc<br>gccacccgcgaagagcagatcgccgttgccgaggtgacccgactgcgtcaaggttggggcgcctgg<br>ccggtatgtgctgcacgagcgggtgcgcgctga (SEQ ID NO: 40)<br>gcatgcaaaacggtgacgttgaccgtcgacgaaccgcgatgcgggtgaccacgatgaaatcgcgg<br>gtgatcgacatcgtcgaagagaacgggttctcagtcgacgaccgcgacgacctgtatcccgcggcc<br>ggcgtgcaggtccatgacgccgacaccatcgtgctgcggcgtagccgtccgctgcagatctcgctg<br>gatggtcacgacgctaagcaggtgtggacgaccgcgtcgacggtggacgaggcgctggcccaactc<br>gcgatgaccgacacggcgccggccgcggcttctcgcgccagccgcgtcccgctgtccgggatggcg<br>ctaccggtcgtcagcgccaagacggtgcagctcaacgacggcgggttggtgcgcacggtgcacttg<br>ccggcccccaatgtcgcggggctgctgagtgcggccggcgtgccgctgttgcaaagcgaccacgtg<br>gtgcccgccgcgacggccccgatcgtcgaaggcatgcagatccaggtgacccgcaatcggatcaag<br>aaggtcaccgagcggctgccgctgccgccgaacgcgcgtcgtgtcgaggacccggagatgaacatg<br>agccgggaggtcgtcgaagacccgggggttccggggacccaggatgtgacgttcgcggtagctgag<br>gtcaacggcgtcgagaccggccgtttgcccgtcgccaacgtcgtggtgacccggcccacgaagcc<br>gtggtgcgggtgggcaccaagcccggtaccgaggtgcccccggtgatcgacggaagcatctgggac<br>gcgatcgccggctgtgaggccggtggcaactgggcgatcaacaccggcaacgggtattacggtggt<br>gtgcagtttgaccagggcacctggaggccaacggcgggctgcggtatgcacccgcgctgacctc<br>gccacccgcgaagagcagatcgccgttgccgaggtgacccgactgcgtcaaggttggggcgcctgg<br>ccggtatgtgctgcacgagcgggtgcgcgctga (SEQ ID NO: 41)<br>MLRLVVGALLLVLAFAGGYAVAACKTVTLTVDGTAMRVTTMKSRV<br>IDIVEENGFSVDDRDDLYPAAGVQVHDADTIVLRRSRPLQISLDGHDA<br>KQVWTTASTVDEALAQLAMTDTAPAAASRASRVPLSGN4ALPVVSA<br>KTVQLNDGGLVRTVHLPAPNVAGLLSAAGVPLLQSDHVVPAATAPI<br>VEGMQ1QVTRNR1KKVTERLPLPPNARRVEDPEMNMSREVVEDPGVP<br>GTQDVTFAVAEVNGVETGRLPVANVVVTPAHEAVVRVGTKPGTEVP<br>PVTDGSIWDAIAGCEAGGNWATNTGNGYYGGVQFDQGTWEANGGL<br>RYAPRADLATREEQIAVAEVTRLRQGWGAWPVCAARAGAR (SEQ<br>ID NO: 42)<br>ACKTVTLTVDGTAMRVTTMKSRVTDIVEENGFSVDDRDDLYPAAGV<br>QVHDADTIVLRRSRPLQISLDGHDAKQVWTTASTVDEALAQLAMTD<br>TAPAAASRASRVPLSGMALPVVSAKTVQLNDGGLVRTVHLPAPNVA<br>GLLSAAGVPLLQSDHVVPAATAPrVEGMQIQVTRNRIKKVTERLPLPP<br>NARRVEDPEMNMSREVVEDPGVPGTQDVTFAVAEVNGVETGRLPV<br>ANVVVTPAHEAVVRVGTKPGTEVPPVIDGSIWDAIAGCEAGGNWAI<br>NTGNGYYGGVQFDQGTWEANGGLRYAPRADLATREEQIAVAEVTR<br>LRQGWGAWPVCAARAGAR (SEQ ID NO: 43) |
| RpfD | atgacaccgggtttgcttactactgcgggtgctggccgaccacgtgacaggtgcgccaggatcgta<br>tgcacggtgttcatcgaaaccgccgttgtcgcgaccatgtttgtcgcgttgttgggtctgtccacc<br>atcagctcgaaagccgacgacatcgattgggacgccatcgcgcaatgcgaatccggcggcaattgg<br>gcggccaacaccggtaacgggttatacggtggtctgcagatcagccaggcgacgtgggattccaac<br>ggtggtgtcgggtcgccggcggccgagtcccagcaacagatcgaggtcgcagacaacattatg<br>aaaacccaaggcccgggtcgtggccgaaatgtagttcttgtagtcagggagacgcaccgctggc<br>tcgctcacccacatcctgacgttcctcgcggccgagactggaggttgttcggggagcagggacgat<br>tga (SEQ ID NO: 44)<br>aagcttttgctgggcctgagcaccattagcagcaaagcggatgacatcgactgggatgcgattgcg<br>cagtgtgagagcggtggcaattgggcagcgaataccggcaatggcctgtacggcggtctgcagatc<br>tcccaggcgacgtgggacagcaatggtggcgtcggcagcccggctgccgcgtcccacaacaacag<br>atcgaggtggcagataacattatgaaaacgcagggtccgggtgcttggccaaaatgctccagctgc<br>agccagggtgacgcaccgctgggcagcctgacccacattctgacgttcctggcagcggaaaccggt<br>ggttgtagcggtagccgcgatgac (SEQ ID NO: 45)<br>accccggactcctcaccacagctggagctggcaggcccagagacagatgcgccaggatcgtgtgc<br>accgtgttcatcgagaccgccgtggtggctaccatgttcgtggccctgctgggcctgagcaccatc<br>agcagcaaggccgacgacatcgactgggacgccatcgcccagtgtgaatccggccggaaactgggcc<br>gccaataccggcaatggcctgtacggcggcctgcagatcagccaggctacctgggactccaacgga<br>ggagtgggaagccctgcgcgctgatcccctcagcagcagatcgaggtggccgacaacatcatgaaga<br>cccaaggccctggcgcctggcctaagtgttccagctgtagccagggcgatgctcctctgggcagcc<br>tgacccacatcctgacctttctcgccgccgagacaggcggatgtagcggaagcagggacgactaa<br>ga (SEQ ID NO: 46)<br>LLGLSTISSKADDIDWDAIAQCESGGNWAANTGNGLYGGLQISQAT<br>WDSNGGVGSPAAASPQQQIEVADNIMKTQGPGAWPKCSSCSQGDAP<br>LGSLTHILTFLAAETGGCSGSRDD (SEQ ID NO: 47)<br>TPGLLTTAGAGRPRDRCARIVCTVFIETAVVATMFVALLGLSTISSKA |

TABLE 3-continued

| Construct | nucleotide sequence<br>amino acid sequence |
|---|---|
| | DDIDWDAIAQCESGGNWAANTGNGLYGGLQISQATWDSNGGVGSP<br>AAASPQQQIEVADNIMKTQGPGAWPKCSSCSQGDAPLGSLTHILTFL<br>AAETGGCSGSRDD (SEQ ID NO: 48) |
| RpfE | ttgaagaacgcccgtacgacgctcatcgccgccgcgattgccgggacgttggtgaccacgtcacca<br>gccggtatcgccaatgccgacgacgcgggcttggacccaaacgccgcagccggcccggatgccgtg<br>ggctttgacccgaacctgccgccggccccggacgctgcacccgtcgatactccgccggctccggag<br>gacgcgggctttgatcccaacctccccccgccgctggccccggacttcctgtccccgcctgcggag<br>gaagcgcctcccgtgcccgtggcctacagcgtgaactgggacgcgatcgcgcagtgcgagtccggt<br>ggaaactggtcgatcaacaccggtaacggttactacggcggcctgcggttcaccgccggcacctgg<br>cgtgccaacggtggctcggggtccgcggccaacgcgagccgggaggagcagatccgggtggctgag<br>aacgtgctgcgttcgcagggtatccgcgcctggccggtctgcggccgccgcggctga<br>(SEQ ID NO: 49)<br>LKNARTTLIAAAIAGTLVTTSPAGIANADDAGLDPNAAAGPDAVGFD<br>PNLPPAPDAAPVDTPPAPEDAGFDPNLPPPLAPDFLSPPAEEAPPVPVA<br>YSVNWDAIAQCESGGNWSINTGNGYYGGLRFTAGTWRANGGSGSA<br>ANASREEQIRVAENVLRSQGIRAWPVCGRRG (SEQ ID NO: 50) |

In some embodiments, the fusion protein comprises at least four *Mycobacterium tuberculosis* (Mtb) antigens. In some embodiments, the fusion protein comprises at least five Mtb antigens. In some embodiments, the fusion protein comprises at least six Mtb antigens. In some embodiments, the fusion protein comprises from at least three to at least six Mtb antigens. In some embodiments, the fusion protein comprises from at least three to at least five Mtb antigens. In some embodiments, the fusion protein comprises at least three or at least four Mtb antigens. In some embodiments, the fusion protein comprises from at least four to at least six Mtb antigens. In some embodiments, the fusion protein comprises at least four or at least five Mtb antigens.

In some embodiments, the fusion protein comprises ESAT6, Rv1733c, Rv2626c, and RpfD Mtb antigens. In some embodiments, the fusion protein comprises ESAT6, Rv1733c, Rv2626c, and RpfB Mtb antigens. In some embodiments, the fusion protein comprises RpfB, ESAT6, Rv1733c, and Rv2626c Mtb antigens. In some embodiments, the fusion protein comprises Ag85B, ESAT6, Rv1733c, Rv2626c, and RpfD Mtb antigens. In some embodiments, the fusion protein comprises Ag85B, ESAT6, Rv1733c, Rv2626c, and RpfB Mtb antigens. In some embodiments, the fusion protein comprises PPE51, Rv1733c, Rv2628c, and RpfD Mtb antigens. In some embodiments, the fusion protein comprises PPE51, Rv1733c, Rv2628c, and RpfB Mtb antigens. In some embodiments, the fusion protein comprises Rv3407, Rv1733c, Rv2626c, and RpfB Mtb antigens. In some embodiments, the fusion protein comprises Rv3407, Rv1733c, Rv2626c, and RpfD Mtb antigens.

In any of the embodiments of fusion proteins set forth herein, the individual Mtb antigens can be present in any order. For example, for a fusion protein comprising ESAT6, Rv1733c, Rv2626c, and RpfD Mtb antigens, the first (or N-terminal) antigen may be ESAT6, Rv1733c, Rv2626c, or RpfD; the second antigen may be ESAT6, Rv1733c, Rv2626c, or RpfD; the third antigen may be ESAT6, Rv1733c, Rv2626c, or RpfD; and the fourth (or C-terminal) antigen may be ESAT6, Rv1733c, Rv2626c, or RpfD. Likewise for every fusion protein disclosed herein.

Individual Mtb antigens may be linked together in a C-terminus to N-terminus manner without any linker (i.e., the C-terminus of ESAT6 linked directly to the N-terminus of Rv1733c). Alternately, a linker may be present between any two Mtb antigens within any of the fusion proteins disclosed herein. In some embodiments, the linker is a segment of DNA or RNA optionally containing one or more restrictions sites, wherein the linker is inserted between nucleic acid molecules encoding two Mtb antigens of any of the fusion proteins disclosed herein. Table 5 shows representative primers for particular Mtb antigens used to introduce restriction sites into a fusion protein construct.

In some embodiments, the fusion protein comprises ESAT6-Rv1733c-Rv2626c-RpfD (Construct A; nucleotide sequence is SEQ ID NO:51 (*E. coli* optimized; inserted EcoRI, SacI, and HindIII restriction sites, respectively, are bolded and underlined) and SEQ ID NO:52 (human optimized; inserted BstBI, PvuI, and AscI restriction sites, respectively, are bolded and underlined); corresponding amino acid sequences are SEQ ID NO:53 (*E. coli* optimized) and SEQ ID NO:54 (human optimized); see Table 4).

In some embodiments, the fusion protein comprises ESAT6-Rv1733c-Rv2626c-RpfB (Construct B; nucleotide sequence is SEQ ID NO:55, wherein inserted EcoRI, SacI, and HindIII restrictions sites, respectively, are bolded and underlined; amino acid sequence is SEQ ID NO:56; see Table 4).

In some embodiments, the fusion protein comprises RpfB-ESAT6-Rv1733c-Rv2626c (Construct C; nucleotide sequence is SEQ ID NO:57, wherein inserted BamHI, EcoRI, and SacI restrictions sites, respectively, are bolded and underlined; amino acid sequence is SEQ ID NO:58; see Table 4).

In some embodiments, the fusion protein comprises Ag85B-ESAT6-Rv1733c-Rv2626c-RpfD (Construct D; nucleotide sequence is SEQ ID NO:59 (*E. coli* optimized; inserted BamHI, EcoR1, SacI, and HindIII restriction sites, respectively, are bolded and underlined) and SEQ ID NO:60 (human optimized; inserted XmaI, BstBI, PvuI, and AscI restriction sites, respectively, are bolded and underlined); amino acid sequence is SEQ ID NO:61 (*E. coli* optimized) and SEQ ID NO:62 (human optimized); see Table 4).

In some embodiments, the fusion protein comprises PPE51-Rv1733c-Rv2628c-RpfD (Construct E; nucleotide sequence is SEQ ID NO:63, wherein inserted EcoRI, SacI, and HindIII restrictions sites, respectively, are bolded and underlined; amino acid sequence is SEQ ID NO:64; see Table 4).

In some embodiments, the fusion protein comprises PPE51-Rv1733c-Rv2628c-RpfB (Construct F; nucleotide sequence is SEQ ID NO:65, wherein inserted EcoRI, SalI, and HindIII restrictions sites, respectively, are bolded and underlined; amino acid sequence is SEQ ID NO:66; see Table 4).

In some embodiments, the fusion protein comprises Rv3407-Rv1733c-Rv2626c-RpfB (Construct G; nucleotide sequence is SEQ ID NO:67, wherein inserted EcoRI, SacI, and HindIII restrictions sites, respectively, are bolded and underlined; amino acid sequence is SEQ ID NO:68; see Table 4).

In some embodiments, the fusion protein comprises Rv3407-Rv1733c-Rv2626c-RpfD (Construct H; nucleotide sequence is SEQ ID NO:69, wherein inserted EcoRI, SacI, and HindIII restrictions sites, respectively, are bolded and underlined; amino acid sequence is SEQ ID NO:70; see Table 4).

In some embodiments, the fusion protein comprises PPE51-Rv1733c-Rv2626c-RpfD (Construct I; nucleotide sequence is SEQ ID NO:71, wherein inserted EcoRI, SacI, and HindIII restrictions sites, respectively, are bolded and underlined; amino acid sequence is SEQ ID NO:72; see Table 4).

In some embodiments, the fusion protein comprises PPE51-Rv1733c-Rv2626c-RpfB (Construct J; nucleotide sequence is SEQ ID NO:73, wherein inserted EcoRI, SacI, and HindIII restrictions sites, respectively, are bolded and underlined; amino acid sequence is SEQ ID NO:74; see Table 4).

| Construct | nucleotide sequence<br>amino acid sequence |
|---|---|
| A | atgacagagcagcagtggaatttcgcgggtatcgaggccgcggcaagcgcaatccagggaaatgtc<br>acgtccattcattccctccttgacgaggggaagcagtccctgaccaagctcgcagcggcctggggc<br>ggtagcggttcggaggcgtaccagggtgtccagcaaaaatgggacgccacggctaccgagctgaac<br>aacgcgctgcagaacctggcgcggacgatcagcgaagccggtcaggcaatggcttcgaccgaaggc<br>aacgtcactgggatgttcgcagaattcatgattgcgactacccgtgatcgtgagggcgcgaccatg<br>atcacgttccgtctgcgtctgccgtgtcgcaccattttgcgcgtgttttcgcgtaacccgctggtc<br>cgcggtaccgaccgtctggaggccccggggtccaagacagccgtgcatgtgtatgctcaccag<br>gctcaaacccgtcaccggctactgccactgttatcgatcacgaaggcgtgattgactccaatacc<br>acggcaacctccgcaccggcctcgcaccaagattacggttcctgcgcgttgggtggtgaatggtatt<br>gaacgcagcggcgaagttaatgccaaaccgggtaccaaaagcggtgaccgtgtgggcatctgggtc<br>gatagcgccggtcagctggtcgacgagccggcaccgccagccgcgtgatcgccgattctagacgc<br>gcaattctgatccgcgttcgcaatgcgagctggcagcacgatattgatagcctgttttgcacccaa<br>cgtgagctcatgaccacggcgcgtgatatcatgaatgcgggtgtcacctgtgttggcgagcacgaa<br>acgttgaccgcagcagcacagtacatgcgcgaacatgatatcggcgcattgccgatttgcggcgac<br>gatgatcgtctgcacggtatgctgaccgaccgcgatatcgttatcaaggtctggccgcaggcttg<br>gacccgaacaccgcgaccgccggtgaactggcacgtgacagcatctattacgtcgacgcgaacgcc<br>agcattcaagagatgctgaacgtgatggaagagcatcaggtgcgtcgtgtcccggttatcagcgaa<br>catcgtctggttggtatcgttaccgaagccgacatcgcacgtcacctgccggagcacgcgattgtt<br>cagttcgtgaaagcgatttgcagcccgatggcgttggcgtctaagctttgctgggcctgagcacc<br>attagcagcaaagcggatgacatcgactgggatgcgattgcgcagtgtgagagcggtggcaattgg<br>gcagcgaataccggcaatggcctgtacgcggtctgcagatctcccaggcgacgtgggacagcaat<br>ggtggcgtcggcagccggctgccgcgtccccacaacaacagatcgaggtggcagataacattatg<br>aaaacgcagggtccgggtgcttggccaaaatgctccagctgcagccagggtgacgcaccgctgggc<br>agcctgacccacattctgacgttcctggcagcggaaaccggtggttgtagcggtagccgcgatga<br>c = (SEQ ID NO: 51)<br>atgaccgagcagcagtggaacttcgccggcatcgaagctgccgctagcgccatccaaggcaacgtg<br>accagcatccacagcctgctggacgagggcaagcagagcctgaccaagctggctgctgcttgggc<br>ggatccggaagcgaagcctaccagggcgtgcagcagaagtggacgccacagccaccggctgaac<br>aacgccctgcagaacctcgccagaaccatcagcgaggccggacaggctatggccagcacagagggc<br>aatgtgaccggcatgttcgccttcgaaatcgccaccaccagggacagggaaggcgctaccatgatc<br>accttcaggctgaggctccctgcaggaccatcctgagggtgttcagcaggaaccccctggtgagg<br>ggcaccgacagactggaagcgtgcaggacagcaggagccacgtgtatgccaccaggctcagacc<br>aggcaccctgctaccgccaccgtgatcgaccacgagggcgtgatcgactccaacaccaccgccacc<br>agcgctcctcccagaaccaagatcacagtgcccgccaggtgggtggtgaacggcatcgagaggagc<br>ggcgaggtgaacgccaagcctggaaccaagagcggcgacagggtgggcatttgggtcgatagcgcc<br>ggccagctggtggatgaacctgctccccctgccagagccatcgccgataggcatcctgatcagg<br>gtgaggaacgccagctggcagcacgacatcgacagcctgttctgcacccaaaggcgatcgacaaca<br>gccagggacatcatgaacgccggcgtgacctgcgtgggagagcatgaaaccctcaccgccgccgcc<br>caatacatgagggagcacgacatcggcgccctgcccatctgtggagacgacgacaggctgcacggc<br>atgctgaccgacagggacatcgtgatcaaggcctggctgccggcctcgatcctaacaccgctaca<br>gccggcgagctggccagagacagcatctactacgtggacgccaacgccagcatccaggagatgctc<br>aacgtgatggaggagcaccaggtgagaagggtgcctgtgatcagcgagcacaggctggtgggcatc<br>gtgaccgaggccgatatcgctaggcacctgcccgagcacgccatcgtgcagttcgtgaaggccatc<br>tgcagcccatggctctggccagcggcgcgcccaccccggactcctcaccacagctggagctggc<br>aggccagagacagatgcgccaggatcgtgtgcaccgtgttcatcgagaccgccgtggtggctacc<br>atgttcgtggccctgctgggcctgagcaccatcagcagcaaggccgacgacatcgactgggacgcc<br>atcgcccagtgtgaatccggcggaaactgggccgccaataccggcaatggcctgtacgcggcctg<br>cagatcagccaggctacctgggactccaacggaggagtgggaagccctgccgctgcttcccctcag<br>cagcagatcgaggtggccgacaacatcatgaagaccaaggccctggcgcctggcctaagtgttcc<br>agctgtagccagggcgatgctcctctgggcagcctgacccacatcctgaccttttctcgccgcgag<br>acaggcggatgtagcggaagcagggacgactaatgatag (SEQ ID NO: 52)<br>MTEQQWNFAGIEAAASAIQGNVTSIHSLLDEGKQSLTKLAAAWGGS<br>GSEAYQGVQQKWDATATELNNALQNLARTISEAGQAMASTEGNVT<br>GMFAEFMIATTRDREGATMITFRLRLPCRTILRVFSRNPLVRGTDRLE<br>APGVQDSRSHVYAHQAQTRHPATATVIDHEGVIDSNTTATSAPPRTKI<br>TVPARWVVNGIERSGEVNAKPGTKSGDRVGIWVDSAGQLVDEPAPP<br>ARAIADSRRAILIRVRNASWQHDIDSLFCTQRELMTTARDIMNAGVT<br>CVGEHETLTAAAQYMREHDIGALPICGDDDRLHGMLTDRDIVIKGLA<br>AGLDPNTATAGELARDSIYYVDANASIQEMLNVMEEHQVRRVPVISE |

-continued

| Construct | nucleotide sequence<br>amino acid sequence |
|---|---|
| | HRLVGIVTEADIARHLPEHAIVQFVKAICSPMALASKLLLGLSTISSKA<br>DDIDWDAIAQCESGGNWAANTGNGLYGGLQISQATWDSNGGVGSP<br>AAASPQQQIEVADNIMKTQGPGAWPKCSSCSQGDAPLGSLTHILTFL<br>AAETGGCSGSRDD (SEQ ID NO: 53)<br>MTEQQWNFAGIEAAASAIQGNVTSIHSLLDEGKQSLTKLAAAWGGS<br>GSEAYQGVQQKWDATATELNNALNLARTISEAGQAMASTEGNVTG<br>MFAFEIATTRDREGATMITFRLRLPCRTILRVFSRNPLVRGTDRLEAV<br>QDSRSHVYAHQAQTRHPATATVIDHEGVIDSNTTATSAPPRTKITVPA<br>RWVVNGIERSGEVNAKPGTKSGDRVGIWVDSAGQLVDEPAPPARAI<br>ADRAILIRVRNASWQHDIDSLFCTQRRSTTARDIMNAGVTCVGEHET<br>LTAAAQYMREHDIGALPICGDDDRLHGMLTDRDIVIKGLAAGLDPNT<br>ATAGELARDSIYYVDANASIQEMLNVMEEHQVRRVPVISEHRLVGIV<br>TEADIARHLPEHAIVQFVKAICSPMALASGAPTPGLLTTAGAGRPRDR<br>CARIVCTVFIETAVVATMFVALLGLSTISSKADDIDWDAIAQCESGGN<br>WAANTGNGLYGGLQISQATWDSNGGVGSPAAASPQQQIEVADNIMK<br>TQGPGAWPKCSSCSQGDAPLGSLTHILTFLAAETGGCSGSRDD (SEQ ID NO: 54) |
| B | atgacagagcagcagtggaatttcgcgggtatcgaggccgcggcaagcgcaatccagggaaatgtc<br>acgtccattcattccctccttgacgaggggaagcagtccctgaccaagctcgcagcggcctgggc<br>ggtagcggttcggaggcgtaccagggtgtccagcaaaaatgggacgccacggctaccgagctgaac<br>aacgcgctgcagaacctggcgcggacgatcagcgaagccggtcaggcaatggatcgaccgaaggca<br>acgtcactgggatgttcgcagaattcatgattgcgactaccgtgatcgtgagggcgcgaccatga<br>tcacgttccgtctgcgtctgccgtgtcgcaccattttgcgcgtgtttcgcgtaaccgctggtcc<br>gcggtaccgaccgtctggaggccgttgtcatgctgctggcggttaccgtgagcctgctgacgatcc<br>cattcgcagcggcagctggcacggccgtccaagacagccgtagccatgtgtatgctcaccaggctc<br>aaacccgtcacccggctactgccactgttatcgatcacgaaggcgtgattgactccaataccacgg<br>caacctccgcaccgcctcgcaccaagattacggttcctgcgcgttgggtggtgaatggtattgaac<br>gcagcggcgaagttaatgccaaaccgggtaccaaaagcggtgaccgtgtgggcatctgggtcgata<br>gcgccggtcagctggtcgacgagccggcaccgccagcgcgtgcgatcgccgatcgggcgctggctg<br>ccctgggtctgtggctgagcgtggcagcggtcgccggtcgcttgctggcgctgacgcgcgcaattc<br>tgatccgcgttcgcaatgcgagctggcagcacgatattgatagcctgttttgcacccaacgtgagc<br>tcatgaccacgcgcgtgatatcatgaatgcgggtgtcacctgtgttggcgagcacgaaacgttga<br>ccgcagcagcacagtacatgcgcgaacatgatatcggcgcattgccgatttgcggcgacgatgatc<br>gtctgcacggtatgctgaccgaccgcgatatcgttatcaagggtctggccgcaggcttggacccga<br>acaccgcgaccgccggtgaactgccacgtgaacagcatctattacgtcgacgcgaacgccagcattc<br>aagagatgctgaacgtgatggaagagcatcaggtgcgtcgtgtcccggttatcagcgaacatcgtc<br>tggttggtatcgttaccgaagccgacatcgcacgtcacctgccggagcacgcggattgttcagttcg<br>tgaaagcgatttgcagcccgatggcgttggcgtctcgtcaaaagggcgacacaaaatttattctaa<br>atgcaaaagcttgcatgcaaaacggtgacgttgaccgtcgacggaaccgcgatgcgggtgaccacga<br>tgaaatcgcgggtgatcgacatcgtcgaagagaacgggttctcagtcgacgaccgcgacgacctgt<br>atcccgcggccggcgtgcaggtccatgacgccgacaccatcgtgctgcggcgtagccgtccgctgc<br>agatctcgctggatggtcacgacgctaagcaggtgtggacgaccgcgtcgacggtggacgaggcgc<br>tggccaactcgcgatgaccgacacggcgccggccgggcttctcgcgccagccgcgtcccgctgt<br>ccgggatggcgctaccggtcgtcagcgccaagacggtgcagctcaacgacggcgggttggtgcgca<br>cggtgcacttgccggccccaatgtcgcggggctgctgagtgcggccggcgtgccgctgttgcaaa<br>gcgaccacgtggtgcccgccgcgacggcccccgatcgtcgaaggcatgcagatccaggtgacccgca<br>atcggatcaagaaggtcaccgagcggctgccgctgccgccgaaccgcgtcgtgtcgaggacccgg<br>agatgaacatgagccgggaggtcgtcgaagacccgggggttccggggacccaggatgtgacgttcg<br>cggtagctgaggtcaacggcgtcgagaccggccgtttgcccgtcgccaacgtcgtggtgaccccgg<br>cccacgaagccgtggtgcgggtgggcaccaagcccggtaccgaggtgccccggtgatcgacggaa<br>gcatctgggacgcgatcgccggctgtgaggccggtggcaactgggcgatcaacaccggcaacggt<br>attacggtggtgtgcagtttgaccagggcacctgggaggccaacggcgggctgcggtatgcaccc<br>gcgctgacctcgccaccccgcgaagagcagatcgccgttgccgaggtgacccgactcgtcaaggtt<br>ggggcgcctggccggtatgtgctgcacgagcgggtgcgcgctga (SEQ ID NO: 55)<br>MTEQQWNFAGIEAAASAIQGNVTSIHSLLDEGKQSLTKLAAAWGGS<br>GSEAYQGVQQKWDATATELNNALQNLARTISEAGQAMASTEGNVT<br>GMFAEFMIATTRDREGATMITFRLRLPCRTILRVFSRNPLVRGTDRLE<br>AVVMLLAVTVSLLTIPFAAAAGTAVQDSRSHVYAHQAQTRHPATAT<br>VIDHEGVIDSNTTATSAPPRTKITVPARWVVNGIERSGEVNAKPGTKS<br>GDRVGIWVDSAGQLVDEPAPPARAIADAALAALGLWLSVAAVAGA<br>LLALTRAILIRVRNASWQHDIDSLFCTQRELMTTARDIMNAGVTCVG<br>EHETLTAAAQYMREHDIGALPICGDDDRLHGMLTDRDTVIKGLAAGL<br>DPNTATAGELARDSIYYVDANASIQEMLNVMEEHQVRRVPVISEHRL<br>VGIVTEADIARHLPEHAIVQFVKAICSPMALASRQKGDTKFILNAKLA<br>CKTVTLTVDGTAMRVTTMKSRVIDIVEENGFSVDDRDDLYPAAGVQ<br>VHDADTIVLRRSRPLQISLDGHDAKQVWTTASTVDEALAQLAMTDT<br>APAAASRASRVPLSGMALPVVSAKTVQLNDGGLVRTVHLPAPNVAG<br>LLSAAGVPLLQSDHVVPAATAPIVEGMQIQVTRNRIKKVTERLPLPPN<br>ARRVEDPEMNMSREVVEDPGVPGTQDVTFAVAEVNGVETGRLPVA<br>NVVVTPAHEAVVRVGTKPGTEVPPVIDGSIWDAIAGCEAGGNWAINT<br>GNGYYGGVQFDQGTWEANGGLRYAPRADLATREEQIAVAEVTRLR<br>QGWGAWPVCAARAGAR (SEQ ID NO: 56) |
| C | atgaagcttgcatgcaaaacggtgacgttgaccgtcgacggaaccgcgatgcgggtgaccacgatg<br>aaatcgcgggtgatcgacatcgtcgaagagaacgggttctcagtcgacgaccgcgacgacctgtat |

| Construct | nucleotide sequence<br>amino acid sequence |
|---|---|
| | cccgcggccggcgtgcaggtccatgacgccgacaccatcgtgctgcggcgtagccgtccgctgcag<br>atctcgctggatggtcacgacgctaagcaggtgtggacgaccgcgtgacggtggacgaggcgctg<br>gcccaactcgcgatgaccgacacggcgccggccgcggcttctcgcgccagccgcgtcccgctgtcc<br>gggatggcgctaccggtcgtcagcgccaagacggtgcagctcaacgacggcgggttggtgcgcacg<br>gtgcacttgccggcccccaatgtcgcggggctgctgagtgcggccggcgtgccgctgttgcaaagc<br>gaccacgtggtgccccgccgcgacgccccgatcgtcgaaggcatgcagatccaggtgacccgcaat<br>cggatcaagaaggtcaccgagcggctgccgctgccgccgaacgcgcgtcgtgtcgaggacccggag<br>atgaacatgagccgggaggtcgtcgaagacccggggggttccggggacccaggatgtgacgttcgcg<br>gtagctgaggtcaacggcgtcgagaccggccgtttgcccgtcgccaacgtcgtggtgaccccggcc<br>cacgaagccgtggtgcgggtgggcaccaagcccggtaccgaggtgccccggtgatcgacggaagc<br>atctgggacgcgatcgccggctgtgaggccggtgcaactggcgatcaacaccggcaacgggtat<br>tacggtggtgtgcagtttgaccagggcacctgggaggccaacggcgggctgcggtatgcaccccgc<br>gctgacctcgccacccgcgaagagcagatcgccgttgccgaggtgaccgactgcgtcaaggttgg<br>ggcgcctggccggtatgtgctgcacgagcgggtgcgcgcggatccatgacagagcagcagtggaat<br>ttcgcgggtatcgaggccgcggcaagcgcaatccagggaaatgtcacgtccattcattccctcctt<br>gacgaggggaagcagtccctgaccaagctcgcagcggcctggggcggtagcggttcggaggcgtac<br>cagggtgtccagcaaaaatgggacgccacggctaccgagctgaacaacgcgctgcagaacctggcg<br>cggacgatcagcgaagccggtcaggcaatggcttcgaccgaaggcaacgtcactgggatgttcgca<br>gaattcatgattgcgactacccgtgatcgtgagggcgcgcactgttccgtctgcgtctg<br>ccgtgtcgcaccattttgcgcgtgttttcgcgtaacccgctggtccgcggtaccgaccgtctggag<br>gccgttgtcatgctgctggcggttaccgtgagcctgctgacgatcccattcgcagcggcagctggc<br>acggccgtccaagacagccgtagccatgtgtatgctcaccaggctcaaacccgtcacccggctact<br>gccactgttatcgatcacgaaggcgtgattgactccaatacccacgcaacctccgcaccgcctcgc<br>accaagattacggttcctgcgcgttgggtggtgaatggtattgaacgcagcggcgaagttaatgcc<br>aaaccgggtaccaaaagcggtgaccgtgtgggcatctgggtcgatagcgccggtcagctggtcgac<br>gagccggcaccgccagcgcgtgcgatcgccgatgcggcgctggctgccctgggtctgtggctgagc<br>gtggcagcggtcgccggtgcgttgctggcgctgacgcgcgcaattctgatccgcgttcgcaatgcg<br>agctggcagcacgatattgatagcctgttttgcacccaacgtgagctcatgaccacggcgcgtgat<br>atcatgaatgcgggtgtcacctgtgttggcgagcacgaaacgttgaccgcagcagcacagtacatg<br>cgcgaacatgatatcggcgcattgccgatttgcggcgacgatgatcgtctgcacggtatgctgacc<br>gaccgcgatatcgttatcaagggtctggccgcaggcttggacccgaacaccgcgaccgccggtgaa<br>ctggcacgtgacagcatctattacgtcgacgcgaacgccagcattcaagagatgctgaacgtgatg<br>gaagagcatcaggtgcgtcgtgtcccggttatcagcgaacatcgtctggttggtatcgttaccgaa<br>gccgacatcgcacgtcacctgccggagcacgcgattgttcagttcgtgaaagcgatttgcagcccg<br>atggcgttggcgtctcgtcaaaagggcgacacaaaatttattctaaatgcatga<br>(SEQ ID NO: 57)<br>MKLACKTVTLTVDGTAMRVTTMKSRVIDIVEENGFSVDDRDDLYPA<br>AGVQVHDADTIVLRRSRPLQISLDGHDAKQVWTTASTVDEALAQLA<br>MTDTAPAAASRASRVPLSGMALPVVSAKTVQLNDGGLVRTVHLPAP<br>NVAGLLSAAGVPLLQSDHVVPAATAPIVEGMQIQVTRNRIKKVTERL<br>PLPPNARRVEDPEMNMSREVVEDPGVPGTQDVTFAVAEVNGVETGR<br>LPVANVVVTPAHEAVVRVGTKPGTEVPPVIDGSTWDAIAGCEAGGN<br>WAINTGNGYYGGVQFDQGTWEANGGLRYAPRADLATREEQIAVAE<br>VTRLRQGWGAWPVCAARAGARGSMTEQQWNFAGIEAAASAIQGNV<br>TSIHSLLDEGKQSLTKLAAAWGGSGSEAYQGVQQKWDATATELNNA<br>LQNLARTISEAGQAMASTEGNVTGMFAEFMIATTRDREGATMFTFRL<br>RLPCRTILRVFSRNPLVRGTDRLEAVVMLLAVTVSLLTIPFAAAAGTA<br>VQDSRSHVYAHQAQTRHPATATVIDHEGVIDSNTTATSAPPRTKITVP<br>ARWVVNGIERSGEVNAKPGTKSGDRVGIWVDSAGQLVDEPAPPARA<br>IADAALAALGLWLSVAAVAGALLALTRAILIRVRNASWQHDIDSLFC<br>TQRELMTTARDTMNAGVTCVGEHETLTAAAQYMREHDIGALPICGD<br>DDRLHGMLTDRDIVIKGLAAGLDPNTATAGELARDSIYYVDANASIQ<br>EMLNVMEEHQVRRVPVISEHRLVGIVTEADIARHLPEHAIVQFVKAIC<br>SPMALASRQKGDTKFILNA (SEQ ID NO: 58) |
| D | atgtttagccgtcctggcctgccagttgaatacctgcaagttccgagcccgtccatgggtcgtgac<br>attaaggtgcagttccagagcggcggtaacaatagcccggctgtgtacctgctggacggtctgcgt<br>gcgcaggatgattacaacggctgggacatcaatacccggcatttgagtggtattaccagtcgggt<br>ctgagcattgtgatgccggttggcggtcaaagcagctcctatagcgattggtacagcccggcatgc<br>ggcaaggctggttgccaaacctacaagtgggaaactttcttgaccagcgagctgccgcaatggttg<br>agcgccaaccgtcggtcaaaccgaccggtagcgctgctattggcctgtccatgccggcagcagc<br>gcgatgatcttggcggcataccatccgcagcagtttatctacgccgtagcctgagcgcattgctg<br>gacccgagccaaggcatgggtccgagcctgattggtctggcaatgggtgacgcaggtggttacaaa<br>gcggccgatatgtgggcccatctagcgacccggcatgggagcgtaatgacccgacccagcaaatt<br>ccgaaactggtggcgaataacacgcgcctgtgggtctactgtggcaatggtacgccgaacgagctg<br>ggtggcgcgaatatccctgcggagtttctggaaaactttgttcgcagcgaacctgaaattccag<br>gacgcgtataacgcagccggtggtcacaatgcggttttcaatttcccgccaaatggcactcatagc<br>tgggagtactgggtgcgcagttgaacgcaatgaaggcgatctgcaatcctctctgggtgcgggc<br>ggatccatgacagagcagcagtggaatttcgcgggtatcgaggccgcggcaagcgcaatccaggga<br>aatgtcacgtccattcattccctccttgacgaggggaagcagtccctgaccaagctcgcagcggcc<br>tggggcggtagcggttcggaggcgtaccagggtgtccagcaaaaatgggacgccacggctaccgag<br>ctgaacaacgcgctgcagaacctggcgcggacgatcagcgaagccggtcaggcaatggcttcgacc<br>gaaggcaacgtcactgggatgttcgcagaattcatgattgcgactacccgtgatcgtgagggcgcg<br>accatgatcacgttccgtctgcgtctgccgtgtcgcaccattttgcgcgtgttttcgcgtaacccg<br>ctggtccgcggtaccgaccgtctggaggccccggggtccaagacagccgtagccatgtgtatgct<br>caccaggctcaaacccgtcacccggctactgccactgttatcgatcacgaaggcgtgattgactcc |

| Construct | nucleotide sequence<br>amino acid sequence |
|---|---|
| | aataccacggcaacctccgcaccgcctcgcaccaagattacggttcctgcgcgttgggtggtgaat<br>ggtattgaacgcagcggcgaagttaatgccaaaccgggtaccaaaagcggtgaccgtgtgggcatc<br>tgggtcgatagcgccggtcagctggtcgacgagccggcaccgccagcgcgtgcgatcgccgattct<br>agacgcgcaattctgatccgcgttcgcaatgcgagctggcagcacgatattgatagcctgttttgc<br>acccaacgtgagctcatgaccacggcgcgtgatatcatgaatgcgggtgtcacctgtgttggcgag<br>cacgaaacgttgaccgcagcagcacagtacatgcgcgaacatgatatcggcgcattgccgatttgc<br>ggcgacgatgatcgtctgcacggtatgctgaccgaccgcgatatcgttatcaagggtctggccgca<br>ggcttggacccgaacaccgcgaccgccggtgaactggcacgtgacagcatctattacgtcgacgcg<br>aacgccagcattcaagagatgctgaacgtgatggaagagcatcaggtgcgtcgtgtcccggttatc<br>agcgaacatcgtctggttggtatcgttaccgaagccgacatcgcacgtcacctgccggagcacgcg<br>attgttcagttcgtgaaagcgatttgcagcccgatgggcgttggcgtctaagctttgctgggcctg<br>agcaccattagcagcaaagcggatgacatcgactgggatgcgattgcgcagtgtgagagcggtggc<br>aattgggcagcgaataccggcaatggcctgtacgcggtctgcagatctcccaggcgacgtgggac<br>agcaatggtggcgtcggcagcccggctgccgcgtcccacaacaacagatcgaggtggcagataac<br>attatgaaaacgcagggtccgggtgcttggccaaaatgctccagctgcagccagggtgacgcaccg<br>ctgggcagcctgacccacattctgacgttcctggcagcggaaaccggtggttgtagcggtagccgc<br>gatgac (SEQ ID NO: 59) |
| | atgttctccaggcccggcctgcctgtcgagtatctgcaggtcccctcccctccatgggcagagac<br>atcaaggtgcagttccaatccggaggcaacaacagccccgccgtgtatctcctcgacggcctgagg<br>gctcaggacgactacaacggctgggacatcaacacccccgccttcgagtggtactaccagtccgga<br>ctgagcatcgtcatgcccgtgggcggccagagctccttctacagcgactggtatagccctgcctgc<br>ggcaaagccggatgccagacctacaagtgggagacctttctgaccagcgaactgccccagtggctg<br>tccgccaatagggccgtcaaacctaccggctccgctgccatcggactgagcatggccggaagctcc<br>gctatgatcctggccgcctaccaccccagcaatttatctacgctggcagcctgtccgctctgctg<br>gatcctagccaaggcatgggccctagcctcattggcctggccatgggcgatgctggcggctataag<br>gccgccgatatgtgggcccctagctccgatcctgcctgggagaggaatgaccccacccagcagatc<br>cccagctggtggccaacaacacaaggctctgggtgtactgcggcaatggcaccccccaacgaactg<br>ggcggagccaacattcccgccgagttcctggagaacttcgtcaggagcagcaacctgaagttccag<br>gacgcctacaatgccgccgaggccacaacgctgtgttcaacttccctcccaacggcacccacagc<br>tgggagtattggggcgctcagctgaacgccatgaaaggcgacctccagagctccctgggagctgga<br>cccgggaccgagcagcagtggaacttcgccggcatcgaagctgccgctagcgccatccaaggcaac<br>gtgaccagcatccacagcctgctggacgagggcaagcagaagcctgaccaagctggctgctgcttgg<br>ggcggatccggaagcgaagcctaccagggcgtgcagcagaagtgggacgccacagccaccgagctg<br>aacaacgccctgcagaacctcgccagaaccatcagcgaggccggacaggctatggcagcacagag<br>ggcaatgtgaccggcatgttcgccttcgaaatcgccaccaccaggacagggaaggcgctaccatg<br>atcaccttcaggctgaggctccctcgcaggaaccatcctgaggtgttcagcaggaaccccctggtg<br>aggggcaccgacagactggaagccgtgcaggacagcaggagccacgtgtatgcccaccaggctcag<br>accaggcaccctgctaccgccaccgtgatcgaccacgagggcgtgatcgactccaacaccaccgcc<br>accagcgctcctcccagaaccaagatcacagtgcccgccaggtgggtggtgaacggcatcgagagg<br>agcggcgaggtgaacgccaagcctggaaccaagagcggcgacagggtgggcatttgggtcgatagc<br>gccggccagctggtggatgaacctgctcccctgccagagccatcgccgatagggccatcctgatc<br>agggtgaggaacgccagctggcagcacgacatcgacagcctgttctgcacccaaaggcgatcgaca<br>acagccagggacatcatgaacgccggcgtgacctgcgtgggagagcatgaaaccctcaccgccgcc<br>gcccaatacatgagggagcacgacatcggcgccctgcccatctgtggagacgacgacaggctgcac<br>ggcatgctgaccgacagggacatcgtgatcaagggcctggctgccggcctcgatcctaacaccgct<br>acagccggcgagctggccagagacagcatctactacgtggacgccaacgccagcatccaggagatg<br>ctcaacgtgatggaggagcaccaggtgagaagggtgcctgtgatcagcgagcacaggctggtgggc<br>atcgtgaccgaggccgatatcgctaggcacctgccccgagcacgccatcgtgcagttcgtgaaggcc<br>atctgcagcccatggctctggccagcggcgcgcccaccccggactcctcaccacagctggagct<br>ggcaggcccagagacagatgcgccaggatcgtgtgcaccgtgttcatcgagaccgccgtggtggct<br>accatgttcgtggccctgctgggcctgagcaccatcagcagcaaggccgacgacatcgactgggac<br>gccatcgcccagtgtgaatccggcggaaactgggcgccaatacggcaatggcctgtacggcggc<br>ctgcagatcagccaggctacctgggactccaacggaggagtgggaagccctgccgctgcttcccct<br>cagcagcagatcgaggtggccgacaacatcatgaagacccaaggccctggcgcctggcctaagtgt<br>tccagctgtagccagggcgatgctcctctgggcagcctgacccacatcctgacctttctcgccgcc<br>gagacaggcggatgtagcggaagcagggacgactaatgatag (SEQ ID NO: 60) |
| | MFSRPGLPVEYLQVPSPSMGRDIKVQFQSGGNNSPAVYLLDGLRAQD<br>DYNGWDINTPAFEWYYQSGLSIVMPVGGQSSFYSDWYSPACGKAGC<br>QTYKWETFLTSELPQWLSANRAVKPTGSAAIGLSMAGSSAMILAAY<br>HPQQFIYAGSLSALLDPSQGMGPSLIGLAMGDAGGYKAADMWGPSS<br>DPAWERNDPTQQIPKLVANNTRLWVYCGNGTPNELGGANIPAEFLE<br>NFVRSSNLKFQDAYNAAGGHNAVFNFPPNGTHSWEYWGAQLNAMK<br>GDLQSSLGAGGSMTEQQWNFAGIEAAASAIQGNVTSIHSLLDEGKQS<br>LTKLAAAWGGSGSEAYQGVQQKWDATATELNNALQNLARTISEAG<br>QAMASTEGNVTGMFAEFMIATTRDREGATMITFRLRLPCRTILRVFSR<br>NPLVRGTDRLEAPGVQDSRSHVYAHQAQTRHPATATVIDHEGVTDSN<br>TTATSAPPRTKITVPARWVVNGIERSGEVNAKPGTKSGDRVGIWVDS<br>AGQLVDEPAPPARAIADSRRAILIRVRNASWQHDIDSLFCTQRELMTT<br>ARDIMNAGVTCVGEHETLTAAAQYMREHDIGALPICGDDDRLHGML<br>TDRDIVIKGLAAGLDPNTATAGELARDSIYYVDANASIQEMLNVMEE<br>HQVRRVPVISEHRLVGIVTEADIARHLPEHAIVQFVKAICSPMALASK<br>LLLGLSTISSKADDIDWDAIAQCESGGNWAANTGNGLYGGLQISQAT<br>WDSNGGVGSPAAASPQQQIEVADNIMKTQGPGAWPKCSSCSQGDAP<br>LGSLTHILTFLAAETGGCSGSRDD (SEQ ID NO: 61) |
| | MFSRPGLPVEYLQVPSPSMGRDIKVQFQSGGNNSPAVYLLDGLRAQD<br>DYNGWDINTPAFEWYYQSGLSIVMPVGGQSSFYSDWYSPACGKAGC |

| Construct | nucleotide sequence<br>amino acid sequence |
|---|---|
| | QTYKWETFLTSELPQWLSANRAVKPTGSAAIGLSMAGSSAMILAAY<br>HPQQFTYAGSLSALLDPSQGMGPSLIGLAMGDAGGYKAADMWGPSS<br>DPAWERNDPTQQIPKLVANNTRLWVYCGNGTPNELGGANIPAEFLE<br>NFVRSSNLKFQDAYNAAGGHNAVFNFPPNGTHSWEYWGAQLNAMK<br>GDLQSSLGAGPGTEQQWNFAGIEAAASAIQGNVTSIHSLLDEGKQSL<br>TKLAAAWGGSGSEAYQGVQQKWDATATELNNALQNLARTTSEAGQ<br>AMASTEGNVTGMFAFEIATTRDREGATMITFRLRLPCRTILRVFSRNP<br>LVRGTDRLEAVQDSRSHVYAHQAQTRHPATATVIDHEGVIDSNTTAT<br>SAPPRTKITVPARWVVNGIERSGEVNAKPGTKSGDRVGIWVDSAGQL<br>VDEPAPPARAIADRAILIRVRNASWQHDIDSLFCTQRRSTTARDIMNA<br>GVTCVGEHETLTAAAQYMREHDIGALPICGDDDRLHGMLTDRDIVIK<br>GLAAGLDPNTATAGELARDSIYYVDANASIQEMLNVMEEHQVRRVP<br>VISEHRLVGIVTEADIARHLPEHAIVQFVKAICSPMALASGAPTPGLLT<br>TAGAGRPRDRCARJVCTVFIETAVVATMFVALLGLSTISSKADDIDW<br>DAIAQCESGGNWAANTGNGLYGGLQISQATWDSNGGVGSPAAASPQ<br>QQTEVADNIMKTQGPGAWPKCSSCSQGDAPLGSLTHTLTFLAAETGG<br>CSGSRDD (SEQ ID NO: 62) |
| E | atggattttgcgctgctgccgccggaagtgaacagcgcgcgcatgtataccggcccgggcgcgggc<br>agcctgctggcggcggcgggcggctgggatagcctggcggcggaactggcgaccaccgcggaagcg<br>tatggcagcgtgctgagcggcctggcggcgctgcattggcgcggcccggcggcggaaagcatggcg<br>gtgagcgccgtatattggctggctgtataccaccgcggaaaaaacccagcagaccgcgattcaggc<br>gcgcgcggcggcgctggctttgaacaggcgtatgcgatgaccctgccgccgccggtggtggcggc<br>gaaccgcattcagctgctggcgctgattgcgaccaacttttttggccagaacaccgcggcgattgc<br>ggcgaccgaagcgcagtatgcggaaatgtgggcgcaggatgcggcggcgatgtatggctatgcgac<br>cgcgagcgcggcggcggcgctgctgaccccgtttagcccgccgcgccagaccaccaacccggcggg<br>cctgaccgcgcaggcggcggcggtgagccaggcgaccgatccgctgagcctgctgattgaaaccgt<br>gacccaggcgctgcaggcgctgaccattccgagctttattccggaagattttaccttcgtggatgc<br>gattttgcgggctatgcgaccgtgggcgtgacccaggatgtggaaagctttgtggcggcaccat<br>tggcgcggaaagcaacctgggcctgctgaacgtgggcgatgaaaaccgggcggaagtgaccccggg<br>cgattttggcattggcgaactggtgagcgcgaccagcccgggcggcggcgtgagcgcgagcggcgc<br>gggcggcgcggcgagcgtgggcaacaccgtgctggcgagcgtgggccgcgcgaacagcattggcca<br>gctgagcgtgccgccgagctgggcggcgccgagcacccgcccggtgagcgcgctgagcccggcggg<br>cctgaccaccctgccgggcaccgatgtggcggaacatggcatgccgggcgtgccgggcgtgccggt<br>ggcggcgggccgcgagcggcgtgctgccgcgctatggcgtgcgcctgaccgtgatggcgcatcc<br>gccggcggcgggcgaattcatgattgcgactaccgtgatcgtgaggggcgaccatgatcacgtt<br>ccgtctgcgctctgccgtgtcgcaccatttttgcgcgtgttttcgcgtaacccgctggtccgcggtac<br>cgaccgtctggaggccgttgtcatgctgctggcggttaccgtgagcctgctgacgatcccattcgc<br>agcggcagctggcacggccgtccaagacagccgtagccatgtgtatgctcaccaggctcaaaccccg<br>tcaccccggctactgccactgttatcgatcacgaaggcgtgattgactccaataccacggcaacctc<br>cgcaccgcctcgcaccaagattacggttcctgcgcgttgggtggtgaatggtattgaacgcagcgg<br>cgaagttaatgccaaaccgggtaccaaaagcggtgaccgtgtgggcatctgggtcgatagcgccgg<br>tcagctggtcgacgagccggcaccgccagcgcgtgcgatcgccgatgcggcgctggctgccctggg<br>tctgtggctgagcgtggcagcgctgccggtgcgttgctggcgcgcgcaattctgatccg<br>cgttcgcaatgcgagctggcagcacgatattgatagcctgttttgcacccaacgtgagctcatgtc<br>cacgcaacgaccgaggcactccggtattcgggctgttggccctacgcatgggccggccgatgtgg<br>tcggataggcaggtgggggtgcaccaggaggcgatgatgaatctagcgatatggcaccgcgcaa<br>ggtgcaatccgccaccatctatcaggtgaccgatcgctcgcacgacgggcgcacagcacgggtgcc<br>tggtgacgagatcactagcaccgtgtccggttggttgtcggagttgggcacccaaagccgttggc<br>cgatgagcttgcgcgtgcggtgcggatcggcgactggcccgctgcgtacgcaatcggtgagcacct<br>gtccgttgagattgccgttgcggtaagctttgctgggcctgagcaccattagcagcaaagcgga<br>tgacatcgactgggatgcgattgcgcagtgtgagagcggtggcagcggtgaataccggcaa<br>tggcctgtacggcggtctgcagatctcccaggcgacgtgggacagcaatggtggcgtcggcagccc<br>ggctgccgcgtcccacaacaacagatcgaggtggcagataacattatgaaaacgcagggtccggg<br>tgcttggccaaaatgctccagctgcagccagggtgacgcaccgctgggcagcctgacccacattct<br>gacgttcctggcagcggaaaccggtggttgtagcggtagccgcgatgactga<br>(SEQ ID NO: 63)<br>MDFALLPPEVNSARMYTGPGAGSLLAAAGGWDSLAAELATTAEAY<br>GSVLSGLAALHWRGPAAESMAVTAAPYIGWLYTTAEKTQQTAIQAR<br>AAALAFEQAYAMTLPPPVVAANRIQLLALIATNFFGQNTAAIAATEA<br>QYAEMWAQDAAAMYGYATASAAAALLTPFSPPRQTTNPAGLTAQA<br>AAVSQATDPLSLLIETVTQALQALTIPSFIPEDFTFLDAIFAGYATVGV<br>TQDVESFVAGTIGAESNLGLLNVGDENPAEVTPGDFGIGELVSATSPG<br>GGVSASGAGGAASVGNTVLASVGRANSIGQLSVPPSWAAPSTRPVSA<br>LSPAGLTTLPGTDVAEHGMPGVPGVPVAAGRASGVLPRYGVRLTVM<br>AHPPAAGEFEFMIATTRDREGATMTTFRLRLPCRTILRVFSRNPLVRGT<br>DRLEAVVMLLAVTVSLLTIPFAAAAGTAVQDSRSHVYAHQAQTRHP<br>ATATVIDHEGVIDSNTTATSAPPRTKITVPARWVVNGIERSGEVNAKP<br>GTKSGDRVGIWVDSAGQLVDEPAPPARAIADAALAALGLWLSVAAV<br>AGALLALTRAILIRVRNASWQHDIDSLFCTQRELMSTQRPRHSGIRAV<br>GPYAWAGRCGRIGRWGVHQEAMMNLAIWHPRKVQSATIYQVTDRS<br>HDGRTARVPGDEITSTVSGWLSELGTQSPLADELARAVRIGDWPAAY<br>AIGEHLSVEIAVAVKLLLGLSTISSKADDIDWDAIAQCESGGNWAAN<br>TGNGLYGGLQISQATWDSNGGVGSPAAASPQQQIEVADNIMKTQGP<br>GAWPKCSSCSQGDAPLGSLTHILTFLAAETGGCSGSRDD (SEQ ID<br>NO: 64) |

| Construct | nucleotide sequence<br>amino acid sequence |
|---|---|
| F | atggattttgcgctgctgccgccggaagtgaacagcgcgcgcatgtataccggcccgggcgcgggc<br>agcctgctggcggcggcggcggctgggatagcctggcggcggaactggcgaccaccgcggaagcg<br>tatggcagcgtgctgagcggcctggcggcgctgcattggcgcggcccggcggcggaaagcatggcg<br>gtgaccgcggcgccgtatattggctggctgtataccaccgcggaaaaaacccagcagaccgcgatt<br>caggcgcgcgcggcggcgctggcgtttgaacaggcgtatgcgatgaccctgccgccgccggtggtg<br>gcggcgaaccgcattcagctgctggcgctgaaatgcgaccaactttttttggccagaacaccgcggcg<br>attgcggcgaccgaagcgcagtatgcggaaatgtgggcgcaggatgcggcggcgatgtatggctat<br>gcgaccgcgagcgcggcggcggcgctgctgaccccgtttagcccgccgcgccagaccaccaacccg<br>gcgggcctgaccgcgcaggcggcggcggtgagccaggcgaccgatccgctgagcctgctgattgaa<br>accgtgacccaggcgctgcaggcgctgaccattccgagctttattccggaagattttacctttctg<br>gatgcgattttgcgggctatgcgaccgtgggcgtgacccaggatgtggaaagctttgtggcgggc<br>accattggcgcggaaagcaacctgggcctgctgaacgtgggcgatgaaaacccggcggaagtgacc<br>ccgggcgattttggcattggcgaactggtgagcgcgaccagcccgggcggcggcgtgagcgcgagc<br>ggcgcgggcggcgcggcgagcggcaacaccgtgctggcgagcgtgggccgcgcgaacagcatt<br>ggccagctgagcgtgccgccgagctgggcggcgccgagcacccgccggtgagcgcgctgagcccg<br>gcgggcctgaccacctgccgggcaccgatgtggcggaacatggcatgccgggcgtgccgggcgtg<br>ccggtggcggcgggccgcgcgagcggcgtgctgccgcgctatggcgtgcgcctgaccgtgatggcg<br>catccgccggcggcgggcgaattcatgattgcgactacccgtgatcgtgagggcgcgaccatgatc<br>acgttccgtctgcgtctgccgtgtcgcaccatttttgcgcgtgttttcgcgtaacccgctggtccgc<br>ggtaccgaccgtctggaggccgttgtcatgctgctggcggttaccgtgagcctgctgacgatccca<br>ttcgcagcggcagctggcacggccgtccaagacagccgtagccatgtgtatgctcaccaggctcaa<br>acccgtcacccggctactgccactgttatcgatcacgaaggcgtgattgactccaataccacggca<br>acctccgcaccgcctcgcaccaagattacggttcctgcgcgttgggtggtgaatggtattgaacgc<br>agcggcgaagttaatgccaaaccgggtaccaaaagcggtgaccgtgtgggcatctgggtcgatagc<br>gccggtcagctggtcgacgagccggcaccgccagcgcgtgcgatcgccgatgcggcgctggctgcc<br>ctgggtctgtggctgagcgtgagcggtcgccggtcgttgctggcgctgaccgcggcaattctg<br>atccgcgttcgcaatgcgagctggcagcacgatattgatagcctgttttgcacccaacgtgagctc<br>atgtccacgcaacgaccgaggcactccggtattcgggctgttggcccctacgcatgggcggcgga<br>tgtggtcggataggcaggtgggggggtgcaccaggaggcgatgatgaatctagcgatatggcacccg<br>cgcaaggtcaatccgccaccatctatcaggtgaccgatcgctcgacgacgggcgcacagcacgg<br>gtgcctggtgacgagatcactagcaccgtgtccggttggttgtcggagttgggcacccaaagcccg<br>ttggccgatgagcttgcgcgtgcggtgcggatcggcgactggccccgctgcgtacgcaatcggtgag<br>cacctgtccgttgagattgccgttgcggtcaagcttgcatgcaaaacggtgacgttgaccgtcgac<br>ggaaccgcgatgcgggtgaccacgatgaaatcgcgggtgatcgacatcgtcgaagagaacgggttc<br>tcagtcgacgaccgcgacgacctgtatcccgcggccggccggcaggtccatgacgccgacaccatc<br>gtgctgcgcgctagccgtccgctgcagatctcgctggatggtcacgacgctaagcaggtgtggacg<br>accgcgtcgacggtggacgaggcgctggcccaactcgcgatgaccgacacggcgccggccgcggct<br>tctcgcgccagccgcgtcccgctgtccgggatggcgctaccggtcgtcagcgccaagacggtgcag<br>ctcaacgacggcgggttggtgcgcacggtgcacttgccggccccaatgtcgcggggcgtcgctgagt<br>gcggccggcgtgccgctgttgcaaagcgaccacgtggtgcccgccgcgacggccccgatcgtcgaa<br>ggcatgcagatccaggtgacccgcaatcggatcaagaaggtcaccgagcggctgccgctgccgccg<br>aacgcgcgtcgtgtcgaggacccggagatgaacatgagccgggaggtcgtcgaagacccgggggtt<br>ccggggaccaggatgtgacgttcgcggtagctgaggtcaacggtcgaggacgcgccgttgccc<br>gtcgccaacgtcgtggtgaccccggcccacgaagccgtggtgcgggtgggcaccaagcccggtacc<br>gaggtgcccccggtgatcgacggaagcatctgggacgcgatcgccggctgtgaggccggtggcaac<br>tgggcgatcaacaccggcaacgggtattacgtggtgtgcagtttgaccagggcacctgggaggcc<br>aacgcggggctgcggtatgcaccccgcgctgacctcgccacccgcgaagagcagatcgccgttgcc<br>gaggtgacccgactgcgtcaaggttggggcgcctggccggtatgtgctgcacgagcgggtgcgcgc<br>tga (SEQ ID NO: 65)<br>MDFALLPPEVNSARMYTGPGAGSLLAAAGGWDSLAAELATTAEAY<br>GSVLSGLAALHWRGPAAESMAVTAAPYIGWLYTTAEKTQQTAIQAR<br>AAALAFEQAYAMTLPPPVVAANRIQLLALIATNFFGQNTAAIAATEA<br>QYAEMWAQDAAAMYGYATASAAAALLTPFSPPRQTTNPAGLTAQA<br>AAVSQATDPLSLLIETVTQALQALTIPSFIPEDFTFLDAIFAGYATVGV<br>TQDVESFVAGTIGAESNLGLLNVGDENPAEVTPGDFGIGELVSATSPG<br>GGVSASGAGGAASVGNTVLASVGRANSIGQLSVPPSWAAPSTRPVSA<br>LSPAGLTTLPGTDVAEHGMPGVPGVPVAAGRASGVLPRYGVRLTVM<br>AHPPAAGEFMIATTRDREGATMITFRLRLPCRTILRVFSRNPLVRGTD<br>RLEAVVMLLAVTVSLLTIPFAAAAGTAVQDSRSHVYAHQAQTRHPA<br>TATVIDHEGVIDSNTTATSAPPRTKITVPARWVVNGIERSGEVNAKPG<br>TKSGDRVGIWDSAGQLVDEPAPPARAIADAALAALGLWLSVAAVA<br>GALLALTRAILIRVRNASWQHDIDSLFCTQRELMSTQRPRHSGIRAVG<br>PYAWAGRCGRIGRWGVHQEAMMNLAIWHPRKVQSATIYQVTDRSH<br>DGRTARVPGDEITSTVSGWLSELGTQSPLADELARAVRIGDWPAAYA<br>IGEHLSVEIAVAVKLACKTVTLTVDGTAMRVTTMKSRVIDIVEENGF<br>SVDDRDDLYPAAGVQVHDADTIVLRRSRPLQISLDGHDAKQVWTTA<br>STVDEALAQLAMTDTAPAAASRASRVPLSGMALPVVSAKTVQLNDG<br>GLVRTVHLPAPNVAGLLSAAGVPLLQSDHVVPAATAPIVEGMQIQVT<br>RNRIKKVTERLPLPPNARRVEDPEMNMSREVVEDPGVPGTQDVTFAV<br>AEVNGVETGRLPVANVVVTPAHEAVVRVGTKPGTEVPPVIDSIWD<br>AIAGCEAGGNWAINTGNGYYGVQFDQGTWEANGGLRYAPRADLA<br>TREEQIAVAEVTRLRQGWGAWPVCAARAGAR (SEQ ID NO: 66) |
| G | atgcgtgcgactgtgggtctggttgaggcgattggcattcgcgagctgcgccaacatgccagccgt<br>tacttggctcgtgtcgaggcgggtgaagaactgggcgtgacgaataagggtcgtctggtcgcccgt |

-continued

| Construct | nucleotide sequence<br>amino acid sequence |
|---|---|
| | ctgattccggttcaggcagctgagcgttctcgcgaggcgctgattgaatccggcgtcctgatcccg<br>gctcgccgtccgcaaaacctgctggacgtgacggcggagccagctcgtggtcgcaaacgcacgctg<br>tctgatgtcctgaacgaaatgcgcgacgagcaggaattcatgattgcgactacccgtgatcgtgag<br>ggcgcgaccatgatcacgttccgtctgcgtctgccgtgtcgcaccattttgcgcgtgttttcgcgt<br>aacccgctggtccgcggtaccgaccgtctggaggccgttgtcatgctgctggcggttaccgtgagc<br>ctgctgacgatcccattcgcagcggcagctggcacggccgtccaagacagccgtagccatgtgtat<br>gctcaccaggctcaaacccgtcacccggctactgccactgttatcgatcacgaaggcgtgattgac<br>tccaataccacggcaacctccgcaccgcctcgcaccaagattacggttcctgcgcgttgggtggtg<br>aatggtattgaacgcagcggcgaagttaatgccaaacgggtaccaaaagcggtgaccgtgtgggc<br>atctgggtcgatagcgccggtcagctggtcgacgagccggcaccgccagcgcgtgcgatcgccgat<br>gcggcgctggctgccctgggtctgtggctgagcgtggcagcggtcgccggtgcgttgctggcgctg<br>acgcgcgcaattctgatccgcgttcgcaatgcgagctggcagcacgatattgatagcctgttttgc<br>acccaacgtgagctcatgaccacggcgcgtgatatcatgaatgcgggtgtcacctgtgttggcgag<br>cacgaaacgttgaccgcagcagcacagtacatgcgcgaacatgatatcggcgcattgccgatttgc<br>ggcgacgatgatcgtctgcacggtatgctgaccgaccgcgatatcgttatcaagggtctggccgca<br>ggcttggacccgaacaccgcgaccgccggtgaactggcacgtgacagcatctattacgtcgacgcg<br>aacgccagcattcaagagatgctgaacgtgatggaagagcatcaggtgcgtcgtgtcccggttatc<br>agcgaacatcgtctggttggtatcgttaccgaagccgacatcgcacgtcacctgccggagcacgcg<br>attgttcagttcgtgaaagcgatttgcagcccgatggcgttggcgtctcgtcaaaagggcgacaca<br>aaatttattctaaatgcaaagcttgcatgcaaaacggtgacgttgaccgtcgacggaaccgcgatg<br>cgggtgaccacgatgaaatcgcgggtgatcgacatcgtcgaagagaacgggtctcagtcgacgac<br>cgcgacgacctgtatcccgcggccggcgtgcaggtccatgacgccgacaccatcgtgctgcggcgt<br>agccgtccgctgcagatctcgctggatggtcacgacgctaaggtgtggaccgacgcgtcgacg<br>gtggacgaggcgctggcccaactcgcgatgaccgacacggcgccggccgcggcttctcgcgccagc<br>cgcgtcccgctgtccgggatggcgctaccggtcgtcagcgccaagacggtgcagctcaacgacggc<br>gggttggtgcgcacggtgcacttgccggcccccaatgtcgcggggctgctgagtgcggccggcgtg<br>ccgctgttgcaaagcgaccacgtggtgcccgccgcgacggcccccgatcgtcgaaggcatgcagatc<br>caggtgacccgcaatcggatcaagaaggtcaccgagcggctgccgctgccgccaacgcgcgtcgt<br>gtcgaggacccggagatgaacatgagccgggaggtcgtcgaagacccgggggttccggggacccag<br>gatgtgacgttcgcggtagctgaggtcaacggcgtcgagaccggccgtttgcccgtcgccaacgtc<br>gtggtgaccccggcccacgaagccgtggtgcgggtgggcaccaagccccggtaccgaggtgccccg<br>gtgatcgacggaagcatctgggacgcgatcgccggcgtgtgaggccggtggcaactgggcgatcaac<br>accggcaacgggtattacgtggtgtgcagtttgaccagggcacctgggaggccaacggcgggctg<br>cggtatgcaccccgcgctgacctcgccacccgcgaagagcagatcgccgttgccgaggtgacccga<br>ctgcgtcaaggttgggcgcctggccggtatgtgctgcacgagcgggtgcgcgctga<br>(SEQ ID NO: 67)<br>MRATVGLVEAIGIRELRQHASRYLARVEAGEELGVTNKGRLVARLIP<br>VQAAERSREALIESGVLIPARRPQNLLDVTAEPARGRKRTLSDVLNE<br>MRDEQEFMIATTRDREGATMITFRLRLPCRTILRVFSRNPLVRGTDRL<br>EAVVMLLAVTVSLLTIPFAAAAGTAVQDSRSHVYAHQAQTRHPATA<br>TVIDHEGVIDSNTTATSAPPRTKITVPARWVNGTERSGEVNAKPGTK<br>SGDRVGIWVDSAGQLVDEPAPPARAIADAALAALGLWLSVAAVAGA<br>LLALTRAILIRVRNASWQHDIDSLFCTQRELMTTARDIMNAGVTCVG<br>EHETLTAAAQYMREHDIGALPICGDDDRLHGMLTDRDIVIKGLAAGL<br>DPNTATAGELARDSIYYVDANASIQEMLNVMEEHQVRRVPVISEHRL<br>VGIVTEADIARHLPEHAIVQFVKAICSPMALASRQKGDTKFILNAKLA<br>CKTVTLTVDGTAMRVTTMKSRVIDIVEENGFSVDDRDDLYPAAGVQ<br>VHDADTIVLRRSRPLQISLDGHDAKQVWTTASTVDEALAQLAMTDT<br>APAAASRASRVPLSGMALPWSAKTVQLNDGGLVRTVHLPAPNVAG<br>LLSAAGVPLLQSDHVVPAATAPIVEGMQIQVTRNRIKKVTERLPLPPN<br>ARRVEDPEMNMSREVVEDPGVPGTQDVTFAVAEVNGVETGRLPVA<br>NVVVTPAHEAVVRVGTKPGTEVPPVIDGSIWDAIAGCEAGGNWAINT<br>GNGYYGGVQFDQGTWEANGGLRYAPRADLATREEQIAVAEVTRLR<br>QGWGAWPVCAARAGAR (SEQ ID NO: 68) |
| H | atgcgtgcgactgtgggtctggttgaggcgattggcattcgcgagctgcgccaacatgccagccgt<br>tacttggctcgtgtcgaggcgggtgaagaactgggcgtgacgaataagggtcgtctggtcgcccgt<br>ctgattccggttcaggcagctgagcgttctcgcgaggcgctgattgaatccggcgtcctgatcccg<br>gctcgccgtccgcaaaacctgctggacgtgacggcggagccagctcgtggtcgcaaacgcacgctg<br>tctgatgtcctgaacgaaatgcgcgacgagcaggaattcatgattgcgactacccgtgatcgtgag<br>ggcgcgaccatgatcacgttccgtctgcgtctgccgtgtcgcaccattttgcgcgtgttttcgcgt<br>aacccgctggtccgcggtaccgaccgtctggaggccgttgtcatgctgctggcggttaccgtgagc<br>ctgctgacgatcccattcgcagcggcagctggcacggccgtccaagacagccgtagccatgtgtat<br>gctcaccaggctcaaacccgtcacccggctactgccactgttatcgatcacgaaggcgtgattgac<br>tccaataccacggcaacctccgcaccgcctcgcaccaagattacggttcctgcgcgttgggtggtg<br>aatggtattgaacgcagcggcgaagttaatgccaaacgggtaccaaaagcggtgaccgtgtgggc<br>atctgggtcgatagcgccggtcagctggtcgacgagccggcaccgccagcgcgtgcgatcgccgat<br>gcggcgctggctgccctgggtctgtggctgagcgtggcagcggtcgccggtgcgttgctggcgctg<br>acgcgcgcaattctgatccgcgttcgcaatgcgagctggcagcacgatattgatagcctgttttgc<br>acccaacgtgagctcatgaccacggcgcgtgatatcatgaatgcgggtgtcacctgtgttggcgag<br>cacgaaacgttgaccgcagcagcacagtacatgcgcgaacatgatatcggcgcattgccgatttgc<br>ggcgacgatgatcgtctgcacggtatgctgaccgaccgcgatatcgttatcaagggtctggccgca<br>ggcttggacccgaacaccgcgaccgccggtgaactggcacgtgacagcatctattacgtcgacgcg<br>aacgccagcattcaagagatgctgaacgtgatggaagagcatcaggtgcgtcgtgtcccggttatc<br>agcgaacatcgtctggttggtatcgttaccgaagccgacatcgcacgtcacctgccggagcacgcg<br>attgttcagttcgtgaaagcgatttgcagcccgatggcgttggcgtctcgtcaaaagggcgacaca |

| Construct | nucleotide sequence<br>amino acid sequence |
|---|---|
| | aaatttattctaaatgcaaagcttttgctgggcctgagcaccattagcagcaaagcggatgacatc<br>gactgggatgcgattgcgcagtgtgagagcggtggcaattgggcagcgaataccggcaatggcctg<br>tacggcggtctgcagatctcccaggcgacgtgggacagcaatggtggcgtcggcagcccggctgcc<br>gcgtccccacaacaacagatcgaggtggcagataacattatgaaacgcagggtccgggtgcttgg<br>ccaaaatgctccagctgcagccagggtgacgcaccgctgggcagcctgacccacattctgacgttc<br>ctggcagcggaaaccggttgtagcggtagccgcgatgactga (SEQ ID NO: 69)<br>MRATVGLVEAIGIRELRQHASRYLARVEAGEELGVTNKGRLVARLIP<br>VQAAERSREALIESGVLIPARRPQNLLDVTAEPARGRKRTLSDVLNE<br>MRDEQEFMIATTRDREGATMITFRLRLPCRTILRVFSRNPLVRGTDRL<br>EAVVMLLAVTVSLLTIPFAAAAGTAVQDSRSHVYAHQAQTRHPATA<br>TVIDHEGVIDSNTTATSAPPRTKITVPARWVVNGIERSGEVNAKPGTK<br>SGDRVGIWVDSAGQLVDEPAPPARAIADAALAALGLWLSVAAVAGA<br>LLALTRAILIRVRNASWQHDIDSLFCTQRELMTTARDIMNAGVTCVG<br>EHETLTAAAQYMREHDIGALPICGDDDRLHGMLTDRDIVIKGLAAGL<br>DPNTATAGELARDSIYYVDANASIQEMLNVMEEHQVRRVPVISEHRL<br>VGIVTEADIARHLPEHAIVQFVKAICSPMALASRQKGDTKFILNAKLL<br>LGLSTISSKADDIDWDAIAQCESGGNWAANTGNGLYGGLQISQATW<br>DSNGGVGSPAAASPQQQIEVADNIMKTQGPGAWPKCSSCSQGDAPL<br>GSLTHILTFLAAETGGCSGSRDD (SEQ ID NO: 70) |
| I | atggattttgcgctgctgccgccggaagtgaacagcgcgcgcatgtataccggcccgggcgcgggc<br>agcctgctggcggcggcgggcggctgggatagcctggcggcggaactggcgaccaccgcggaagcg<br>tatggcagcgtgctgagcggcctggcggcgctgcattggcgcggccggcggcggaaagcatggcg<br>gtgaccgcggcgccgtatattggctggctgtataccaccgcggaaaaaacccagcagaccgcgatt<br>caggcgcgcgcggcggcgctggcgtttgaacaggcgtatgcgatgaccctgccgccgccggtggtg<br>gcggcgaaccgcattcagctgctggcgctgattgcgaccaacttttttggccagaacaccgcggcg<br>attgcggcgaccgaagcgcagtatgcggaaatgtgggcgcaggatgcggccggcgatgtatggctat<br>gcgaccgcgagcgcggcggcggcgctgctgaccccgtttagcccgccgcgccagaccaccaacccg<br>gcgggcctgaccgcgcaggcggcggcggtgagccaggcgaccgatccgctgagcctgctgattgaa<br>accgtgacccaggcgctgcaggcgctgaccattccgagctttattccggaagattttacctttctg<br>gatgcgattttttgcgggctatgcgaccgtgggcgtgacccaggatgtggaaagctttgtggcgggc<br>accattggcgcggaaagcaacctgggcctgctgaacgtgggcgatgaaaaccggcggaagtgacc<br>ccgggcgattttggcattggcgaactggtgagcgcgaccagcccgggcggcggcgtgagcgcgagc<br>ggcgcgggcggcgcggcgagcgtgggcaacaccgtgctggcgagcgtgggccgcgcgaacagcatt<br>ggccagctgagcgtgccgccgagctgggcggcgccgagcacccgcccggtgagcgcgctgagcccg<br>gcgggcctgaccaccctgccgggcaccgatgtggcggaacatggcatgccgggcgtgccgggcgtg<br>ccggtggcggcgggccgcgcgagcggcgtgctgccgcgctatggcgtgcgcctgaccgtgatggcg<br>catccgccggcggcgggcgaatttatgacagagcagcagtggaatttcgcgggtatcgaggccgcg<br>gcaagcgcaatccagggaaatgtcacgtccattcattccctccttgacgaggggaagcagtccctg<br>accaagctcgcagcggcctggggcggtagcggttcggaggcgtaccagggtgtccagcaaaaatgg<br>gacgccacggctaccgagctgaacaacgcgctgcagaacctggcgcggacgatcagcgaagccggt<br>caggcaatggcttcgaccgaaggcaacgtcactgggatgttcgcagaattcatgattgcgactacc<br>cgtgatcgtgagggcgcgaccatgatcacgttccgtctgcgtctgccgtgtcgcaccatttttgcgc<br>gtgttttcgcgtaaccgctggtccgcggtaccgaccgtctggaggccgttgtcatgctgctggcg<br>gttaccgtgagcctgctgacgatcccattcgcagcggcagctggcacggccgtccaagacagccgt<br>agccatgtgtatgctcaccaggctcaaacccgtcaccggctactgccactgttatcgatcacgaa<br>ggcgtgattgactccaataccacggcaacctccgcaccgcctcgcaccaagattacggttcctgcg<br>cgttgggtggtgaatggtattgaacgcagcggcgaagttaatgccaaaccgggtaccaaaagcggt<br>gaccgtgtgggcatctgggtcgatagcgccggtcagctggtcgacgagccggcaccgccagcgt<br>gcgatcgccgatgcggcgctgctgccctgggtctgtggctgagcgtggcagcggtcgccggtgcg<br>ttgctggcgctgacgcgcgcaattctgatccgcgttcgcaatgcgagctggcagcacgatattgat<br>agcctgttttgcacccaacgtgagctcatgaccacggcgcgtgatatcatgaatgcgggtgtcacc<br>tgtgttggcgagcacgaaacgttgaccgcagcagcacagtacatgcgcgaacatgatatcggcgca<br>ttgccgatttgcggcgacgatgatcgtctgcacggtatgctgaccgaccgcgatatcgttatcaag<br>ggtctggccgcaggcttggacccgaacaccgcgaccgccggtgaactggcacgtgacagcatctat<br>tacgtcgacgcgaacgccagcattcaagagatgctgaacgtgatggaagagcatcaggtgcgtcgt<br>gtcccggttatcagcgaacatcgtctggttggtatcgttaccgaagccgacatcgcacgtcacctg<br>ccggagcacgcgattgttcagttcgtgaaagcgatttgcagcccgatggcgttggcgtctcgtcaa<br>aagggcgacacaaaatttattctaaatgcaaagctttgctgggcctgagcaccattagcagcaaa<br>gcggatgacatcgactgggatgcgattgcgcagtgtgagagcggtggcaattgggcagcgaatacc<br>ggcaatggcctgtacggcggtctgcagatctcccaggcgacgtgggacagcaatggtggcgtcggc<br>agcccggctgccgcgtccccacaacaacagatcgaggtggcagataacattatgaaaacgcaggt<br>ccgggtgcttggccaaaatgctccagctgcagccagggtgacgcaccgctgggcagcctgacccac<br>attctgacgttcctggcagcggaaaccggtggttgtagcggtagccgcgatgactga<br>(SEQ ID NO: 71)<br>MDFALLPPEVNSARMYTGPGAGSLLAAAGGWDSLAAELATTAEAY<br>GSVLSGLAALHWRGPAAESMAVTAAPYIGWLYTTAEKTQQTAIQAR<br>AAALAFEQAYAMTLPPPVVAANRIQLLALIATNFFGQNTAAIAATEA<br>QYAEMWAQDAAAMYGYATASAAAALLTPFSPPRQTTNPAGLTAQA<br>AAVSQATDPLSLLIETVTQALQALTIPSFIPEDFTFLDAIFAGYATVGV<br>TQDVESFVAGTIGAESNLGLLNVGDENPAEVTPGDFGIGELVSATSPG<br>GGVSASGAGGAASVGNTVLASVGRANSIGQLSVPPSWAAPSTRPVSA<br>LSPAGLTTLPGTDVAEHGMPGVPGVPVAAGRASGVLPRYGVRLTVM<br>AHPPAAGEFMIATTPvDREGATMITFRLRLPCRTILRVFSRNPLVRGTD<br>RLEAVVMLLAVTVSLLTIPFAAAAGTAVQDSRSHVYAHQAQTRHPA<br>TATVIDHEGVIDSNTTATSAPPRTKITVPARWVVNGIERSGEVNAKPG |

| Construct | nucleotide sequence<br>amino acid sequence |
|---|---|
| | TKSGDRVGIWVDSAGQLVDEPAPPARAIADAALAALGLWLSVAAVA<br>GALLALTRAILIRVRNASWQHDIDSLFCTQRELMTTARDIMNAGVTC<br>VGEHETLTAAAQYMREHDIGALPICGDDDRLHGMLTDRDIVIKGLAA<br>GLDPNTATAGELARDSIYYVDANASIQEMLNVMEEHQVRRVPVISEH<br>RLVGIVTEADIARHLPEHAIVQFVKAICSPMALASRQKGDTKFILNAK<br>LLLGLSTISSKADDIDWDAIAQCESGGNWAANTGNGLYGGLQISQAT<br>WDSNGGVGSPAAASPQQQIEVADNIMKTQGPGAWPKCSSCSQGDAP<br>LGSLTHILTFLAAETGGCSGSRDDKMK (SEQ ID NO: 72) |
| J | atggattttgcgctgctgccgccggaagtgaacagcgcgcgcatgtataccggcccgggcgcgggc<br>agcctgctggcggcggcggcggctgggatagcctggcggcggaactggcgaccaccgcggaagcg<br>tatggcagcgtgctgagcggcctggcggcgctgcattggcgcggcccggcggcggaaagcatggcg<br>gtgaccgcggcgccgtatattggctggctgtataccaccgcggaaaaaacccagcagaccgcgatt<br>caggcgcgcgcggcggcgctggcgtttgaacaggcgtatgcgatgaccctgccgccgccggtggtg<br>gcggcgaaccgcattcagctgctggcgctgattgcgaccaacttttttggccagaacaccgcggcg<br>attgcggcgaccgaagcgcagtatgcggaaatgtgggcgcaggatgcggcggcgatgtatggctat<br>gcgaccgcgagcgcggcggcggcgctgctgaccccgtttagcccgccgcgccagaccaccaacccg<br>gcgggcctgaccgcgcaggcggcggcggtgagccaggcgaccgatccgctgagcctgctgattgaa<br>accgtgacccaggcgctgcagctgaccattccgagctttattccggaagattttaccttctg<br>gatgcgattttcgcgggctatgcgaccgtgggcgtgaccccaggatgtggaaagctttgtggcgggc<br>accattggcgcggaaagcaacctgggcctgctgaacgtgggcgatgaaaacccggcggaagtgacc<br>ccgggcgattttggcattggcgaactggtgagcgcgaccagcccgggcggcggcgtgagcgcgagc<br>ggcgcggggcggcgcggcgagcgtgggcaacaccgtgctggcgagcgtgggccgcgcgaacagcatt<br>ggccagctgagcgtgccgccgagctggcggcgccgagcacccgccggtgagcgcgctgagcccg<br>gcgggcctgaccaccctgccgggcaccgatgtggcggaacatggcatgccgggcgtgccgggcgtg<br>ccggtggcggcgggccgcgcgagcggcgtgctgccgcgctatggcgtgcgcctgaccgtgatggcg<br>catccgccggcggcgggcgaatttatgacagagcagcagtggaatttcgcgggtatcgaggccgcg<br>gaagcgcaatccaggggaaatgtcacgtccattcattccctccttgacgaggggaagcagtccctga<br>ccaagctcgcagcggcctggggcggtagcggttcggaggcgtaccagggtgtccagcaaaaatggg<br>acgccacggctaccgagctgaacaacgcgctgcagaacctggcgcggacgatcagcgaagccggtc<br>aggcaatggcttcgaccgaaggcaacgtcactgggatgttcgc<b>gaattc</b>atgattgcgactaccc<br>gtgatcgtgaggcgcgaccatgatcacgttccgtctgctctgcctgtcgccgtgtcgcaccattttgcgcg<br>tgttttcgcgtaacccgctggtccgcggtaccgaccgtctggaggccgttgtcatgctgctggcgg<br>ttaccgtgagcctgctgacgatcccattcgcagcggcagctggcacggccgtccaagacagccgta<br>gccatgtgtatgctcaccaggctcaaaccgtcacccggctactgccactgttatcgatcacgaag<br>gcgtgattgactccaataccacggcaacctccgcaccgcctcgcaccaagattacggttcctgcgc<br>gttgggtggtgaatggtattgaacgcagcggcgaagttaatgccaaacgggtaccaaaagcggtg<br>accgtgtgggcatctgggtcgatagcgccggtcagctggtcgacgagccggcaccgccagcgcgtg<br>cgatcgccgatgcggcgctggctgccctgggtctgtggctgagcgtggcagcggtcgccggtgcgt<br>tgctggcgctgacgcgcgcaattctgatccgcgttcgcaatgcgagctggcacgatattgata<br>gcctgttttgcacccaacgt<b>gagctc</b>atgaccacggcgcgtgatatcatgaatgcgggtgtcacct<br>gtgttggcgagcacgaaacgttgaccgcagcagcacagtacatgcgcgaacatgatatcggcgcat<br>tgccgatttgcggcgacgatgatcgtctgcacggtatgctgaccgaccgcgatatcgttatcaagg<br>gtctggccgcaggcttggaccgaacaccgcgaccgccggtgaactggcgacagcatctatt<br>acgtcgacgcgaacgccagcattcaagagatgctgaacgtgatggaagagcatcaggtcgctcgtg<br>tcccggttatcagcgaacatcgtctggttggtatcgttaccgaagccgacatcgcacgtcacctgc<br>cggagcacgcgattgttcagttcgtgaaagcgatttgcagcccgatggcgttggcgtctcgtcaaa<br>agggcgacacaaaatttattctaaatgc<b>aaagctt</b>gcatgcaaaacggtgacgttgaccgtcgcg<br>gaaccgcgatgcgggtgaccacgatgaaatcgcgggtgatcgacatcgtcgaagagaacgggttct<br>cagtcgacgaccgcgacgacctgtatcccgcggccggcgtgcaggtccatgacgccgacaccatcg<br>tgctgcggcgtagccgtccgctgcagatctcgctggatggtcacgacgctaagcaggtgtggacga<br>ccgcgtcgacggtggacgaggcgctggccaactcgcgatgaccgacacggcgccggccggcgctt<br>ctcgcgccagccgcgtcccgctgtccgggatggcgctaccggtcgtcagcgccaagacggtggcagc<br>tcaacgacggcgggttggtgcgcacggtgcacttgccggccccaatgtcgcggggctgctgagtg<br>cggccggcgtgccgctgttgcaaagcgaccacgtggtgcccgccgcgacggccccgatcgtcgaag<br>gcatgcagatccaggtgacccgcaatcggatcaagaaggtcaccgagcggctgccgctgccgccga<br>acgcgcgtcgtgtcgagggaccggagatgaacatgagcgggaggtcgtcgaagaccgggggttc<br>cggggacccaggatgtgacgttcgcggtagctgaggtcaacggcgtcgagaccggccgtttgcccg<br>tcgccaacgtcgtggtgaccccggcccacgaagccgtggtgcgggtgggcaccaagcccggtaccg<br>aggtgccccggtgatcgacgaagcatctgggacgcgatcgccggctgtgaggccggtggcaact<br>gggcgatcaacaccggcaacgggtattacggtggtgtgcagtttgaccagggcacctggggagcca<br>acggcgggctgcggtatgcaccccgcgctgacctcgccacccgcgaagagcagatcgccgttgccg<br>aggtgacccgactgcgtcaaggttggggcgcctggccggtatgtgctgcacgagcgggtgcgcgct<br>ga (SEQ ID NO: 73)<br>MDFALLPPEVNSARMYTGPGAGSLLAAAGGWDSLAAELATTAEAY<br>GSVLSGLAALHWRGPAAESMAVTAAPYIGWLYTTAEKTQQTAIQAR<br>AAALAFEQAYAMTLPPPVVAANRIQLLALIATNFFGQNTAAIAATEA<br>QYAEMWAQDAAAMYGYATASAAAALLTPFSPPRQTTNPAGLTAQA<br>AAVSQATDPLSLLIETVTQALQALTIPSFIPEDFTFLDAIFAGYATVGV<br>TQDVESFVAGTIGAESNLGLLNVGDENPAEVTPGDFGTGELVSATSPG<br>GGVSASGAGGAASVGNTVLASVGRANSIGQLSVPPSWAAPSTRPVSA<br>LSPAGLTTLPGTDVAEHGMPGVPGVPVAAGRASGVLPRYGVRLTVM<br>AHPPAAGEFMIATTRDREGATMITFRLRLPCRTILRVFSRNPLVRGTD<br>RLEAVVMLLAVTVSLLTIPFAAAAGTAVQDSRSHVYAHQAQTRHPA<br>TATVIDHEGVIDSNTTATSAPPRTKITVPARWVVNGIERSGEVNAKPG<br>TKSGDRVGIWVDSAGQLVDEPAPPARAIADAALAALGLWLSVAAVA |

| Construct | nucleotide sequence<br>amino acid sequence |
|---|---|
| | GALLALTRAILIRVRNASWQHDIDSLFCTQRELMTTARDIMNAGVTC<br>VGEHETLTAAAQYMREHDIGALPICGDDDRLHGMLTDRDIVIKGLAA<br>GLDPNTATAGELARDSIYYVDANASIQEMLNVMEEHQVRRVPVISEH<br>RLVGIVTEADIARHLPEHAIVQFVKAICSPMALASRQKGDTKFILNAK<br>LACKTVTLTVDGTAMRVTTMKSRVIDIVEENGFSVDDRDDLYPAAG<br>VQVHDADTIVLRRSRPLQISLDGHDAKQVWTTASTVDEALAQLAMT<br>DTAPAAASRASRVPLSGMALPVVSAKTVQLNDGGLVRTVHLPAPNV<br>AGLLSAAGVPLLQSDHVVPAATAPIVEGMQIQVTRNRIKKVTERLPLP<br>PNARRVEDPEMNMSREVVEDPGVPGTQDVTFAVAEVNGVETGRLPV<br>ANVVVTPAHEAVVRVGTKPGTEVPPVIDGSIWDAIAGCEAGGNWAI<br>NTGNGYYGGVQFDQGTWEANGGLRYAPRADLATREEQIAVAEVTR<br>LRQGWGAWPVCAARAGAR (SEQ ID NO: 74) |

Any Mtb antigen, including any Mtb antigen within any of the fusion proteins described herein, can have an amino acid sequence that is 100%, or from 70% to 99.9%, identical to the particular amino acid sequence listed in Tables 1-4. The amino acid sequence of any individual Mtb antigen, including any Mtb antigen within any of the fusion proteins described herein, can be at least 70%, at least 75%, at least 80%, at least 85%, at least 90%, at least 95%, at least 96%, at least 97%, at least 98%, or at least 99% identical to the particular amino acid sequence listed in Tables 1-4. Identity or similarity with respect to an amino acid or nucleotide sequence is defined herein as the percentage of amino acid residues (or nucleotide residues as the case may be) in the particular Mtb antigen that are identical (i.e., same residue) with the amino acid or nucleotide sequence for the Mtb antigen shown in Tables 1-4, after aligning the sequences and introducing gaps, if necessary, to achieve the maximum percent sequence identity. Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Any amino acid number calculated as a % identity can be rounded up or down, as the case may be, to the closest whole number.

Any Mtb antigen, including any Mtb antigen within any of the fusion proteins described herein, can be fragments of the particular amino acid sequence listed in Tables 1-3. The amino acid sequence of any individual Mtb antigen, including any Mtb antigen within any of the fusion proteins described herein, can be missing consecutive amino acids constituting at least 20%, at least 15%, at least 10%, at least 5%, at least 4%, at least 3%, at least 2%, or at least 1%, of the particular amino acid sequence listed in Tables 1-3. The omitted consecutive amino acids may be from the C-terminus or N-terminus portion of the antigen. Alternately, the omitted consecutive amino acids may be from the internal portion of the antigen, thus retaining at least its C-terminus and N-terminus amino acids of the antigen.

Any Mtb antigen, including any Mtb antigen within any of the fusion proteins described herein, can have one or more amino acid additions, deletions, or substitutions compared to the particular amino acid sequence listed in Tables 1-3. Any individual Mtb antigen, including any Mtb antigen within any of the fusion proteins described herein, can have at least one, at least two, at least three, at least four, at least five, at least six, at least seven, at least eight, at least nine, at least ten, at least eleven, or at least twelve amino acid additions, deletions, or substitutions compared to the particular amino acid sequence listed in Tables 1-3. The amino acid additions, deletions, or substitutions can take place at any amino acid position within the Mtb antigen.

Where a particular Mtb antigen, including any Mtb antigen within any of the fusion proteins described herein, comprises at least one or more substitutions, the substituted amino acid(s) can each be, independently, any naturally occurring amino acid or any non-naturally occurring amino acid. Thus, a particular Mtb antigen may comprise one or more amino acid substitutions that are naturally occurring amino acids and/or one or more amino acid substitutions that are non-naturally occurring amino acids. Individual amino acid substitutions are selected from any one of the following: 1) the set of amino acids with nonpolar sidechains, for example, Ala, Cys, Ile, Leu, Met, Phe, Pro, Val; 2) the set of amino acids with negatively charged side chains, for example, Asp, Glu; 3) the set of amino acids with positively charged sidechains, for example, Arg, His, Lys; and 4) the set of amino acids with uncharged polar sidechains, for example, Asn, Cys, Gln, Gly, His, Met, Phe, Ser, Thr, Trp, Tyr, to which are added Cys, Gly, Met and Phe. Substitutions of a member of one class with another member of the same class are contemplated herein. Naturally occurring amino acids include, for example, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Non-naturally occurring amino acids include, for example, norleucine, ornithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Briefly, these procedures involve chemically activating a suppressor tRNA with a non-naturally occurring amino acid residue followed by in vitro transcription and translation of the RNA.

The Mtb antigens, including any Mtb antigen within any of the fusion proteins described herein, which are modified as described herein retain their ability to elicit an immune response against *Mycobacterium tuberculosis*. That is, modification of a particular Mtb antigen, including any Mtb antigen within any of the fusion proteins described herein, will still allow the resultant Mtb antigen, or fusion protein comprising the same, to elicit an immune response against *Mycobacterium tuberculosis*.

The present disclosure also provides nucleic acid molecules encoding any of the fusion proteins described herein that comprise at least three *Mycobacterium tuberculosis*

(Mtb) antigens. In some embodiments, the fusion protein comprises at least one acute Mtb antigen, at least one latent Mtb antigen, and at least one resuscitation Mtb antigen. In some embodiments, the fusion protein comprises at least two latent Mtb antigens and at least one resuscitation Mtb antigen.

The nucleic acid molecules described herein and in Tables 1-4 are representative. That is, the specific sequences recited in Tables 1-4 are simply one example of a nucleic acid molecule that can encode a particular Mtb antigen within a fusion protein. One skilled in the art having knowledge of the genetic code can routinely prepare and design a plethora of nucleic acid molecules encoding the same Mtb antigen. The length and nucleotide content of any particular nucleic acid molecule is dictated by the desired amino acid sequence of the encoded Mtb antigen. The nucleic acid molecule sequences shown in Tables 1-4 are DNA, although RNA nucleic acid molecules are also contemplated.

TABLE 5

| Primer name | Sequence |
| --- | --- |
| 85B For NdeI | ata gat cat atg ttt agc cgt cct ggc ctg c (SEQ ID NO: 75) |
| 85B Rev EcoRI nostop | tta aga gaa ttc gcc cgc acc cag aga gga t (SEQ ID NO: 76) |
| ESAT-6 For BamHI | aac gtt gga tcc atg aca gag cag cag tgg aa (SEQ ID NO: 77) |
| ESAT-6 Rev EcoRI ns | ata cta gaa ttc tgc gaa cat ccc agt gac gt (SEQ ID NO: 78) |
| 1733 For EcoRI | aac tta gaa ttc atg att gcg act acc cgt gat (SEQ ID NO: 79) |
| 1733 In1 Rev Xma | gat ata ccc ggg ggc ctc cag acg gtc ggt (SEQ ID NO: 80) |
| 1733 Out For Xma | aac gaa ccc ggg gtc caa gac agc cgt agc c (SEQ ID NO: 81) |
| 1733 Out Rev Xba | taa gta tct aga atc ggc gat cgc acg cgc t (SEQ ID NO: 82) |
| 1733 In2 For Xba | ata gaa tct aga cgc gca att ctg atc cgc gt (SEQ ID NO: 83) |
| 1733 Rev ns SacI | aga taa gag ctc acg ttg ggt gca aaa cag gc (SEQ ID NO: 84) |
| 2626 For SacI | ata gaa gag ctc atg acc acg gcg cgt gat a (SEQ ID NO: 85) |
| 2626 Rev HindIII ns | taa aga aag ctt tgc att tag aat aaa ttt tgt gtc (SEQ ID NO: 86) |
| RpfD For HindIII | taa cta aag ctt ttg ctg ggc ctg agc acc (SEQ ID NO: 87) |

TABLE 5-continued

| Primer name | Sequence |
| --- | --- |
| RpfD Rev XhoI stop | atc taa ctc gag cta gtc atc gcg gct acc gct (SEQ ID NO: 88) |
| ESAT6 For NdeI | taa gat cat atg aca gag cag cag tgg aat tc (SEQ ID NO: 89) |
| ESAT-6 Rev EcoRI ns | ata cta gaa ttc tgc gaa cat ccc agt gac gt (SEQ ID NO: 90) |

The present disclosure also provides vectors encoding any of the Mtb antigens, including Mtb antigens within any of the fusion proteins described herein, including any of the modified versions described herein. The vector can be capable of expressing an Mtb antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding an Mtb antigen, which the transformed host cell is cultured and maintained under conditions wherein expression of the antigen takes place.

In some embodiments, coding sequences can be optimized for stability and high levels of expression. In some instances, codons are selected to reduce secondary structure formation of the RNA such as that formed due to intramolecular bonding.

In some embodiments, the vectors can comprise regulatory elements for gene expression of the coding sequences of the nucleic acid. The regulatory elements can be a promoter, an enhancer an initiation codon, a stop codon, or a polyadenylation signal. In some embodiments, the vector can comprise heterologous nucleic acid encoding an Mtb antigen and can further comprise an initiation codon, which is upstream of the antigen coding sequence, and a stop codon, which is downstream of the antigen coding sequence. The initiation and termination codon are in frame with the antigen coding sequence.

The vector can also comprise a promoter that is operably linked to the antigen coding sequence. The promoter operably linked to the Mtb antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter, or the like. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Representative examples of promoters include the bacteriophage T7 promoter, bacteriophage T3 promoter, SP6 promoter, lac operator-promoter, tac promoter, mycobacterial Hsp60 promoter, SV40 late promoter, SV40 early promoter, RSV-LTR promoter, CMV IE promoter, SV40 early promoter or SV40 late promoter and the CMV IE promoter.

The vector can also comprise a polyadenylation signal, which can be downstream of the antigen coding sequence. The polyadenylation signal can be a SV40 polyadeylation signal, LTR polyadenylation signal, CMV polyadeylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus BoNT-A, BoNT-B, BoNT-E, and BoNT-F antigen sequences. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The vector can also comprise a regulatory sequence, which can be well suited for gene expression in a mammalian or human cell into which the vector is administered. The consensus coding sequence can comprise a codon, which can allow more efficient transcription of the coding sequence in the host cell.

The vector can be pSE420 (Invitrogen, San Diego, Calif.) or pET28b (EMD Millipore, Billerca, Mass.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

In some embodiments, the vector is a viral vector. Suitable viral vectors include, but are not limited to, an adenovirus vector, vaccinia virus vector, and paramyxovirus vector. Suitable adenovirus vectors include, but are not limited to, adenovirus 4, adenovirus 5, chimpanzee adenovirus 3, chimpanzee adenovirus 63, and chimpanzee adenovirus 68. A suitable vaccinia virus vector includes, but is not limited to, modified vaccinia Ankara (MVA). Suitable paramyxovirus vectors include, but are not limited to, modified parainfluenza virus (PIV2) and recombinant human parainfluenza virus (rHPIV2). In some embodiments, the vector is present within a composition comprising a pharmaceutically acceptable carrier. One skilled in the art is readily familiar with numerous vectors, many of which are commercially available.

The present disclosure also provides host cells comprising any of the nucleic acid molecules or vectors disclosed herein. The host cells can be used, for example, to express the Mtb antigens, or fragments of thereof. The Mtb antigens, or fragments thereof, can also be expressed in cells in vivo. The host cell that is transformed (for example, transfected) to produce the Mtb antigens, or fragments of thereof can be an immortalised mammalian cell line, such as those of lymphoid origin (for example, a myeloma, hybridoma, trioma or quadroma cell line). The host cell can also include normal lymphoid cells, such as B-cells, that have been immortalized by transformation with a virus (for example, the Epstein-Barr virus).

In some embodiments, the host cells include, but are not limited to: bacterial cells, such as *E. coli, Caulobacter crescentus, Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda* (for example, Sf9 and Sf21 cell lines, and expresSF™ cells (Protein Sciences Corp., Meriden, Conn., USA)), *Drosophila* S2 cells, and *Trichoplusia* in High Five® Cells (Invitrogen, Carlsbad, Calif., USA); and mammalian cells, such as COS1 and COS7 cells, Chinese hamster ovary (CHO) cells, NS0 myeloma cells, NIH 3T3 cells, 293 cells, Procell92S, perC6, HEPG2 cells, HeLa cells, L cells, HeLa, MDCK, HEK293, WI38, murine ES cell lines (for example, from strains 129/SV, C57/BL6, DBA-1, 129/SVJ), K562, Jurkat cells, and BW5147. Other useful mammalian cell lines are well known and readily available from the American Type Culture Collection ("ATCC") (Manassas, Va., USA) and the National Institute of General Medical Sciences (NIGMS) Human Genetic Cell Repository at the Coriell Cell Repositories (Camden, N.J., USA). In some embodiments, the cell is a recombinant BCG. These cell types are only representative and are not meant to be an exhaustive list.

Among other considerations, some of which are described above, a host cell strain may be chosen for its ability to process the expressed Mtb antigens, or fragment thereof, in the desired fashion. Post-translational modifications of the polypeptide include, but are not limited to, glycosylation, acetylation, carboxylation, phosphorylation, lipidation, and acylation, and it is an aspect of the present disclosure to provide Mtb antigens thereof with one or more of these post-translational modifications.

In some embodiments, the recombinant BCG has been genetically engineered to express a functional endosomalytic protein that is bioactive at pH values near neutrality (e.g. about pH 6-8 or about 6.5 to 7.5). The endosomalytic protein is active within Mycobacteria-containing endosomes, which typically have an internal pH near neutrality. The activity of the endosomalytic protein produced by the rBCG results in disruption of the endosome, permitting the rBCG to escape from the endosome and into the cytoplasm of the cell. In some embodiments, the endosomalytic protein that is introduced into the rBCG by genetic engineering is Perfringolysin O (PfoA) from *Clostridium perfringens* or a mutant thereof, such as PfoA$_{G137Q}$, as described in WO 2007/058663, which is incorporated herein by reference in its entirety.

In some embodiments, the *Mycobacteria* are attenuated, as exemplified by BCG. However, those of skill in the art will recognize that other attenuated and nonattenuated *Mycobacteria* exist which would also be suitable for use herein. Examples of additional types of *Mycobacteria* include, but are not limited to, *M. tuberculosis* strain CDC1551, *M. tuberculosis* strain Beijing, *M. tuberculosis* strain H37Ra (ATCC#:25177), *M. tuberculosis* strain H37Rv (ATCC#:25618), *M. bovis* (ATCC#:19211 and 27291), *M. fortuitum* (ATCC#:15073), *M. smegmatis* (ATCC#:12051 and 12549), *M. intracellulare* (ATCC#: 35772 and 13209), *M. kansasii* (ATCC#:21982 and 35775) *M. avium* (ATCC#:19421 and 25291), *M. gallinarum* (ATCC#:19711), *M. vaccae* (ATCC#:15483 and 23024), *M. leprae* (ATCC#:), *M. marinarum* (ATCC#:11566 and 11567), and *M. microtti* (ATCC#:11152).

Examples of attenuated *Mycobacterium* strains include, but are not restricted To, *M. tuberculosis* pantothenate auxotroph strain, *M. tuberculosis* rpoV mutant strain, *M. tuberculosis* leucine auxotroph strain, BCG Danish strain (ATCC #35733), BCG Japanese strain (ATCC #35737), BCG Chicago strain (ATCC #27289), BCG Copenhagen strain (ATCC #: 27290), BCG Pasteur strain (ATCC #: 35734), BCG Glaxo strain (ATCC #: 35741), BCG Connaught strain (ATCC #35745), BCG Montreal (ATCC #35746), BCG1331 strain, BCG Tokyo strain, BCG Moreau strain, BCG-Pasteur Aeras, and BCG Moscow strain.

In some embodiments, the cell comprising the one or more vector(s) is present within a composition comprising a pharmaceutically acceptable carrier.

In some embodiments, the Mtb antigen, or fragment thereof, is labeled with a detectable marker. Detectable markers include, but are not limited to, radioactive isotopes (such as $P^{32}$ and $S^{35}$), enzymes (such as horseradish peroxidase, chloramphenicol acetyltransferase (CAT), β-galactosidase (β-gal), and the like), fluorochromes, chromophores, colloidal gold, dyes, and biotin. The labeled Mtb antigens, or fragments thereof, can be used to carry out diagnostic procedures in a variety of cell or tissue types. For imaging procedures, in vitro or in vivo, the Mtb antigens can be labeled with additional agents, such as NMR contrasting agents, X-ray contrasting agents, or quantum dots. Methods for attaching a detectable agent to polypeptides are known in the art. The Mtb antigens can also be attached to an insoluble support (such as a bead, a glass or plastic slide, or the like).

In some embodiments, the Mtb antigens, or fragment thereof, can be conjugated to a therapeutic agent including, but not limited to, radioisotopes (such as $^{111}$In or $^{90}$Y), toxins (such as tetanus toxoid or ricin), toxoids, and chemotherapeutic agents.

In some embodiments, the Mtb antigens, or fragments thereof, can be conjugated to an imaging agent. Imaging agents include, for example, a labeling moiety (such as biotin, fluorescent moieties, radioactive moieties, histidine tag or other peptide tags) for easy isolation or detection.

The present disclosure also provides compositions comprising at least three *Mycobacterium tuberculosis* (Mtb) antigens, wherein the composition comprises: at least one acute Mtb antigen, at least one latent Mtb antigen, and at least one resuscitation Mtb antigen; or at least two latent Mtb antigens, and at least one resuscitation Mtb antigen. In some embodiments, the at least three Mtb antigens are not present in a fusion protein. In some embodiments, the at least three Mtb antigens are in the form of a protein and not nucleic acid molecules encoding the Mtb antigens.

In some embodiments, the acute Mtb antigen is Ag85B, ESAT6, MPT64, PPE15, PPE51, or Rv3615c. In some embodiments, the latent Mtb antigen is Rv1733c, Rv2626c, Rv3407, or Rv2628c. In some embodiments, the first and/or second transmembrane region of Rv1733c is deleted (Rv1733cΔTM). In some embodiments, the resuscitation Mtb antigen is RpfB, RpfD, or RpfE. In some embodiments, the composition comprises at least four Mtb antigens. In some embodiments, the composition comprises: ESAT6, Rv1733c, Rv2626c, and RpfD Mtb antigens; ESAT6, Rv1733c, Rv2626c, and RpfB Mtb antigens; RpfB, ESAT6, Rv1733c, and Rv2626c Mtb antigens; Ag85B, ESAT6, Rv1733c, Rv2626c, and RpfD Mtb antigens; Ag85B, ESAT6, Rv1733c, Rv2626c, and RpfB Mtb antigens; PPE51, Rv1733c, Rv2628c, and RpfD Mtb antigens; PPE51, Rv1733c, Rv2628c, and RpfB Mtb antigens; Rv3407, Rv1733c, Rv2626c, and RpfB Mtb antigens; or Rv3407, Rv1733c, Rv2626c, and RpfD Mtb antigens. In some embodiments, the composition further comprises a pharmaceutically acceptable carrier.

The present disclosure also provides compositions comprising at least three *Mycobacterium tuberculosis* (Mtb) antigens, wherein the composition comprises: at least one acute Mtb antigen, at least one latent Mtb antigen, and at least one resuscitation Mtb antigen; or at least two latent Mtb antigens, and at least one resuscitation Mtb antigen; wherein the composition comprises at least one nucleic acid molecule encoding at least one of the Mtb antigens. In some embodiments, the composition comprises one Mtb antigen in protein form and one or two nucleic acid molecules encoding two Mtb antigens. In some embodiments, the composition comprises two Mtb antigens in protein form, optionally as a fusion protein, and one nucleic acid molecule encoding one Mtb antigen. Thus, the present composition is a mixture of a protein Mtb antigen(s) and nucleic acid molecule(s) encoding an Mtb antigen(s).

In some embodiments, at least two Mtb antigens are encoded by one or more nucleic acid molecules within one or more vectors. In some embodiments, the one or more vectors is one or more viral vectors. In some embodiments, the one or more viral vectors are any one or more of adenovirus vector, vaccinia virus vector, or paramyxovirus vector. In some embodiments, the adenovirus vector is adenovirus 4, adenovirus 5, chimpanzee adenovirus 3, chimpanzee adenovirus 63, or chimpanzee adenovirus 68. In some embodiments, the one or more vaccinia virus vector is modified vaccinia Ankara (MVA). In some embodiments, the one or more paramyxovirus vectors are any one or more of modified parainfluenza virus (PIV2 or PIV3) or recombinant human parainfluenza virus (rHPIV2). In some embodiments, the at least two Mtb antigens are encoded by a single nucleic acid molecule within the same expression vector as a fusion protein.

In some embodiments, the acute Mtb antigen is Ag85B, ESAT6, MPT64, PPE15, PPE51, or Rv3615c. In some embodiments, the latent Mtb antigen is Rv1733c, Rv2626c, Rv3407, or Rv2628c. In some embodiments, the first and/or second transmembrane region of Rv1733c is deleted. In some embodiments, the resuscitation Mtb antigen is RpfB, RpfD, or RpfE. In some embodiments, the composition comprises at least four Mtb antigens. In some embodiments, the composition comprises: ESAT6, Rv1733c, Rv2626c, and RpfD Mtb antigens; ESAT6, Rv1733c, Rv2626c, and RpfB Mtb antigens; RpfB, ESAT6, Rv1733c, and Rv2626c Mtb antigens; Ag85B, ESAT6, Rv1733c, Rv2626c, and RpfD Mtb antigens; Ag85B, ESAT6, Rv1733c, Rv2626c, and RpfB Mtb antigens; PPE51, Rv1733c, Rv2628c, and RpfD Mtb antigens; PPE51, Rv1733c, Rv2628c, and RpfB Mtb antigens; Rv3407, Rv1733c, Rv2626c, and RpfB Mtb antigens; or Rv3407, Rv1733c, Rv2626c, and RpfD Mtb antigens; wherein any two or more Mtb antigens can be within a fusion protein. In some embodiments, the composition comprises at least four Mtb antigens. In some embodiments, the composition further comprises a pharmaceutically acceptable carrier.

In some embodiments, where a rBCG is used as the vehicle to deliver the Mtb antigens, or fusion proteins, or nucleic acids and or vectors comprising or encoding the same, expression of all or part of the Dos R regulon is not up-regulated in the rBCG. In some embodiments, one or more of the following Dos R regulon antigens are not up-regulated in the rBCG: Rv1738, Rv2623, Rv2031c, Rv2032, Rv2626c, Rv2005c, Rv3127, Rv1733c, Rv1996, Rv2628c, Rv0079, Rv3130c, Rv3131, Rv1813c, Rv2006, Rv2029c, Rv2627c, Rv2030c, Rv3132c, and Rv2629. In some embodiments, the rBCG does not comprise up-regulation of: 1) one or more Mtb antigens, including "classical" Mtb antigens such as 85A, 85B and TB 10.4; and 2) at least one Mtb resuscitation antigen selected from Rv0867c, Rv1009, Rv1884c, Rv2389c, Rv2450c, Rv0288, Rv1009, Rv0685, Rv0824c, Rv1349, Rv2744c, Rv3347c, Rv1130, and Rv1169c. In some embodiments, the rBCG does not include the expression of the following combinations: classical antigens Rv1886c, Rv3804c; resuscitation antigens Rv0867c, Rv1884c, Rv2389c; and Mtb-specific antigen Rv3407. In some embodiments, the rBCG does not include the expression of the following combination: Rv3804c, Rv1886c, and Rv3407, or in addition with Rv3133c, and with the combination of Rv0867c, Rv1884c, and Rv2389c. In some embodiments, the rBCG does not include the expression of the following combination: TB10.4, Ag85B, Ag85A, and Rv3407. In some embodiments, the cell is not a rBCG.

The present disclosure also provides compositions comprising any one or more of the fusion proteins, Mtb antigens, nucleic acid molecules encoding Mtb antigens, including fusion proteins thereof, cells, and/or vectors and a pharmaceutically acceptable carrier. Compositions include, for example, pharmaceutical compositions. A pharmaceutically acceptable carrier refers to at least one component of a pharmaceutical preparation that is normally used for administration of active ingredients. As such, a carrier can contain any pharmaceutical excipient used in the art and any form of vehicle for administration. Carriers include, but are not limited to, phosphate buffered saline, physiological saline, water, citrate/sucrose/Tween formulations and emulsions such as, for example, oil/water emulsions.

The compositions can also include an active therapeutic agent and a variety of other pharmaceutically acceptable components. See Remington's Pharmaceutical Science (15th ed., Mack Publishing Company, Easton, Pa. (1980)). The desired form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents include, but are not limited to, distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Solid formulations of the compositions for oral administration can contain suitable carriers or excipients, such as corn starch, gelatin, lactose, *acacia*, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include *acacia*, methylcellulose, sodium carboxymethylcellulose, polyvinylpyrrolidone (Povidone™), hydroxypropyl methylcellulose, sucrose, starch, and ethylcellulose. Lubricants that can be used include magnesium stearates, stearic acid, silicone fluid, talc, waxes, oils, and colloidal silica. Additional excipients include, for example, colorants, taste-masking agents, solubility aids, suspension agents, compressing agents, enteric coatings, sustained release aids, and the like.

In some embodiments, the compositions can be administered in the form of a depot injection or implant preparation, which can be formulated in such a manner as to permit a sustained release. An exemplary composition comprises any one or more of the compositions described herein formulated in aqueous buffer.

In some embodiments, liquid formulations of a pharmaceutical composition for oral administration prepared in water or other aqueous vehicles can contain various suspending agents such as methylcellulose, alginates, tragacanth, pectin, kelgin, carrageenan, *acacia*, polyvinylpyrrolidone, and polyvinyl alcohol. Liquid formulations of pharmaceutical compositions can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In some embodiments, liquid formulations of a pharmaceutical composition for injection can comprise various carriers such as vegetable oils, dimethylacetamide, dimethylformamide, ethyl lactate, ethyl carbonate, isopropyl myristate, ethanol, polyols such as, for example, glycerol, propylene glycol, liquid polyethylene glycol, and the like. In some embodiments, the composition includes a citrate/sucrose/tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid such as, for example, ethyl oleate.

The compositions can be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. In some embodiments, for topical applications, the pharmaceutical compositions can be formulated in a suitable ointment. In some embodiments, a topical semi-solid ointment formulation typically comprises a concentration of the active ingredient from about 1 to 20%, or from 5 to 10%, in a carrier, such as a pharmaceutical cream base. Some examples of formulations of a composition for topical use include, but are not limited to, drops, tinctures, lotions, creams, solutions, and ointments containing the active ingredient and various supports and vehicles.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect (see Langer, Science, 1990, 249, 1527 and Hanes, Advanced Drug Delivery Reviews, 1997, 28, 97). A sterile injectable preparation such as, for example, a sterile injectable aqueous or oleaginous suspension can also be prepared. This suspension may be formulated according to techniques known in the art using suitable dispersing, wetting, and suspending agents. In some embodiments, the pharmaceutical composition can be delivered in a microencapsulation device so as to reduce or prevent a host immune response against the protein.

Effective doses of the compositions of the present disclosure, for the treatment of a condition vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

In some embodiments, the compositions can be administered to a subject by injection intravenously, subcutaneously, intraperitoneally, intramuscularly, intramedullarily, intraventricularly, intraepidurally, intraarterially, intravascularly, intraarticularly, intrasynovially, intrasternally, intrathecally, intrahepatically, intraspinally, intratumorly, intracranially, enteral, intrapulmonary, transmucosal, intrauterine, sublingual, or locally at sites of inflammation or tumor growth by using standard methods. Alternately, the compositions can be administered to a subject by routes including oral, nasal, ophthalmic, rectal, or topical. The most typical route of administration is intravascular, subcutaneous, or intramuscular, although other routes can be effective. In some embodiments, compositions are administered as a sustained release composition or device, such as a Medipad™ device. The composition can also be administered via the respiratory tract, for example, using a dry powder inhalation device, nebulizer, or a metered dose inhaler. The composition can also be administered by traditional syringes, needleless injection devices, "microprojectile bombardment gone guns," or other physical methods such as electroporation ("EP"), "hydrodynamic method", or ultrasound.

In some embodiments, the composition can be administered to a subject by sustained release administration, by such means as depot injections of erodible implants directly applied during surgery or by implantation of an infusion pump or a biocompatible sustained release implant into the subject. Alternately, the composition can be administered to a subject by injectable depot routes of administration, such as by using 1-, 3-, or 6-month depot injectable or biodegradable materials and methods, or by applying to the skin of the subject a transdermal patch containing the composition, and leaving the patch in contact with the subject's skin, generally for 1 to 5 hours per patch.

In some embodiments, the compositions comprise about 1 nanogram to about 10 mg of nucleic acid. In some embodiments, the compositions comprise: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg.

In some embodiments, the compositions comprise about 5 nanograms to about 10 mg of nucleic acid molecule. In some embodiments, the compositions comprise about 25 nanograms to about 5 mg of nucleic acid molecule. In some embodiments, the compositions contain about 50 nanograms to about 1 mg of nucleic acid molecule. In some embodiments, the compositions contain about 0.1 to about 500 micrograms of nucleic acid molecule. In some embodiments, the compositions contain about 1 to about 350 micrograms of nucleic acid molecule. In some embodiments, the compositions contain about 5 to about 250 micrograms of nucleic acid molecule. In some embodiments, the compositions contain about to about 200 micrograms of nucleic acid molecule. In some embodiments, the compositions contain about 15 to about 150 micrograms of nucleic acid molecule. In some embodiments, the compositions contain about 20 to about 100 micrograms of nucleic acid molecule. In some embodiments, the compositions contain about 25 to about 75 micrograms of nucleic acid molecule. In some embodiments, the compositions contain about 30 to about 50 micrograms of nucleic acid molecule. In some embodiments, the compositions contain about 35 to about 40 micrograms of nucleic acid molecule. In some embodiments, the compositions contain about 100 to about 200 micrograms of nucleic acid molecule. In some embodiments, the compositions comprise about 10 to about 100 micrograms of nucleic acid molecule. In some embodiments, the compositions comprise about 20 to about 80 micrograms of nucleic acid molecule. In some embodiments, the compositions comprise about 25 to about 60 micrograms of nucleic acid molecule. In some embodiments, the compositions comprise about 30 nanograms to about 50 micrograms of nucleic acid molecule. In some embodiments, the compositions comprise about 35 nanograms to about 45 micrograms of nucleic acid molecule. In some embodiments, the compositions contain about 0.1 to about 500 micrograms of nucleic acid molecule. In some embodiments, the compositions contain about 1 to about 350 micrograms of nucleic acid molecule. In some embodiments, the compositions contain about 25 to about 250 micrograms of nucleic acid molecule. In some embodiments, the compositions contain about 100 to about 200 micrograms of nucleic acid molecule.

The compositions can be formulated according to the mode of administration to be used. In cases where compositions are injectable pharmaceutical compositions, they are sterile, pyrogen free and particulate free. An isotonic formulation can be used. Generally, additives for isotonicity can include sodium chloride, dextrose, mannitol, sorbitol and lactose. In some cases, isotonic solutions such as phosphate buffered saline are suitable. Stabilizers include gelatin and albumin. In some embodiments, a vasoconstriction agent is added to the formulation.

The compositions can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freund's incomplete adjuvant, LPS analog including monophosphoryl lipid A, muramyl peptides, quinone analogs, vesicles such as squalene and squalane, hyaluronic acid, lipids, liposomes, calcium ions, viral proteins, polyanions, polycations, or nanoparticles, or other known transfection facilitating agents. The transfection facilitating agent is a polyanion, polycation, including poly-L-glutamate (LGS), or lipid. The transfection facilitating agent is poly-L-glutamate, and more suitably, the poly-L-glutamate is present in the composition at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalane, and hyaluronic acid can also be used administered in conjunction with the genetic construct. In some embodiments, the plasmid compositions can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. In some embodiments, the transfection facilitating agent is a polyanion, polycation, including poly-L-glutamate (LGS), or lipid. Concentration of the transfection agent in the composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP 1, TAP2 and functional fragments thereof.

The plasmid compositions can further comprise a genetic vaccine facilitator agent as described in U.S. Ser. No. 021,579 filed Apr. 1, 1994, which is fully incorporated by reference.

The present disclosure also provides kits comprising any of the Mtb antigens, fragments thereof, fusion proteins, nucleic acid molecules, vectors, or cells, described herein. The kit can include, for example, container(s), package(s) or dispenser(s) along with labels and instructions for administration or use.

The present disclosure also provides methods of eliciting an immune response against *Mycobacterium tuberculosis* in a mammal comprising administering to the mammal an immunologically sufficient amount of one or more fusion proteins comprising at least three *Mycobacterium tuberculosis* (Mtb) antigens, wherein at least one fusion protein comprises: at least one acute Mtb antigen, at least one latent Mtb antigen, and at least one resuscitation Mtb antigen; or at least two latent Mtb antigens, and at least one resuscitation Mtb antigen. Any of the fusion proteins described herein can be administered. In some embodiments, the fusion protein comprises at least four Mtb antigens.

The present disclosure also provides methods of eliciting an immune response against *Mycobacterium tuberculosis* in a mammal comprising administering to the mammal an immunologically sufficient amount of a composition comprising at least three *Mycobacterium tuberculosis* (Mtb) antigens, wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier. Any of the compositions comprising three or more Mtb antigens can be administered. In some embodiments, the composition comprises at least four Mtb antigens.

The present disclosure also provides methods of eliciting an immune response against *Mycobacterium tuberculosis* in a mammal comprising administering to the mammal an immunologically sufficient amount of a composition comprising at least three *Mycobacterium tuberculosis* (Mtb) antigens, wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens. Any of the compositions comprising a mixture of one or more Mtb antigen proteins and one or more nucleic acid molecules encoding one or more Mtb antigens described herein can be administered.

The fusion proteins and compositions described herein can be used to treat or prevent tuberculosis. In some embodiments, the method comprises administering to a human a therapeutically- or prophylactically-effective amount of any of the fusion proteins or compositions described herein such that the tuberculosis infection is diminished or prevented.

In some embodiments, the subject being treated will have been previously diagnosed as having tuberculosis. Such subjects will, thus, have been diagnosed as being in need of such treatment. Alternately, the treatment may be intended to prevent a tuberculosis infection in a subject that does not yet have tuberculosis or to a subject that is travelling to an area where tuberculosis is prevalent.

Treatment of a subject suffering from tuberculosis can be monitored using standard methods. Some methods entail determining a baseline value, for example, of an antibody level or profile in a subject, before administering a dosage of agent, and comparing this with a value for the profile or level after treatment. A significant increase such as, for example, greater than the typical margin of experimental error in repeat measurements of the same sample, expressed as one standard deviation from the mean of such measurements in value of the level or profile signals a positive treatment outcome (i.e., that administration of the agent has achieved a desired response). If the value for immune response does not change significantly, or decreases, a negative treatment outcome is indicated.

In other embodiments, a control value such as a mean and standard deviation, of level or profile is determined for a control population. Typically the individuals in the control population have not received prior treatment. Measured values of the level or profile in a subject after administering a therapeutic agent are then compared with the control value. A significant increase relative to the control value, such as greater than one standard deviation from the mean, signals a positive or sufficient treatment outcome. A lack of significant increase or a decrease signals a negative or insufficient treatment outcome. Administration of the therapeutic is generally continued while the level is increasing relative to the control value. As before, attainment of a plateau relative to control values is an indicator that the administration of treatment can be discontinued or reduced in dosage and/or frequency.

In other embodiments, a control value of the level or profile, such as a mean and standard deviation, is determined from a control population of individuals who have undergone treatment with a therapeutic agent and whose levels or profiles have plateaued in response to treatment. Measured values of levels or profiles in a subject are compared with the control value. If the measured level in a subject is not significantly different, such as by more than one standard deviation, from the control value, treatment can be discontinued. If the level in a subject is significantly below the control value, continued administration of agent is warranted. If the level in the subject persists below the control value, then a change in treatment may be indicated.

In other embodiments, a subject who is not presently receiving treatment but has undergone a previous course of treatment is monitored for antibody levels or profiles to determine whether a resumption of treatment is required. The measured level or profile in the subject can be compared with a value previously achieved in the subject after a previous course of treatment. A significant decrease relative to the previous measurement, such as greater than a typical margin of error in repeat measurements of the same sample, is an indication that treatment can be resumed. Alternately, the value measured in a subject can be compared with a control value (mean plus standard deviation) determined in a population of subjects after undergoing a course of treatment. Alternately, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level, such as more than a standard deviation, is an indicator that treatment should be resumed in a subject.

In some methods, a baseline measurement of antibody to a given antigen in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline, such as 50%, 25% or 10%, administration of a further dosage of antigen is administered. In some embodiments, peak or subsequent measured levels less background are compared with reference levels previously determined to constitute a beneficial prophylactic or therapeutic treatment regime in other subjects. If the measured antibody level is significantly less than a reference level, such as less than the mean minus one standard deviation of the reference value in population of subjects benefiting from treatment, administration of an additional dosage of antigen is indicated.

In some embodiments, the subject(s) that can be treated by the above-described methods is an animal, such as a mammal, including, but are not limited to, humans, non-human primates, rodents (including rats, mice, hamsters and guinea pigs) cow, horse, sheep, goat, pig, dog and cat. In most instances, the mammal is a human.

The present disclosure also provides fusion proteins for use in the preparation of a medicament for treating or preventing a *Mycobacterium tuberculosis* infection, wherein the fusion protein comprises at least three *Mycobacterium tuberculosis* (Mtb) antigens, and wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides fusion proteins for use in treating or preventing a *Mycobacterium tuberculosis* infection, wherein the fusion protein comprises at least three *Mycobacterium tuberculosis* (Mtb) antigens, and wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides uses of a fusion protein in the preparation of a medicament for treating or preventing a *Mycobacterium tuberculosis* infection, wherein the fusion protein comprises at least three *Mycobacterium tuberculosis* (Mtb) antigens, and wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides uses of a fusion protein in treating or preventing a *Mycobacterium tuberculosis* infection, wherein the fusion protein comprises at least three *Mycobacterium tuberculosis* (Mtb) antigens, and wherein the fusion protein comprises: at least one acute Mtb antigen, at least one latent Mtb antigen, and at least one resuscitation Mtb antigen; or at least two latent Mtb antigens, and at least one resuscitation Mtb antigen.

The present disclosure also provides compositions for use in the preparation of a medicament for treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides compositions for use in treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides uses of a composition in the preparation of a medicament for treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides uses of a composition in treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier.

The present disclosure also provides compositions for use in the preparation of a medicament for treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides compositions for use in treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides uses of a composition in the preparation of a medicament for treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides uses of a composition in treating or preventing a *Mycobacterium tuberculosis* infection, wherein the composition comprises at least three *Mycobacterium tuberculosis* (Mtb) antigens, and wherein the composition comprises: at least one acute Mtb antigen, at least one latent Mtb antigen, and at least one resuscitation Mtb antigen; or at least two latent Mtb antigens, and at least one resuscitation Mtb antigen; and a pharmaceutically acceptable carrier; wherein the composition comprises at least one nucleic acid molecule encoding at least one of the Mtb antigens.

The present disclosure also provides any of the fusion proteins described herein, or any of the compositions described herein, or any of the cells described herein, or any of the vectors described herein, or any of the methods described herein, or any of the uses described herein, substantially as described with reference to the accompanying examples and/or figures.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Construction of the Antigen Cassette as the Basic Tool for Subsequent Platform Insertion The 5 antigen cassette (Construct D), which was human codon optimized, was synthesized commercially by Aldevron and cloned into pVAX-1. For use in MVA vectors, antigen 85B was synthesized with its native leader sequence. For viral vectors other than MVA, antigen 85B was replaced with genes either containing or not containing the leader sequence, this being achieved using the unique EcoRI and XmaI nuclease target sequences. To clone the 5 antigen cassette into adenoviral or CMV vectors, primers with homology arms were used to PCR amplify the cassette, and this PCR product was recombined into the appropriate region of the BAC.

For recombinant protein expression of Construct D, the 85B, Rv1733, Rv2626, and RpfD genes were synthesized by DNA2.0 and codon optimized for *E. coli* expression. Antigen 85B and RpfD were synthesized without the native leader sequences. Each gene was PCR amplified from the respective DNA2.0 vector with appropriate restriction sites added and cloned into pET28b sequentially. ESAT-6 was PCR amplified from H37Rv DNA.

More specifically, the genes encoding the protein antigens were PCR amplified using the primers in Table 5 and cloned into the pET28b vector (Novagen) via the indicated restriction enzyme sites. ESAT6 was PCR amplified from Mtb and first cloned into the pET23b vector (Novagen). It was subsequently PCR amplified and cloned into pET28b. The genes for antigen 85B, Rv1733c, Rv2626c, and RpfD were all synthesized with their codons optimized for expression in E. coli (DNA2.0). Antigen Ag85B and rpfD were synthesized without the bases encoding the N-terminal signal sequence, and rpfB was PCR amplified from Mtb without the N-terminal signal sequence. The codon optimized genes were PCR amplified and cloned into pET28b creating N-terminal 6xHis-tagged fusion proteins. The genes were cloned with no spacer sequences, only the restriction enzyme sites between each gene. To remove the 2 transmembrane regions of Rv1733c, it was PCR amplified in 3 pieces which were ligated together.

In another embodiment the 4 Ag and 5 Ag proteins were constructed with wild type Rv1733c including the transmembrane regions. The pET28b constructs were cloned in E. coli cloning strains, screened by restriction digest and sequenced to verify each construct.

Example 2

Construction of Recombinant BCG (rBCG) Strains rBCG strains over-expressing antigens involved with active infection, latency, and resuscitation were constructed. The genes of interest were first cloned in a plasmid which allows for their insertion in the chromosome of BCG at the attB integration site (pJFINT-RIAR). Since this plasmid has three different cloning sites, the 5 genes were not fused together but rather split into three groups. Ag85B was fused to ESAT-6 (Ag85B-ESAT6; SEQ ID NO:91 (nucleotide) and SEQ ID NO:92 (amino acid) with Ag85B signal sequence; SEQ ID NO:93 (nucleotide) and SEQ ID NO:94 (amino acid) with 19 kDa lipoprotein signal sequence) and placed in the first cloning site, Rv1733c was cloned by itself, and Rv2626c was fused with RpfD (Rv2626c-RpfD; SEQ ID NO:95 and SEQ ID NO:96 with Ag85B signal sequence; SEQ ID NO:97 and SEQ ID NO:98 with 19 kDa lipoprotein signal sequence) then placed into the third site to create the following construct: Ag85B-ESAT6+Rv1733c+Rv2626c-RpfD. Each insert was placed under the control of the Hsp60 promoter and a signal sequence was added to both fusions, except Rv1733c since it is already a mycobacterial membrane protein. Constructs with two different signal sequences were made; the Ag85B signal sequence which allows for secretion of the fusions, and the 19 kDa lipoprotein signal sequence which anchors them into the membrane to examine which one would allow better expression and/or immunogenicity of the antigens. Both replicating and non-replicating versions of those rBCG strains were constructed. The maps of the plasmids that were used to construct the rBCG strains are shown in FIG. 1A (fusions with the Ag85B signal sequence) and 1B (fusions with the 19 kDa signal sequence).

After the rBCG strains were constructed by integration of the shuttle plasmids in the chromosome of BCG SSI, BCG SSIΔPanCD or other BCG strains, cell lysates and supernatants were prepared to evaluate the relative expression of the different antigens as well as their localization in the rBCG cells. Western blot data using a monoclonal antibody against ESAT-6 as a probe showed the following: the BCG SSI control, which does not have the gene for ESAT-6, showed no reactivity with the monoclonal antibody in either the cell lysate or the culture supernatant; for rBCG expressing the Ag85B-ESAT6 fusion linked to the 19 kDa signal sequence, low levels of the fusion were detected, but only in the cell lysates and not in the culture supernatant of both the replicating and non-replicating rBCG strains, showing that this signal sequence does not result in secretion of the fusion, as expected; the rBCG strain expressing the Ag85B-ESAT6 fusion linked to the Ag85B signal sequence showed a very high level of expression both in the cell lysate and the culture supernatant confirming that this signal sequence does result in the secretion of this fusion (data not shown).

Following the antigen expression studies, a preliminary immunogenicity experiment was carried out in C57/BL6 mice comparing the BCG SSI control and the rBCG strains expressing the fusions with the two different signal sequences. Mice were immunized once sc with either $10^5$ or $10^6$ CFUs of the different BCG strains and were sacrificed 6 weeks later. The splenocytes were stimulated for 72 hours with recombinant Ag85B or ESAT-6 proteins and the levels of antigen specific IFNγ released in the culture supernatants were measured using an ELISA assay. The following results were obtained with the Ag85B-ESAT6 fusions (see, FIG. 2): the BCG SSI control given at the lowest dose showed background levels of IFNγ, similar to what was obtained with the naïve mice, whereas the mice given the highest dose showed higher levels of Ag85B specific IFNγ, but no ESAT6 specific response which was expected since the BCG SSI control does not have the gene for ESAT-6; in contrast, the rBCG strain expressing the Ag85B-ESAT6 fusion linked to the Ag85B signal sequence gave a much stronger Ag85B specific response at both doses, but an ESAT-6 response above background only at the higher dose; similar results were obtained with the rBCG strain expressing the fusion linked to the 19 kDa signal sequence, but only at the higher dose, which is not surprising considering the expression levels were much lower in that strain (data not shown).

DNA sequence of the Ag85B-ESAT6 fusion with the Ag85B signal sequence:

(SEQ ID NO: 91)

```
atgacagacgtgagccgaaagattcgagcttggggacgccgattgat
gatcggcacggcagcggctgtagtccttccgggcctggtggggcttg
ccggcggagcggcaaccgcgggcgcgttctcccggccggggctgccg
gtcgagtacctgcaggtgccgtcgccgtcgatgggccgcgacatcaa
ggttcagttccagagcggtgggaacaactcacctgcggtttatctgc
tcgacggcctgcgcgcccaagacgactacaacggctgggatatcaac
accccggcgttcgagtggtactaccagtcgggactgtcgatagtcat
gccggtcggcgggcagtccagcttctacagcgactggtacagcccgg
cctgcggtaaggctggctgccagacttacaagtgggaaaccttcctg
accagcgagctgccgcaatggttgtccgccaacagggccgtgaagcc
caccggcagcgctgcaatcggcttgtcgatggccggctcgtcggcaa
tgatcttggccgcctaccaccccccagcagttcatctacgccggctcg
ctgtcggccctgctggacccctctcaggggatggggcctagcctgat
cggcctcgcgatgggtgacgccggcggttacaaggccgcagacatgt
ggggtccctcgagtgacccggcatgggagcgcaacgaccctacgcag
cagatccccaagctggtcgcaaacaacacccggctatgggtttattg
cgggaacggcaccccgaacgagttgggcggtgccaacatacccgccg
```

-continued

```
agttcttggagaacttcgttcgtagcagcaacctgaagttccaggat
gcgtacaacgccgcgggcgggcacaacgccgtgttcaacttcccgcc
caacggcacgcacagctgggagtactgggcgctcagctcaacgcca
tgaagggtgacctgcagagttcgttaggcgccggcatgacagagcag
cagtggaatttcgcgggtatcgaggccgcggcaagcgcaatccaggg
aaatgtcacgtccattcattccctccttgacgaggggaagcagtccc
tgaccaagctcgcagcggcctggggcggtagcggttcggaggcgtac
cagggtgtccagcaaaaatgggacgccacggctaccgagctgaacaa
cgcgctgcagaacctggcgcggacgatcagcgaagccggtcaggcaa
tggcttcgaccgaaggcaacgtcactgggatgttcgcatga.
```

Amino acid sequence of the Ag85B-ESAT6 fusion with the Ag85B signal sequence:

(SEQ ID NO: 92)
MTDVSRKIRAWGRRLMIGTAAAVVLPGLVGLAGGAATAGAFSRPGLP
VEYLQVPSPSMGRDIKVQFQSGGNNSPAVYLLDGLRAQDDYNGWDIN
TPAFEWYYQSGLSIVMPVGGQSSFYSDWYSPACGKAGCQTYKWETFL
TSELPQWLSANRAVKPTGSAAIGLSMAGSSAMILAAYHPQQFIYAGS
LSALLDPSQGMGPSLIGLAMGDAGGYKAADMWGPSSDPAWERNDPTQ
QIPKLVANNTRLWVYCGNGTPNELGGANIPAEFLENFVRSSNLKFQD
AYNAAGGHNAVFNFPPNGTHSWEYWGAQLNAMKGDLQSSLGAGMTEQ
QWNFAGIEAAASAIQGNVTSIHSLLDEGKQSLTKLAAAWGGSGSEAY
QGVQQKWDATATELNNALQNLARTISEAGQAMASTEGNVTGMFA.

DNA sequence of the Ag85B-ESAT6 fusion with the 19 kDa signal sequence:

(SEQ ID NO: 93)
atgaagcgtggactgacggtcgcggtagccggagccgccattctggt
cgcaggtattccggatgttcaagcaacaagtcgactacaggaagcgg
tgagaccacgaccgcggcaggtaccacggcaagccccggccggccgg
ggctgccggtcgagtacctgcaggtgccgtcgccgtcgatgggccgc
gacatcaaggttcagttccagagcggtgggaacaactcacctgcggt
ttatctgacgacggcctgcgcgcccaagacgactacaacggctggga
tatcaacaccccggcgttcgagtggtactaccagtcgggactgtcga
tagtcatgccggtcggcgggcagtccagatctacagcgactggtaca
gcccggcctgcggtaaggctggctgccagacttacaagtgggaaacc
ttcctgaccagcgagagccgcaatggttgtccgccaacagggccgtg
aagcccaccggcagcgctgcaatcggcttgtcgatggccggctcgtc
ggcaatgatcttggccgcctaccacccccagcagttcatctacgccg
gctcgctgtcggccagaggacccactcaggggatggggcctagcctg
atcggcctcgcgatgggtgacgccggcggttacaaggccgcagacat
gtggggtccacgagtgacccggcatgggagcgcaacgaccctacgca
gcagatccccaagaggtcgcaaacaacacccggctatgggtttattg
cgggaacggcaccccgaacgagttgggcggtgccaacatacccgccg
agttcttggagaacttcgttcgtagcagcaacctgaagttccaggat
gcgtacaacgccgcgggcgggcacaacgccgtgttcaacttcccgcc
caacggcacgcacagctgggagtactggggcgctcagctcaacgcca
tgaagggtgacctgcagagttcgttaggcgccggcatgacagagcag
cagtggaatttcgcgggtatcgaggccgcggcaagcgcaatccaggg
aaatgtcacgtccattcattccctccttgacgaggggaagcagtccc
tgaccaagctcgcagcggcctggggcggtagcggttcggaggcgtac
cagggtgtccagcaaaaatgggacgccacggctaccgagctgaacaa
cgcgctgcagaacctggcgcggacgatcagcgaagccggtcaggcaa
tggatcgaccgaaggcaacgtcactgggatgttcgcatga.

Amino acid sequence of the Ag85B-ESAT6 fusion with the 19 kDa signal sequence:

(SEQ ID NO: 94)
MKRGLTVAVAGAAILVAGLSGCSSNKSTTGSGETTTAAGTTASPGRP
GLPVEYLQVPSPSMGRDIKVQFQSGGNNSPAVYLLDGLRAQDDYNGW
DINTPAFEWYYQSGLSIVMPVGGQSSFYSDWYSPACGKAGCQTYKWE
TFLTSELPQWLSANRAVKPTGSAAIGLSMAGSSAMILAAYHPQQFIY
AGSLSALLDPSQGMGPSLIGLAMGDAGGYKAADMWGPSSDPAWERND
PTQQIPKLVANNTRLWVYCGNGTPNELGGANIPAEFLENFVRSSNLK
FQDAYNAAGGHNAVFNFPPNGTHSWEYWGAQLNAMKGDLQSSLGAGM
TEQQWNFAGIEAAASAIQGNVTSIHSLLDEGKQSLTKLAAAWGGSGS
EAYQGVQQKWDATATELNNALQNLARTISEAGQAMASTEGNVTGMFA.

DNA sequence of Rv2626c-RpfD fusion with the Ag85B signal sequence:

(SEQ ID NO: 95)
atgacagacgtgagccgaaagattcgagcttggggacgccgattgat
gatcggcacggcagcggctgtagtccttccgggcctggtggggcttg
ccggcggagcggcaaccgcgggcgcgttctccatgaccaccgcacgc
gacatcatgaacgcaggtgtgacctgtgttggcgaacacgagacgct
aaccgctgccgctcaatacatgcgtgagcacgacatcggcgcgttgc
cgatctgcggggacgacgaccggctgcacggcatgctcaccgaccgc
gacattgtgatcaaaggcctggctgcgggcctagacccgaataccgc
cacggctggcgagttggcccgggacagcatctactacgtcgatgcga
acgcaagcatccaggagatgctcaacgtcatggaagaacatcaggtc
cgccgtgttccggtcatctcagagcaccgcttggtcggaatcgtcac
cgaagccgacatcgcccgacacctgcccgagcacgccattgtgcagt
tcgtcaaggcaatctgctcgcccatggccctcgccagcatgacaccg
ggtttgcttactactgcgggtgctggccgaccacgtgacaggtgcgc
caggatcgtatgcacggtgttcatcgaaaccgccgttgtcgcgacca

```
tgtttgtcgcgttgttgggtctgtccaccatcagctcgaaagccgac gacatcgattgggacgccatcgcgcaatgcgaatccggcggcaattg ggcggccaacaccggtaacgggttatacggtggtctgcagatcagcc aggcgacgtgggattccaacggtggtgtcgggtcgccggcggccgcg agtccccagcaacagatcgaggtcgcagacaacattatgaaaaccca aggcccgggtgcgtggccgaaatgtagttcttgtagtcagggagacg caccgctgggctcgctcacccacatcctgacgttcctcgcggccgag actggaggttgttcggggagcagggacgattag.
```

Amino acid sequence of the Rv2626c-RpfD fusion with the Ag85B signal sequence:

```
                                        (SEQ ID NO: 96)
MTDVSRKIRAWGRRLMIGTAAAVVLPGLVGLAGGAATAGAFSMTTAR

DIMNAGVTCVGEHETLTAAAQYMREHDIGALPICGDDDRLHGMLTDR

DIVIKGLAAGLDPNTATAGELARDSIYYVDANASIQEMLNVMEEHQV

RRVPVISEHRLVGIVTEADIARHLPEHAIVQFVKAICSPMALASMTP

GLLTTAGAGRPRDRCARIVCTVFIETAVVATMFVALLGLSTISSKAD

DIDWDAIAQCESGGNWAANTGNGLYGGLQISQATWDSNGGVGSPAAA

SPQQQIEVADNIMKTQGPGAWPKCSSCSQGDAPLGSLTHILTFLAAE

TGGCSGSRDD.
```

DNA sequence of the Rv2626c-RpfD fusion with the 19 kDa signal sequence:

```
                                        (SEQ ID NO: 97)
Atgaagcgtggactgacggtcgcggtagccggagccgccattctggt cgcaggtattccggatgttcaagcaacaagtcgactacaggaagcgg tgagaccacgaccgcggcaggtaccacggcaagcccggcatgacca ccgcacgcgacatcatgaacgcaggtgtgacctgtgttggcgaacac gagacgctaaccgctgccgctcaatacatgcgtgagcacgacatcgg cgcgttgccgatctgcggggacgacgaccggctgcacggcatgctca ccgaccgcgacattgtgatcaaaggcctggctgcgggcctagacccg aataccgccacggctggcgagttggcccgggacagcatctactacgt cgatgcgaacgcaagcatccaggagatgctcaacgtcatggaagaac atcaggtccgccgtgttccggtcatctcagagcaccgcttggtcgga atcgtcaccgaagccgacatcgcccgacacctgcccgagcacgccat tgtgcagttcgtcaaggcaatctgctcgcccatgcccctcgccagca tgacaccgggtttgcttactactgcgggtgctggccgaccacgtgac aggtgcgccaggatcgtatgcacggtgttcatcgaaaccgccgttgt cgcgaccatgtttgtcgcgttgttgggtagtccaccatcagctcgaa agccgacgacatcgattgggacgccatcgcgcaatgcgaatccggcg gcaattgggcggccaacaccggtaacgggttatacggtggtctgcag atcagccaggcgacgtgggattccaacggtggtgtcgggtcgccggc ggccgcgagtccccagcaacagatcgaggtcgcagacaacattatga
```

```
aaacccaaggcccgggtgcgtggccgaaatgtagttcttgtagtcag ggagacgcaccgctgggctcgctcacccacatcctgacgttcctcgc ggccgagactggaggttgttcggggagcagggacgattag.
```

Amino acid sequence of the Rv2626c-RpfD fusion with the 19 kDa signal sequence:

```
                                        (SEQ ID NO: 98)
MKRGLTVAVAGAAILVAGLSGCSSNKSTTGSGETTTAAGTTASPGMT

TARDIMNAGVTCVGEHETLTAAAQYMREHDIGALPICGDDDRLHGML

TDRDIVIKGLAAGLDPNTATAGELARDSIYYVDANASIQEMLNVMEE

HQVRRVPVISEHRLVGIVTEADIARHLPEHAIVQFVKAICSPMALAS

MTPGLLTTAGAGRPRDRCARIVCTVFIETAVVATMFVALLGLSTISS

KADDIDWDAIAQCESGGNWAANTGNGLYGGLQISQATWDSNGGVGSP

AAASPQQQIEVADNIMKTQGPGAWPKCSSCSQGDAPLGSLTHILTFL

AAETGGCSGSRDD.
```

Example 3

Cloning and Overexpression of Fusion Proteins of the Cassette and Variants

Preparation of the Antigen Cassette and its Variants as Fusion Protein Required a Modified Strategy Outline Below:

Cloning:Multiple recombinant fusion proteins were created, of which two are exemplified here: one with four Mtb antigens (ESAT6-Rv1733c-Rv2626c-RpfD), and one with five antigens (Ag85B-ESAT6-Rv1733c-Rv2626c-RpfD). The genes encoding the protein antigens were PCR amplified using the primers in Table 5 and cloned into the pET28b vector (Novagen) via the indicated restriction enzyme sites. ESAT6 was PCR amplified from Mtb and first cloned into the pET23b vector (Novagen). It was subsequently PCR amplified and cloned into pET28b. The genes for antigen 85B, Rv1733c, Rv2626c, and RpfD were all synthesized with their codons optimized for expression in *E. coli* (DNA2.0). Ag85B, and rpfD were synthesized without the bases encoding the N-terminal signal sequence, and rpfB was PCR amplified from Mtb without the N-terminal signal sequence. The codon optimized genes were PCR amplified and cloned into pET28b creating N-terminal 6xHis-tagged fusion proteins. The genes were cloned with no spacer sequences, only the restriction enzyme sites between each gene. To remove the 2 transmembrane regions of Rv1733c, it was PCR amplified in 3 pieces which were ligated together. In another embodiment the 4 Ag and 5 Ag proteins were constructed with wild type Rv1733c including the transmembrane regions. The pET28b constructs were cloned in *E. coli* cloning strains, screened by restriction digest and sequenced to verify each construct. The DNA and amino acid sequences of the 4 Ag and 5 Ag fusions were prepared without the transmembrane regions of Rv1733c. Later versions of these fusions replaced RpfD with RpfB in the 4 Ag fusion, with RpfB placed either at the 5' or the 3' end of the fusion.

Expression:The plasmids encoding Construct D and its variant fusion proteins were transformed into *E. coli* T7 express (NEB) or *E. coli* BL21 DE3 (Novagen). Multiple colonies of each fusion construct were picked and grown overnight shaking at 37° C. in Tryptic Soy Broth (TSB) (Sigma). Overnight cultures were diluted 1:100 in TSB and grown shaking at 37° C. to OD600=0.6. Cultures were induced with 1 mM IPTG and grown shaking at 37° C. for 3 hours. Induced and uninduced aliquots of each culture were run on 4-12% Bis/Tris SDS-PAGE gels to verify induction of the fusion proteins. Colonies expressing each of the fusion proteins were frozen in TSB+20% glycerol at −80° C. as research stocks.

Purification of Fusion Proteins 10 ml cultures were inoculated from glycerol stocks of the BE1726D and its variant fusion constructs and grown overnight shaking at 37° C. The overnight cultures were diluted 1:100 in 250 ml TSB and grown shaking at 37° C. to OD600=0.6. Cultures were induced with 1 mM IPTG and grown shaking at 37° C. for 3 hours. An aliquot of the induced sample was run on a 4-12% Bis/Tris SDS-PAGE gel to confirm induction of the protein. The induced culture was centrifuged at 6,000×g for 10 m and pellets were frozen at −80° C. Pellets were thawed and resuspended in 10 ml BPER buffer (Thermo Scientific), and an aliquot was taken for testing (lysate). Lysozyme (20 u/ml) and DNase I (25 U/ml) was added to help complete cell lysis. The lysed cells were centrifuged at 12,000×g for 10 minutes and the supernatant was collected (soluble fraction). The insoluble pellet was resuspended in 10 ml BPER buffer and a 100 µl aliquot was removed (insoluble fraction). The cells in the resuspended pellet were diluted with 10 ml 10% BPER buffer and the suspension was centrifuged at 12,000×g for 10 minutes. The supernatant was discarded and the pellet was washed again with 10 ml 10% BPER buffer 3 more times. The lysate, soluble and insoluble fractions and washes were run on a 4-12% Bis/Tris SDS-PAGE gel to confirm expression and determine the subcellular localization of the protein. The fusion proteins were found localized to the insoluble pellet in inclusion bodies. The insoluble pellet was resuspended in 10 ml denaturing binding buffer (DBB) (8 M urea, 92 mM $Na_2HPO_4$, 7 mM $NaH_2PO_4$, 10 mM Tris) pH 7.8. The inclusion bodies were lysed by sonication, and the lysate was cleared of debris by centrifugation at 12,000×g for 20 minutes.

Proteins with the transmembrane regions of Rv1733c deleted were purified by column purification. Five (5) ml of HisPur Cobalt resin (Thermo Scientific) was equilibrated with DBB and incubated with 5 ml of cleared lysate. The mixture was rocked at room temperature for 90 minutes. The lysate/resin mixture was then loaded on a 30 ml column and washed with 25 volumes of denaturing wash buffer (8 M urea, 25 mM $Na_2HPO_4$, 75 mM $NaH_2PO_4$, 10 mM Tris, 12 mM sodium deoxycholate, pH 7.8). His-tagged protein was eluted from the Co+ column by eluting with elution buffer (8 M urea, 10 mM Tris, 5% glycerol) pH 8.0 with 50, 100, 350, 500, and 1000 mM imidazole. Eluted proteins were run on a 4-12% Bis/Tris SDS-PAGE gel and clean fractions were dialyzed stepwise from 8M urea, 10 mM Tris, 5% glycerol to 10 mM Tris, 5% glycerol. Dialyzed protein was analyzed by SDS-PAGE for purity, western blot for the presence of each antigen, and was assayed for the presence of residual endotoxin. Pure samples with <0.25 U endotoxin/ml were aliquoted and frozen at −80° C.

Proteins which have wild type Rv1733c were purified using an AKTA purifier (GE Healthcare). After the inclusion bodies were separated by BPER washes as above, the insoluble pellet was resuspended in 10 ml denaturing binding buffer (DBB)+20 mM imidazole. The inclusion bodies were lysed by sonication, and the lysate was cleared of debris by centrifugation at 12,000×g for 20 minutes. Five (5) ml of Ni Sepharose High Performance (GE Healthcare) resin was equilibrated with DBB and incubated with 10 ml of cleared lysate. The mixture was rocked at room temperature for 2 hours. The mixture was then loaded on the AKTA purifier. All the lines used on AKTA purifier were equilibrated with DBB+20 mM imidazole, denaturing wash buffer (8 M urea, 25 mM $Na_2HPO_4$, 75 mM $NaH_2PO_4$, 10 mM Tris, 12 mM sodium deoxycholate, 20 mM imidazole) pH 7.8, or elution buffer (8 M urea, 10 mM Tris, 5% glycerol, 20 mM imidazole), as needed. Proteins were eluted by gradient elution (elution buffer 1: 8 M urea, 10 mM Tris, 5% glycerol, 20 mM imidazole, run from 100% to 0; elution buffer 2: 8 M urea, 10 mM Tris, 5% glycerol, 500 mM imidazole, fun from 0 to 100%) and fractions were collected. The positive fractions were run on a 4-12% Bis-Tris SDS-PAGE gel and were dialyzed stepwise from 8 M urea, 10 mM Tris, 5% glycerol to 10 mM Tris, 5% glycerol. Dialyzed protein was analyzed by SDS-PAGE for purity, western blot for the presence of each antigen, and was assayed for the presence of residual endotoxin. Pure samples with <0.25 U endotoxin/ml were aliquoted and frozen at −80° C.

The foregoing describes the purification of the 4 Ag and 5 Ag proteins that were expressed with 6xHis tags. The proteins can also be expressed without tags. The untagged proteins can be purified by combining chromatographic methods including ion exchange and size exclusion chromatography and filtration methods such as tangential flow.

Example 4

Immunogenicity of the 5 Ag and 4 Ag Fusion Proteins in Mice

Figure 3A:
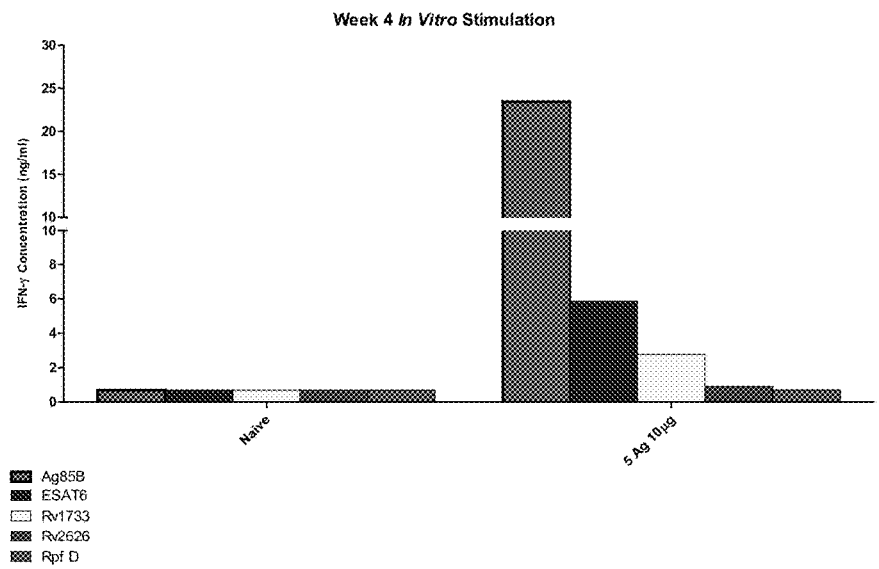
FIGS. 3A and 3B show in vitro stimulation: (A) showing INF-γ induction in splenocytes following protein stimulation and ELISpot; and (B) analysis showing number of splenocytes expressing INF-γ from CB6F1 mice immunized twice with 10 μg of the 5 Ag fusion protein (Construct D) and a synthetic poly I:C adjuvant.
Figure 3B:
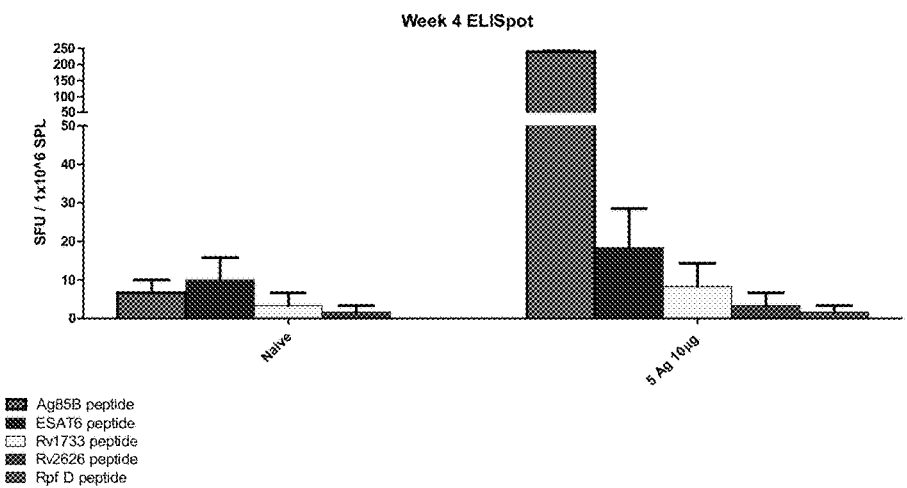

The 5 Ag fusion protein was tested for immunogenicity in CB6F1 mice, adjuvanted with a synthetic poly I:C TLR3 agonist. Multiple other adjuvants, such as TLR4 agonists, were tested and shown to be immunogenic, and thus the embodiment is independent of the adjuvant used, and applicable to many classes of adjuvants. Mice were immunized subcutaneously twice, two weeks apart, with 1 or 10 µg of adjuvanted fusion protein. Two (2) weeks after the second immunization, the mice were sacrificed and splenocytes were isolated. The splenocytes were incubated with recombinant protein antigens for in vitro stimulation and recombinant protein or overlapping peptides for ELISpot analysis. The 5 Ag fusion protein induced significant IFN-γ responses to each antigen that were measurable by both in vitro stimulation and ELISpot (see, FIGS. 3A and 3B). The response to Ag85B, the most immunogenic and first antigen of the fusion protein, was much stronger to the responses to the other antigens.

Figure 4A:
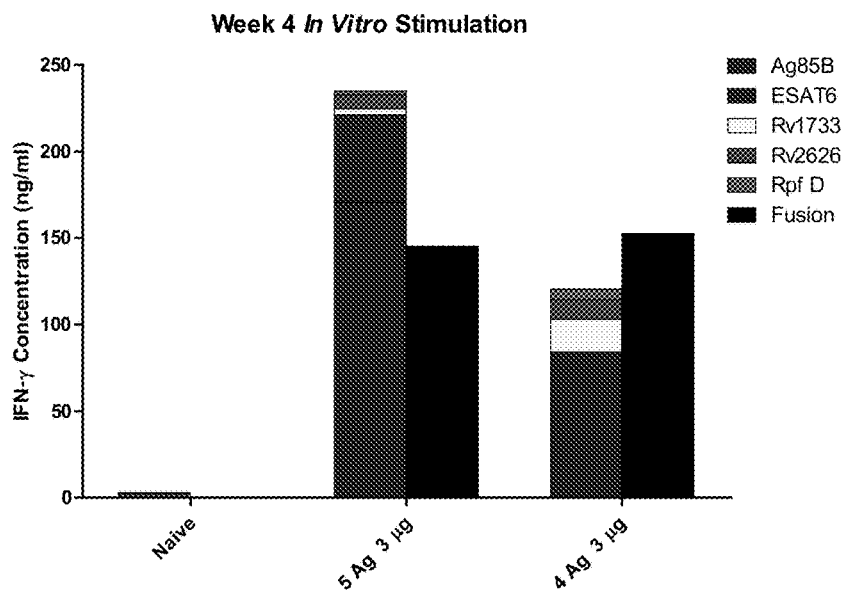
FIGS. 4A and 4B show in vitro stimulation: (A) ELISpot; and (B) analysis of splenocytes from CB6F1 mice immunized twice with 3 μg of the 5 Ag fusion protein (Construct D) or 4 Ag fusion protein (Construct A) and a synthetic MPL TLR4 adjuvant; when Ag85B is removed from the 5 Ag fusion protein, the responses to the other 4 antigens in the 4 Ag protein increase.
Figure 4B:
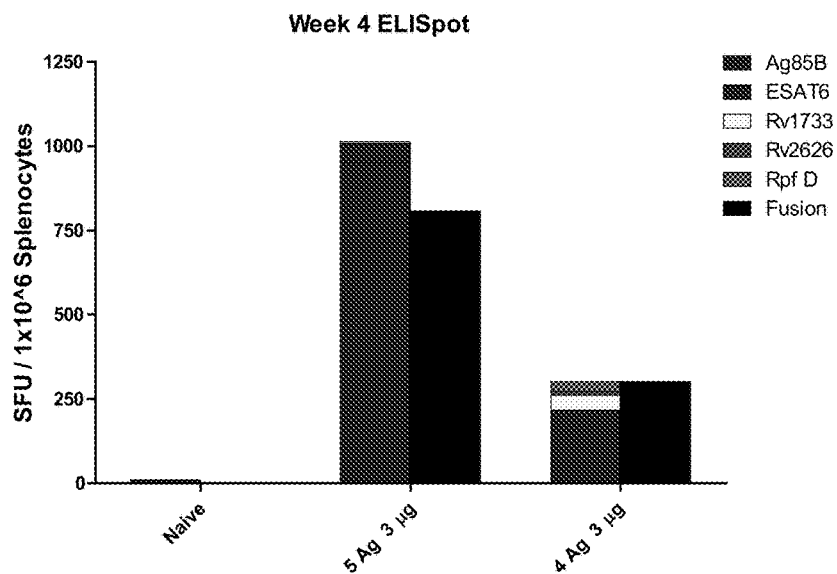

The 4 Ag and 5 Ag proteins were then both tested for immunogenicity in CB6F1 mice, adjuvanted with a synthetic MPL TLR4 agonist. Mice were immunized subcutaneously twice, two weeks apart, with 3 µg adjuvanted fusion protein. Splenocytes were isolated for in vitro stimulation and ELISpot. Splenocytes were stimulated with individual antigens or fusion proteins Immunization with either the 4 Ag or 5 Ag fusion proteins induced IFN-γ responses to all antigens. Responses to ESAT6, Rv1733c, Rv2626c, and RpfD were all higher in the 4 Ag fusion protein, which lacks Ag85B, than the 5 Ag fusion protein (see, FIGS. 4A and 4B).

Figure 5A:
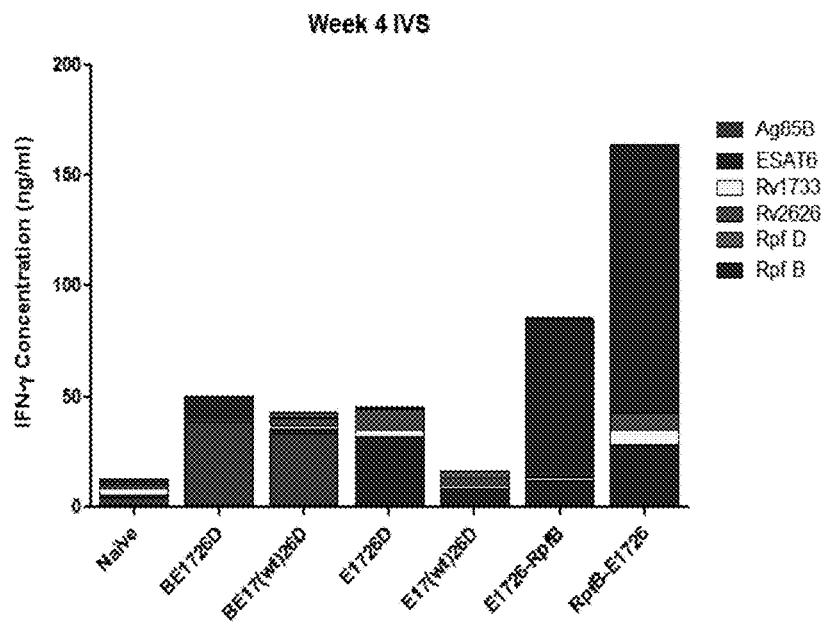
FIGS. 5A and 5B show in vitro stimulation: (A) ELISpot; and (B) analysis of splenocytes from CB6F1 mice immunized twice with 3 μg of the 5 Ag fusion protein (Construct D) and 4 Ag fusion proteins with either wild-type or modified Rv1733 or the 4 Ag protein with RpfD replaced by RpfB, with RpfB either at the 3' or 5' end of the fusion protein; the proteins were adjuvanted with a synthetic poly I:C adjuvant; RpfB induces a much stronger immune response than RpfD, particularly when RpfB is at the 5' end of the fusion protein; neither modified nor wild-type Rv1733 induced a strong immune response.
Figure 5B:
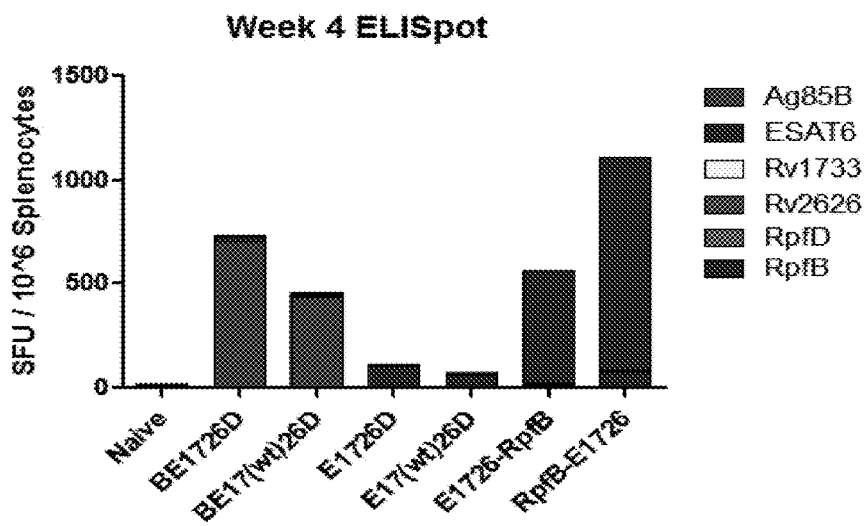

Immunogenicity studies were also performed on the fusion proteins with the wild-type Rv1733c (85B-ESAT6-Rv1733cwt-Rv2626c-RpfD and ESAT6-Rv1733cwt-Rv2626c-RpfD) and the 4 Ag fusions where RpfD was replaced by RpfB (ESAT6-Rv1733c-Rv2626c-RpfB and RpfB-ESAT6-Rv1733c-Rv2626c). These studies compared the immunogenicity of fusion proteins containing the modified Rv1733c with that of fusions containing the wild-type Rv1733c, and also the immunogenicity of fusion proteins containing RpfD with that of fusions containing RpfB. The studies showed that while replacing the modified Rv1733c with the wild-type 1733c did not affect overall immunogenicity, RpfB is significantly more immunogenic than RpfD in these fusions (see, FIGS. 5A and 5B).

Example 5

Ongoing Protective Efficacy

Figure 6A:
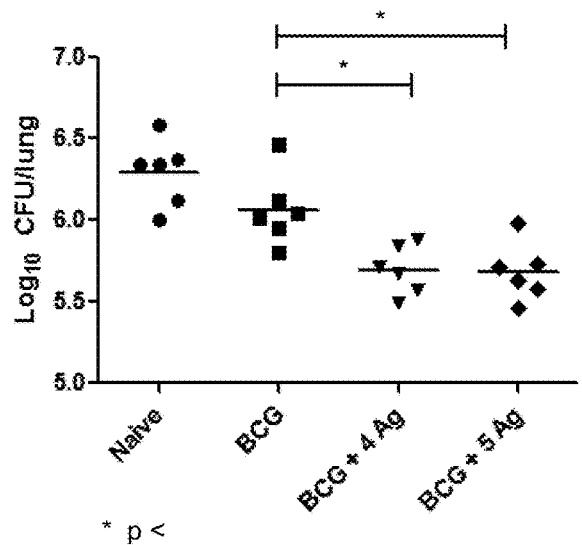
FIGS. 6A and 6B show bacterial numbers in: (A) the lungs and (B) spleen of CB6F1 mice primed with BCG and boosted with either the 4 Ag or 5 Ag fusion protein 4 weeks after challenge with *Mycobacterium tuberculosis* H37Rv.
Figure 6B:
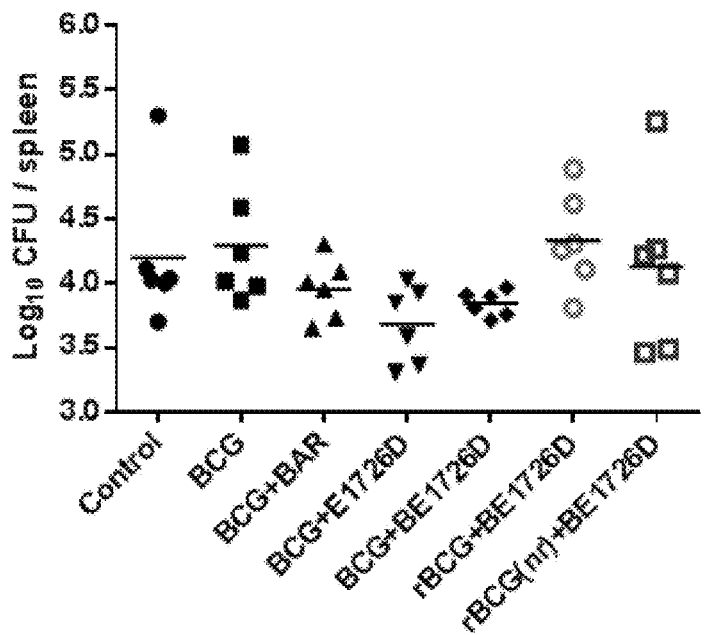

The 5 Ag and 4 Ag fusion proteins (BE1726D, E1726D) were used in a prime boost protection experiment in mice. Mice were primed with BCG SSI and recombinant BCG SSI overexpressing the 5 Mtb antigens that make up the 5 Ag fusion protein. Six (6) and 8 weeks later, the mice were boosted with either the 5 Ag or the 4 Ag protein plus a poly I:C adjuvant. Four (4) weeks after the second boost mice received an aerosol Mtb challenge of 50-100 CFU. Mice were then sacrificed at 4 and 12 weeks post challenge to determine viable bacteria in the lungs (see, FIG. 6A) and spleen (see, FIG. 6B). This experiment determined whether the large response to Ag85B is more protective in mice than the more broad response to the other 4 antigens in the 4 Ag fusion protein.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A fusion protein consisting of four or five antigens, wherein the four or five antigens are *Mycobacterium tuberculosis* antigens, and wherein the fusion protein comprises an amino acid sequence that is at least 98% identical to an amino acid sequence of:
    ESAT6-Rv1733c-Rv2626c-RpfD (SEQ ID NO:53 or SEQ ID NO:54);
    ESAT6-Rv1733c-Rv2626c-RpfB (SEQ ID NO:56);
    RpfB-ESAT6-Rv1733c-Rv2626c (SEQ ID NO:58);
    Ag85B-ESAT6-Rv1733c-Rv2626c-RpfD (SEQ ID NO:61 or SEQ ID NO:62);
    Ag85B-ESAT6-Rv1733c-Rv2626c-RpfB (SEQ ID NO:99 or SEQ ID NO:100);
    PPE51-Rv1733c-Rv2628c-RpfD (SEQ ID NO:64);
    PPE51-Rv1733c-Rv2628c-RpfB (SEQ ID NO:66);
    Rv3407-Rv1733c-Rv2626c-RpfB (SEQ ID NO:68); or
    Rv3407-Rv1733c-Rv2626c-RpfD (SEQ ID NO:70).

2. A pharmaceutical composition comprising the fusion protein according to claim 1 and a pharmaceutically acceptable carrier.

3. The fusion protein according to claim 1, wherein the fusion protein comprises an amino acid sequence at least 98% identical to an amino acid sequence of Ag85B-ESAT6-Rv1733c-Rv2626c-RpfD (SEQ ID NO:61 or SEQ ID NO:62).

4. A fusion protein selected from the group consisting of ESAT6-Rv1733c-Rv2626c-RpfD (SEQ ID NO:53 or SEQ ID NO:54);
    ESAT6-Rv1733c-Rv2626c-RpfB (SEQ ID NO:56);
    RpfB-ESAT6-Rv1733c-Rv2626c (SEQ ID NO:58);
    Ag85B-ESAT6-Rv1733c-Rv2626c-RpfD (SEQ ID NO:61 or SEQ ID NO:62);
    Ag85B-ESAT6-Rv1733c-Rv2626c-RpfB (SEQ ID NO:99 or SEQ ID NO:100);
    PPE51-Rv1733c-Rv2628c-RpfD (SEQ ID NO:64);
    PPE51-Rv1733c-Rv2628c-RpfB (SEQ ID NO:66);
    Rv3407-Rv1733c-Rv2626c-RpfB (SEQ ID NO:68); or
    Rv3407-Rv1733c-Rv2626c-RpfD (SEQ ID NO:70).

5. The fusion protein according to claim 4, where in the fusion protein is Ag85B-ESAT6-Rv1733c-Rv2626c-RpfD (SEQ ID NO:61 or SEQ ID NO:62).

6. A method of eliciting an immune response against *Mycobacterium tuberculosis* in a mammal comprising administering to the mammal an immunologically sufficient amount of the fusion protein according to claim 1.

* * * * *